(12) United States Patent
Guo et al.

(10) Patent No.: US 8,106,064 B2
(45) Date of Patent: Jan. 31, 2012

(54) PYRIMIDINE-2,4-DIONE HIV REVERSE TRANSCRIPTASE INHIBITORS

(75) Inventors: Hongyan Guo, San Mateo, CA (US);
Choung U. Kim, San Carlos, CA (US);
Thorsten A. Kirschberg, Belmont, CA (US); Ill Young Lee, Daejeon (KR);
Michael L. Mitchell, Hayward, CA (US); Jong Chan Son, Daejeon (KR);
Lianhong Xu, Palo Alto, CA (US)

(73) Assignee: Korea Research Institute of Chemical Technology, Daejeon (KR)

( * ) Notice: Subject to any disclaimer, the term of this patent is extended or adjusted under 35 U.S.C. 154(b) by 78 days.

(21) Appl. No.: 11/880,854

(22) Filed: Jul. 24, 2007

(65) Prior Publication Data

US 2008/0070920 A1   Mar. 20, 2008

Related U.S. Application Data

(60) Provisional application No. 60/832,806, filed on Jul. 24, 2006.

(51) Int. Cl.
*A61K 31/505* (2006.01)
(52) U.S. Cl. ........... 514/274; 544/210; 546/268.1
(58) Field of Classification Search .......... 514/274; 544/310; 546/268.1
See application file for complete search history.

(56) References Cited

U.S. PATENT DOCUMENTS

| | | |
|---|---|---|
| 4,656,209 A | 4/1987 | Wehner et al. |
| 5,162,326 A | 11/1992 | Naka et al. |
| 5,461,060 A | 10/1995 | Miyasaka et al. |
| 5,889,013 A | 3/1999 | Kim et al. |
| 5,922,727 A | 7/1999 | Cho et al. |
| 5,998,411 A | 12/1999 | Vig et al. |
| 6,136,815 A | 10/2000 | Son et al. |
| 6,174,998 B1 | 1/2001 | Muhlegger et al. |
| 6,713,486 B1 | 3/2004 | Son et al. |
| 6,987,114 B1 | 1/2006 | Cho et al. |
| 7,250,421 B2 | 7/2007 | Nair et al. |
| 2006/0223834 A1 | 10/2006 | Nair et al. |

FOREIGN PATENT DOCUMENTS

| | | |
|---|---|---|
| EP | 929533 | 7/1999 |
| FR | 2779721 | 12/1999 |
| FR | 2779722 | 12/1999 |
| JP | 08003143 | 1/1996 |
| JP | 10130244 | 5/1998 |
| JP | 10130245 | 5/1998 |
| JP | 10168068 | 6/1998 |
| JP | 2001114767 | 4/2001 |
| JP | 2002284686 | 10/2002 |
| WO | WO 00/51990 | * 9/2000 |
| WO | WO-00/61563 | 10/2000 |
| WO | WO-00/61564 | 10/2000 |
| WO | WO-01/23363 | 4/2001 |
| WO | WO-03/029226 | 4/2003 |
| WO | WO-03/057677 | 7/2003 |

(Continued)

OTHER PUBLICATIONS

Jordan, V. C. Nature Reviews: Drug Discovery, 2, 2003, p. 205.*

(Continued)

*Primary Examiner* — James O Wilson
*Assistant Examiner* — Douglas M Willis
(74) *Attorney, Agent, or Firm* — Edwards Angell Palmer & Dodge LLP; Kongsik Kim; Mark D. Russett

(57) ABSTRACT

The invention is related to pyrimidine-2,4-dione HIV reverse transcriptase inhibitors of Formula (I), (II), or (III):

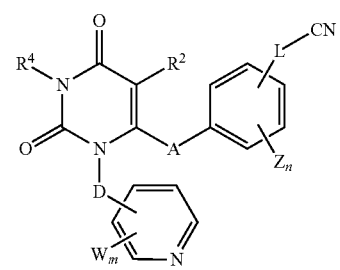

I

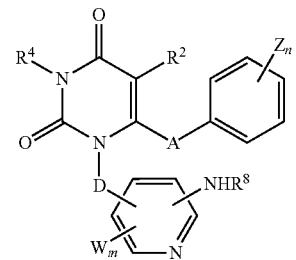

II

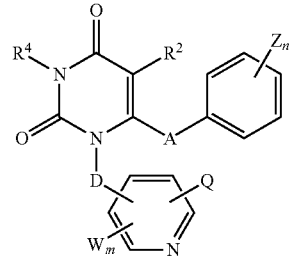

III or a pharmaceutically acceptable salt, thereof, compositions containing such compounds, and therapeutic methods that include the administration of such compounds.

36 Claims, No Drawings

FOREIGN PATENT DOCUMENTS

| WO | WO-03/064511 | 8/2003 |
| WO | WO-2006/070292 | 7/2006 |
| WO | WO-2007/106450 | 9/2007 |
| WO | WO-2008/016522 | 2/2008 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Vippagunta, et al. Advanced Drug Delivery Reviews, 48, 2001, p. 18.*

Patani, et al. Chem. Rev., 96, 1996, pp. 3147-3176.*

Frank D. King. Bioisosteres, Conformational Restriction, and Prodrugs—Case History: An Example of a Conformational Restriction Approach, Medicinal Chemistry: Principles and Practice, Chapter 14, 1994, p. 208.*

Balzarini, J. : Biochemical Pharmacology, vol. 58, No. 1 1999, pp. 1-27.

Database Registry ACS: Jun. 12, 2006 Databse accession No. 887421-82-1(RN).

Database Registry ACS: Jun. 12, 2006, Database accession No. 887421-77-4 (RN).

Database Registry ACS: Jan. 2, 2004, Database accession No. 633320-95-3 (RN).

Datanase Registry ACS: Jun. 12, 2006, Database accession No. 887424-71-7 (RN).

El-Amam, Ali A. et al. Bull. Korean Chem. Soc., vol. 25, No. 7, 2004, pp. 991-996.

Ji, Lei et al. Chem. Pharm Bull. vol. 54., No. 9, 2006, pp. 1248-1253.

Larsen, Janus S. et al. Synthesis, No. 11, 2004, pp. 1874-1878.

Yanping, He et al. Monatshefte Fur Chemie, vol. 136, No. 7, Jul. 1, 2005, pp. 1233-1245.

* cited by examiner

PYRIMIDINE-2,4-DIONE HIV REVERSE TRANSCRIPTASE INHIBITORS

CROSS-REFERENCE TO RELATED APPLICATIONS

This application is filed under 35 U.S.C. 111(a) claiming the benefit under 35 U.S.C. 119(e) to provisional application 60/832,806 filed Jul. 24, 2006 which is herein incorporated by reference in its entirety.

FIELD OF THE INVENTION

This invention relates to novel HIV reverse transcriptase (RT) inhibitors, pharmaceutical compositions thereof, processes for making the novel HIV reverse transcriptase, and methods for inhibiting and treating an HIV infection.

BACKGROUND OF THE INVENTION

In recent years, inhibitors of HIV reverse transcriptase (RT) have become an important class of therapeutic agents for inhibition and treatment of HIV infection in humans. Compounds that inhibit the enzymatic functions of HIV reverse transcriptase inhibit replication of HIV in infected cells. Such compounds are useful in the prevention or treatment of HIV infection in humans, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. Thus, to be effective, new HIV RT inhibitors must be effective not only against wild-type strains of HIV, but must also demonstrate efficacy against the newly emerging mutant strains that are resistant to the commercially available RT inhibitors. Accordingly, there continues to be a need for new HIV RT inhibitors, for example, those targeting the HIV RT in both wild type and mutant strains of HIV.

SUMMARY OF THE INVENTION

Accordingly, in one embodiment, the present invention provides novel HIV RT inhibitor compounds of Formula (I) or (II):

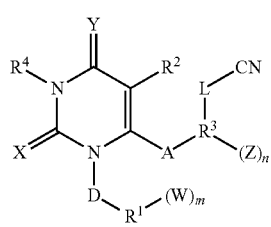

(I)

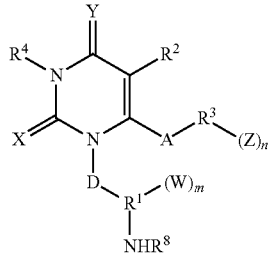

(II)

or a pharmaceutically acceptable salt, solvate, and/or ester thereof, wherein:

X and Y are independently O or S;
A is —O—, —S—, $NR^5$ or —$C(R^6)_2$—;
D is alkylene or substituted alkylene;
L is a covalent bond, alkylene, substituted alkylene, alkenylene, or substituted alkenylene;
$R^1$ is carbocyclyl or heterocyclyl;
$R^2$ is H, halogen, nitro, cyano, alkyl, substituted alkyl, hydroxyalkyl, alkoxyalkyl, alkenyl, substituted alkenyl, alkynyl, or substituted alkynyl, alkoxycarbonyl, amino, alkylamino, dialkyamino, alkylcarbamoyl, dialkylcarbamoyl, cycloalkyl, substituted cycloalkyl, arylalkyl, or substituted arylalkyl;
$R^3$ is a carbocyclyl or heterocyclyl;
$R^4$ is H, alkyl, substituted alkyl, cycloalkyl, substituted cycloalkyl, arylalkyl, substituted arylalkyl;
$R^8$ is H, —C(O)—O-alkyl, —C(O)—O-(substituted alkyl), —C(O)-alkyl-, C(O)-(substituted alkyl).
$R^5$ is H, alkyl, substituted alkyl, arylalkyl, substituted arylalkyl, acyl, or substituted acyl;
each $R^6$ is independently H, alkyl, hydroxyl, alkoxy, cyano, or halo; or
each $R^6$, together with the carbon atom to which they are shown attached, form a —C(O)—, —C(S)—, —$C(NR^7)$—, or cycloalkyl; or
one $R^6$, together with $R^2$, forms a heterocyclyl or substituted heterocyclyl ring;
$R^7$ is H, alkyl, substituted alkyl, hydroxyl, or alkoxy;
each W and Z is independently selected from the group consisting of halo, nitro, hydroxyl, amino, acetamido, trifluoroacetamido, azido, cyano, formyl, carbamoyl, alkyl, substituted alkyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, oxide; and n and m are independently integers of from 0 to 4;
with the following proviso:
when -D-$R^1$—$(W)_m$ or -D-$R^1(NHR^8)$—$(W)_m$ is:

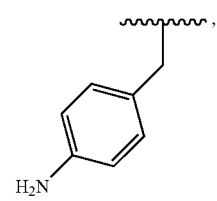

then -A-R³(L-CN)—(Z)ₙ or -A-R³—(Z)ₙ is not:

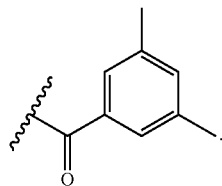

In another embodiment, the present invention provides novel HIV RT inhibitor compounds of Formula (III):

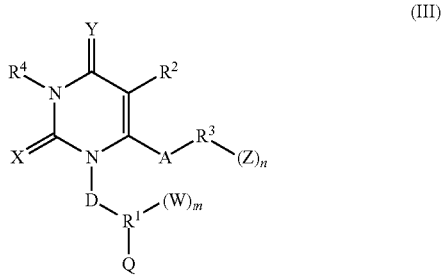

(III)

or pharmaceutically acceptable salt, solvate, and/or ester thereof:
wherein
X and Y are independently O or S;
A is O—, —S—, NR⁵ or —C(R⁶)₂—;
D is alkylene or substituted alkylene;
Q is halo or alkoxy;
R¹ is carbocyclyl or heterocyclyl;
R² is H, halogen, nitro, cyano, alkyl, substituted alkyl, hydroxyalkyl, alkoxyalkyl, alkenyl, substituted alkenyl, alkynyl, or substituted alkynyl, alkoxycarbonyl, amino, alkylamino, dialkyamino, alkylcarbamoyl, dialkylcarbamoyl, cycloalkyl, substituted cycloalkyl, arylalkyl, or substituted arylalkyl;
R³ is a carbocyclyl or heterocyclyl;
R⁴ is H, alkyl, substituted alkyl, cycloalkyl, substituted cycloalkyl, arylalkyl, substituted arylalkyl;
R⁸ is H, —C(O)—O-alkyl, —C(O)—O-(substituted alkyl), —C(O)-alkyl-, C(O)-(substituted alkyl).
R⁵ is H, alkyl, substituted alkyl, arylalkyl, or substituted arylalkyl;
each R⁶ is independently H, alkyl, hydroxyl, alkoxy, or halo; or
  each R⁶, together with the carbon atom to which they are shown attached, form a —C(O)— or —C(NR⁷)—; or
  one R⁶, together with R⁷, forms a heterocyclyl or substituted heterocyclyl ring;
R⁷ is H, alkyl, substituted alkyl, hydroxyl, or alkoxy;
each W and Z is independently selected from the group consisting of halo, nitro, hydroxyl, amino, acetamido, trifluoroacetamido, azido, cyano, formyl, carbamoyl, alkyl, substituted alkyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, oxide; and
n and m are independently integers of from 0 to 4;

with the following provisos:
(a) when D is —CH₂—, R³ is carbocyclyl, and n is 2, then R¹ is heterocyclyl; and
(b) when D is —CH₂—, R¹ is heterocyclyl, Q is halo, R³ is carbocyclyl, and n is 2, then Z is not alkyl.

In another embodiment, the present invention provides a pharmaceutical composition comprising a therapeutically effective amount of a compound of Formula (I), (II), or (III), and a pharmaceutically acceptable carrier.

In another embodiment, the present invention provides a pharmaceutical composition comprising a therapeutically effective amount of a compound of Formula (I), (II), or (III), one or more additional active agents, and a pharmaceutically acceptable carrier.

In another embodiment, the present invention provides a combination pharmaceutical agent comprising: a first pharmaceutical composition comprising a compound of Formula (I), (II), or (III), or a pharmaceutically acceptable salt, solvate, and/or ester thereof; and a second pharmaceutical composition comprising at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof.

In another embodiment, the present invention provides a method for inhibiting HIV reverse transcriptase comprising: administering a therapeutically effective amount of a compound of Formula (I), (II), or (III), or a pharmaceutically acceptable salt, solvate, and/or ester thereof, to a patient in need of such treatment.

In another embodiment, the present invention provides a method for treating or preventing a HIV infection comprising: administering a therapeutically effective amount of a compound of Formula (I), (II), or (III), or a pharmaceutically acceptable salt, solvate, and/or ester thereof, to a patient in need of such treatment.

In another embodiment, the present invention provides a method for treating AIDS or AIDS Related Complex (ARC) comprising: administering a therapeutically effective amount of a compound of Formula (I), (II), or (III), or a pharmaceutically acceptable salt, solvate, and/or ester thereof, to a patient in need of such treatment.

In another embodiment, the present invention provides a method of inhibiting the replication of a retrovirus comprising: contacting said retrovirus with a compound of Formula (I), (II), or (III), or a pharmaceutically acceptable salt, solvate, and/or ester thereof.

In another embodiment of the present invention, each of the above methods further comprises co-administering a therapeutic amount of at least one additional active agent selected from the group consisting of one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended the invention to those claims. On the contrary, the invention is intended to cover all alternatives, modifications, and equivalents, which may be included within the scope of the present invention as defined by the claims.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbone structure.

As used herein, "a compound of the invention" or "a compound of formula (I), (II), or (III)" means a compound of formula (I), (II), or (III) or a pharmaceutically acceptable salt, solvate, or physiologically functional derivative thereof. Similarly, with respect to isolatable intermediates such as for example, compounds of formula (4), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—O$CH_2CH_3$ or -OEt), t-butoxy (—O—$C(CH_3)_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—CH($CH_3$)—), 1,2-ethyl (—$CH_2CH_2$—), 1,1-propyl (—CH($CH_2CH_3$)—), 1,2-propyl (—$CH_2$CH($CH_3$)—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡CH—).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or Sp³ carbon atom, but also an sp² carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp³ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O⁻; =O, —OR, —SR, —S⁻, NR₂, —N⁺R₃, =NR, —CX₃, —CN, —OCN, —SCN, —N=C=O, —NCS, —NO, —NO₂, =N₂, —N₃, —NHC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)(OR)₂, —N(=O)(OR)₂, —N(=O)(O⁻)₂, —N(=O)(OH)₂, —N(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula (I), (II), or (III) should be selected in order to provide a compound which is sufficiently stable to provide a pharmaceutically useful compound which can be formulated into an acceptably stable pharmaceutical composition. Compounds of Formula (I), (II), or (III) which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH₃, etc.), an amine (e.g., —NHCH₃, —N(CH₃)₂, etc.), or a thioalkyl group (e.g., —SCH₃). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH₂CH₂—O—CH₃, etc.), an alkyl amine (e.g., —CH₂NHCH₃, —CH₂N(CH₃)₂, etc.), or a thioalkyl ether (e.g., —CH₂—S—CH₃). If a terminal carbon atom of the alkyl group is replaced with a heteroatom (e.g., O, N, or S), the resulting heteroalkyl groups are, respectively, a hydroxyalkyl group (e.g., —CH₂CH₂—OH), an aminoalkyl group (e.g., —CH₂NH₂), or an alkyl thiol group (e.g., —CH₂CH₂—SH). A heteroalkyl group can have, for example, 1 to 20 carbon atoms, 1 to 10 carbon atoms, or 1 to 6 carbon atoms. A C₁-C₆ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl, and the like.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $Sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $Sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $Sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-5-aryl, -alkylene-5-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate, and phosphonthioate functional groups.

"Linker" or "link" refers to a chemical moiety comprising a covalent bond or a chain or group of atoms that covalently attaches a phosphonate or phosphinate group to a drug. Linkers which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

"Optionally substituted" refers to a particular moiety of the compound of Formula (I), (II), or (III) (e.g., an optionally substituted aryl group) refers to a moiety having 0, 1, 2, or more substituents.

"Ester thereof" means any ester of a compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a compound according to the invention; preferably a pharmaceutically acceptable salt thereof.

"Pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), (II), (III), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Treatment" or "treating" means the administration of a compound or composition according to the present invention to alleviate or eliminate symptoms of the HIV disease and/or to reduce viral load in a patient. The term "treatment" or "treating" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

"Chiral" refers to molecules which have the property of non-superimposability of the mirror image partner, while the term "achiral" refers to molecules which are superimposable on their mirror image partner.

"Stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S, N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Theme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphor-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in Vivo, are useful in diagnostic assays for therapeutic dosing of the compounds of the invention even if they possess no anti-infective activity of their own.

Compounds of Formula (I), (II), or (III)

In one embodiment, the present application provides compounds according to Formula (I) or (II), as described herein.

In another embodiment of the compounds of Formula (I) or (II), A is A is —C($R^6$)$_2$—.

In another embodiment of the compounds of Formula (I) or (II), A is —C($NR^5$)—.

In another embodiment of the compounds of Formula (I) or (II), A is —C(N—$OR^5$)—.

In another embodiment of the compounds of Formula (I) or (II), A is —C(O)—.

In another embodiment of the compounds of Formula (I) or (II), A is —O—.

In another embodiment of the compounds of Formula (I) or (II), A is —$NR^5$.

In another embodiment of the compounds of Formula (I) or (II), $R^3$ is aryl or heteroaryl.

In another embodiment of the compounds of Formula (I) or (II), $R^3$ is phenyl.

In another embodiment of the compounds of Formula (I) or (II), $R^3$ is phenyl and each Z is independently selected from the group consisting of —CN, alkyl, substituted alkyl, halo, and substituted alkenyl.

In another embodiment of the compounds of Formula (I) or (II), $R^3$—(Z)$_n$ or $R^3$(L-CN)—(Z)$_n$ have the following structures:

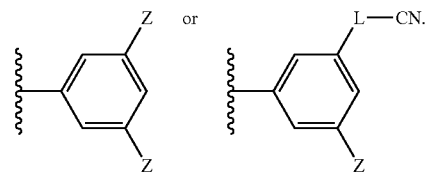

In another embodiment of the compounds of Formula (I) or (II), each Z is independently selected from the group consisting of —CN, —$CH_3$, —CH=CH—CN, —$CH_2CH_2$—CN, Cl, and Br.

In another embodiment of the compounds of Formula (I) or (II), $R^3$—(Z)$_n$ is selected from the group consisting of:

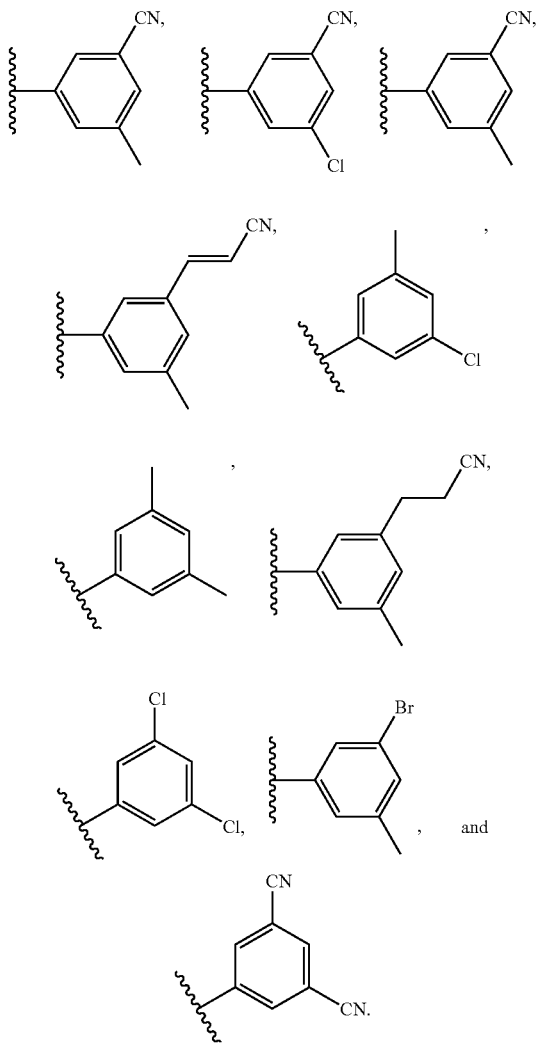

In another embodiment of the compounds of Formula (I) or (II), $R^3$ is phenyl and each Z is independently selected from the group consisting of —CN, alkyl, substituted alkyl, halo, and substituted alkenyl.

In another embodiment of the compounds of Formula (I) or (II), $R^3$—(Z)$_n$ or $R^3$(L-CN)—(Z)$_n$ have the following structures:

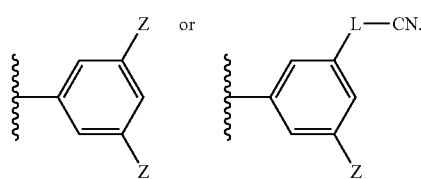

In another embodiment of the compounds of Formula (I) or (II), each Z is independently selected from the group consisting of —CN, —CH$_3$, —CH=CH—CN, —CH$_2$CH$_2$—CN, Cl, and Br.

In another embodiment of the compounds of Formula (I) or (II), R$^3$—(Z)$_n$ is selected from the group consisting of:

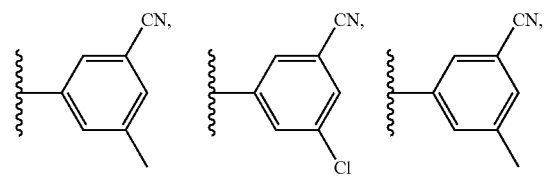

In another embodiment of the compounds of Formula (I) or (II), R$^3$ is phenyl, R$^5$ is H, and each Z is independently selected from the group consisting of —CN, alkyl, substituted alkyl, halo, and substituted alkenyl.

In another embodiment of the compounds of Formula (I) or (II), R$^3$—(Z)$_n$ or R$^3$(L-CN)—(Z)$_n$ have the following structures:

In another embodiment of the compounds of Formula (I) or (II), each Z is independently selected from the group consisting of —CN, —CH$_3$, —CH=CH—CN, —CH$_2$CH$_2$—CN, Cl, and Br.

In another embodiment of the compounds of Formula (I) or (II), R$^3$—(Z)$_n$ is selected from the group consisting of:

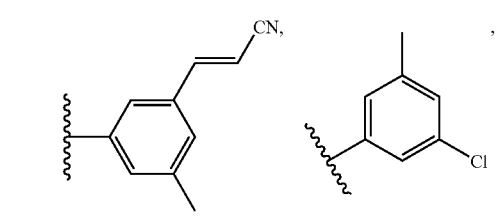

In another embodiment of the compounds of Formula (I) or (II), D is alkylene or substituted alkylene.

In another embodiment of the compounds of Formula (I) or (II), D is methylene.

In another embodiment of the compounds of Formula (I) or (II), R$^1$ is aryl or heteroaryl.

In another embodiment of the compounds of Formula (I) or (II), R$^1$ is phenyl, pyridyl, pyrimidyl, pyridazinyl, and isoxazolyl.

In another embodiment of the compounds of Formula (I) or (II), R$^1$—(W)$_m$ is:

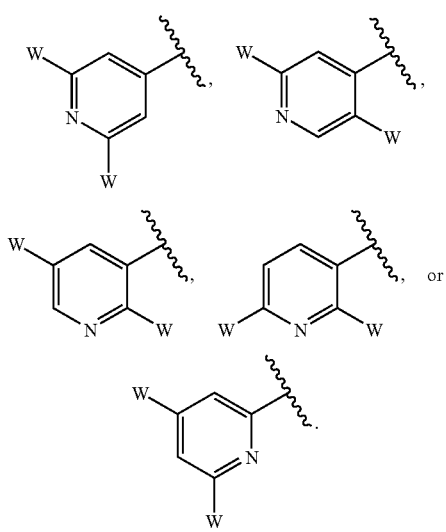

In another embodiment of the compounds of Formula (I) or (II), each W is independently selected from the group consisting of halo, hydroxyl, alkoxyl, amino, substituted amino, -amino-C(O)-alkylene-amino, and sulfonamido.

In another embodiment of the compounds of Formula (I) or (II), $R^1$—(W)$_m$ is selected from the group consisting of:

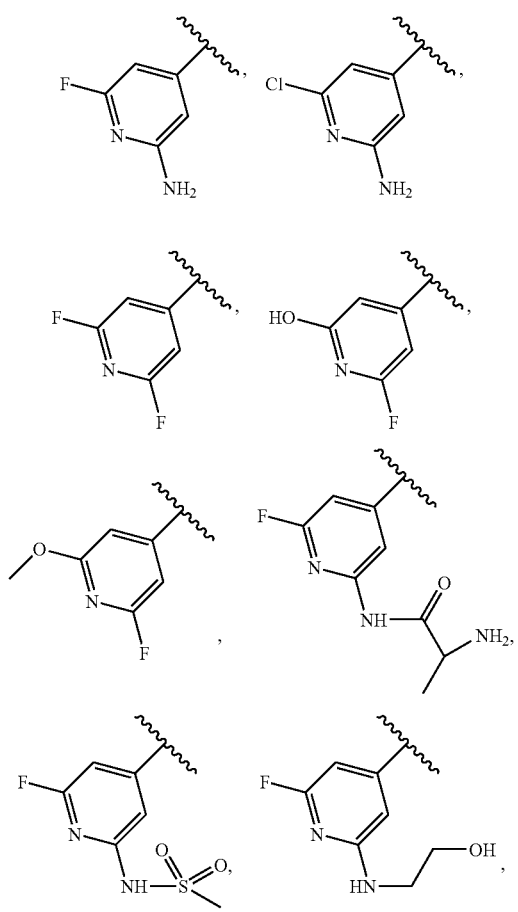

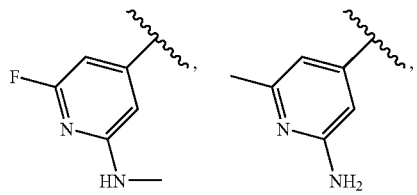

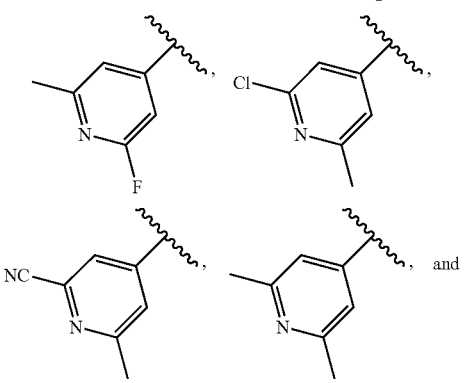

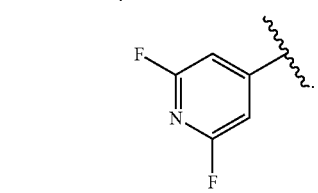

In another embodiment of the compounds of Formula (I) or (II), $R^1$—(W)$_m$ is:

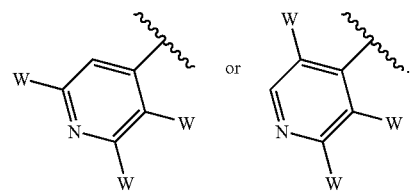

In another embodiment of the compounds of Formula (I) or (II), each W is independently selected from the group consisting of halo, hydroxyl, alkoxy, amino, substituted amino, -amino-C(O)-alkylene-amino, and sulfonamido.

In another embodiment of the compounds of Formula (I) or (II), $R^1$—(W)$_m$ is:

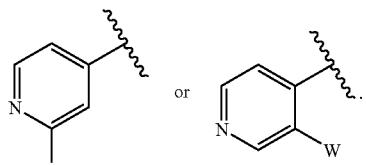

In another embodiment of the compounds of Formula (I) or (II), W is selected from the group consisting of halo, alkyl, cyano, —C(O)-amino, alkoxy, hydroxy, and amino.

In another embodiment of the compounds of Formula (I) or (II), $R^1$—(W)$_m$ is selected from the group consisting of:

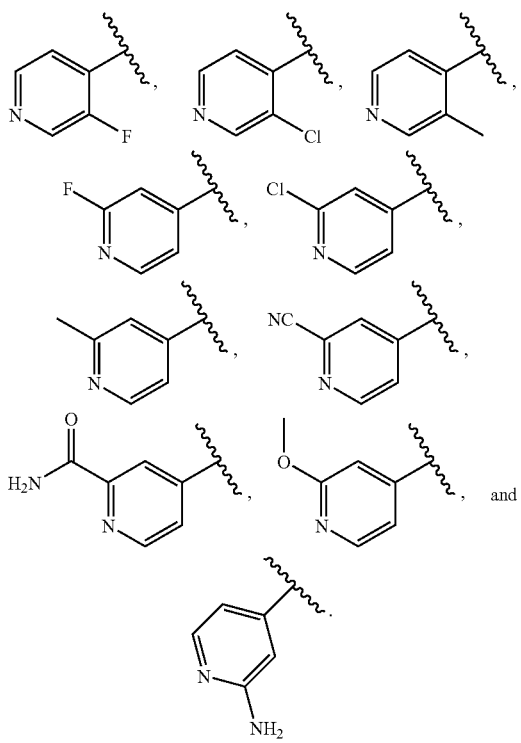

In another embodiment of the compounds of Formula (I) or (II), $R^1$—$(W)_m$ is:

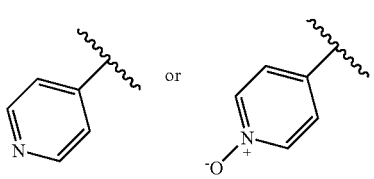

In another embodiment of the compounds of Formula (I) or (II), $R^2$ is alkyl, hydroxyalkyl, alkoxyalkyl, cycloalkyl, substituted cycloalkyl, halo, or amino.

In another embodiment of the compounds of Formula (I) or (II), $R^2$ is alkyl.

In another embodiment of the compounds of Formula (I) or (II), X and Y are both O; A is —C(O)—; D is alkylene; $R^1$ is aryl or heteroaryl; $R^2$ is alkyl; and $R^3$ is aryl.

In another embodiment of the compounds of Formula (I) or (II), X and Y are both O; A is —C(O)—; D is —CH$_2$—; $R^1$ is phenyl, pyridyl, pyrimidyl, pyridazyl, or isoxazolyl; $R^2$ is 2-propyl; and $R^3$ is phenyl. It is preferred that $R^1$ is 4-pyridyl. It is also preferred that each W is independently selected from the group consisting of halo, hydroxyl, alkoxy, amino, substituted amino, -amino-C(O)-alkylene-amino, and sulfonamido. It is also preferred that $R^1$ is phenyl.

In another embodiment of the compounds of Formula (I) or (II), X and Y are both O; A is —C($R^6$)$_2$, —C(N—OR$^5$)—, or —C(NR$^5$)—; D is alkylene; $R^1$ is aryl or heteroaryl; $R^2$ is alkyl; and $R^3$ is aryl. Preferably, $R^6$ is —CHOH or $R^6$, together with $R^2$, forms a heterocyclyl or substituted heterocyclyl.

In another embodiment of the compounds of Formula (I) or (II), the compound is selected from the group consisting of:

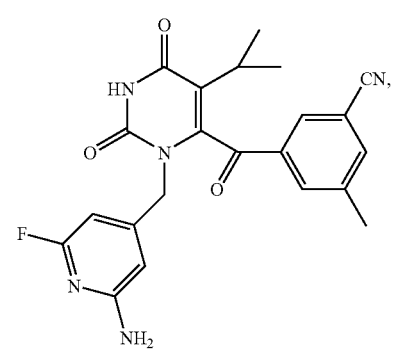

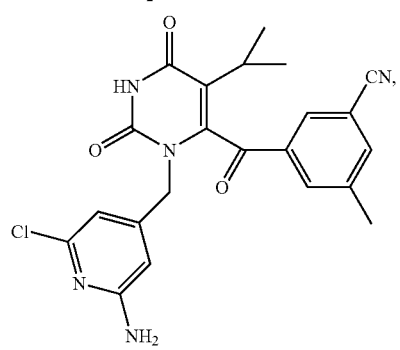

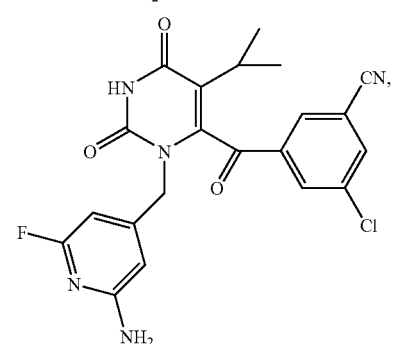

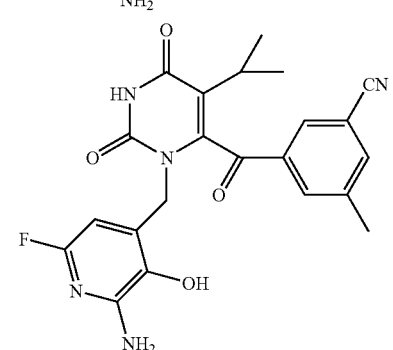

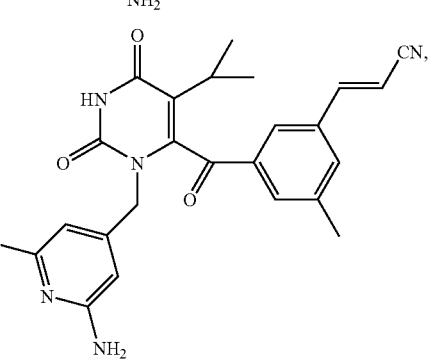

-continued
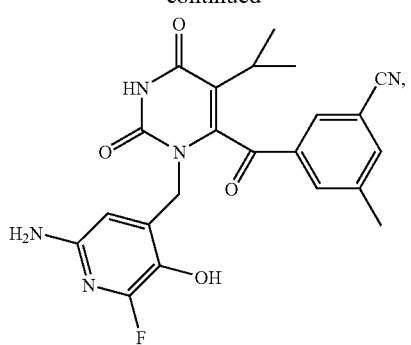
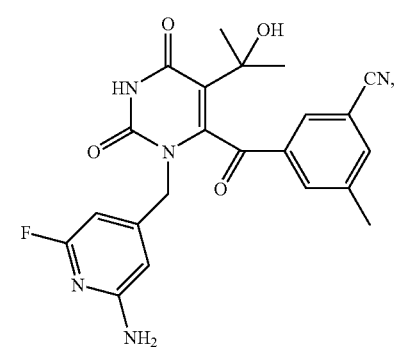
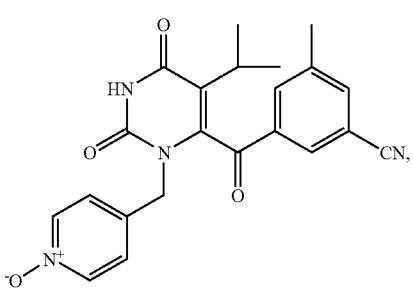
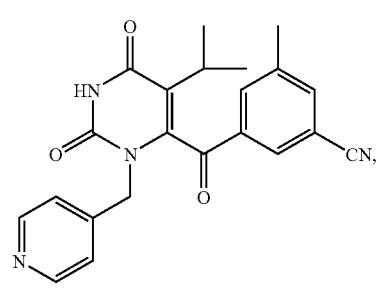
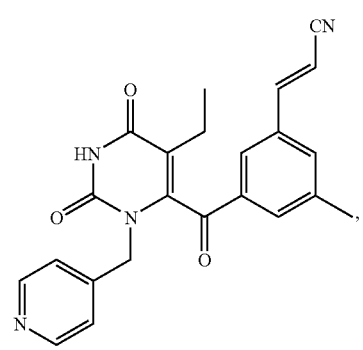
-continued
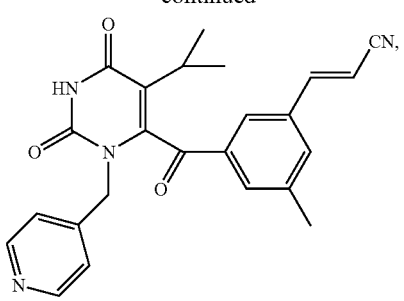
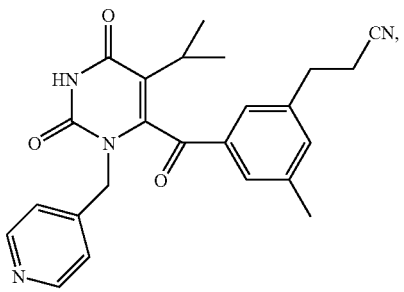
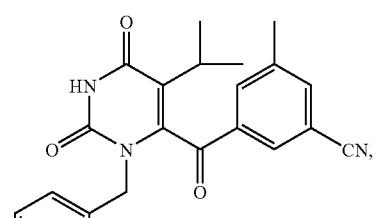
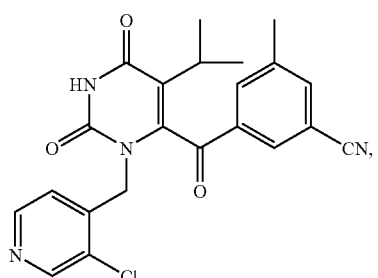
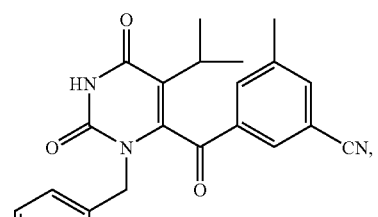
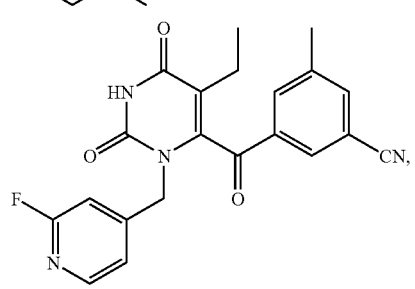

23
-continued
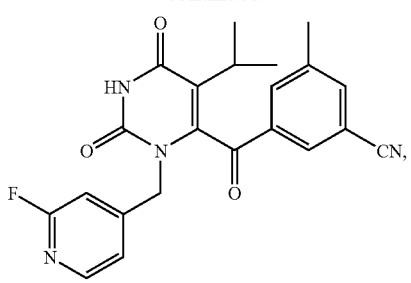
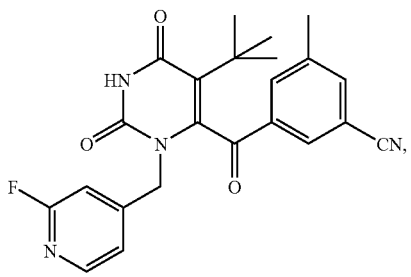
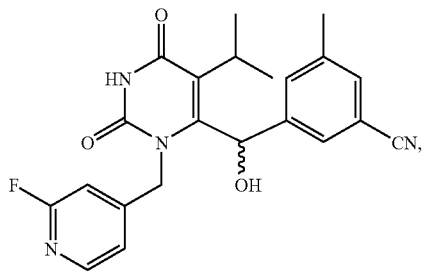
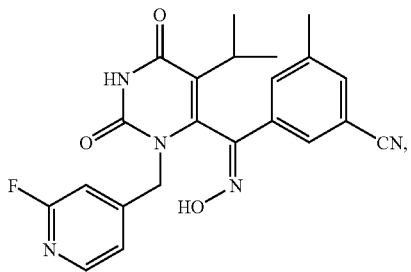
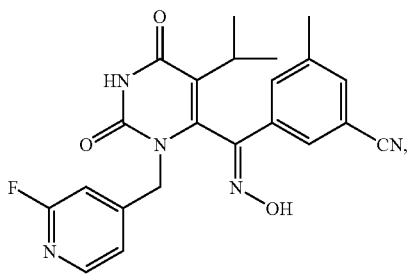
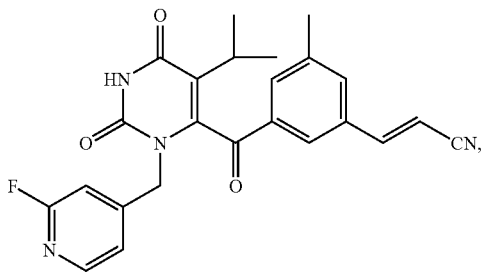
24
-continued
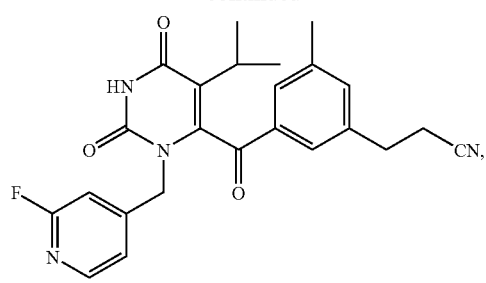
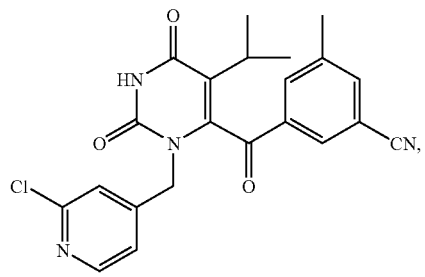
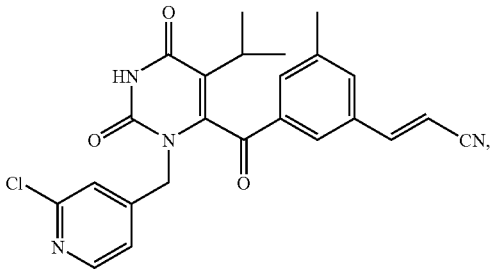
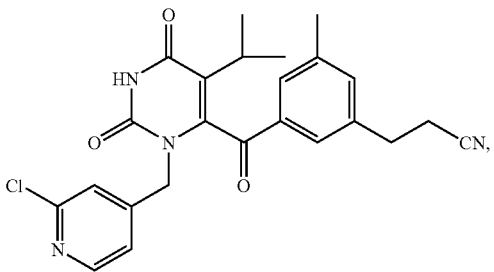
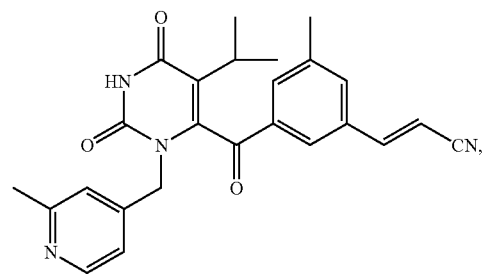
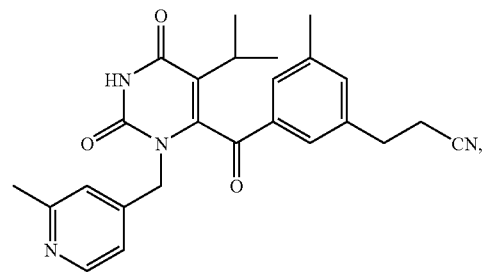

25
-continued
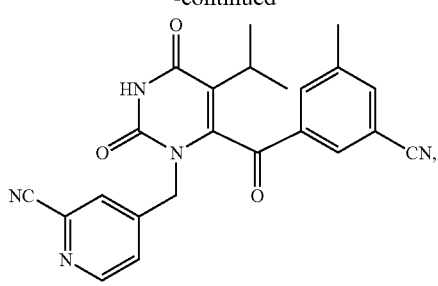
26
-continued
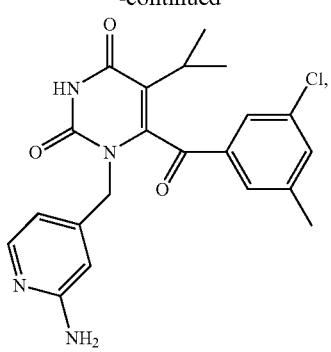
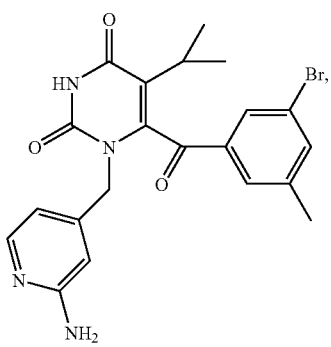
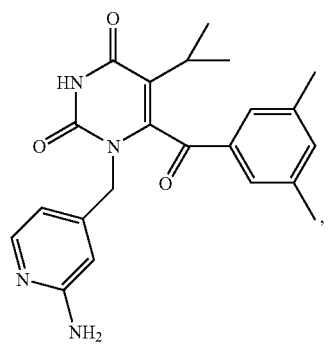
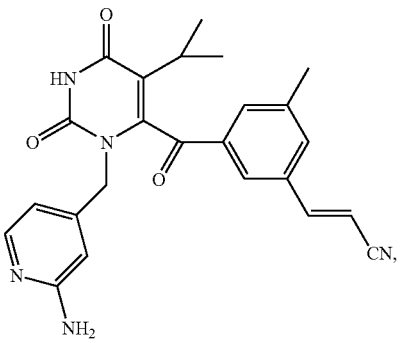
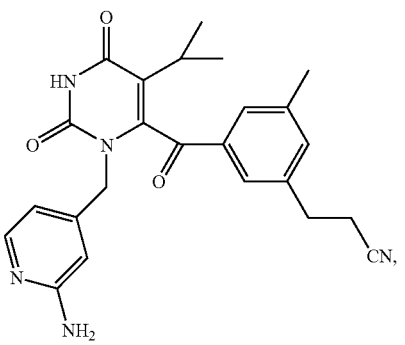

-continued
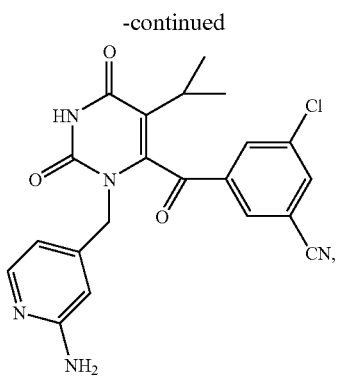
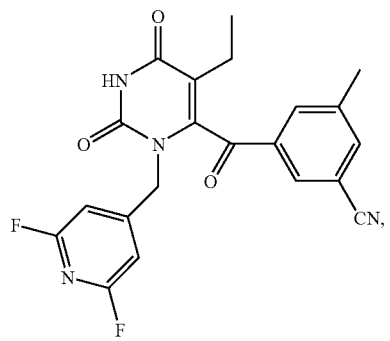
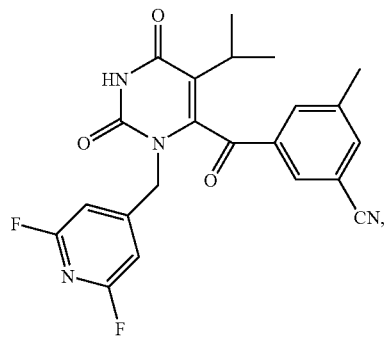
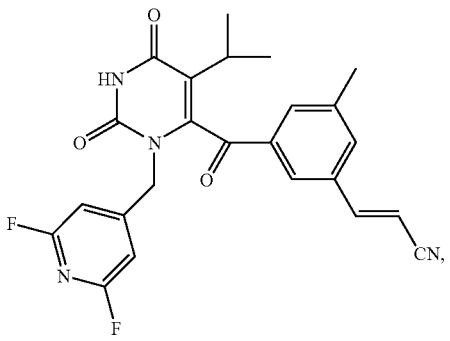
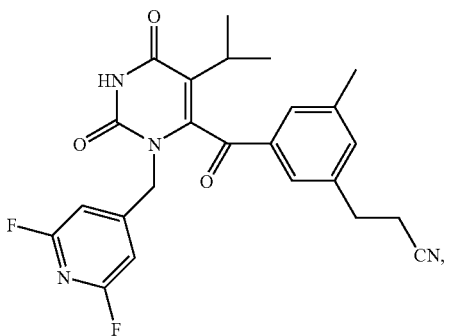
-continued
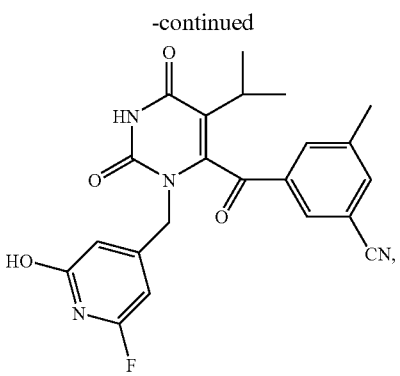
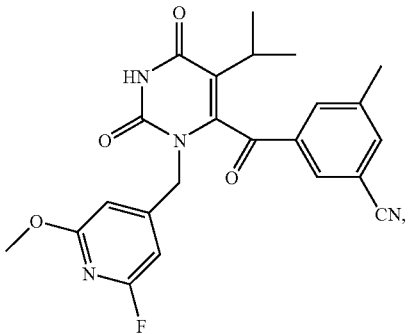
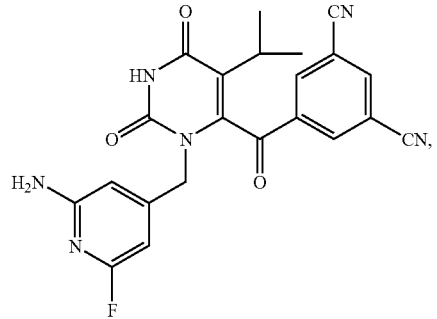
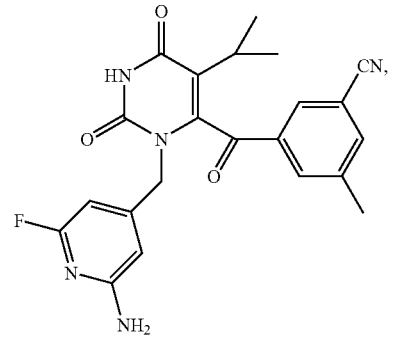
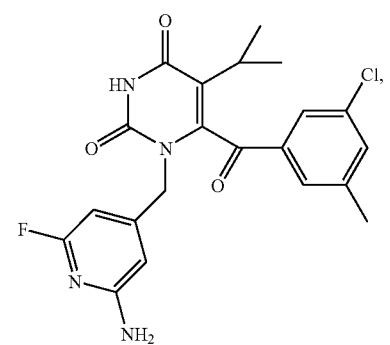

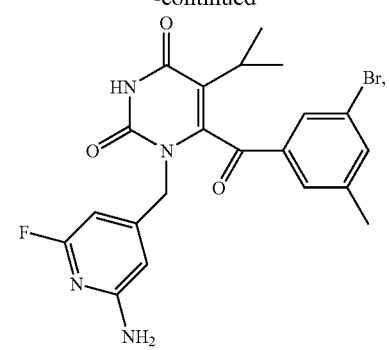
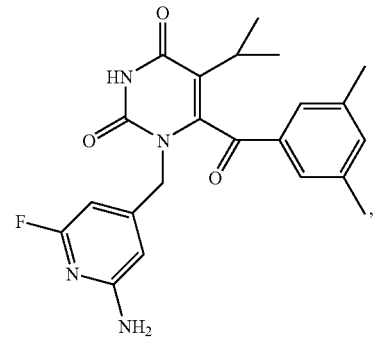
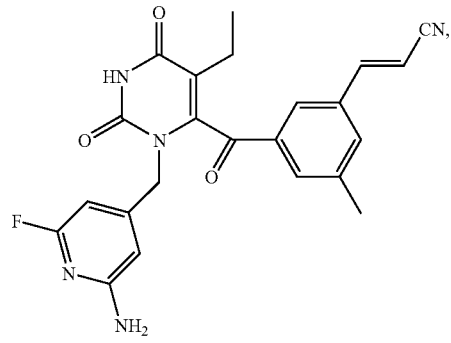
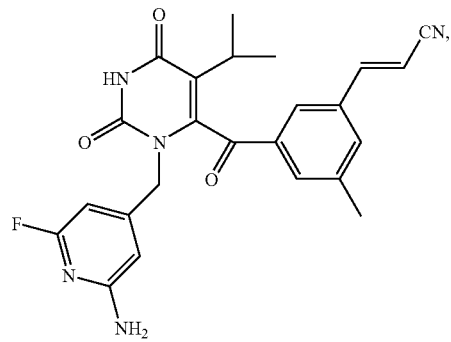
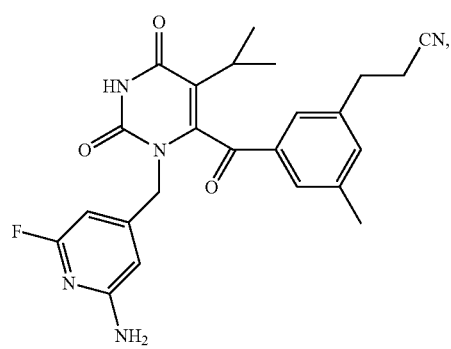
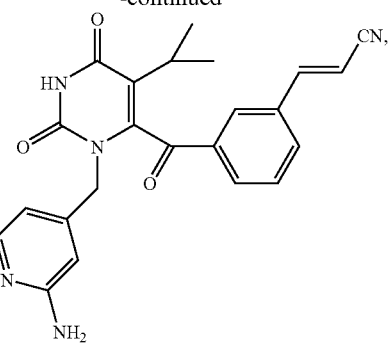
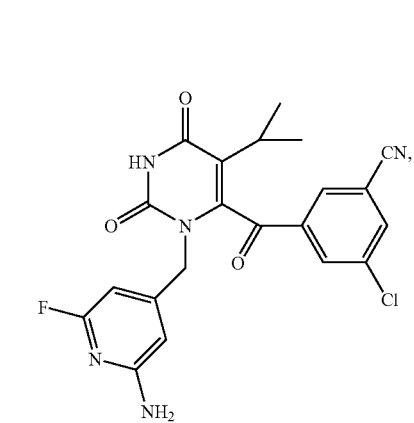
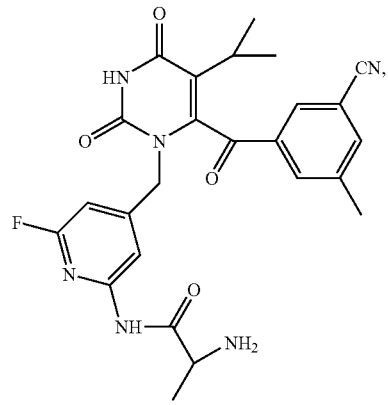
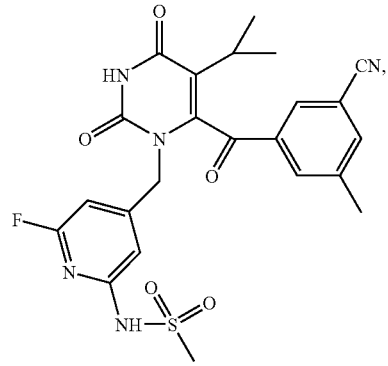

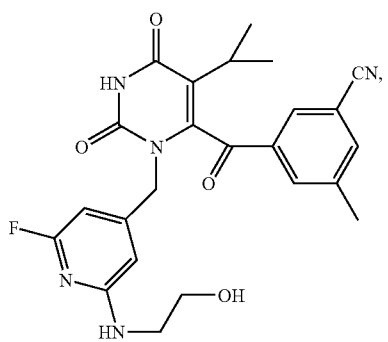
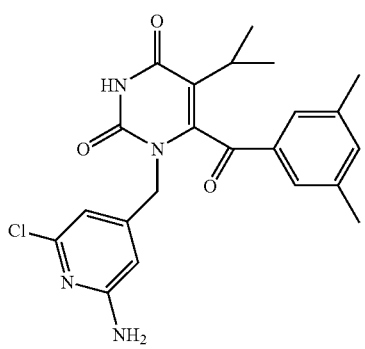
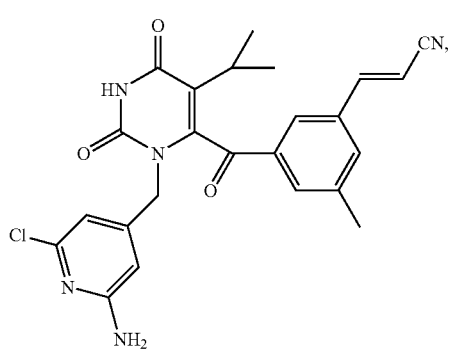
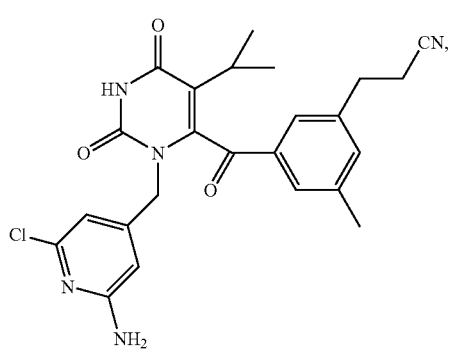
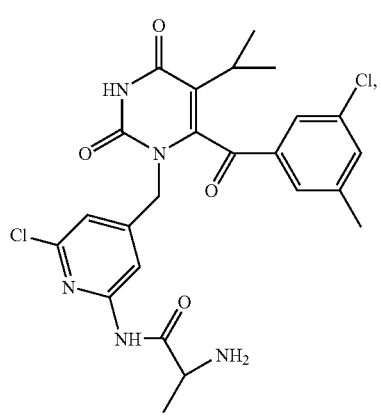

-continued
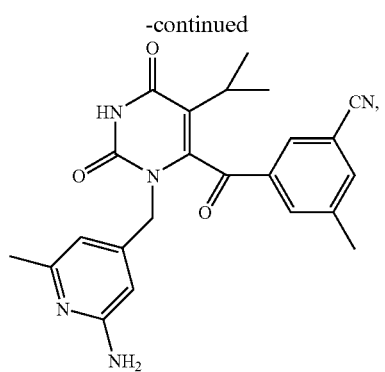
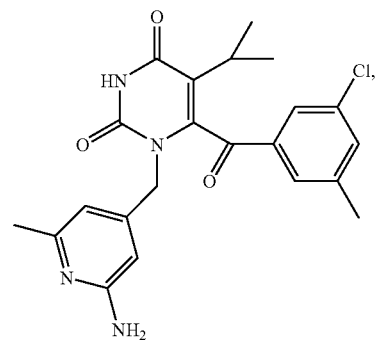
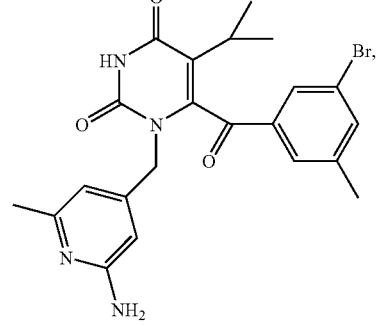
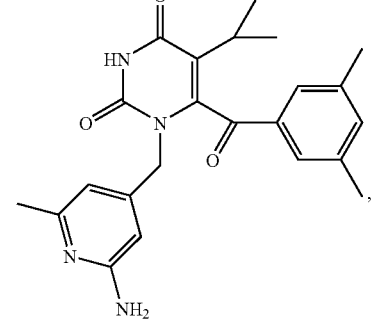
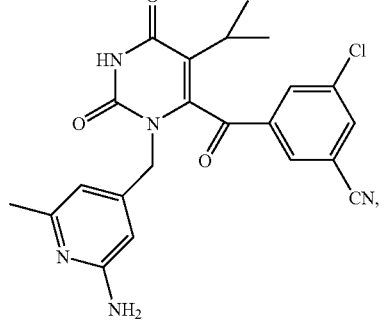
-continued
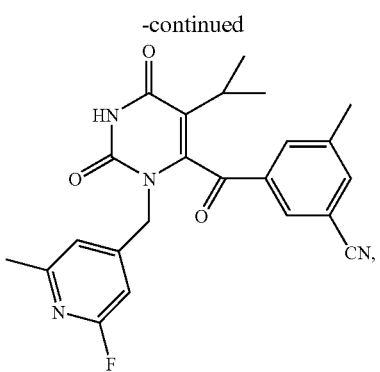
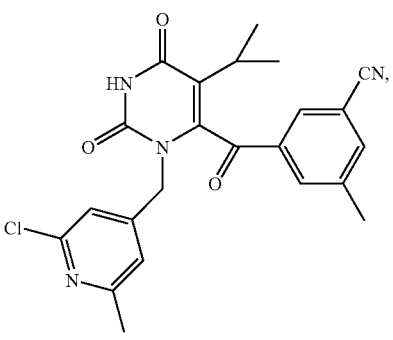
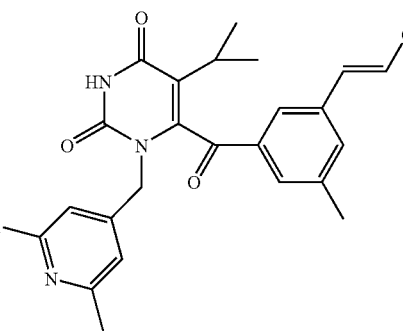
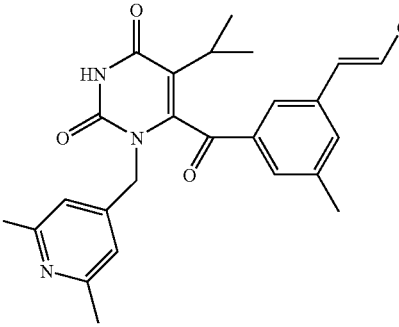
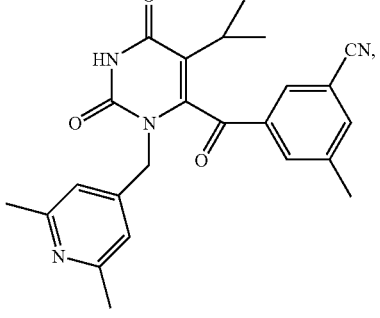

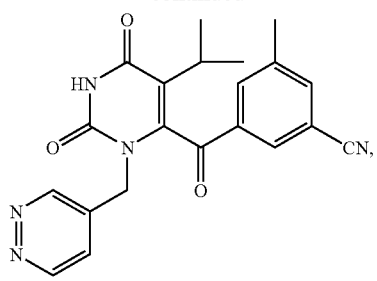
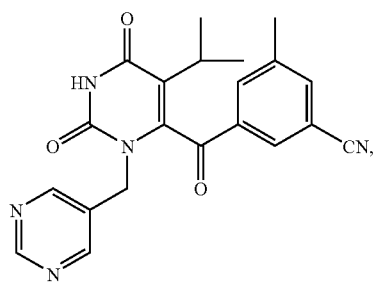
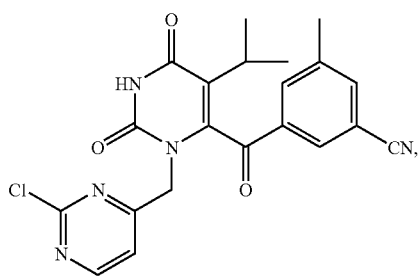
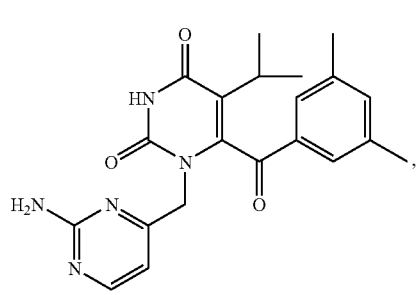
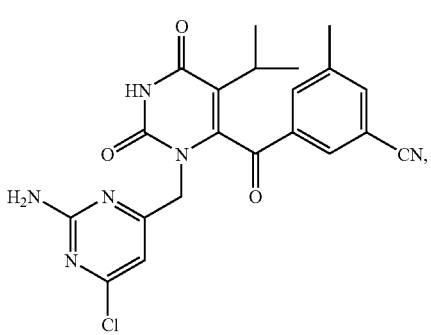
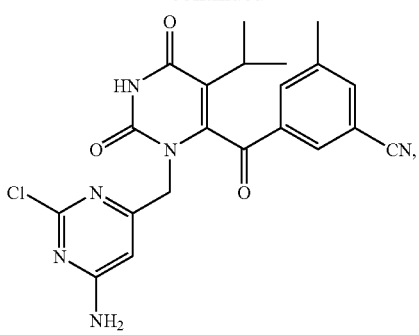
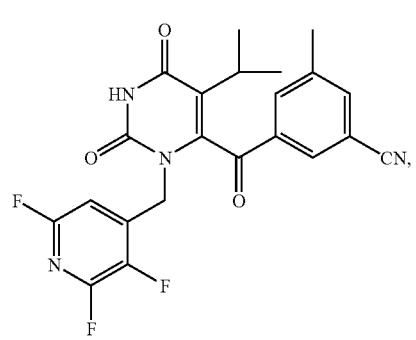
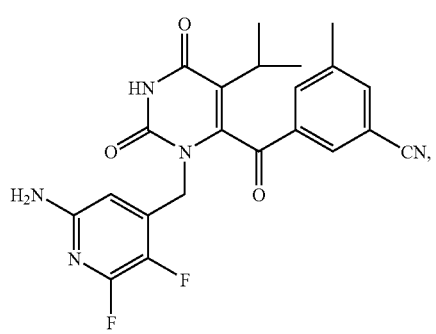
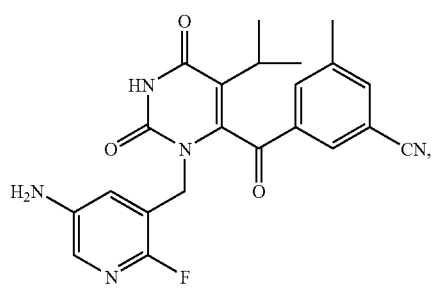
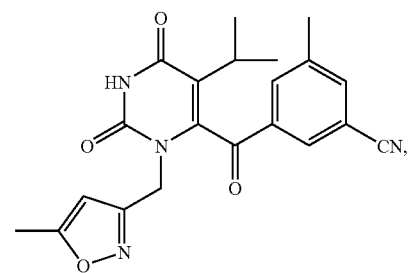

-continued
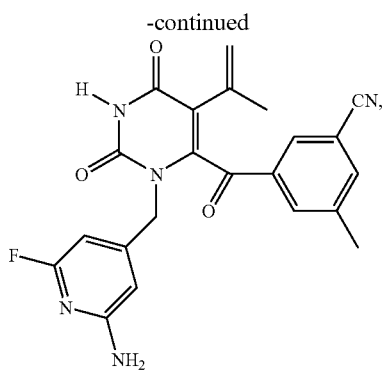
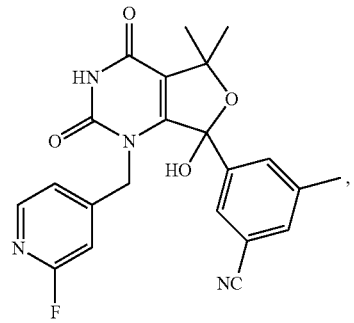
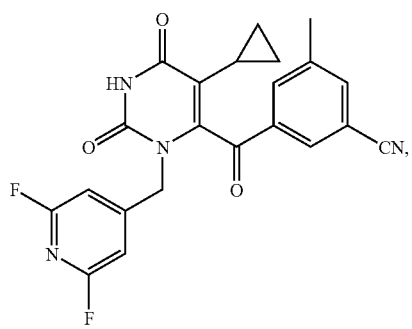
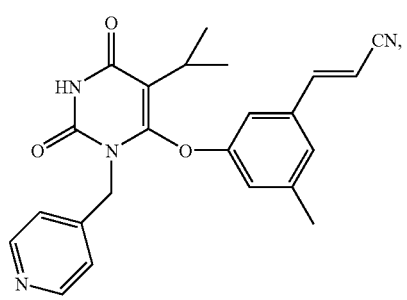
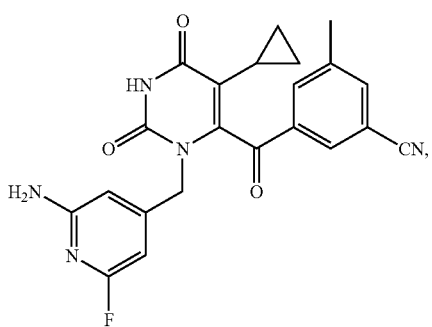
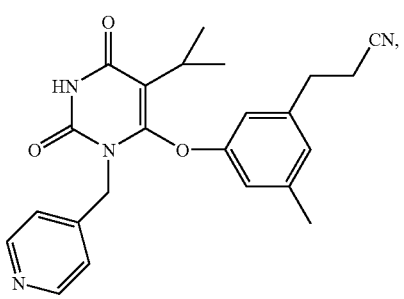
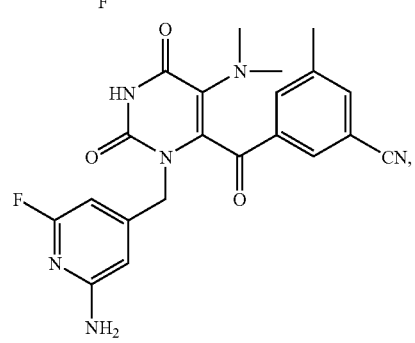
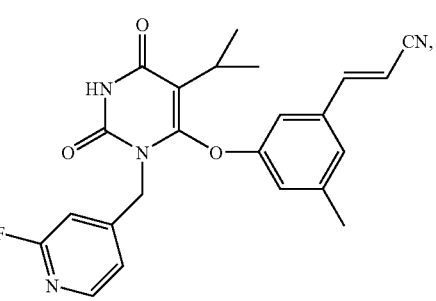
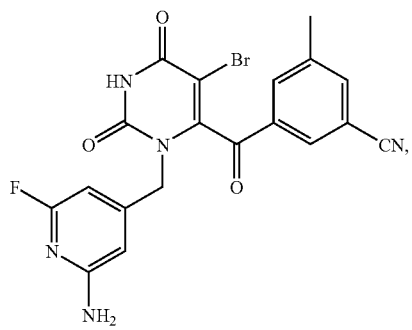
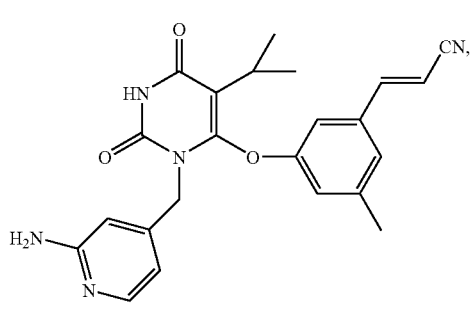

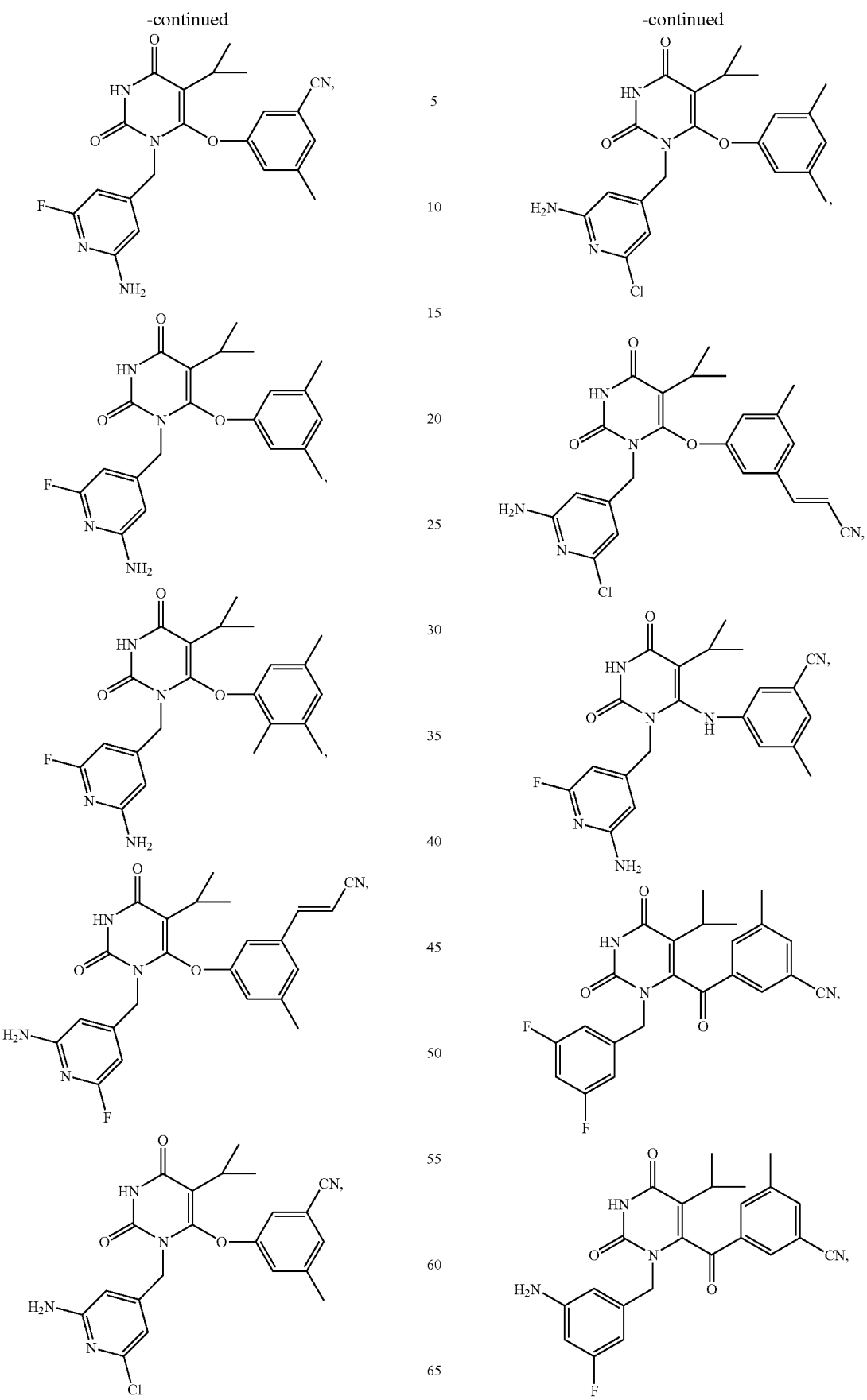

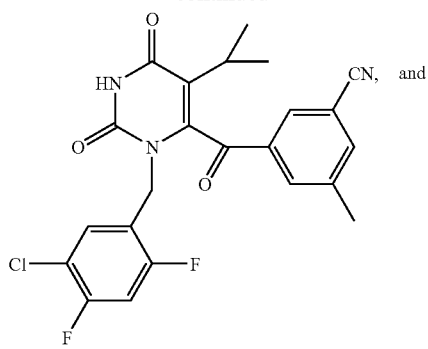

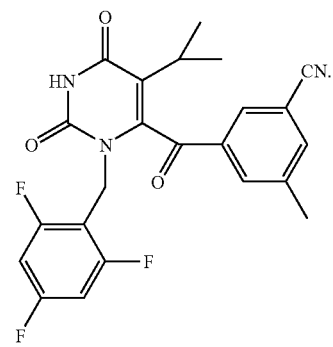

In yet another embodiment of the compounds of Formula (III), R¹ is heteroaryl.

In yet another embodiment of the compounds of Formula (III), R¹ is 4-pyridyl.

In yet another embodiment of the compounds of Formula (III), m is 0.

In yet another embodiment of the compounds of Formula (III), R³ is aryl.

In yet another embodiment of the compounds of Formula (III), R³ is phenyl.

In yet another embodiment of the compounds of Formula (III), n is 2.

In yet another embodiment of the compounds of Formula (III), each Z is independently halo or alkyl.

In yet another embodiment of the compounds of Formula (III), R¹ is 4-pyridyl, m is 0, R³ is phenyl, n is 2, and each Z is independently halo or alkyl.

In yet another embodiment of the compounds of Formula (III), the compound is selected from the group consisting of:

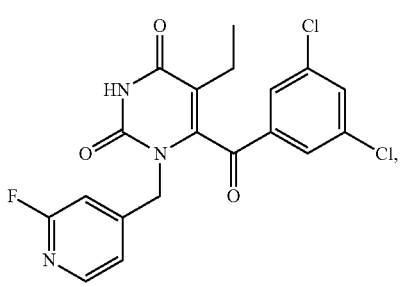

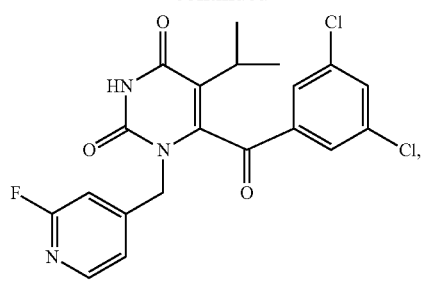

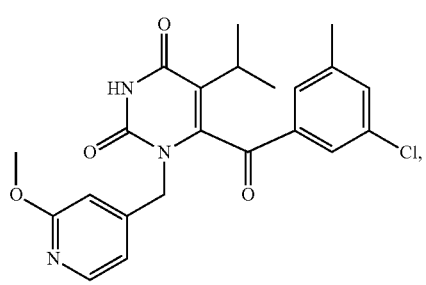

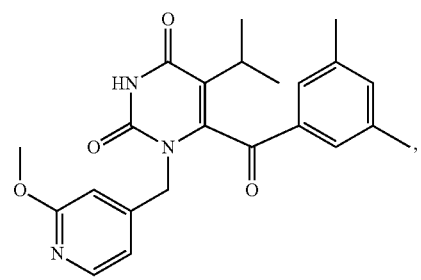

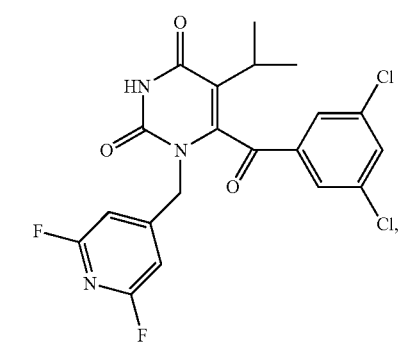

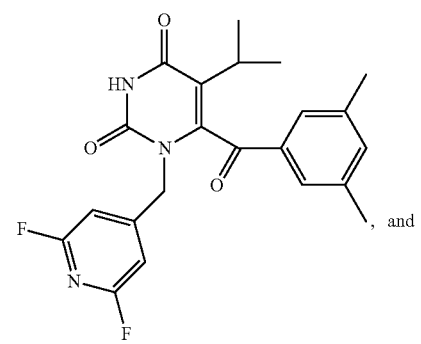

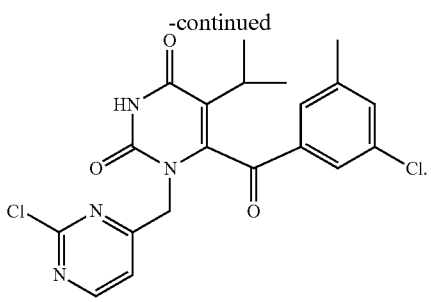

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides a pharmaceutical composition comprising a therapeutically effective amount of a compound of Formula (I), (II), or (III), or a pharmaceutically acceptable salt, solvate, and/or ester thereof, and a pharmaceutically acceptable carrier.

In another embodiment, the present application provides a pharmaceutical composition comprising a therapeutically effective amount of a compound of Formula (I), (II), or (III), or a pharmaceutically acceptable salt, solvate, and/or ester thereof, in combination with at least one additional active therapeutic agent and a pharmaceutically acceptable carrier.

In another embodiment, the present application provides a pharmaceutical composition comprising a therapeutically effective amount of a compound of Formula (I), (II), or (III), and one or more additional active agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present application provides a pharmaceutical composition comprising a therapeutically effective amount of a compound of Formula (I), (II), or (III), and at least one another active agent selected from the group consisting of: (1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, racivir (®-FTC), D-d4FC, emtricitabine, phosphazide, fozivudine tidoxil, apricitibine (AVX754), amdoxovir, KP-1461, and fosalvudine tidoxil (formerly HDP 99.0003); (4) HIV nucleotide inhibitors of reverse transcriptase selected from the group consisting of tenofovir and adefovir; (5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) gp41 inhibitors selected from the group consisting of enfuvirtide, sifuvirtide, FB006M, and TRI-1144; (7) CXCR4 inhibitor, such as AMD-070; (8) entry inhibitor, such as SP01A; (9) gp120 inhibitor, such as BMS-488043 and/or BlockAide/CR; (10) G6PD and NADH-oxidase inhibitor, such as immunitin; (11) CCR5 inhibitors selected from the group consisting of aplaviroc, vicriviroc, maraviroc, PRO-140, INCB15050, PF-232798 (Pfizer), and CCR5 mAb004; (12) other drugs for treating HIV selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040); and (13) any combinations or mixtures of the above.

In another embodiment, the present application provides a combination pharmaceutical agent comprising: a first pharmaceutical composition comprising a compound of Formula (I), (II), or (III), or a pharmaceutically acceptable salt, solvate, and/or ester thereof; and a second pharmaceutical composition comprising at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of Formula (I), (II), or (III) can be administered alone, e.g., without other active therapeutic in ingredients or agents. In another embodiment, the compounds of Formula (I), (II), or (III) are used in combination with one or more active therapeutic ingredients or agents. Preferably, the other active therapeutic ingredients or agents are HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Combinations of the compounds of Formula (I), (II), or (III) are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

Non-limiting examples of suitable anti-infective agents suitable for combining with the compounds of Formula (I), (II), or (III) include: (1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859; (2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, racivir (⊛-FTC), D-d4FC, emtricitabine, phosphazide, fozivudine tidoxil, apricitibine (AVX754), amdoxovir, KP-1461, and fosalvudine tidoxil (formerly HDP 99.0003); (4) HIV nucleotide inhibitors of reverse transcriptase selected from the group consisting of tenofovir and adefovir; (5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) gp41 inhibitors selected from the group consisting of enfuvirtide, sifuvirtide, FB006M, and TRI-1144; (7) CXCR4 inhibitor, such as AMD-070; (8) entry inhibitor, such as SP01A; (9) gp120 inhibitor, such as BMS-488043 and/or BlockAide/CR; (10) G6PD and NADH-oxidase inhibitor, such as immunitin; (11) CCR5 inhibitors selected from the group consisting of aplaviroc, vicriviroc, maraviroc, PRO-140, INCB15050, PF-232798 (Pfizer), and CCR5 mAb004; (12) other drugs for treating HIV selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040); (13) any combinations or mixtures of the above.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In another embodiment, the present invention provides a method for inhibiting HIV RT comprising administering a therapeutically effective amount of a compound of Formula (I), (II), or (III), or a pharmaceutically acceptable salt, solvate, or ester thereof, to a patient in need of such treatment.

In another embodiment, the present invention provides a method for treating or preventing a HIV infection comprising: administering a therapeutically effective amount of a compound of Formula (I), (II), or (III), or a pharmaceutically acceptable salt, solvate, and/or ester thereof, to a patient in need of such treatment.

In another embodiment, the present invention provides a method, further comprising co-administering a therapeutic amount of at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides a method for treating AIDS or AIDS Related Complex (ARC) comprising administering a therapeutically effective amount of a compound of Formula (I), (II), or (III), or a pharmaceutically acceptable salt, solvate, and/or ester thereof, to a patient in need of such treatment.

In another embodiment, the present invention provides a method of co-administering a therapeutic amount of compound of Formula (I), (II), or (III) and at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides a method of inhibiting the replication of a retrovirus comprising contacting said retrovirus with a compound of Formula (I), (II), or (III), or a pharmaceutically acceptable salt, solvate, and/or ester thereof.

In another embodiment, the present invention provides a method of inhibiting the replication of a retrovirus comprising contacting the retrovirus with a compound of Formula (I), (II), or (III) and at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present application provides for the use of a compound of Formulae I, II, or III for the preparation of a medicament for treating or preventing an HIV infection in a patient.

In another embodiment, the present application provides for the use of a compound of Formulae I, II, or III for the preparation of a medicament for treating AIDS or AIDS Related Complex (ARC) in a patient.

In another embodiment, the present application provides for the use of a compound of Formulae I, II, or III for the preparation of a medicament for inhibiting the replication of a retrovirus in a patient.

EXAMPLES

Example A

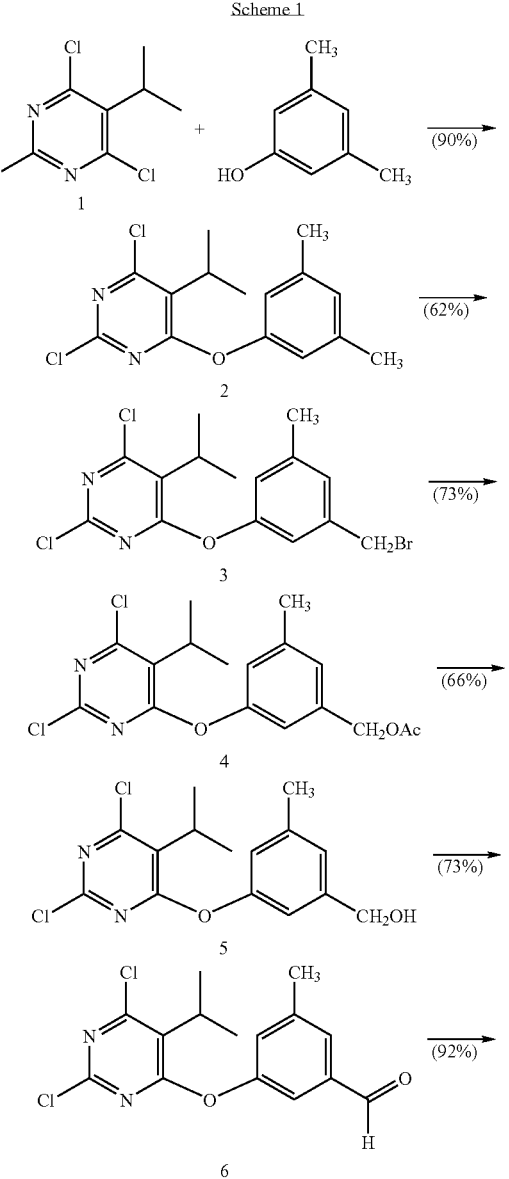

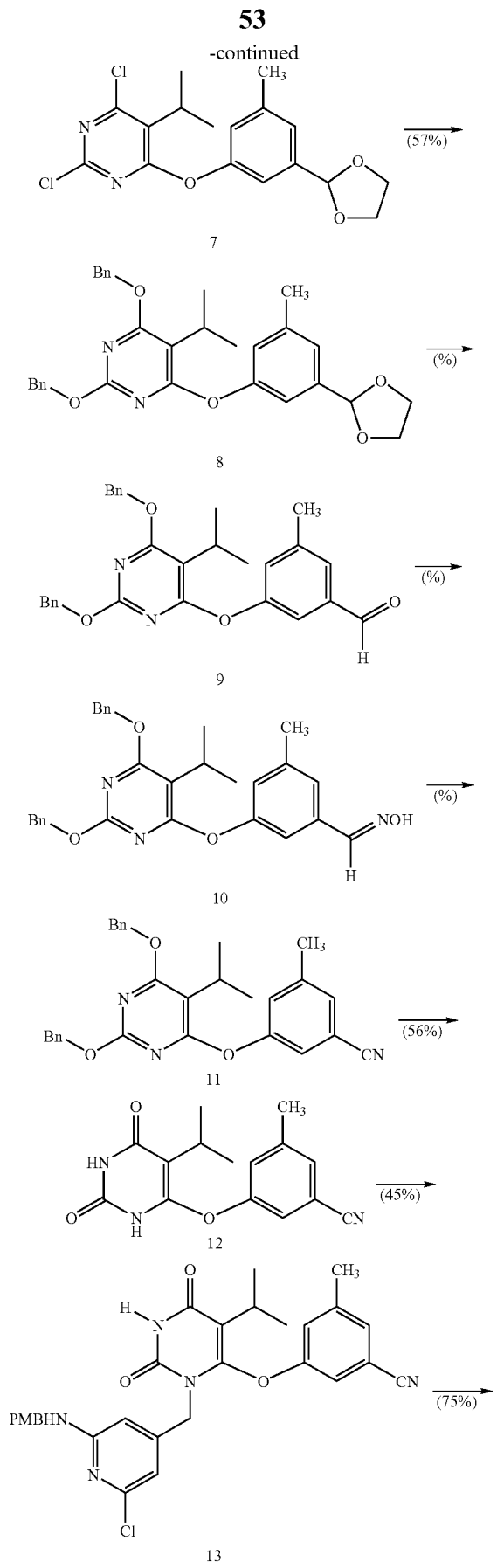

2,4-Dichloro-6-(3,5-dimethyl-phenoxy)-5-isopropyl-pyrimidine (2): To a stirred mixture of 5-isopropyl-2,4,6-trichloropyrimidine (1) (23.68 g, 0.105M), 3,5-dimethylphenol (12.2 g, 0.2M) in anhydrous DMF (200 ml) cooled in a dry ice-acetone bath (−40° C.) under nitrogen atmosphere, was portionwise added 60% sodium hydride (4.2 g, 0.105M). The reaction temperature was then slowly raised to room temperature during 3 hr. The reaction mixture was then diluted with ether, washed with water twice, dried with anhydrous magnesium sulfate, filtered, and evaporated in vacuo to give a crude product as a pale yellow solid. The crude product was purified by silica gel column chromatography (eluent, ether:hexanes (1:9)) to afford 28 g (90%) of a white solid. m.p. 107-108° C.; $^1$H NMR (200 MHz, CDCl$_3$) δ 1.40 (6H, d, J=7.0 Hz), 2.35 (6H, s), 3.58 (1H, m), 6.72 (2H, s), 6.91 (1H, s).

4-(3-Bromomethyl-5-methyl-phenoxy)-2,6-dichloro-5-isopropyl-pyrimidine (3): A mixture of (2) (9.72 g, 31 mmol), NBS (5.56 g, 31 mmol), and benzoyl peroxide (0.756 g, 3.1 mmol) in carbon tetrachloride (60 ml) was refluxed for 3 hr. under a light of 500 W tungsten lamp. After cooling to room temperature, the reaction mixture was filtered and evaporated in vacuo. The residue was purified by silica gel column chromatography (eluent, ether:hexanes (1:19)) to afford 8 g (62%) of a white solid; m.p. 98-101° C.; $^1$H NMR (200 MHz, CDCl$_3$) δ 1.41 (6H, d, J=7.2 Hz), 2.38 (3H, s), 3.59 (1H, m), 4.47 (2H, s), 6.86 (1H, s), 6.97 (1H, s), 7.13 (1H, s).

Acetic acid 3-(2,6-dichloro-5-isopropyl-pyrimidin-4-yloxy)-5-methyl-benzyl ester (4): To a stirred solution of (3) (14.4 g, 36.9 mmol) in anhydrous DMF (50 ml), was added sodium acetate (6.05 g, 73.8 mmol) and the mixture was stirred in an oil bath (90~100° C.) for overnight. After cooling to room temperature, the mixture was partitioned between ether and water. The ether layer was taken, washed with water twice, dried with anhydrous magnesium sulfate, filtered, and evaporated in vacuo. The residue was purified by silica gel column chromatography (eluent, ether: hexanes (from 1:9 to 1:4)) to afford 10 g (73%) of a white solid. m.p. 76-77° C.; $^1$H NMR (200 MHz, CDCl$_3$) δ 1.41 (6H, d, J=7.2 Hz), 2.12 (3H, s), 2.39 (3H, s), 3.58 (1H, m), 5.09 (2H, s), 6.88 (1H, s), 6.93 (1H, s), 7.08 (1H, s).

[3-(2,6-Dichloro-5-isopropyl-pyrimidin-4-yloxy)-5-methyl-phenyl]-methanol (5): To a stirred solution of (4) (5 g, 13.54 mmol) in THF (20 ml) at room temperature, was added lithium hydroxide (649 mg, 27 mmol) followed by distilled water (20 ml). After stirring for 23 hr., THF was removed in vacuo and the residue was partitioned between dichloromethane and water. The organic layer was taken, dried with anhydrous magnesium sulfate, filtered, and evaporated in vacuo. The residue was purified by silica gel column chromatography (eluent, ether: hexanes (from 1:4 to 1:1)) to afford 2.92 g (66%) of a white solid; m.p. 140-141° C.; ¹H NMR (200 MHz, CDCl₃) δ 1.40 (6H, d, J=7.4 Hz), 1.76 (1H, t, J=5.6 Hz), 2.39 (3H, s), 3.58 (1H, m), 4.69 (2H, d, J=5.6 Hz), 6.84 (1H, s), 6.95 (1H, s), 7.09 (1H, s).

3-(2,6-Dichloro-5-isopropyl-pyrimidin-4-yloxy)-5-methyl-benzaldehyde (6): A mixture of (5) (2.36 g, 7.22 mmol), PCC (1.56 g, 7.22 mmol), and dried celite (2 g) was stirred in dichloromethane (20 ml) for 2 hr. at room temperature. The mixture was then filtered through a short silica gel pad and washed with EA. The combined filtrate was evaporated in vacuo and the residue was purified by silica gel column chromatography (eluent, EA:hexanes (1:15)) to afford 1.71 g (73%) of a pale yellow syrup; ¹H NMR (200 MHz, CDCl₃) δ 1.42 (6H, d, J=7.2 Hz), 2.49 (3H, s), 3.61 (1H, m), 7.20 (1H, s), 7.44 (1H, s), 7.62 (1H, s), 10.01 (1H, s).

2,4-Dichloro-6-(3-[1,3]dioxolan-2-yl-5-methyl-phenoxy)-5-isopropyl-pyrimidine (7): A mixture of (6) (1.71 g, 5.25 mmol), ethylene glycol (0.88 ml, 15.75 mmol), and p-toluenesulfonic acid (263 mg, 0.26 mmol) in toluene (20 ml) was refluxed for 3 hr., using a reflux condenser equipped with a Dean-Stark trap. After cooling to room temperature, the mixture was diluted with EA, washed with aqueous saturated sodium bicarbonate solution, dried with anhydrous magnesium sulfate, filtered, and evaporated in vacuo. The residue was purified by silica gel column chromatography (eluent, EA:hexanes (1:15)) to afford 1.79 g (92%) of a colorless syrup; ¹H NMR (200 MHz, CDCl₃) δ 1.40 (6H, d, J=7.0 Hz), 2.40 (3H, s), 3.58 (1H, m), 3.99-4.16 (4H, m), 5.82 (1H, s), 6.92 (1H, s), 7.03 (1H, s), 7.21 (1H, s).

2,4-Bis-benzyloxy-6-(3-[1,3]dioxolan-2-yl-5-methyl-phenoxy)-5-isopropyl-pyrimidine (8): To a stirred anhydrous benzyl alcohol (10 ml) under nitrogen atmosphere at room temperature, was added sodium metal (285 mg, 12.41 mmol). After 1 hr., (7) (1.91 g, 5.17 mmol) in anhydrous benzyl alcohol (7 ml) was added. After stirring for overnight at room temperature, the mixture was evaporated in vacuo. The residue was dissolved in dichloromethane, filtered through a celite pad and the pad was washed with dichloromethane. The combined filtrate was then evaporated in vacuo and the residue was purified by silica gel column chromatography (eluent, EA:hexanes (1:10)) to afford 1.52 g (57%) of a colorless syrup; ¹H NMR (200 MHz, CDCl₃) δ 1.30 (6H, d, J=7.2 Hz), 2.39 (3H, s), 3.43 (1H, m), 4.02-4.13 (4H, m), 5.12 (2H, s), 5.42 (2H, s), 5.81 (1H, s), 6.92 (1H, s), 7.07 (1H, s), 7.16 (1H, s), 7.20-7.43 (10H, m).

3-(2,6-Bis-benzyloxy-5-isopropyl-pyrimidin-4-yloxy)-5-methyl-benzaldehyde (9): An unseparable mixture (monobenzyl- and di-benzyl) was obtained and carried to the next step directly without separation.

3-(2,6-Bis-benzyloxy-5-isopropyl-pyrimidin-4-yloxy)-5-methyl-benzaldehyde oxime (10): An unseparable mixture (mono-benzyl- and di-benzyl) was obtained and carried to the next step directly without separation.

3-(2,6-Bis-benzyloxy-5-isopropyl-pyrimidin-4-yloxy)-5-methyl-benzonitrile (11): An unseparable mixture (monobenzyl- and di-benzyl) was obtained and carried to the next step directly without separation.

3-(5-Isopropyl-2,6-dioxo-1,2,3,6-tetrahydro-pyrimidin-4-yloxy)-5-methyl-benzonitrile (12): Compound (II) (20.89 g) in anhydrous ethanol (30 ml) was stirred with 10% palladium on carbon (300 mg) under an atmosphere of hydrogen. After 6 hr., the mixture was filtered through celite pad and the filtrate was evaporated in vacuo. The residue was purified by silica gel column chromatography (eluent, dichloromethane:methanol (95:5)) to afford 1 g of a white solid; m.p. 272-275° C.; ¹H NMR (200 MHz, DMSO-d₆) δ 1.06 (6H, d, J=7.4 Hz), 2.36 (3H, s), 2.78 (1H, m), 7.33 (1H, s), 7.45 (1H, s), 7.55 (1H, s), 11.05 (1H, s), 11.34 (1H, s); m/z (EI) 285 (M+).

3-{3-[2-Chloro-6-(4-methoxy-benzylamino)-pyridin-4-ylmethyl]-5-isopropyl-2,6-dioxo-1,2,3,6-tetrahydro-pyrimidin-4-yloxy}-5-methyl-benzonitrile (13): To a stirred solution of 2-chloro-6-(p-methoxybenzylamino)-4-pyridinemethanol (278 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with (12) (285 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo to give a pale yellow foam. The crude product was purified by silica gel column chromatography (eluent, EA:hexanes (1:2)) to afford 244 mg (45%) of a white solid; ¹H NMR (200 MHz, CD₃OD/CDCl₃) δ 1.10 (6H, d, J=7.0 Hz), 2.32 (3H, s), 2.62 (1H, m), 3.81 (3H, s), 4.31 (2H, s), 4.71 (2H, s), 5.98 (1H, s), 6.24 (1H, s), 6.76 (1H, s), 6.87-6.91 (3H, m), 7.18-7.28 (3H, m).

Example A

To a stirred solution of the compound 13 (205 mg, 0.3761 mmol) in acetonitrile (4 ml) and glacial acetic acid (2 ml) at room temperature, was added CAN (412 mg, 0.7522 mmol) followed by distilled water (2 ml). After 30 min., the mixture was diluted with EA, washed with water, dried with anhydrous magnesium sulfate, filtered, and evaporated in vacuo to give a brown syrup. The crude product was purified by silica gel column chromatography (eluent, EA: hexanes (from 1:2 to 3:2)) to afford 120 mg (75%) of Example A as a pale yellow solid; m.p. 227-228° C.; ¹H NMR (200 MHz, DMSO-d₆) δ 1.03 (6H, d, J=6.8 Hz), 2.30 (3H, s), 2.56 (1H, m), 4.62 (2H, s), 6.08 (1H, s), 6.30 (1H, s), 6.33 (2H, s), 7.30 (1H, s), 7.39 (1H, s), 7.54 (1H, s), 11.57 (1H, s).

Example B

Scheme 2

14

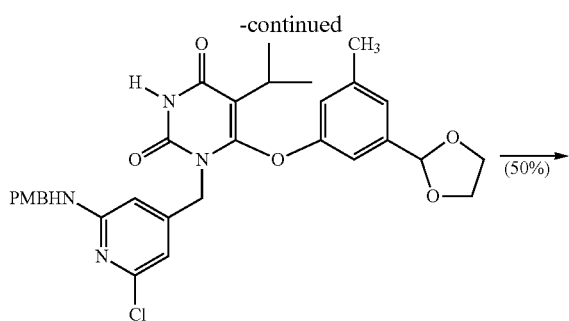

1-[2-Chloro-6-(4-methoxy-benzylamino)-pyridin-4-ylmethyl]-6-(3-[1,3]dioxolan-2-yl-5-methyl-phenoxy)-5-isopropyl-1H-pyrimidine-2,4-dione (15)

To a stirred solution of 2-chloro-6-(p-methoxybenzylamino)-4-pyridinemethanol (790 mg, 2.84 mmol) in chloroform (28 ml) at 0° C. (ice bath), was added triethylamine (597 µl, 4.26 mmol) followed by methanesulfonyl chloride (256 µl, 3.41 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with (14) (945 mg, 2.84 mmol), anhydrous powdered potassium carbonate (392 mg, 2.84 mmol), and lithium iodide (381 mg, 2.84 mmol). Anhydrous DMF (15 ml) was then added into the mixture and stirred for overnight at room temperature. The mixture was evaporated in vacuo. The residue was dissolved in methanol-dichloromethane (1:9), filtered through a celite pad, and the pad was washed with dichloromethane. The combined filtrate was evaporated in vacuo and the residue was purified by silica gel column chromatography (eluent, EA:hexanes (1:2)) to afford 963 mg (57%) of a white foam; $^1$H NMR (200 MHz, CDCl$_3$) δ 1.11 (6H, d, J=7.0 Hz), 2.30 (3H, s), 2.72 (1H, m), 3.79 (3H, s), 3.93-4.06 (4H, m), 4.30 (2H, d, J=5.4 Hz), 4.67 (2H, s), 5.04 (1H, t, J=5.4 Hz), 5.67 (1H, s), 5.96 (1H, s), 6.36 (1H, s), 6.57 (1H, s), 6.79 (1H, s), 6.85 (2H, d, J=8.4 Hz), 7.01 (1H, s), 7.22 (2H, d, J=8.4 Hz), 9.01 (1H, s).

3-{3-[2-Chloro-6-(4-methoxy-benzylamino)-pyridin-4-ylmethyl]-5-isopropyl-2,6-dioxo-1,2,3,6-tetrahydro-pyrimidin-4-yloxy}-5-methyl-benzaldehyde (16): A mixture of (15) (908 mg, 1.53 mmol), PPTS (77 mg, 0.31 mmol), and water (7 drops) in acetone (10 ml) was heated under reflux for 3 hr. After cooling to room temperature, the mixture was evaporated in vacuo and the residue was purified by silica gel column chromatography (eluent, EA:hexanes (1:2)) to afford 350 mg (50%) of a white foam; $^1$H NMR (200 MHz, CDCl$_3$) δ 1.11 (6H, d, J=6.8 Hz), 2.40 (3H, s), 2.68 (1H, m), 3.80 (3H, s), 4.29 (2H, d, J=5.4 Hz), 4.72 (2H, s), 5.02 (1H, t, J=5.4 Hz), 6.01 (1H, s), 6.26 (1H, s), 6.85-6.89 (3H, m), 7.09 (1H, s), 7.21-7.27 (2H, m), 7.40 (1H, s), 8.98 (1H, s), 9.89 (1H, s).

3-(3-{3-[2-Chloro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (17)

To a stirred solution of (16) (335 mg, 0.611 mmol) and diethyl cyanomethylphosphonate (104 µl, 0.64 mmol) in THF (10 ml) at 0° C. (ice bath) under nitrogen atmosphere, was added potassium t-butoxide (151 mg, 1.34 mmol). After stirring for 1 hr., the mixture was stirred for overnight at room temperature. The mixture was then diluted with EA, washed with aqueous saturated ammonium chloride solution, dried with anhydrous magnesium sulfate, filtered, and evaporated in vacuo. The residue was purified by silica gel column chromatography (eluent, EA:hexanes (1:2)) to afford 243 mg (70%) of a white foam; $^1$H NMR (200 MHz, CDCl$_3$) δ 1.10 (6H, d, J=6.8 Hz), 2.32 (3H, s), 2.68 (1H, m), 3.78 (3H, s), 4.30 (2H, d, J=5.2 Hz), 4.68 (2H, s), 5.23 (1H, t, J=5.2 Hz), 5.82 (1H, d, J=16.6 Hz), 6.05 (1H, s), 6.21 (1H, s), 6.62 (2H, s), 6.84-6.90 (2H, m), 6.97 (1H, s), 7.18-7.27 (3H, m), 9.63 (1H, s).

Example B

To a stirred solution of (17) (220 mg, 0.38 mmol) in acetonitrile (4 ml) at room temperature, was added CAN (422 mg, 0.77 mmol) followed by distilled water (2 ml). After 25 min., the mixture was diluted with EA, washed with water, dried with anhydrous magnesium sulfate, filtered, and evaporated in vacuo to give a brown syrup. The crude product was purified by silica gel column chromatography (eluent, EA:hexanes (1:1)) to afford 154 mg (88%) of Example B as a pale yellow solid; $^1$H NMR (200 MHz, CD$_3$OD/CDCl$_3$) δ 1.11 (6H, d, J=7.0 Hz), 2.29 (3H, s), 2.71 (1H, m), 4.73 (2H, s), 5.91 (1H, d, J=16.6 Hz), 6.16 (1H, s), 6.29 (1H, s), 6.70 (1H, s), 6.75 (1H, s), 7.02 (1H, s), 7.32 (1H, d, J=16.6 Hz).

Example C

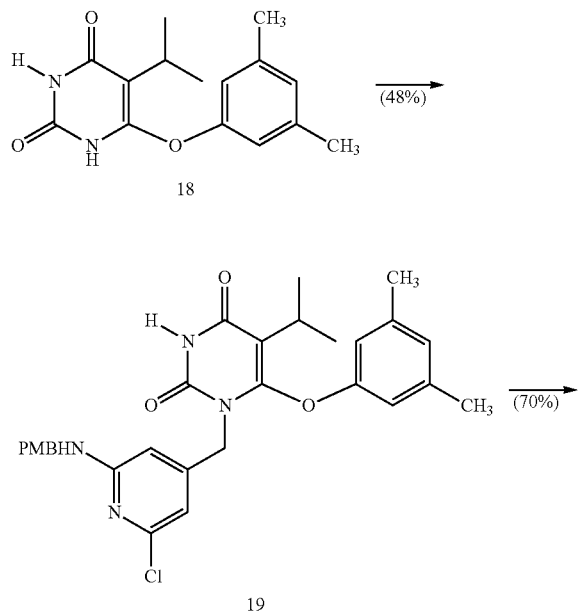

1-[2-Chloro-6-(4-methoxy-benzylamino)-pyridin-4-ylm-ethyl]-6-(3,5-dimethyl-phenoxy)-5-isopropyl-1H-pyrimi-dine-2,4-dione (19): To a stirred solution of 2-chloro-6-(p-methoxybenzylamino)-4-pyridinemethanol (278 mg, 1 mmol) in chloroform (10 ml) at 0° C. (ice bath), was added triethylamine (210 µl, 1.5 mmol) and methanesulfonyl chloride (90 µl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with (18) (274 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo to give a pale yellow foam. The crude product was purified by silica gel column chromatography (eluent, dichloromethane:EA (7:1)) to afford 260 mg (48%) of a white solid; m.p. 223-225° C.; $^1$H NMR (200 MHz, CDCl$_3$) δ 1.11 (6H, d, J=6.8 Hz), 2.26 (6H, s), 2.74 (1H, m), 3.79 (3H, s), 4.31 (2H, d, J=5.4 Hz), 4.67 (2H, s), 5.01 (1H, t, J=5.4 Hz), 6.05 (1H, s), 6.35 (1H, s), 6.40 (2H, s), 6.74 (1H, s), 6.83-6.88 (2H, m), 7.20-7.27 (2H, m), 8.87 (1H, s).

Example C

To a stirred solution of the (19) (226 mg, 0.4232 mmol) in acetonitrile (4 ml) and glacial acetic acid (2 ml) at room temperature, was added CAN (464 mg, 0.8464 mmol) followed by distilled water (2 ml). After 30 min., the mixture was diluted with EA, washed with water, dried with anhydrous magnesium sulfate, filtered, and evaporated in vacuo to give a brown syrup. The crude product was purified by silica gel column chromatography (eluent, EA: hexanes (from 1:2 to 1:1)) to afford 123 mg (70%) of Example C as a white solid; m.p. 238-239° C.; $^1$H NMR (300 MHz, CDCl$_3$) δ 1.19 (6H, d, J=6.9 Hz), 2.29 (6H, s), 2.77 (1H, m), 4.72 (4H, s), 6.29 (1H, s), 6.38 (1H, s), 6.46 (2H, s), 6.76 (1H, s), 9.43 (1H, s); HRMS (EI) Calcd. 414.145869, Found 414.144933.

Example D

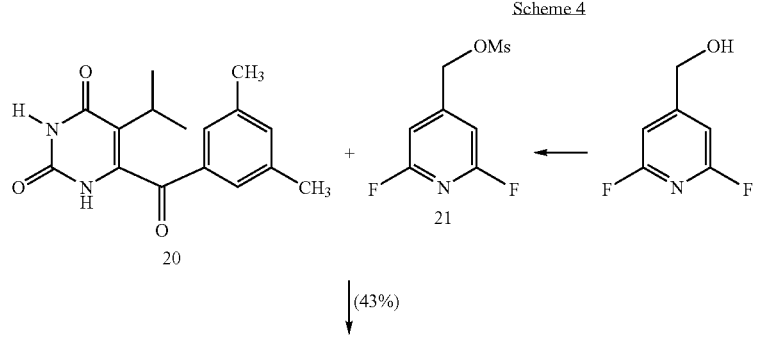

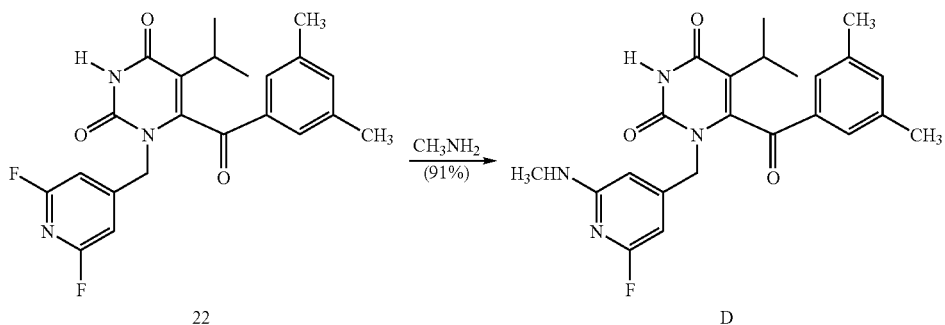

1-(2,6-Difluoro-pyridin-4-ylmethyl)-6-(3,5-dimethyl-benzoyl)-5-isopropyl-1H-pyrimidine-2,4-dione (22): To a stirred solution of (2,6-Difluoro-pyridin-4-yl)-methanol (870 mg, 6 mmol) in chloroform (30 ml) at 0° C. (ice bath), was added triethylamine (1.26 ml, 9 mmol) followed by methanesulfonyl chloride (540 μl, 7.2 mmol). After stirring for 1.5 hr., the mixture was diluted with dichloromethane, washed with aqueous saturated sodium bicarbonate solution, dried with anhydrous magnesium sulfate, filtered, and evaporated in vacuo to give (21). The residue was further dried in high vacuo and mixed with (20) (1.7 g, 6 mmol), anhydrous powdered potassium carbonate (816 mg, 6 mmol), lithium iodide (804 mg, 6 mmol). Anhydrous DMF (30 ml) was then added into the mixture and stirred for overnight at room temperature. The mixture was evaporated in vacuo. The residue was dissolved in methanol-dichloromethane (1:9), filtered through celite pad, and evaporated in vacuo to give a light yellow foam. The crude product was purified by silica gel column chromatography (eluent, EA:hexanes (from 1:2 to 1:1)) to afford 1.07 g (43%) of a white solid; m.p. 185-187° C.; $^1$H NMR (200 MHz, CDCl$_3$) δ 1.10 (3H, d, J=6.9 Hz), 1.19 (3H, d, J=6.9 Hz), 2.20-2.37 (7H, m), 4.63 (1H, d, J=16.9 Hz), 4.82 (1H, d, J=16.9 Hz), 6.48 (2H, s), 7.25 (1H, s), 7.34 (2H, s), 9.24 (1H, s); HRMS (EI) Calcd. 413.155098, Found 413.154694.

Example D

To a 100 ml steel bomb, were placed (22) (372 mg, 0.9 mmol), methylamine hydrochloride (607 mg, 9 mmol), triethylamine (1.25 ml, 9 mmol), and methanol (15 ml). The mixture was then heated for 5 hr in an oil bath (100~120° C.). The mixture was cooled to room temperature, evaporated in vacuo, and the residue was purified by silica gel column chromatography (eluent, EA:hexanes (1:2)) to afford 348 mg (91%) of compound 4 as a white solid; m.p. 204-205° C.; $^1$H NMR (300 MHz, CDCl$_3$) δ 1.14 (3H, d, J=6.9 Hz), 1.22 (3H, d, J=6.9 Hz), 2.30-2.39 (7H, m), 2.77 (3H, d, J=5.1 Hz), 4.12 (1H, d, J=16.2 Hz), 4.74 (1H, q, J=5.1 Hz), 4.95 (1H, d, J=16.2 Hz), 5.79 (1H, s), 5.85 (1H, s), 7.27 (1H, s), 7.37 (2H, s), 9.56 (1H, s); HRMS (EI) Calcd. 424.191069, Found 424.191074.

Example E

Scheme 5

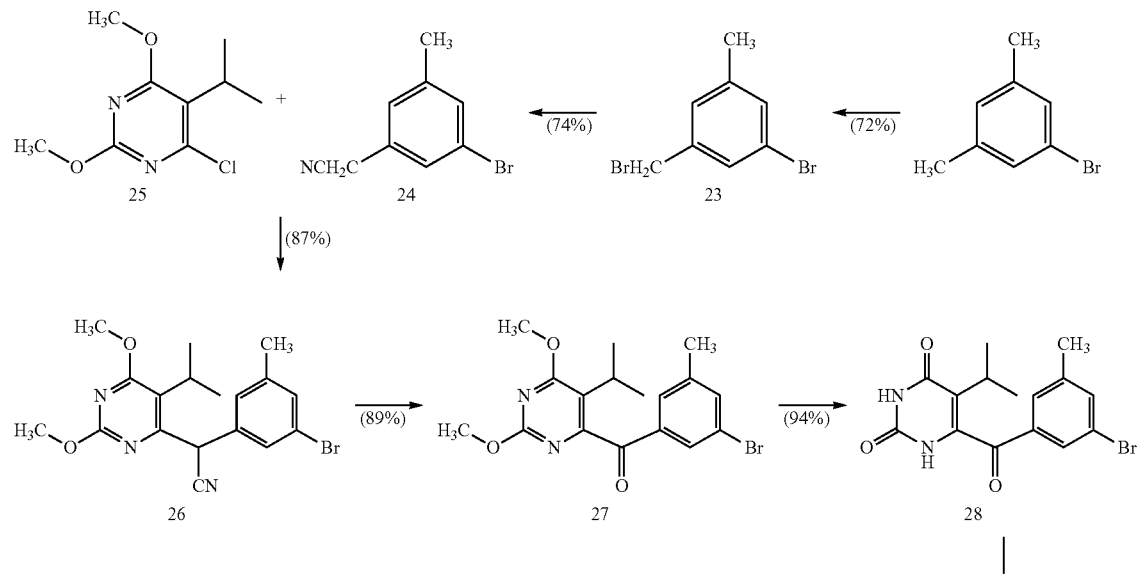

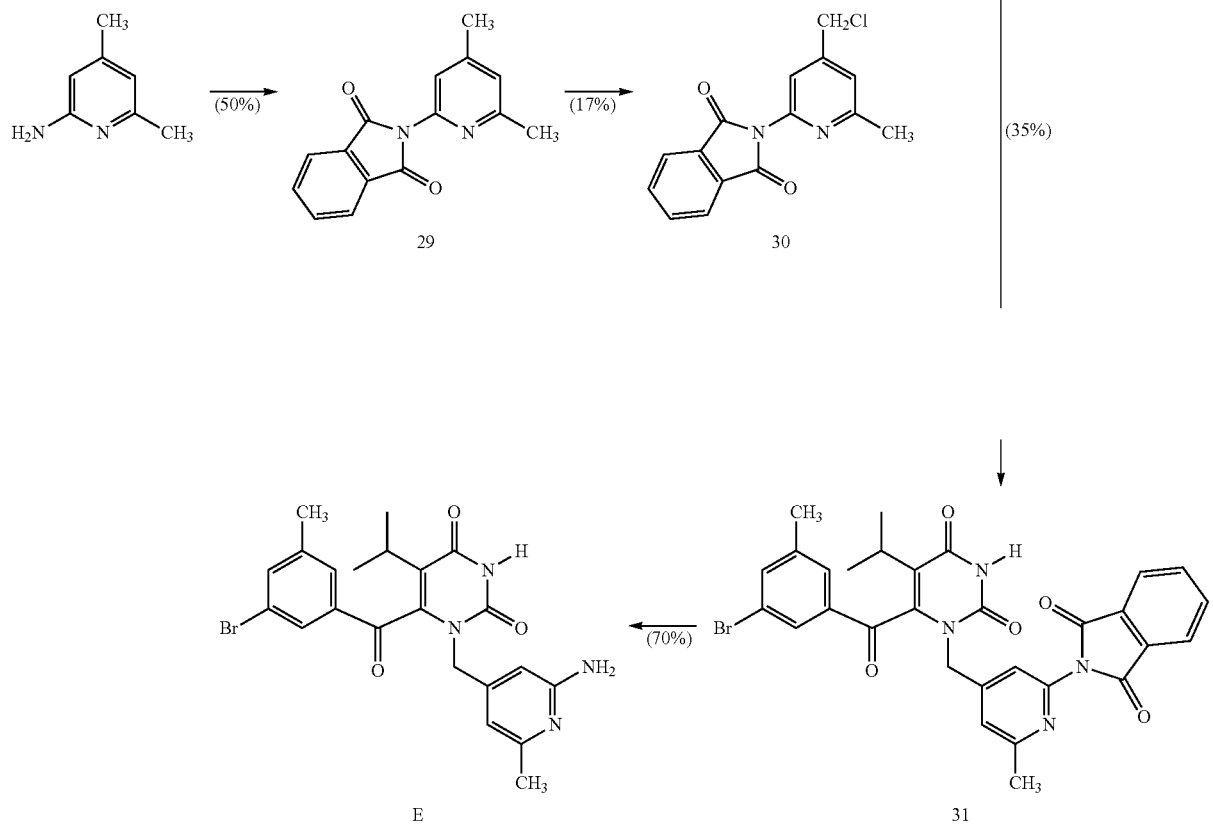

1-Bromo-3-bromomethyl-5-methyl-benzene (23): The mixture of 3,5-dimethylbromobenzene (80.25 g, 0.43M), NBS (77 g, 0.43M), and benzoyl peroxide (5.2 g, 0.021M) in carbon tetrachloride (400 ml) was refluxed for 3 hr. under a light of 500 W tungsten light. After cooling to room temperature, the mixture was filtered and the filtrate was evaporated in vacuo to give a white solid, which was purified by silica gel column chromatography (eluent, hexane) to afford 82 g (72%) of a white solid; m.p. 46-47° C.; $^1$H NMR (200 MHz, CDCl$_3$) δδ 2.32 (3H, s), 4.38 (2H, s), 7.12 (1H, s), 7.25 (1H, s), 7.33 (1H, s).

(3-Bromo-5-methyl-phenyl)-acetonitrile (24): To a flask equipped with additional funnel, was placed potassium cyanide (29.6 g, 0.45M) and distilled water (30 ml). The mixture was heated up to 70° C. in an oil bath. With stirring, (23) (80 g, 0.3M) in ethanol (150 ml) was then dropwise added for 1 hr. through the addition funnel. After completion of addition, the mixture was refluxed for 2 hr. After cooling to room temperature, ether was added to the mixture. The mixture was washed with water, dried with anhydrous magnesium sulfate, filtered, and evaporated in vacuo to give a brown residue, which was purified by silica gel column chromatography (eluent, ether:hexanes (1:3)) to afford 47 g (74%) of a light brown oil; $^1$H NMR (200 MHz, CDCl$_3$) δ 2.33 (3H, s), 3.68 (2H, s), 7.08 (1H, s), 7.28 (1H, s), 7.29 (1H, s).

(3-Bromo-5-methyl-phenyl)-(5-isopropyl-2,6-dimethoxy-pyrimidin-4-yl)-acetonitrile (26): To a stirred mixture of (25) (47.63 g, 0.22M) and (24) (42 g, 0.2M) in anhydrous DMF (220 ml) in an ice-water bath under an atmosphere of nitrogen, was portionwise added 60% sodium hydride (16 g, 0.4M). After stirring for 1 hr., the mixture was stirred at room temperature for overnight. The mixture was neutralized with aqueous saturated ammonium chloride solution. The crude product was extracted with ether and purified by silica gel column chromatography (eluent, ether:hexanes (1:7)) to afford 68 g (87%) of a white solid; m.p. 123-124° C.; $^1$H NMR (200 MHz, CDCl$_3$) δ 1.11 (3H, d, J=6.9 Hz), 1.15 (3H, D, J=6.9 Hz), 2.32 (3H, s), 2.97 (1H, m), 4.00 (3H, s), 4.01 (3H, s), 5.34 (1H, s), 7.14 (1H, s), 7.28 (1H, s), 7.31 (1H, s).

(3-Bromo-5-methyl-phenyl)-(5-isopropyl-2,6-dimethoxy-pyrimidin-4-yl)-methanone (27): To a stirred solution of (26) (40 g, 0.1M) in anhydrous DMF (300 ml) in a water bath under an atmosphere of nitrogen, was portionwise added 60% sodium hydride (4.92 g, 0.12M). After 30 min., oxygen gas was bubbled into the reaction mixture for 2 hr. The mixture was neutralized with aqueous saturated ammonium chloride solution. The crude product was extracted with ether and purified by silica gel column chromatography (eluent, ether:hexanes (1:9)) to afford 34.6 g (89%) of a white solid; m.p. 122-123° C.; $^1$H NMR (200 MHz, CDCl$_3$) δ 1.17 (6H, d, J=7.1 Hz), 2.36 (3H, s), 2.77 (1H, m), 3.92 (3H, s), 4.05 (3H, s), 7.54-7.56 (2H, m), 7.75 (1H, m).

6-(3-Bromo-5-methyl-benzoyl)-5-isopropyl-1H-pyrimidine-2,4-dione (28): Compound (27) (34.6 g, 91 mmol) was refluxed with conc. HCl (200 ml) for 3 hr. After cooling to room temperature, the white precipitate was collected by filtration, washed with cold water and hexane, and dried in high vacuo to afford 30 g (94%) of a white solid; m.p. 266-

267° C.; $^1$H NMR (200 MHz, DMSO-d$_6$) δ 1.05 (6H, d, J=6.8 Hz), 2.26 (1H, m), 2.40 (3H, s), 7.82 (2H, s), 7.93 (1H, s), 11.02 (1H, s), 11.17 (1H, s).

2-(4,6-Dimethyl-pyridin-2-yl)-isoindole-1,3-dione (29): To a mixture of 24,6-Dimethyl-pyridin-2-ylamine (24.4 g, 0.2 mol) and phthalic anhydride (29.6 g, 0.2 mol) in toluene (160 ml), was added triethylamine (2.8 ml, 0.02 mol). The mixture was refluxed for 5 hr. After cooling to room temperature, the mixture was evaporated in vacuo and the residue was suspended in acetic anhydride (250 ml). The mixture was then heated to reflux until the solid dissolves completely. After cooling to room temperature, the mixture was evaporated in vacuo. The residue was dissolved in dichloromethane, washed with saturated aqueous sodium bicarbonate solution, dried with anhydrous magnesium sulfate, filtered, and evaporated in vacuo to give a white solid. The crude product was then purified by silica gel column chromatography (eluent, dichloromethane:EA (9:1)) to afford 24.9 g (50%) of a white solid; $^1$H NMR (200 MHz, CDCl$_3$) δ 2.38 (3H, s), 2.56 (3H, s), 7.02 (1H, s), 7.06 (1H, s), 7.74-7.95 (4H, m).

2-(4-Chloromethyl-6-methyl-pyridin-2-yl)-isoindole-1,3-dione (30): A mixture of (29) (2.52 g, 10 mmol)), N-chlorosuccinimide (1.6 g, 12 mmol), and benzoyl peroxide (1.21 g, 5 mmol) in carbon tetrachloride (50 ml) was refluxed for 2 hr. After cooling to room temperature, the mixture was filtered and the filtrate was evaporated in vacuo. The residue was purified by silica gel column chromatography (eluent, dichloromethane:EA (95:5)) to afford 493 mg (17%) of a yellow solid; $^1$H NMR (200 MHz, CDCl$_3$) δ 2.63 (3H, s), 4.48 (2H, s), 7.27 (1H, s), 7.28 (1H, s), 7.76-7.98 (4H, m); m/z (EI) 286 (M$^+$).

2-{4-[6-(3-Bromo-5-methyl-benzoyl)-5-isopropyl-2,4-dioxo-3,4-dihydro-2 H-pyrimidin-1-ylmethyl]-6-methyl-pyridin-2-yl}-isoindole-1,3-dione (31): To a mixture of (28) (351 mg, 1 mmol), (30) (287 mg, 1 mmol), anhydrous powdered potassium carbonate (138 mg, 1 mmol), and lithium iodide (134 mg, 1 mmol), was added DMF (5 ml). The mixture was stirred for overnight at room temperature. The mixture was then evaporated in vacuo and the residue was purified by silica gel column chromatography (eluent, EA: hexanes (from 1:2 to 1:1)) to afford 211 mg (35%) of a white solid; $^1$H NMR (200 MHz, CDCl$_3$) δ 1.13 (3H, d, J=7.2 Hz), 1.20 (3H, d, J=7.2 Hz), 2.17-2.40 (4H, m), 2.47 (3H, s), 4.49 (1H, d, J=16.0 Hz), 5.15 (1H, d, J=16.0 Hz), 6.84 (1H, s), 6.91 (1H, s), 7.36 (1H, s), 7.53 (1H, s), 7.61 (1H, s), 7.77-7.96 (4H, m), 9.30 (1H, s).

Example E

To a stirred solution of (31) (211 mg, 0.35 mmol) in ethanol (5 ml), was added aqueous 4M sodium hydroxide solution (0.5 ml). The mixture was refluxed for 5 hr. After cooling to room temperature, the mixture was evaporated in vacuo and the residue was purified by silica gel column chromatography (eluent, dichloromethane:methanol (95:5)) to afford 116 mg (70%) of Example E as a yellow solid; m.p. 261-262° C.; $^1$H NMR (200 MHz, CDCl$_3$) δ 1.13 (3H, d, J=7.0 Hz), 1.21 (3H, d, J=7.0 Hz), 2.17-2.40 (7H, m), 4.23 (1H, d, J=16.1 Hz), 4.45 (2H, S), 5.09 (1H, d, J=16.1 Hz), 5.97 (1H, s), 6.05 (1H, s), 7.35 (1H, s), 7.54 (1H, s), 7.73 (1H, s), 9.50 (1H, s); HRMS (EI) Calcd. 470.093788, Found 470.095352.

Example F

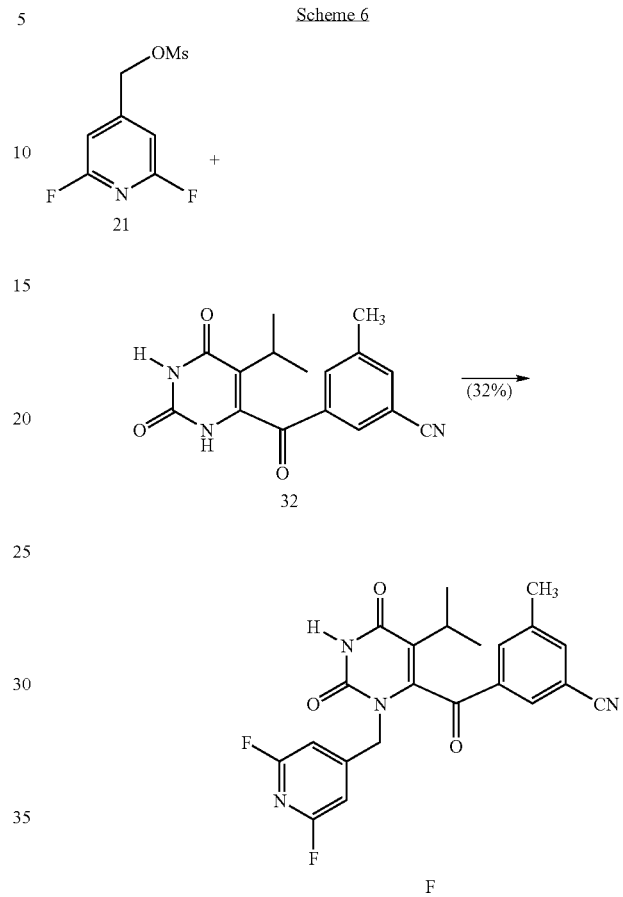

Scheme 6

Example F

To a stirred solution of 2,6-difluoro-4-pyridinemethanol (435 mg, 3 mmol) in chloroform (30 ml) at 0° C. (ice bath), was added triethylamine (630 μl, 4.5 mmol) followed by methanesulfonyl chloride (270 μl, 3.6 mmol). After stirring for 1.5 hr., the mixture was diluted with dichloromethane, washed with aqueous saturated sodium bicarbonate solution, dried with anhydrous magnesium sulfate, filtered, and evaporated in vacuo to give (21). The residue was further dried in high vacuo and mixed with (32) (891 mg, 3 mmol), anhydrous powdered potassium carbonate (408 mg, 3 mmol), lithium iodide (402 mg, 3 mmol). Anhydrous DMF (15 ml) was then added into the mixture and stirred for overnight at room temperature. The mixture was evaporated in vacuo. The residue was dissolved in methanol-dichloromethane (1:9), filtered through celite pad and evaporated in vacuo to give a light yellow foam. The crude product was purified by silica gel column chromatography (eluent, EA:hexanes (1:2)) to afford 443 mg (32%) of compound 6 as a white solid; m.p. 227-229° C.; $^1$H NMR (300 MHz, CDCl$_3$) δ 1.14 (3H, d, J=6.6 Hz), 1.25 (3H, d, J=6.6 Hz), 2.23 (1H, m), 2.47 (3H, s), 4.76 (2H, s), 6.55 (2H, s), 7.76 (2H, s), 7.95 (1H, s), 8.67 (1H, s); m/z (EI) 424 (M$^+$); HRMS (EI) Calcd. 424.134697, Found 424.135406.

Preparation of Compound 32 is described in the section describing the preparation of Example DC.

Example G

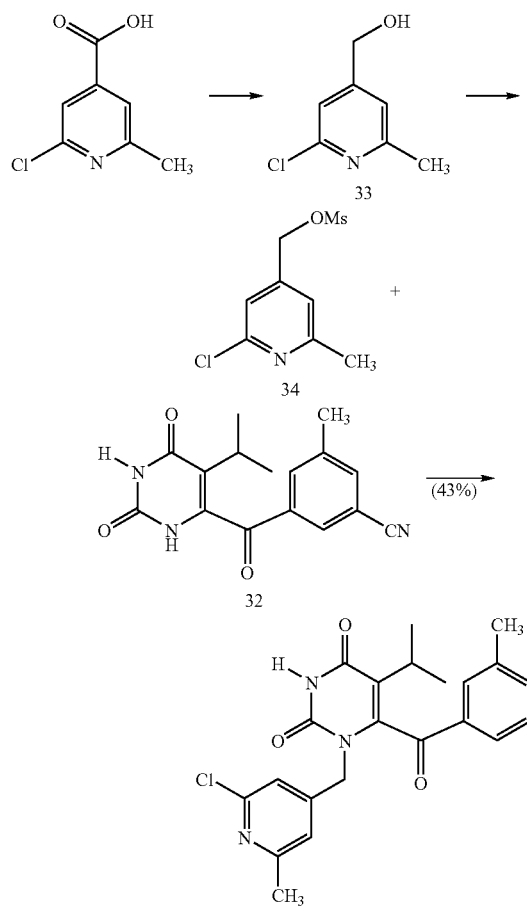

(2-Chloro-6-methyl-pyridin-4-yl)-methanol (33): To a stirred solution of 2-Chloro-6-methyl-isonicotinic acid (2 g, 11.65 mmol) in anhydrous THF (40 ml) cooled in an ice bath, was added 1M borane-methyl sulfide complex (6 ml, 60 mmol). After 1 hr, the mixture was stirred for 48 hr at room temperature. The mixture was cooled in an ice bath and conc. HCl (18 ml) was added and stirred for 30 min. The mixture was then basified by addition of 50% aqueous NaOH (15 ml). The product was extracted with dichloromethane, dried with anhydrous potassium carbonate, filtered, and evaporated in vacuo. The crude product was purified by silica gel column chromatography (eluent, methanol:dichloromethane (5:95)) to afford 1.3 g (71%) of a pale yellow solid; m.p. 112-113° C.; $^1$H NMR (200 MHz, CDCl$_3$) δ 2.26 (1H, t, J=5.4 Hz), 2.52 (3H, s), 4.70 (2H, d, J=5.4 Hz), 7.15 (1H, s), 7.16 (1H, s); m/z (EI) 157 (M$^+$).

Example G

To a stirred solution of (33) (315 mg, 2 mmol) in chloroform (20 ml) at 0° C. (ice bath), was added triethylamine (420 μl, 3 mmol) followed by methanesulfonyl chloride (180 μl, 2.4 mmol). After stirring for 1.5 hr, the mixture was diluted with dichloromethane, washed with aqueous saturated sodium bicarbonate solution, dried with anhydrous magnesium sulfate, filtered, and evaporated in vacuo to give (34), which was then mixed with (32) (594 mg, 2 mmol), anhydrous powdered potassium carbonate (276 mg, 2 mmol), lithium iodide (268 mg, 2 mmol). Anhydrous DMF (10 ml) was then added into the mixture and stirred for overnight at room temperature. The mixture was evaporated in vacuo. The residue was dissolved in methanol-dichloromethane (1:9), filtered through Celite pad, and evaporated in vacuo to give a light yellow foam. The crude product was purified by silica gel column chromatography (eluent, EA:hexanes (1:2)) to afford 378 mg (43%) of Example G as a white solid; m.p. 205-206° C.; $^1$H NMR (200 MHz, CDCl$_3$) δ 1.13 (3H, d, J=7.0 Hz), 1.22 (3H, d, J=7.0 Hz), 2.18 (1H, m), 2.40 (3H, s), 2.43 (3H, s), 4.35 (1H, d, J=16.1 Hz), 5.15 (1H, d, J=16.1 Hz), 6.71 (1H, s), 6.74 (1H, s), 7.68 (1H, s), 7.69 (1H, s), 7.82 (1H, s), 8.64 (1H, s); m/z (EI) 436 (M$^+$); HRMS (EI) Calcd. 436.130003, Found 436.13021.

Example H

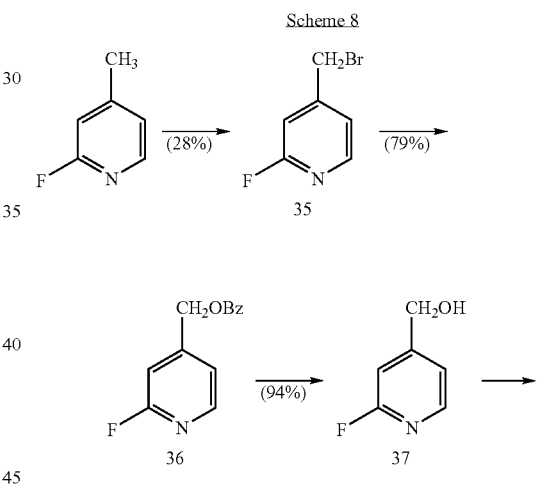

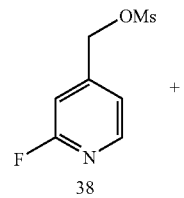

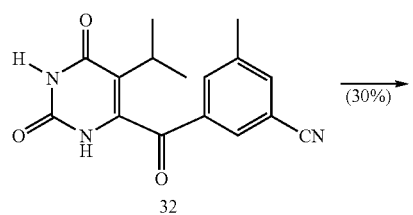

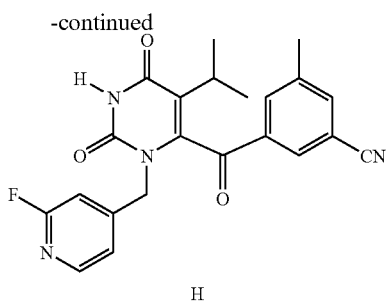

H

4-Bromomethyl-2-fluoro-pyridine (35): The mixture of 2-Fluoro-4-methyl-pyridine (10 g, 90 mmol), N-bromosuccinimide (19.2 g, 108 mmol), and benzoyl peroxide (2.18 g, 9 mmol) in carbon tetrachloride (100 ml) was refluxed for 5 hr under a light of 500 W tungsten light. After cooling to room temperature, the mixture was filtered and the filtrate was evaporated in vacuo to give a brown oil, which was purified by silica gel column chromatography (eluent, ether:hexane (1:9)) to afford 4.85 g (28%) of a pale brown oil; $^1$H NMR (200 MHz, CDCl$_3$) δ: 4.40 (2H, s), 6.95 (1H, m), 7.19 (1H, m), 8.18 (1H, d, J=5.2 Hz); m/z (EI): 189 (M$^+$), 191 (M+2$^+$).

Benzoic acid 2-fluoro-pyridin-4-ylmethyl ester (36): The mixture of 4-Bromomethyl-2-fluoro-pyridine (35) (4.85 g, 25.5 mmol) and sodium benzoate (5.51 g, 38.25 mmol) in DMF (60 ml) was stirred at room temperature for 3 hr. Ether was then added and the mixture was washed with water, dried with anhydrous magnesium sulfate, filtered, and evaporated in vacuo. The residue was purified by silica gel column chromatography (eluent, ether:hexane (1:4)) to afford 4.68 g (79%) of a colorless oil; $^1$H NMR (200 MHz, CDCl$_3$) δ: 5.41 (2H, s), 7.11 (1H, m), 7.45-7.66 (3H, m), 8.08-8.12 (2H, m), 8.23 (1H, d, J=5.4 Hz); m/z (EI): 231 (M$^+$).

(2-Fluoro-pyridin-4-yl)-methanol (37): To a stirred solution of Benzoic acid 2-fluoro-pyridin-4-ylmethyl ester (36) (4.536 g, 19.62 mmol) in anhydrous methanol (40 ml) cooled in an ice bath, was added sodium methoxide (1.06 g, 19.62 mmol). After stirring for 30 min., excess ammonium chloride was added to the mixture. The mixture was then evaporated in vacuo and the residue was purified by silica gel column chromatography (eluent, ether:hexane (1:1)) to afford 2.34 g (94%) of a white solid; m.p. 70-71° C.; $^1$H NMR (200 MHz, CDCl$_3$) δ: 2.40 (1H, t, J=4.0 Hz), 4.78 (2H, d, J=4 Hz), 6.97 (1H, s), 7.15 (1H, m), 8.15 (1H, d, J=5.0 Hz); m/z (EI): 127 (M$^+$).

Example H

To a stirred solution of (2-Fluoro-pyridin-4-yl)-methanol (37) (381 mg, 3 mmol) in chloroform (30 ml) at 0° C. (ice bath), was added triethylamine (630 μl, 4.5 mmol) followed by methanesulfonyl chloride (270 μl, 3.6 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo to provide Methanesulfonic acid 2-fluoro-pyridin-4-ylmethyl ester (38). A flask was charged with Methanesulfonic acid 2-fluoro-pyridin-4-ylmethyl ester (38) from above, 3-(5-Isopropyl-2,6-dioxo-1,2,3,6-tetrahydro-pyrimidine-4-carbonyl)-5-methyl-benzonitrile (32) (891 mg, 3 mmol), anhydrous powdered potassium carbonate (408 mg, 3 mmol), and lithium iodide (402 mg, 3 mmol). Anhydrous DMF (15 ml) was then added into the mixture and stirred for 5.5 hr at room temperature. The mixture was evaporated in vacuo. The residue was dissolved in methanol-dichloromethane (1:9), filtered through celite pad, and evaporated in vacuo to give a pale yellow foam. The crude product was purified by silica gel column chromatography (eluent, methanol:chloroform (2:98)) to afford 366 mg (30%) of Example H as a pale yellow foam, which was recrystallized from chloroform-ether to give a white solid; $^1$H NMR (200 MHz, CDCl$_3$) δ: 1.12 (3H, d, J=6.8 Hz), 1.23 (3H, d, J=6.8 Hz), 2.25 (1H, m), 2.42 (3H, s), 4.66 (1H, d, J=16.7 Hz), 4.93 (1H, d, J=16.7 Hz), 6.61 (1H, s), 6.90 (1H, d, J=5.3 Hz), 7.71 (2H, s), 7.91 (1H, s), 8.04 (1H, d, J=5.3 Hz), 9.44 (1H, s); m/z (EI): 406 (M$^+$); HRMS (EI) Calcd. 406.144104, Found 406.144119.

Example I

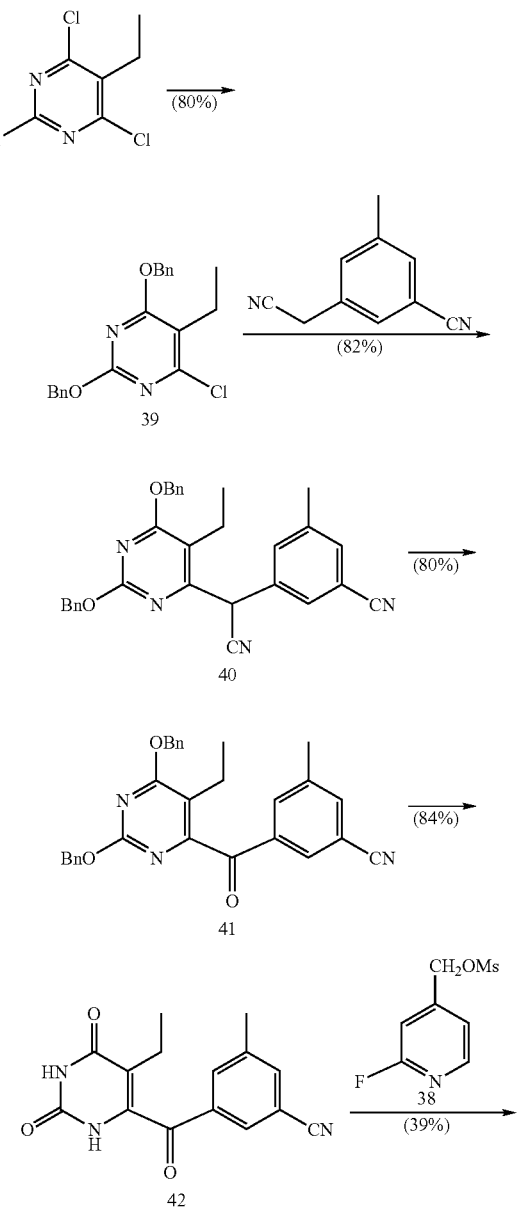

Scheme 9

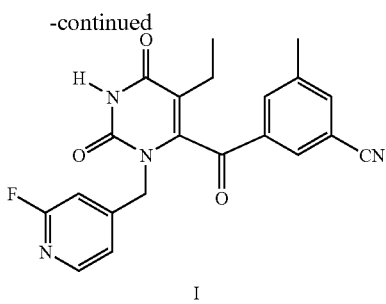

I 2,4-Bis-benzyloxy-6-chloro-5-ethyl-pyrimidine (39): To a stirred solution of benzyl alcohol (80 ml) in water bath, was added sodium metal (2.17 g, 94.6 mmol) under nitrogen atmosphere. After complete reaction of sodium metal, the mixture was cooled in an ice bath and 2,4,6-Trichloro-5-ethyl-pyrimidine (10.5 g, 49.6 mmol) was added portionwise. After stirring for 30 min in an ice bath, the reaction mixture was stirred at room temperature for overnight. Excess benzyl alcohol was evaporated in vacuo and the residue was dissolved in ether, washed with water, dried with anhydrous magnesium sulfate, filtered, and evaporated in vacuo to give a pale yellow oil. The crude product was purified by silica gel column chromatography (eluent, ether:hexane (4:96)) to give 14 g (80%) of a white solid; m.p. 53-54° C.; $^1$H NMR (200 MHz, CDCl$_3$) δ: 1.14 (3H, t, J=7.4 Hz), 2.70 (2H, q, J=7.4 Hz), 5.41 (2H, s), 5.45 (2H, s), 7.34-7.53 (10H, m); m/z (EI): 354 (M$^+$).

3-[(2,6-Bis-benzyloxy-5-ethyl-pyrimidin-4-yl)-cyano-methyl]-5-methyl-benzonitrile (40): To a stirred mixture of 2,4-Bis-benzyloxy-6-chloro-5-ethyl-pyrimidine (39) (9.89 g, 27.87 mmol) and 3-Cyanomethyl-5-methyl-benzonitrile (4.15 g, 26.55 mmol) in anhydrous DMF (50 ml) in an ice-water bath under an atmosphere of nitrogen, was portionwise added 60% sodium hydride (2.34 g, 58.4 mmol). After stirring for 1 hr, the mixture was stirred at room temperature for overnight. The mixture was neutralized with aqueous saturated ammonium chloride solution. The crude product was extracted with ether and recrystallized from dichloromethane-hexane to afford 10.3 g (82%) a pale yellow solid; m.p. 139-141° C.; $^1$H NMR (200 MHz, CDCl$_3$) δ: 1.00 (3H, t, J=7.6 Hz), 2.37 (3H, s), 2.52-2.58 (2H, m), 5.29 (1H, s), 5.49 (4H, s), 7.27-7.50 (10H, m); m/z (EI): 474 (M$^+$).

3-(2,6-Bis-benzyloxy-5-ethyl-pyrimidine-4-carbonyl)-5-methyl-benzonitrile (41): To a stirred solution of 3-[(2,6-Bis-benzyloxy-5-ethyl-pyrimidin-4-yl)-cyano-methyl]-5-methyl-benzonitrile (40) (10 g, 21.1 mmol) in anhydrous DMF (80 ml) in a water bath under an atmosphere of nitrogen, was portionwise added 60% sodium hydride (869 mg, 21.7 mmol). After 30 min, oxygen gas was bubbled into the reaction mixture for 5 hr. The mixture was neutralized with aqueous saturated ammonium chloride solution. The crude product was extracted with ether and recrystallized from dichloromethane-hexane to afford 8 g (80%) of a white solid; m.p. 123-124° C.; $^1$H NMR (200 MHz, CDCl$_3$) δ: 1.09 (3H, t, J=7.4 Hz), 2.43 (3H, s), 2.50 (2H, q, J=7.4 Hz), 5.35 (2H, s), 5.50 (2H, s), 7.27-7.46 (10H, m), 7.67 (1H, s), 7.87 (1H, s), 7.92 (1H, s); m/z (EI): 463 (M$^+$).

3-(5-Ethyl-2,6-dioxo-1,2,3,6-tetrahydro-pyrimidine-4-carbonyl)-5-methyl-benzonitrile (42): 3-(2,6-Bis-benzyloxy-5-ethyl-pyrimidine-4-carbonyl)-5-methyl-benzonitrile (41) (4.5 g, 9.7 mmol) in anhydrous ethanol (30 ml) and THF (30 ml) was stirred with 10% palladium on carbon (250 mg) under an atmosphere of hydrogen. After 1.5 hr, the mixture was filtered through celite pad and the filtrate was evaporated in vacuo. The residue was purified by silica gel column chromatography (eluent, chloroform:methanol (95:5)) to afford 20.3 g (84%) of a white solid; m.p. 253-254° C.; $^1$H NMR (200 MHz, DMSO-d$_6$) δ: 0.84 (3H, t, J=7.0 Hz), 1.96 (2H, q, J=7.0 Hz), 2.45 (3H, s), 8.06 (1H, s), 8.11 (1H, s), 8.33 (1H, s), 11.05 (1H, s), 8.28 (1H, s); m/z (EI): 283 (M$^+$).

Example I

To a flask containing Methanesulfonic acid 2-fluoro-pyridin-4-ylmethyl ester (38) (1 mmol), 3-(5-Ethyl-2,6-dioxo-1,2,3,6-tetrahydro-pyrimidine-4-carbonyl)-5-methyl-benzonitrile (42) (283 mg, 1 mmol), anhydrous powdered potassium carbonate (138 mg, 1 mmol), lithium iodide (134 mg, 1 mmol) was added anhydrous DMF (5 ml) and stirred for overnight at room temperature. The mixture was evaporated in vacuo. The residue was dissolved in methanol-dichloromethane (1:9), filtered through celite pad, and evaporated in vacuo to give a light yellow foam. The crude product was purified by silica gel column chromatography (eluent, methanol:chloroform (2:98)) to afford 154 mg (39%) of compound 9 as a white solid; m.p. 171-172° C.; $^1$H NMR (200 MHz, CDCl$_3$) δ: 0.96 (3H, t, J=7.4 Hz), 1.97 (1H, br. s), 2.25 (1H, br. s), 2.42 (3H, s), 4.82 (2H, br. d), 6.67 (1H, s), 6.92 (1H, d, J=3.8 Hz), 7.71 (1H, s), 7.78 (1H, s), 7.96 (1H, s), 8.02 (1H, d, J=5.4 Hz), 10.31 (1H, s); m/z (EI): 392 (M$^+$).

Example J

Scheme 10

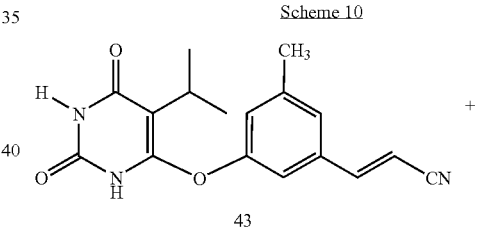

43

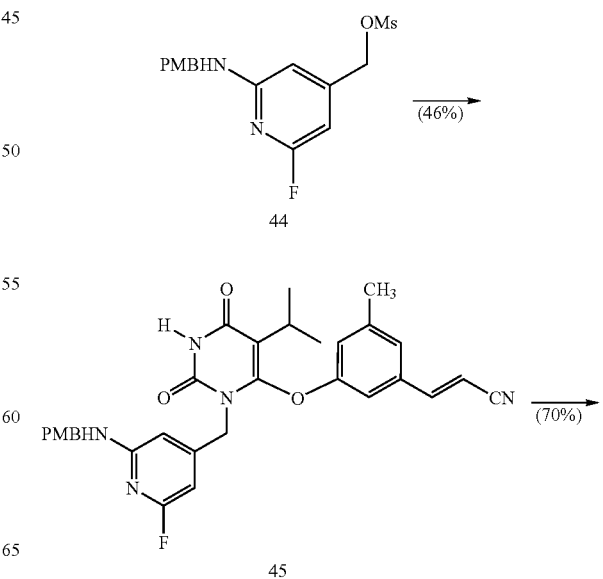

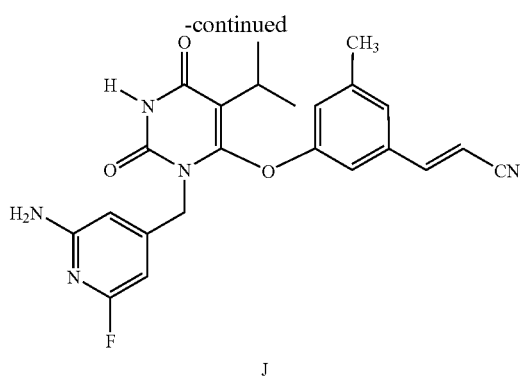

J 3-(3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (45): To a flask containing Methanesulfonic acid 2-fluoro-6-(4-methoxy-benzylamino)-pyridin-4-ylmethyl ester (44) (1 mmol), 3-[3-(5-Isopropyl-2,6-dioxo-1,2,3,6-tetrahydro-pyrimidin-4-yloxy)-5-methyl-phenyl]-acrylonitrile (43) (311 mg, 1 mmol), anhydrous powdered potassium carbonate (138 mg, 1 mmol), lithium iodide (134 mg, 1 mmol) was added anhydrous DMF (5 ml) and stirred for overnight at room temperature. The mixture was evaporated in vacuo. The residue was dissolved in methanol-dichloromethane (1:9), filtered through celite pad, and the filtrate was evaporated in vacuo to give a pale yellow foam. The crude product was purified by silica gel column chromatography (eluent, EA:hexane (1:2); The fraction of Rf=0.19 was collected) to afford 255 mg (46%) of a white foam; $^1$H NMR (300 MHz, CDCl$_3$) δ: 1.10 (6H, d, J=6.9 Hz), 2.32 (3H, s), 2.68 (1H, m), 3.79 (3H, s), 4.31 (2H, d, J=5.5 Hz), 4.73 (2H, s), 5.02 (1H, t, J=5.5 Hz), 5.81 (1H, d, J=16.6 Hz), 5.85 (1H, s), 5.98 (1H, s), 6.64 (2H, s), 6.86-6.89 (2H, m), 6.98 (1H, s), 7.20-7.24 (3H, m), 8.98 (1H, s).

Preparation of Compound 44 is described in the section describing the preparation of Example DC.

Example J

To a stirred solution of the 3-(3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (45) (166 mg, 0.2987 mmol) in acetonitrile (4 ml) at room temperature, was added CAN (327 mg, 0.5975 mmol) followed by distilled water (2 ml). After 30 min, the mixture was diluted with EA, washed with water, dried with anhydrous magnesium sulfate, filtered, and evaporated in vacuo to give a brown syrup. The crude product was purified by silica gel column chromatography (eluent, EA:hexane (1:1)) to afford 91 mg (70%) of Example J as a pale yellow solid; $^1$H NMR (200 MHz, CD$_3$OD/CDCl$_3$) δ: 1.12 (6H, d, J=7.0 Hz), 2.35 (3H, s), 2.71 (1H, s), 4.76 (2H, s), 5.90 (1H, s), 5.94 (1H, 1, J=16.8 Hz), 6.10 (1H, s), 6.73 (1H, s), 6.78 (1H, s), 7.04 (1H, s), 7.33 (1H, d, J=16.8 Hz); m/z (LC/Mass, EI): 436 (M+H$^+$).

Example K

Scheme 11

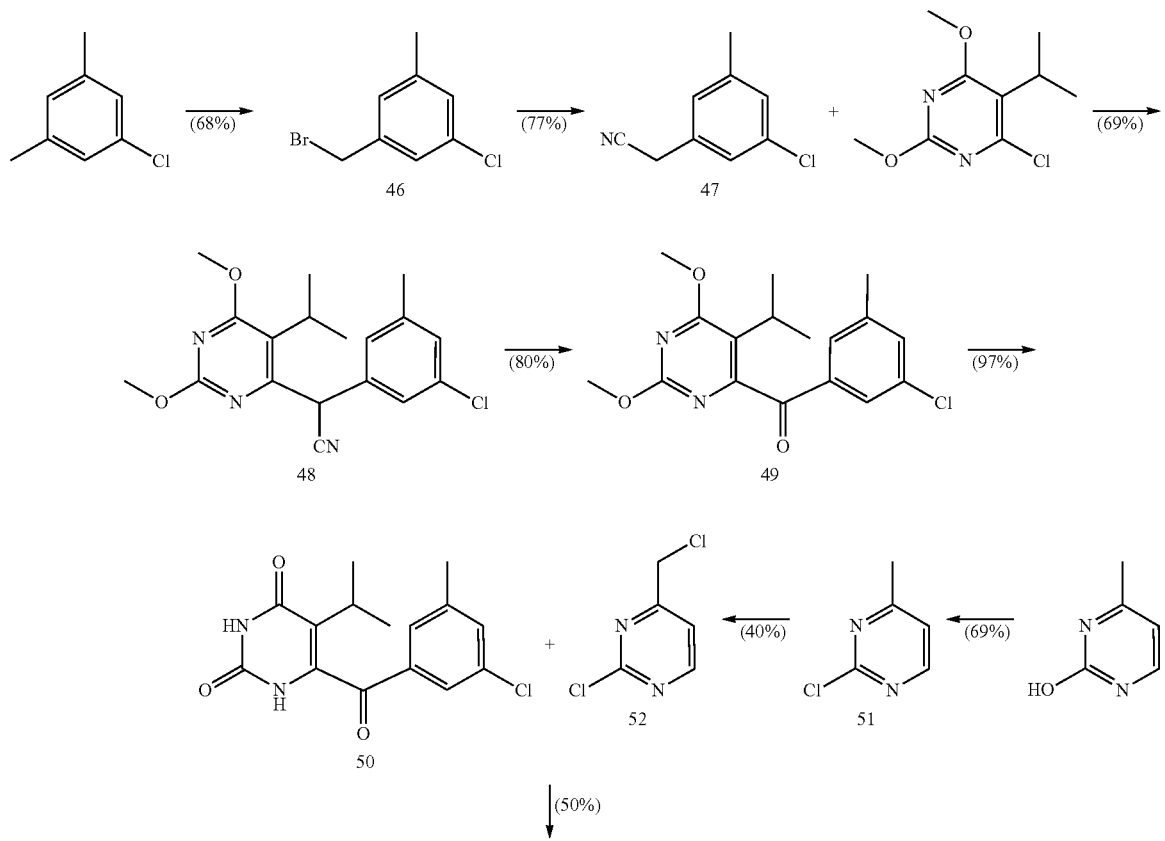

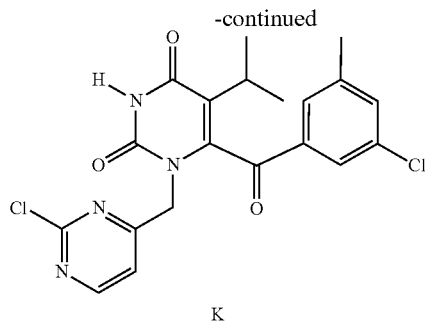

K

1-Bromomethyl-3-chloro-5-methyl-benzene (46): The mixture of 1-Chloro-3,5-dimethyl-benzene (32 g, 0.23 mol) and N-bromosuccinimide (40.5 g, 0.23M) in carbon tetrachloride (400 ml) was refluxed for 3 hr under a light of 500 W tungsten light. After cooling to room temperature, the mixture was filtered and the filtrate was evaporated in vacuo and the residue was purified by silica gel column chromatography (eluent, hexane) to afford 33 g (68%) of a white solid. $^1$H NMR (200 MHz, CDCl$_3$) δ: 2.32 (3H, s), 4.39 (2H, s), 7.10 (2H, s), 7.18 (1H, s).

(3-Chloro-5-methyl-phenyl)-acetonitrile (47): To a flask equipped with additional funnel, was placed potassium cyanide (29.6 g, 0.45 mol) and distilled water (55 ml). The mixture was heated up to 70° C. in an oil bath. With stirring, 1-Bromomethyl-3-chloro-5-methyl-benzene (46) (35 g, 0.16 mol) in ethanol (180 ml) was then dropwise added over 1 hr through the addition funnel. After completion of addition, the mixture was refluxed for 8 hr. After cooling to room temperature, ether was added to the mixture. The mixture was washed with water, dried with anhydrous magnesium sulfate, filtered, and evaporated in vacuo and the residue was purified by silica gel column chromatography (eluent, ether:hexane (1:9)) to afford 20 g (77%) of a pale brown oil. $^1$H NMR (200 MHz, CDCl$_3$) δ: 2.31 (3H, s), 3.66 (2H, s), 7.02 (1H, s), 7.09 (2H, s).

(3-Chloro-5-methyl-phenyl)-(5-isopropyl-2,6-dimethoxy-pyrimidin-4-yl)-acetonitrile (48): To a stirred mixture of 4-Chloro-5-isopropyl-2,6-dimethoxy-pyrimidine (23.8 g, 0.11 mol) and (3-Chloro-5-methyl-phenyl)-acetonitrile (47) (16.6 g, 0.1 mol) in anhydrous DMF (200 ml) in an ice-water bath under an atmosphere of nitrogen, was portionwise added 60% sodium hydride (8.8 g, 0.22 mol). After stirring for 1 hr, the mixture was stirred at room temperature for overnight. The mixture was neutralized with aqueous saturated ammonium chloride solution. The crude product was extracted with ether and purified by silica gel column chromatography (eluent, EA:hexane (1:10)) to afford 24 g (69%) of a white solid. m.p. 105-106° C.; $^1$H NMR (200 MHz, CDCl$_3$) δ: 1.11 (3H, d, J=7.1 Hz), 1.15 (3H, d, J=7.1 Hz), 2.32 (3H, s), 3.00 (1H, m), 4.00 (3H, s), 4.02 (3H, s), 5.33 (1H, s), 7.10-7.16 (3H, m).

(3-Chloro-5-methyl-phenyl)-(5-isopropyl-2,6-dimethoxy-pyrimidin-4-yl)-methanone (49): To a stirred solution of (48) (7.56 g, 21.88 mmol) in anhydrous DMF (100 ml) in a water bath under an atmosphere of nitrogen, was portionwise added 60% sodium hydride (1.05 g, 26 mmol). After 30 min, oxygen gas was bubbled into the reaction mixture for 4 hr. The mixture was neutralized with aqueous saturated ammonium chloride solution. The crude product was extracted with ether and purified by silica gel column chromatography (eluent, ether:hexane (1:4)) to afford 5.87 g (80%) of a white solid. m.p. 119-120° C.; $^1$H NMR (200 MHz, CDCl$_3$) δ: 1.19 (6H, d, J=7.1 Hz), 2.38 (3H, s), 2.80 (1H, m), 3.93 (3H, s), 4.06 (3H, s), 7.40-7.61 (3H, m).

6-(3-Chloro-5-methyl-benzoyl)-5-isopropyl-1H-pyrimidine-2,4-dione (50): (3-Chloro-5-methyl-phenyl)-(5-isopropyl-2,6-dimethoxy-pyrimidin-4-yl)-methanone (49) (3.4 g, 10 mmol) was refluxed with concentrated HCl (35 ml) for 4 hr. After cooling to room temperature, the white precipitate was collected by filtration, washed with cold water and hexane, and dried in high vacuo to afford 3 g (97%) of a white solid. m.p. 254-255° C.; $^1$H NMR (200 MHz, CDCl$_3$/CD$_3$OD) δ: 1.17 (6H, d, J=6.9 Hz), 2.25-2.45 (4H, m), 7.50-7.71 (3H, m); HRMS (EI): Calc. 306.077120, Found 306.076851.

2-Chloro-4-methyl-pyrimidine (51): To a stirred mixture of 4-Methyl-pyrimidin-2-ol (29.3 g, 0.2 mol) in phosphorus (III) oxychloride (200 ml) was added N,N-diethylaniline (31.8 ml, 0.2 mol). The mixture was refluxed for 6 hr. After cooling to room temperature, the mixture was evaporated in vacuo and ether was added to the residue. The ether layer was taken, washed with 2N aqueous sodium hydroxide solution, dried with anhydrous magnesium sulfate, filtered, and evaporated in vacuo. The residue was purified by silica gel column chromatography (eluent, ether:hexane (1:1)) to afford 18 g (69%) of a white solid. $^1$H NMR (200 MHz, CDCl$_3$) δ: 2.55 (3H, s), 7.14 (1H, d, J=4.6 Hz), 8.47 (1H, d, J=4.6 Hz).

2-Chloro-4-chloromethyl-pyrimidine (52): The mixture of 2-Chloro-4-methyl-pyrimidine (51) (6.48 g, 50 mmol), N-chloro succinimide (8.0 g, 60 mmol), and benzoyl peroxide (2.42 g, 10 mmol) in carbon tetrachloride (100 ml) was refluxed for 22 hr. After cooling to room temperature, the mixture was filtered and the filtrate was evaporated in vacuo and the residue was purified by silica gel column chromatography (eluent, ether:hexane (1:2)) to afford 3.3 g (40%). $^1$H NMR (200 MHz, CDCl$_3$) δ: 4.57 (2H, s), 7.50 (1H, d, J=5.2 Hz), 8.65 (1H, d, J=5.2 Hz).

Example K

To a mixture of 2-Chloro-4-chloromethyl-pyrimidine (52) (492 mg, 3 mmol), 6-(3-Chloro-5-methyl-benzoyl)-5-isopropyl-1H-pyrimidine-2,4-dione (50) 919.5 mg, 3 mmol), anhydrous powdered potassium carbonate (414 mg, 3 mmol), and lithium iodide (402 mg, 3 mmol), was added DMF (15 ml) and the mixture was stirred for overnight at room temperature. The mixture was evaporated in vacuo and the residue was purified by silica gel column chromatography (eluent, EA:hexane (1:2)) to afford 653 mg (50%) of Example K as an amber solid. m.p. 219-222° C.; $^1$H NMR (200 MHz, CDCl$_3$) δ: 1.18 (3H, d, J=7.0 Hz), 1.22 (3H, d, J=7.0 Hz), 2.29 (1H, m), 2.41 (3H, s), 4.68 (1H, d, J=17.2 Hz), 4.99 (1H, d, J=17.2 Hz), 7.10 (1H, d, J=5.0 Hz), 7.44 (1H, s), 7.59 (1H, s), 7.67

(1H, s), 8.48 (1H, d, J=5.0 Hz), 9.28 (1H, s); HRMS (EI): Calcd. 432.076023, Found 432.075596.

Examples L, M, N, O, P, Q, and R

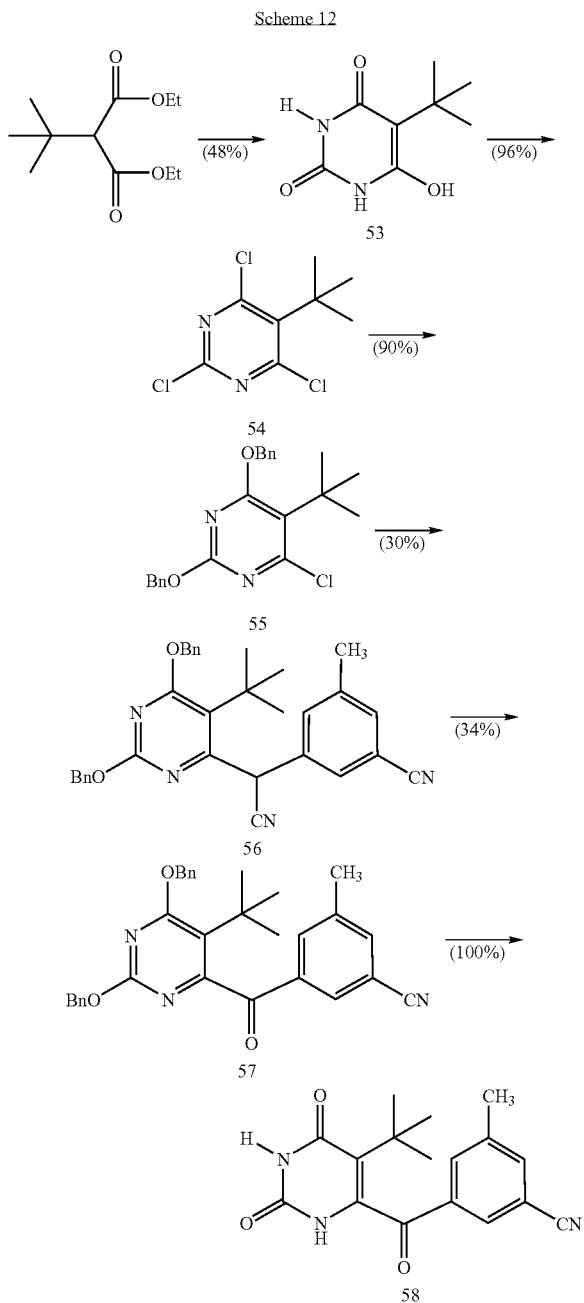

Scheme 12

5-tert-Butyl-6-hydroxy-1H-pyrimidine-2,4-dione (53): To a stirred solution of sodium ethoxide (prepared from 2.55 g of sodium, 10 mmol) in ethanol (60 ml), was added diethyl tert-butylmalonate (20 g, 92 mmol). The mixture was heated up to reflux. Urea (5.83 g, 97 mmol) in hot ethanol (50 ml) was added and the mixture was refluxed for 6 hr. The mixture was then evaporated in vacuo and the residue was dissolved in water (80 ml). The solution was washed with ether and the water layer was cooled in an ice bath and acidified by the addition of conc. hydrochloric acid. The precipitate was filtered, washed with cold water and n-hexane, and dried in vacuo to give 8.22 g (48%) of a white solid. m.p. 247-248° C.; $^1$H NMR (200 MHz, DMSO-d$_6$) δ 1.00 (9H, s), 2.83 (1H, s), 11.11 (2H, s).

5-tert-Butyl-2,4,6-trichloro-pyrimidine (54): To a stirred phosphorus oxychloride (75 ml), was added 5-tert-Butyl-6-hydroxy-1H-pyrimidine-2,4-dione (8 g, 43.43 mmol) and N,N-diethyl aniline (14.2 ml, 86.86 mmol). The mixture was refluxed for 23 hr. After cooling to room temperature, the mixture was evaporated in vacuo and the residue was poured onto crushed ice to give a precipitate. The precipitate was filtered and washed with cold water several times. The crude product was purified by silica gel column chromatography (eluent, ether:hexanes (1:9)) to afford 10 g (96%) of a white solid. m.p. 58-59° C.; $^1$H NMR (200 MHz, CDCl$_3$) δ 1.66 (9H, s).

2,4-Bis-benzyloxy-5-tert-butyl-6-chloro-pyrimidine (55): To a stirred anhydrous benzyl alcohol (80 ml), was added pieces of sodium metal (1.73 g, 75 mmol). After the reaction completed, the mixture was cooled in an ice bath and 5-tert-Butyl-2,4,6-trichloro-pyrimidine (9 g, 37.5 mmol) was added. After 1 hr., the mixture was stirred at room temperature for overnight and evaporated in vacuo. The residue was dissolved in ethyl acetate, washed with water, dried with anhydrous magnesium sulfate, filtered, and evaporated in vacuo. The crude product was purified by silica gel column chromatography (eluent, ether:hexanes (1:19)) to afford 13 g (90%) of a white solid. m.p. 96° C.; $^1$H NMR (200 MHz, CDCl$_3$) δ 1.50 (9H, s), 5.37 (2H, s), 5.41 (2H, s), 7.34-7.46 (10H, m).

3-[(2,6-Bis-benzyloxy-5-tert-butyl-pyrimidin-4-yl)-cyano-methyl]-5-methyl-benzonitrile (56): To a stirred mixture of 2,4-Bis-benzyloxy-5-tert-butyl-6-chloro-pyrimidine (3.8 g, 10 mmol) and 3-cyano-5-methylphenyl acetonitrile (1.56 g, 10 mmol) in anhydrous DMF (20 ml) at 0° C. (ice bath) under nitrogen atmosphere, was portionwise added 60% sodium hydride (880 mg, 22 mmol). After stirring for 1 hr., the mixture was further stirred at room temperature for overnight. The mixture was then neutralized with aqueous saturated ammonium chloride solution and the crude product was extracted with ether and purified by silica gel column chromatography (eluent, EA:hexanes (1:10)) to afford 1.48 g (30%) of the title compound as a colorless syrup. m.p. 126-128° C.; $^1$H NMR (200 MHz, CDCl$_3$) δ 1.46 (9H, s), 2.36 (3H, s), 5.29 (1H, d, J=12.2 Hz), 5.38 (1H, d, J=12.2 Hz), 5.46 (2H, s), 5.98 (1H, s), 7.22-7.46 (10H, m); m/z (EI) 502 (M$^+$).

3-(2,6-Bis-benzyloxy-5-tert-butyl-pyrimidine-4-carbonyl)-5-methyl-benzonitrile (57): To a stirred solution of (56) (1.43 g, 2.8 mmol) in anhydrous DMF (10 ml) under nitrogen atmosphere, was added 60% sodium hydride (114 mg, 2.8 mmol). After 10 min., oxygen was bubbled into the reaction mixture for 4.5 hr. The mixture was partitioned between ether and aqueous saturated ammonium chloride solution. The organic layer was taken, washed with water twice, dried with anhydrous magnesium sulfate, filtered, and evaporated in vacuo. The residue was then purified by silica gel column chromatography (eluent, ether:hexanes (1:9)) to afford 486 mg (34%) of the title compound as a colorless syrup. $^1$H NMR (200 MHz, CDCl$_3$) δ 1.27 (9H, s), 2.44 (3H, s), 5.31 (2H, s), 5.53 (2H, s), 7.28-7.48 (10H, m), 7.66 (1H, s), 7.77 (1H, s), 7.88 (1H, s).

3-(5-tert-Butyl-2,6-dioxo-1,2,3,6-tetrahydro-pyrimidine-4-carbonyl)-5-methyl-benzonitrile (58): The solution of (57) (1.1 g, 2.237 mmol) in ethanol (20 ml) was stirred in the presence of 10% palladium on carbon under an atmosphere of hydrogen. After 1.5 hr., the mixture was filtered through celite pad and the filtrate was evaporated in vacuo. The residue was purified by silica gel column chromatography (eluent, methanol:chloroform (5:95)) to afford 786 mg (quantitative) of the title compound as a white solid. m.p. 270-271° C.; $^1$H NMR (200 MHz, CDCl$_3$) δ 1.00 (9H, s), 2.47 (3H, s), 7.70 (1H, s), 7.86 (1H, s), 8.02 (1H, s), 10.74 (1H, s), 11.01 (1H, s); m/z (EI) 311 (M$^+$).

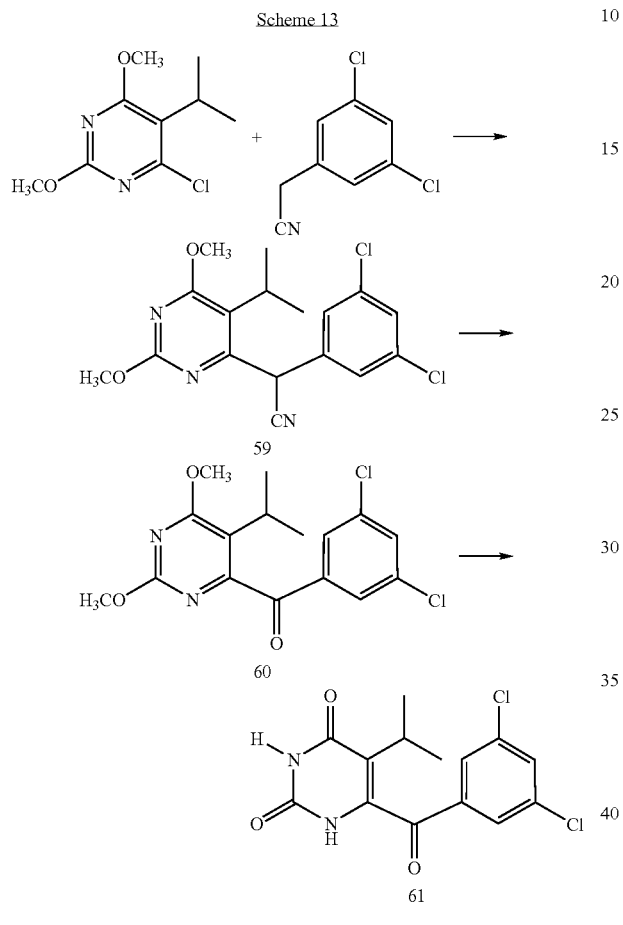

(3,5-Dichloro-phenyl)-(5-isopropyl-2,6-dimethoxy-pyrimidin-4-yl)-acetonitrile (59): To a stirred mixture of 4-Chloro-5-isopropyl-2,6-dimethoxy-pyrimidine (9.8 g, 45 mmol) and (3,5-Dichloro-phenyl)-acetonitrile (8.0 g, 43 mmol) in anhydrous DMF (70 ml) at 0° C. (ice bath) under nitrogen atmosphere, was portionwise added 60% sodium hydride (3.44 g, 86 mmol). After stirring for 1 hr., the mixture was further stirred at room temperature for overnight. The mixture was then neutralized with aqueous saturated ammonium chloride solution and the crude product was extracted with ethyl acetate and purified by silica gel column chromatography (eluent, EA:hexanes (1:9)) to afford 9.6 g (61%) of the title compound as a white solid. m.p. 135-136° C.; $^1$H NMR (200 MHz, CDCl$_3$) δ 1.13 (3H, d, J=7.0 Hz), 1.18 (3H, d, J=7.0 Hz), 2.97 (1H, m), 3.99 (6H, s), 5.33 (1H, s), 7.25-7.33 (3H, m).

(3,5-Dichloro-phenyl)-(5-isopropyl-2,6-dimethoxy-pyrimidin-4-yl)-methanone (60): To a stirred solution of (59) (9.6 g, 26 mmol) in anhydrous DMF (100 ml) under nitrogen atmosphere, was added 60% sodium hydride (1.05 g, 26 mmol). After 10 min., oxygen was bubbled into the reaction mixture for 4 hr. The mixture was partitioned between ether and aqueous saturated ammonium chloride solution. The organic layer was taken, washed with water twice, dried with anhydrous magnesium sulfate, filtered, and evaporated in vacuo. The residue was then purified by silica gel column chromatography (eluent, ether:hexanes (1:10)) to afford 7.36 g (80%) of the title compound as a white solid. m.p. 120-121° C.; $^1$H NMR (200 MHz, CDCl$_3$) δ 1.22 (6H, d, J=7.0 Hz), 2.86 (1H, m), 3.96 (6H, s), 4.09 (3H, s), 7.60-7.74 (3H, m).

6-(3,5-Dichloro-benzoyl)-5-isopropyl-1H-pyrimidine-2,4-dione (61): Compound (60) (2.0 g, 5.6 mmol) was refluxed with conc. HCl (30 ml) for 3 hr. After cooling to room temperature, the white precipitate was collected by filtration, washed with cold water, and dried in high vacuo to afford 1.6 g (87%) of the title compound as a white solid. m.p. 252-253° C.; $^1$H NMR (200 MHz, CDCl$_3$/CD$_3$OD) δ 1.11 (6H, d, J=6.9 Hz), 2.33 (1H, m), 7.61-7.73 (3H, m); HRMS (EI) Calcd. 326.0225, Found 326.0240.

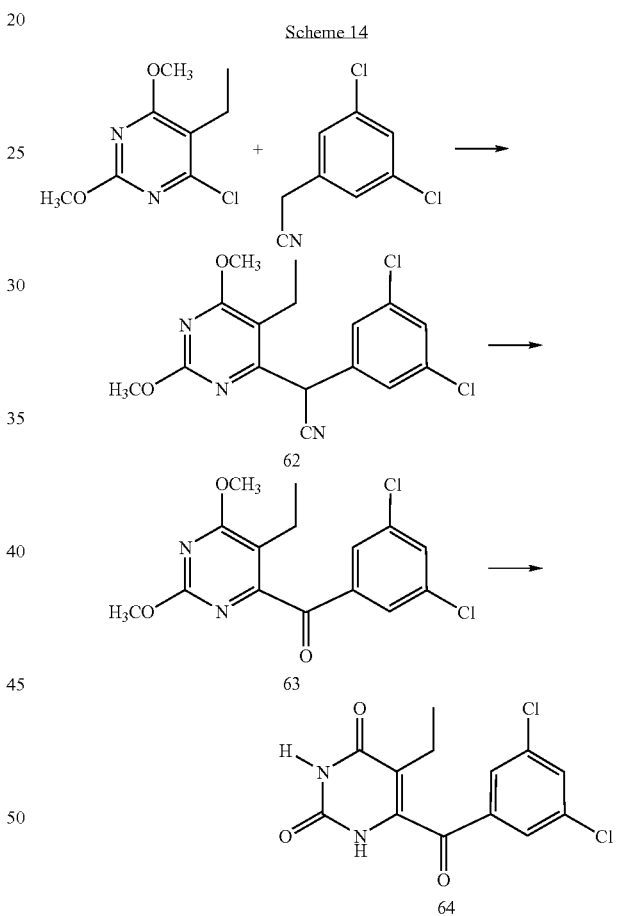

(3,5-Dichloro-phenyl)-(5-ethyl-2,6-dimethoxy-pyrimidin-4-yl)-acetonitrile (62): To a stirred mixture of 4-Chloro-5-ethyl-2,6-dimethoxy-pyrimidine (1.42 g, 7 mmol) and (3,5-Dichloro-phenyl)-acetonitrile (1.3 g, 7 mmol) in anhydrous DMF (14 ml) at 0° C. (ice bath) under nitrogen atmosphere, was portionwise added 60% sodium hydride (616 mg, 15.44 mmol). After stirring for 1 hr., the mixture was further stirred at room temperature for 18 hr. The mixture was then neutralized with aqueous saturated ammonium chloride solution and the crude product was extracted with ethyl acetate and purified by silica gel column chromatography (eluent, EA:hexanes (1:10)) to afford 2.1 g (85%) of the title compound as a white solid. m.p. 121-122° C.; $^1$H NMR (200 MHz, CDCl$_3$) δ 1.03 (3H, t, J=7.4 Hz), 2.03-2.57 (2H, m), 3.98 (6H, s), 5.23 (1H, s), 7.33 (3H, s).

(3,5-Dichloro-phenyl)-(5-ethyl-2,6-dimethoxy-pyrimidin-4-yl)-methanone (63): To a stirred solution of (62) (1.97 g, 5.59 mmol) in anhydrous DMF (25 ml) under nitrogen atmosphere, was added 60% sodium hydride (224 mg, 5.59 mmol). After 10 min., oxygen was bubbled into the reaction mixture for 4 hr. The mixture was partitioned between ether and aqueous saturated ammonium chloride solution. The organic layer was taken, washed with water twice, dried with anhydrous magnesium sulfate, filtered, and evaporated in vacuo. The residue was then purified by silica gel column chromatography (eluent, ether:hexanes (1:30)) to afford 1.37 g (72%) of the title compound as a white solid. m.p. 118-119° C.; $^1$H NMR (200 MHz, CDCl$_3$) δ 1.09 (3H, t, J=7.4 Hz), 2.46 (2H, q, J=7.4 Hz), 3.95 (3H, s), 4.08 (3H, s), 7.58 (1H, t, J=1.8 Hz), 7.56 (2H, d, J=1.8 Hz).

6-(3,5-Dichloro-benzoyl)-5-ethyl-1H-pyrimidine-2,4-dione (64): Compound (63) (1.26 g, 3.69 mmol) was refluxed with conc. HCl (20 ml) for 5 hr. After cooling to room temperature, the white precipitate was collected by filtration, washed with cold water, and dried in high vacuo to afford 1.08 g (93%) of the title compound as a white solid. m.p. 242-243° C.; $^1$H NMR (200 MHz, CDCl$_3$/CD$_3$OD) δ 0.90 (3H, t, J=7.5 Hz), 2.07 (2H, q, J=7.5 Hz), 7.59 (1H, t, J=1.8 Hz), 7.67 (2H, d, J=1.8 Hz); HRMS (EI) Calcd. 312.0068, Found 312.0049.

Scheme 15

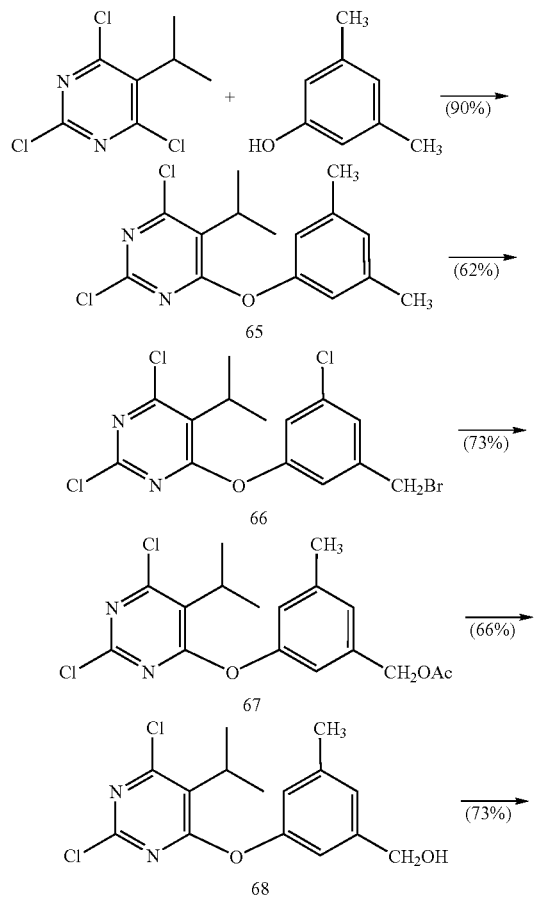

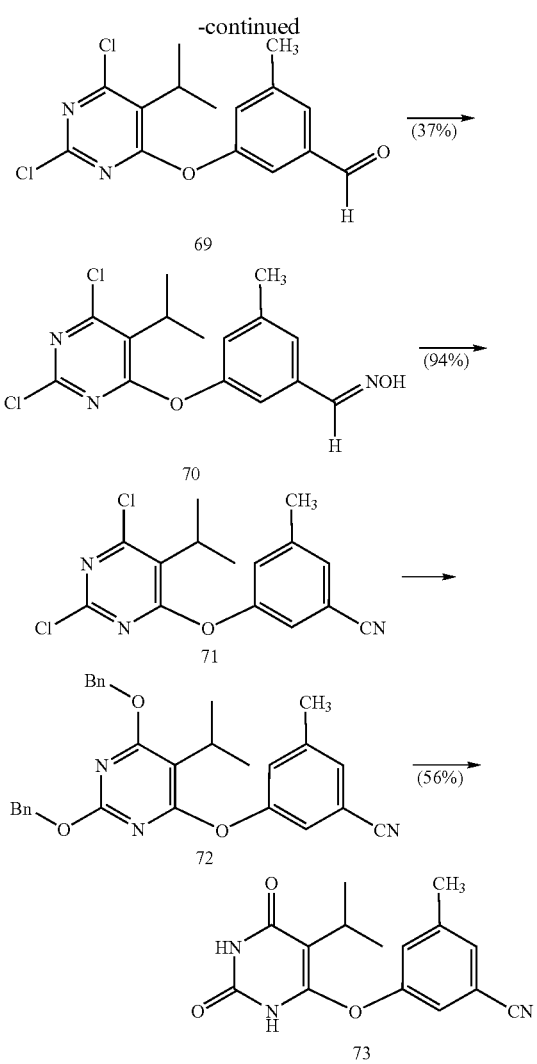

2,4-Dichloro-6-(3,5-dimethyl-phenoxy)-5-isopropyl-pyrimidine (65): To a stirred mixture of 2,4,6-Trichloro-5-isopropyl-pyrimidine (23.68 g, 0.105M), 3,5-dimethylphenol (12.2 g, 0.2M) in anhydrous DMF (200 ml) cooled in a dry ice-acetone bath (−40° C.) under nitrogen atmosphere, was portionwise added 60% sodium hydride (4.2 g, 0.105M). The reaction temperature was then slowly raised to room temperature during 3 hr. The reaction mixture was then diluted with ether, washed with water twice, dried with anhydrous magnesium sulfate, filtered, and evaporated in vacuo to give a crude product as a pale yellow solid. The crude product was purified by silica gel column chromatography (eluent, ether:hexanes (1:9)) to afford 28 g (90%) a white solid. m.p. 107-108° C.; $^1$H NMR (200 MHz, CDCl$_3$) δ 1.40 (6H, d, J=7.0 Hz), 2.35 (6H, s), 3.58 (1H, m), 6.72 (2H, s), 6.91 (1H, s).

4-(3-Bromomethyl-5-methyl-phenoxy)-2,6-dichloro-5-isopropyl-pyrimidine (66): A mixture of (65) (9.72 g, 31 mmol), NBS (5.56 g, 31 mmol), and benzoyl peroxide (0.756 g, 3.1 mmol) in carbon tetrachloride (60 ml) was refluxed for 3 hr. under a light of 500 W tungsten lamp. After cooling to room temperature, the reaction mixture was filtered and evaporated in vacuo. The residue was purified by silica gel column chromatography (eluent, ether:hexanes (1:19)) to afford 8 g (62%) of a white solid. m.p. 98-101° C.; $^1$H NMR (200 MHz, CDCl$_3$) δ 1.41 (6H, d, J=7.2 Hz), 2.38 (3H, s), 3.59 (1H, m), 4.47 (2H, s), 6.86 (1H, s), 6.97 (1H, s), 7.13 (1H, s).

Acetic acid 3-(2,6-dichloro-5-isopropyl-pyrimidin-4-yloxy)-5-methyl-benzyl ester (67): To a stirred solution of (66) (14.4 g, 36.9 mmol) in anhydrous DMF-(50 ml), was added sodium acetate (6.05 g, 73.8 mmol) and the mixture was stirred in an oil bath (90~100° C.) for overnight. After cooling to room temperature, the mixture was partitioned between ether and water. The ether layer was taken, washed with water twice, dried with anhydrous magnesium sulfate, filtered, and evaporated in vacuo. The residue was purified by silica gel column chromatography (eluent, ether: hexanes (from 1:9 to 1:4)) to afford 10 g (73%) of a white solid. m.p. 76-77° C.; $^1$H NMR (200 MHz, CDCl$_3$) δ 1.41 (6H, d, J=7.2 Hz), 2.12 (3H, s), 2.39 (3H, s), 3.58 (1H, m), 5.09 (2H, s), 6.88 (1H, s), 6.93 (1H, s), 7.08 (1H, s).

[3-(2,6-Dichloro-5-isopropyl-pyrimidin-4-yloxy)-5-methyl-phenyl]-methanol (68): To a stirred solution of (67) (5 g, 13.54 mmol) in THF (20 ml) at room temperature, was added lithium hydroxide (649 mg, 27 mmol) followed by distilled water (20 ml). After stirring for 23 hr., THF was removed in vacuo and the residue was partitioned between dichloromethane and water. The organic layer was taken, dried with anhydrous magnesium sulfate, filtered, and evaporated in vacuo. The residue was purified by silica gel column chromatography (eluent, ether: hexanes (from 1:4 to 1:1)) to afford 2.92 g (66%) of a white solid. m.p. 140-141° C.; $^1$H NMR (200 MHz, CDCl$_3$) δ 1.40 (6H, d, J=7.4 Hz), 1.76 (1H, t, J=5.6 Hz), 2.39 (3H, s), 3.58 (1H, m), 4.69 (2H, d, J=5.6 Hz), 6.84 (1H, s), 6.95 (1H, s), 7.09 (1H, s).

3-(2,6-Dichloro-5-isopropyl-pyrimidin-4-yloxy)-5-methyl-benzaldehyde (69): A mixture of (68) (2.36 g, 7.22 mmol), pyridinium chlorochromate (1.56 g, 7.22 mmol), and dried celite (2 g) was stirred in dichloromethane (20 ml) for 2 hr. at room temperature. The mixture was then filtered through a short silica gel pad and washed with EA. The combined filtrate was evaporated in vacuo and the residue was purified by silica gel column chromatography (eluent, EA:hexanes (1:15)) to afford 1.71 g (73%) of a pale yellow syrup. $^1$H NMR (200 MHz, CDCl$_3$) δ 1.42 (6H, d, J=7.2 Hz), 2.49 (3H, s), 3.61 (1H, m), 7.20 (1H, s), 7.44 (1H, s), 7.62 (1H, s), 10.01 (1H, s).

3-(2,6-Dichloro-5-isopropyl-pyrimidin-4-yloxy)-5-methyl-benzaldehyde oxime (70): A mixture of (69) (11.66 g, 35.8 mmol), hydroxyamine hydrochloride (2.98 g, 42.96 mmol), and triethyl amine (7.48 ml, 53.7 mmol) in ethanol (100 ml) was refluxed for 2 hr. After cooling to room temperature, the mixture was evaporated in vacuo and the residue was purified by silica gel column chromatography (eluent, ether:hexanes (1:9)) to afford 4.5 g (37%) of a white solid. m.p. 185-187° C.; $^1$H NMR (200 MHz, CDCl$_3$) δ 1.40 (6H, d, J=7.0 Hz), 2.40 (3H, s), 3.58 (1H, m), 6.94 (1H, s), 7.16 (1H, s), 7.28 (1H, s), 7.51 (1H, s), 8.10 (1H, s).

3-(2,6-Dichloro-5-isopropyl-pyrimidin-4-yloxy)-5-methyl-benzonitrile (71): To a stirred solution of (70) (4.4 g, 12.93 mmol) in acetonitrile (40 ml), was added triphenylphosphine (13.56 g, 51.73 mmol) and carbon tetrachloride (2.5 ml, 25.86 mmol). After 30 min., carbon tetrachloride (5 ml) was added and the mixture was stirred for 1 hr. The mixture was diluted with ether, washed with water, dried with anhydrous magnesium sulfate, filtered, and evaporated in vacuo. The residue was purified by silica gel column chromatography (eluent, ether:hexanes (1:4)) to afford 3.82 g (94%) of a white solid. m.p. 143-144° C.; $^1$H NMR (200 MHz, CDCl$_3$) δ 1.40 (6H, d, J=7.0 Hz), 2.45 (3H, s), 3.60 (1H, m), 7.18 (1H, m), 7.25 (1H, m), 7.40 (1H, m).

3-(2,6-Bis-benzyloxy-5-isopropyl-pyrimidin-4-yloxy)-5-methyl-benzonitrile (72): Sodium (0.48 g, 21 mmol) was reacted with anhydrous benzyl alcohol (20 ml) under nitrogen at room temperature. The mixture was then cooled in an ice bath and (71) (3.22 g, 10 mmol) was added. After 1 hr., the mixture was stirred at room temperature for overnight. The mixture was evaporated in vacuo and the residue was dissolved in ether, washed with water, dried with anhydrous magnesium sulfate, filtered, and evaporated in vacuo. The residue was purified by silica gel column chromatography (eluent, ether:hexanes (1:9)) to afford 3.18 g (68%) of a colorless syrup. $^1$H NMR (200 MHz, CDCl$_3$) δ 1.28 (6H, d, J=7.2 Hz), 2.39 (3H, s), 3.40 (1H, m), 5.14 (2H, s), 5.42 (2H, s), 7.13-7.44 (13H, m).

3-(5-Isopropyl-2,6-dioxo-1,2,3,6-tetrahydro-pyrimidin-4-yloxy)-5-methyl-benzonitrile (73): Compound (72) (2.89 g) in anhydrous ethanol (30 ml) was stirred with 10% palladium on carbon (300 mg) under an atmosphere of hydrogen. After 6 hr., the mixture was filtered through celite pad and the filtrate was evaporated in vacuo. The residue was purified by silica gel column chromatography (eluent, dichloromethane:methanol (95:5)) to afford 1 g of the title compound as a white solid. m.p. 272-275° C.; $^1$H NMR (200 MHz, DMSO-d$_6$) δ 1.06 (6H, d, J=7.4 Hz), 2.36 (3H, s), 2.78 (1H, m), 7.33 (1H, s), 7.45 (1H, s), 7.55 (1H, s), 11.05 (1H, s), 11.34 (1H, s); m/z (EI) 285 (M$^+$).

Scheme 16

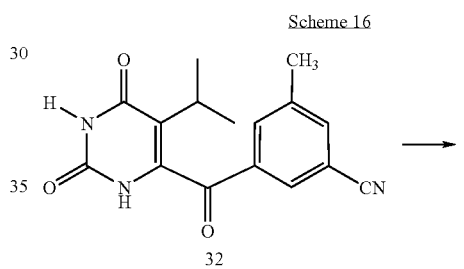

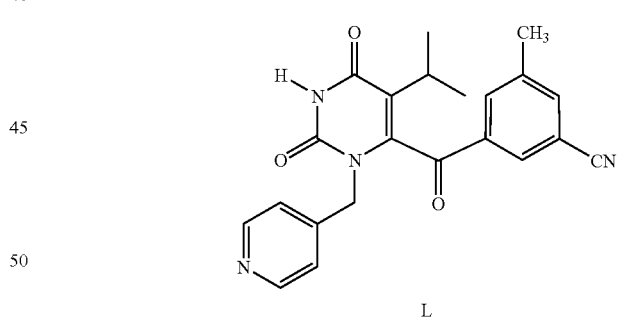

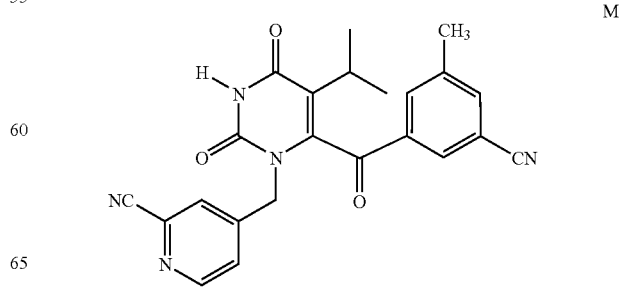

-continued

N
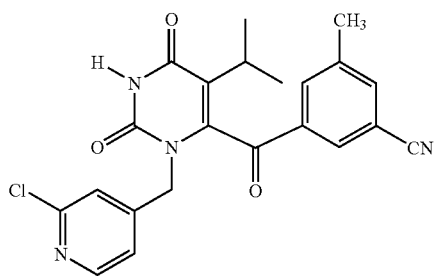

O
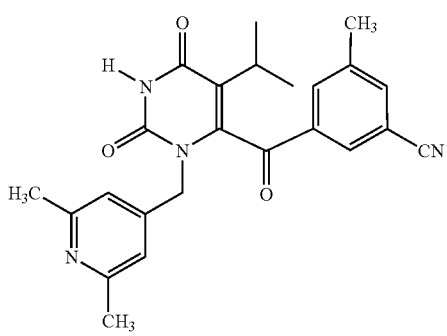

P
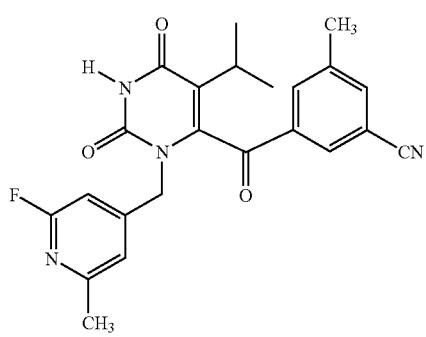

Q
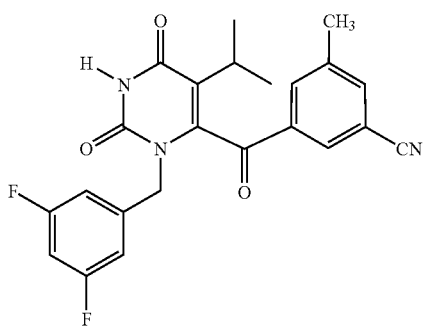

R
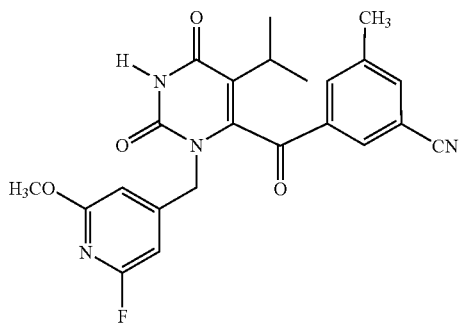

Example L

To a stirred solution of (32) (297 mg, 1 mmol), anhydrous powdered potassium carbonate (134 mg, 1 mmol), and lithium iodide (134 mg, 1 mmol) in DMF (5 ml) at room temperature, was added 4-chloromethylpyridine hydrochloride (154 mg, 1 mmol).

After stirring for overnight, the mixture was evaporated in vacuo and the residue was purified by silica gel column chromatography (eluent, EA:hexanes (2:1)) to afford 200 mg (51%) of a white solid. m.p. 208-209° C.; $^1$H-NMR (200 MHz, CDCl$_3$) δ 1.11 (3H, d, J=6.9 Hz), 1.20 (3H, d, J=6.8 Hz), 2.22 (1H, m), 2.38 (3H, s), 4.55 (1H, d, J=16.3 Hz), 5.05 (1H, d, J=16.3 Hz), 6.96 (1H, dd, J=1.6 Hz, 4.6 Hz), 7.62 (1H, s), 7.66 (1H, s), 7.86 (1H, s); HRMS (EI) Calcd, 388.153419, Found 388.153541.

Example M

To a stirred solution of 2-cyanopyridine-4-methanol (134 mg, 1 mmol) in chloroform (10 ml) cooled in an ice bath under nitrogen atmosphere, was added triethylamine (210 μl, 1.5 mmol) and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (32) (297 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, methanol:chloroform (2:98)) to afford 160 mg (38%) of a white foam. Recrystallization from chloroform/ether/hexane resulted a white solid. m.p. 224-225° C.; $^1$H-NMR (200 MHz, CDCl$_3$) δ 1.18 (3H, d, J=7.0 Hz), 1.22 (3H, d, J=7.0 Hz), 2.25 (1H, m), 2.49 (3H, s), 4.71 (1H, d, J=16.2 Hz), 4.87 (1H, d, J=16.2 Hz), 7.30 (1H, m), 7.48 (1H, s), 7.78 (1H, s), 7.87 (1H, s), 7.97 (1H, s), 8.58 (1H, d, J=5.1 Hz), 9.96 (1H, s); HRMS (EI) Calcd, 413.148694, Found 413.148790.

Example N

To a stirred solution of 2-chloropyridine-4-methanol (143 mg, 1 mmol) in chloroform (10 ml) cooled in an ice bath under nitrogen atmosphere, was added triethylamine (210 μl, 1.5 mmol) and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (32) (297 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 120 mg (28%) a white foam. Recrystallization from chloroform/ether/hexane resulted in a white solid. m.p. 206-207° C.; $^1$H-NMR (200 MHz, CDCl$_3$) δ 1.13 (3H, d, J=6.9 Hz), 1.23 (3H, d, J=6.9 Hz), 2.18 (1H, m), 2.43 (3H, s), 4.51 (1H, d, J=16.4 Hz), 5.06

(1H, d, J=16.4 Hz), 6.91-6.96 (2H, m), 7.66 (1H, s), 7.70 (1H, s), 7.88 (1H, s), 8.19 (1H, d, J=0.8 Hz, 5.5 Hz), 8.98 (1H, s); m/z (EI) 422 (M+); HRMS (EI) Calcd, 422.114525, Found 422.114568.

Example O

To a stirred solution of (32) (297 mg, 1 mmol), anhydrous powdered potassium carbonate (134 mg, 1 mmol), and lithium iodide (134 mg, 1 mmol) in DMF (5 ml) at room temperature, was added 2,6-dimethyl-4-chloromethylpyridine hydrochloride (192 mg, 1 mmol).
After stirring for overnight, the mixture was evaporated in vacuo and the residue was purified by silica gel column chromatography (eluent, EA:hexanes (1:2)) to afford 171 mg (41%) of a white solid. m.p. 235-237° C.; 1H-NMR (200 MHz, CDCl$_3$) δ 1.10 (3H, d, J=6.9 Hz), 1.21 (3H, d, J=6.9 Hz), 2.10-2.40 (10H, m), 4.31 (1H, d, J=16.0 Hz), 5.25 (1H, d, J=16.0 Hz), 6.54 (2H, s), 7.60 (1H, s), 7.61 (1H, s), 7.77 (1H, s), 9.38 (1H, s); m/z (EI) 416 (M+); HRMS (EI) Calcd, 416.186218, Found 416.184841.

Example P

To a stirred solution of (32) (297 mg, 1 mmol), anhydrous powdered potassium carbonate (134 mg, 1 mmol), and lithium iodide (134 mg, 1 mmol) in DMF (5 ml) at room temperature, was added 2-fluoro-6-methyl-4-chloromethylpyridine (160 mg, 1 mmol).
After stirring for overnight, the mixture was evaporated in vacuo and the residue was purified by silica gel column chromatography (eluent, EA:hexanes (1:2)) to afford 205 mg (49%) of a white solid. m.p. 208-209° C.; 1H-NMR (200 MHz, CDCl$_3$) δ 1.13 (3H, d, J=6.8 Hz), 1.23 (3H, d, J=6.8 Hz), 2.25 (1H, m), 2.37 (3H, s), 2.42 (3H, s), 4.51 (1H, d, J=16.2 Hz), 5.05 (1H, d, J=16.2 Hz), 6.37 (1H, s), 6.70 (1H, s), 7.69 (2H, s), 7.86 (1H, s), 9.48 (1H, s); HRMS (EI) Calcd, 420.159332, Found 420.159769.

Example Q

To a stirred solution of (32) (297 mg, 1 mmol) and anhydrous powdered potassium carbonate (134 mg, 1 mmol) in DMF (5 ml) at room temperature, was added 3,5-difluorobenzyl bromide (207 mg, 1 mmol). After stirring for overnight, the mixture was evaporated in vacuo and the residue was purified by silica gel column chromatography (eluent, EA:hexanes (1:5)) to afford 200 mg (47%) of a white solid. m.p. 239-240° C.; 1H-NMR (200 MHz, DMSO-d$_6$) δ 1.03 (3H, d, J=6.6 Hz), 1.10 (3H, d, J=6.6 Hz) 2.10 (1H, m), 2.35 (3H, s), 4.48 (1H, d, J=17.2 Hz), 4.84 (1H, d, J=17.2 Hz), 6.80-6.97 (3H, m), 7.94 (1H, s), 8.07 (1H, s), 8.31 (1H, s), 11.62 (1H, s); m/z (EI) 423 (M+).

Example R

To a stirred solution of 2-fluoro-6-methoxypyridine-4-methanol (157 mg, 1 mmol) in chloroform (10 ml) cooled in an ice bath under nitrogen atmosphere, was added triethylamine (210 μl, 1.5 mmol) and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (32) (297 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, methanol:chloroform (2:98)) to afford 240 mg (55%) of a colorless syrup. m.p. 135-136° C.; 1H-NMR (200 MHz, CDCl$_3$) δ 1.12 (3H, d, J=7.0 Hz), 1.22 (3H, d, J=7.0 Hz), 2.22 (1H, m), 3.81 (3H, s), 4.43 (1H, d, J=16.6 Hz), 5.08 (1H, d, J=16.6 Hz), 6.11 (1H, s), 6.23 (1H, s), 7.68 (2H, s), 7.87 (1H, s), 8.88 (1H, s); m/z (EI) 436 [M+].

Examples S, T, U, V, and W

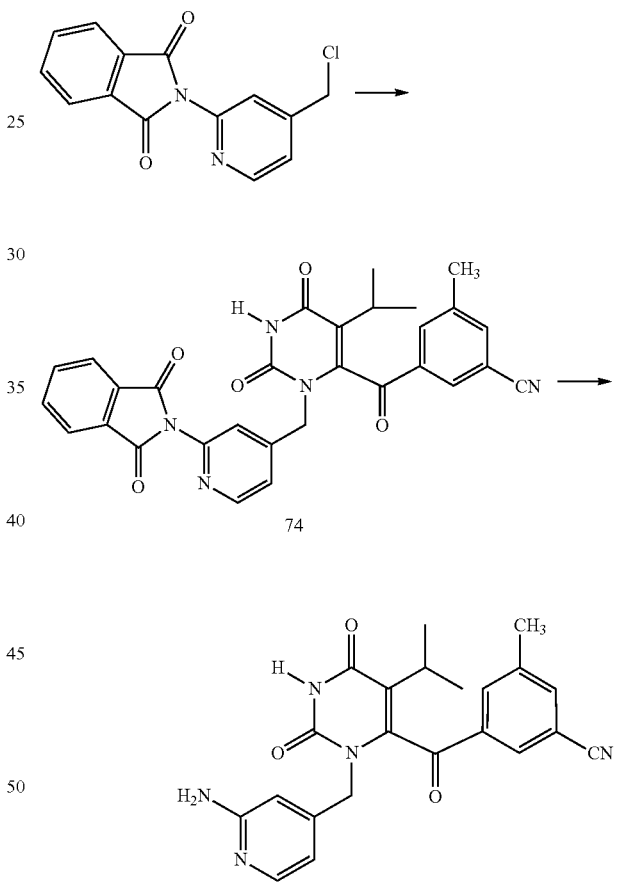

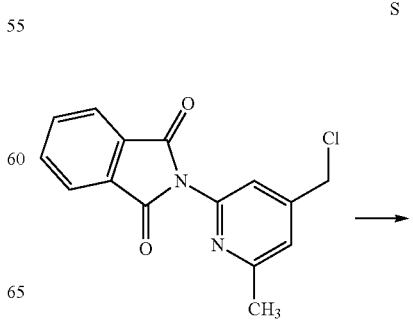

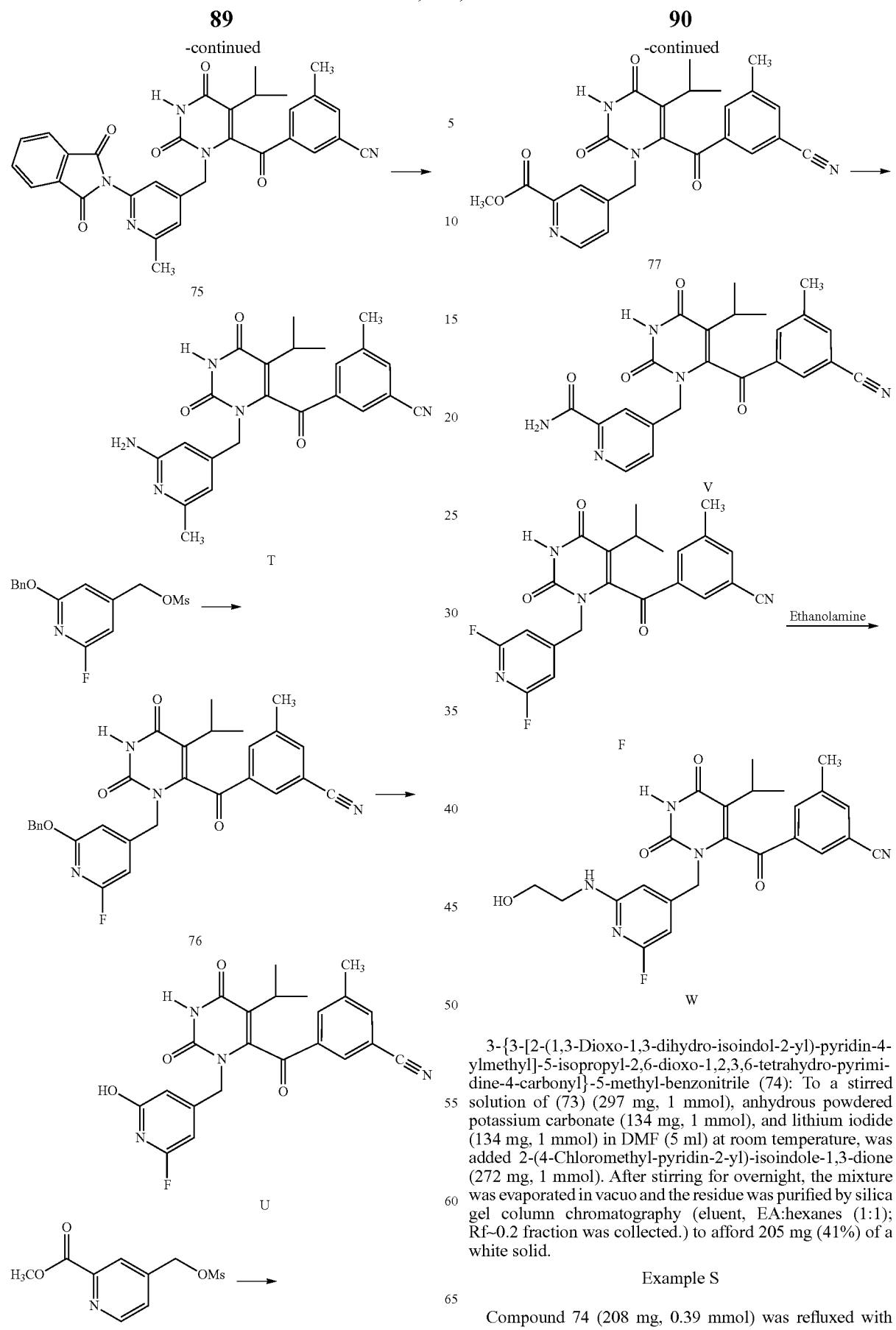

3-{3-[2-(1,3-Dioxo-1,3-dihydro-isoindol-2-yl)-pyridin-4-ylmethyl]-5-isopropyl-2,6-dioxo-1,2,3,6-tetrahydro-pyrimidine-4-carbonyl}-5-methyl-benzonitrile (74): To a stirred solution of (73) (297 mg, 1 mmol), anhydrous powdered potassium carbonate (134 mg, 1 mmol), and lithium iodide (134 mg, 1 mmol) in DMF (5 ml) at room temperature, was added 2-(4-Chloromethyl-pyridin-2-yl)-isoindole-1,3-dione (272 mg, 1 mmol). After stirring for overnight, the mixture was evaporated in vacuo and the residue was purified by silica gel column chromatography (eluent, EA:hexanes (1:1); Rf~0.2 fraction was collected.) to afford 205 mg (41%) of a white solid.

Example S

Compound 74 (208 mg, 0.39 mmol) was refluxed with hydrazine monohydrate (0.6 ml) in toluene (4 ml) and THF (4 ml). After cooling to room temperature, the mixture was evaporated in vacuo and the residue was purified by silica gel column chromatography (eluent, methanol:chloroform (1:9)) to afford 60 mg (62%) of a white solid. m.p. 203-204° C.; $^1$H-NMR (200 MHz, CDCl$_3$) δ 1.13 (3H, d, J=6.9 Hz), 1.22 (3H, d, J=6.9 Hz), 2.24 (1H, m), 2.41 (3H, s), 4.28 (1H, d, J=16.3 Hz), 5.04 (2H, s), 5.17 (1H, d, J=16.3 Hz), 6.15 (1H, s), 6.19 (1H, d, J=5.3 Hz), 7.63 (1H, s), 7.71 (1H, s), 7.83-7.88 (2H, m), 11.8 (1H, s); m/z (EI) 403 (M$^+$); HRMS (EI) Calcd, 403.164452, Found 403.164440.

3-{3-[2-(1,3-Dioxo-1,3-dihydro-isoindol-2-yl)-6-methyl-pyridin-4-ylmethyl]-5-isopropyl-2,6-dioxo-1,2,3,6-tetrahydro-pyrimidine-4-carbonyl}-5-methyl-benzonitrile (75): To a stirred solution of (73) (297 mg, 1 mmol), anhydrous powdered potassium carbonate (134 mg, 1 mmol), and lithium iodide (134 mg, 1 mmol) in DMF (5 ml) at room temperature, was added 2-(4-Chloromethyl-6-methyl-pyridin-2-yl)-isoindole-1,3-dione (286 mg, 1 mmol). After stirring for overnight, the mixture was evaporated in vacuo and the residue was purified by silica gel column chromatography (eluent, EA:hexanes (2:1); Rf~0.2 fraction was collected.) to afford 250 mg (45%) of a white solid.

Example T

Compound 75 (320 mg, 0.585 mmol) was refluxed with hydrazine monohydrate (0.6 ml) in toluene (4 ml) and THF (4 ml) for 4 hr. After cooling to room temperature, the mixture was evaporated in vacuo and the residue was purified by silica gel column chromatography (eluent, methanol:dichloromethane (5:95)) to afford 170 mg (70%) of a white solid. m.p. 255-256° C.; $^1$H-NMR (200 MHz, CDCl$_3$) δ 1.14 (3H, d, J=6.8 Hz), 1.23 (3H, d, J=6.8 Hz), 2.18-2.28 (4H, m), 2.41 (3H, s), 4.14 (1H, d, J=13.5 Hz), 4.81 (2H, s), 5.17 (1H, d, J=13.5 Hz), 5.99 (2H, s), 7.64 (1H, s), 7.69 (1H, s), 7.84 (1H, s); m/z (EI) 417 (M$^+$); HRMS (EI) Calcd, 417.180654, Found 417.180090.

3-[3-(2-Benzyloxy-6-fluoro-pyridin-4-ylmethyl)-5-isopropyl-2,6-dioxo-1,2,3,6-tetrahydro-pyrimidine-4-carbonyl]-5-methyl-benzonitrile (76): To a stirred solution of 2-fluoro-6-benzylpyridine-4-methanol (233 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (73) (297 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, methanol:chloroform (2:98)) to afford 260 mg (50%) of a colorless syrup. $^1$H-NMR (200 MHz, CDCl$_3$) δ 1.11 (3H, d, J=6.8 Hz), 1.21 (3H, d, J=6.8 Hz), 2.21 (1H, m), 2.34 (3H, s), 4.40 (1H, d, J=16.4 Hz), 5.09 (1H, d, J=16.4 Hz), 5.20 (2H, d, J=3.2 Hz), 6.14 (1H, s), 6.22 (1H, s), 7.34-7.50 (5H, m), 7.51 (1H, s), 7.65 (1H, s), 7.85 (1H, s), 8.81 (1H, s).

Example U

Compound 76 (220 mg, 0.429 mmol) was stirred with 10% palladium on carbon (50 mg) in anhydrous ethanol (10 ml) and THF (5 ml) at room temperature under an atmosphere of hydrogen. After 4 hr., the reaction mixture was filtered through celite pad and the pad was washed with ethanol and chloroform. The combined filtrate was evaporated in vacuo and the residue was purified by silica gel column chromatography (eluent, methanol:chloroform (5:95)) to afford 175 mg (96%) of a pale yellow solid. m.p. 264-265° C.; $^1$H-NMR (200 MHz, CDCl$_3$) δ 1.14 (3H, d, J=6.8 Hz), 1.22 (3H, d, J=6.8 Hz), 2.25 (1H, m), 2.44 (3H, s), 4.59 (1H, d, J=16.8 Hz), 4.95 (1H, d, J=16.8 Hz), 6.18 (1H, s), 6.29 (1H, s), 7.71 (1H, s), 7.82 (1H, s), 7.93 (1H, s), 10.33 (1H, br. s), 10.47 (1H, br. s), 10.91 (1H, br. s); m/z (EI) 422 [M$^+$].

4-[6-(3-Cyano-5-methyl-benzoyl)-5-isopropyl-2,4-dioxo-3,4-dihydro-2 H-pyrimidin-1-ylmethyl]-pyridine-2-carboxylic acid methyl ester (77): To a stirred solution of 2-methoxycarbonylpyridine-4-methanol (222 mg, 1.3 mmol) in chloroform (10 ml) cooled in an ice bath under nitrogen atmosphere, was added triethylamine (279 µl, 2 mmol) and methanesulfonyl chloride (120 µl, 1.5 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (73) (394 mg, 1.3 mmol), powdered anhydrous potassium carbonate (183 mg, 1.3 mmol), and lithium iodide (178 mg, 1.3 mmol). DMF (7 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (4:1)) to afford 271 mg (45%) of a white foam. $^1$H-NMR (200 MHz, CDCl$_3$) δ 1.13 (3H, d, J=6.8 Hz), 1.23 (3H, d, J=6.8 Hz), 2.23 (1H, m), 2.37 (3H, s), 4.00 (3H, s), 4.66 (1H, d, J=17.0 Hz), 5.11 (1H, d, J=17.0 Hz), 7.23 (1H, m), 7.65 (2H, s), 7.73 (1H, s), 7.88 (1H, s), 8.55 (1H, d, J=5.2 Hz), 9.56 (1H, s).

Example V

Compound 77 (248 mg, 0.555 mmol) was stirred with ammonium hydroxide (5 ml) in methanol (5 ml) for overnight at room temperature. The mixture was evaporated in vacuo and the residue was purified by silica gel column chromatography (eluent, methanol:chloroform (5:95)) to afford 177 mg (74%) of a white solid. m.p. 251-252° C.; $^1$H-NMR (200 MHz, DMSO-d$_6$) δ 1.03 (3H, d, J=6.6 Hz), 1.10 (3H, d, J=6.6 Hz), 2.11 (1H, m), 2.34 (3H, s), 4.72 (2H, s), 7.30 (1H, d, J=5.0 Hz), 7.62 (1H, s), 7.69 (1H, s), 7.95 (1H, s), 8.01 (1H, s), 8.06 (1H, s), 8.31 (1H, d, J=6.4 Hz), 8.41 (1H, d, J=5.0 Hz), 11.69 (1H, s); m/z (EI) 431 [M$^+$].

Example W

Example F (200 mg, 0.47 mmol) was refluxed with ethanolamine (57 µl, 0.94 mmol) in toluene (2 ml) for 4 hr. After cooling to room temperature, the mixture was evaporated in vacuo and the residue was purified by silica gel column chromatography (eluent, EA:hexanes (3:1)) to afford 213 mg (98%) of a white solid. m.p. 194-195° C.; $^1$H-NMR (300 MHz, CDCl$_3$) δ 1.12 (3H, d, J=6.9 Hz), 1.23 (3H, d, J=6.9 Hz), 2.17 (1H, br. s), 2.22 (1H, m), 2.42 (3H, s), 3.35-3.40 (2H, m), 3.76-3.81 (2H, m), 4.20 (1H, d, J=16.2 Hz), 4.98 (1H, t, J=5.4 Hz), 5.21 (1H, d, J=1625 Hz), 5.70 (1H, s), 5.87

(1H, s), 7.66 (1H, s), 7.71 (1H, s), 7.82 (1H, s), 8.57 (1H, s); HRMS (EI) Calcd, 465.181233, Found 465.182434.
Examples X, Y, Z, AA, AB, AC, and AD
Scheme 18
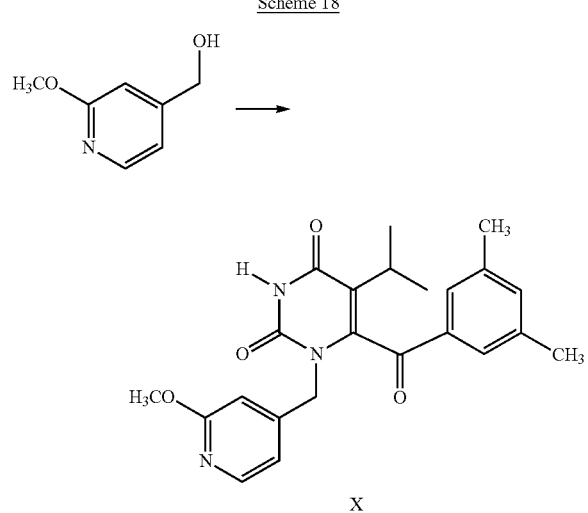
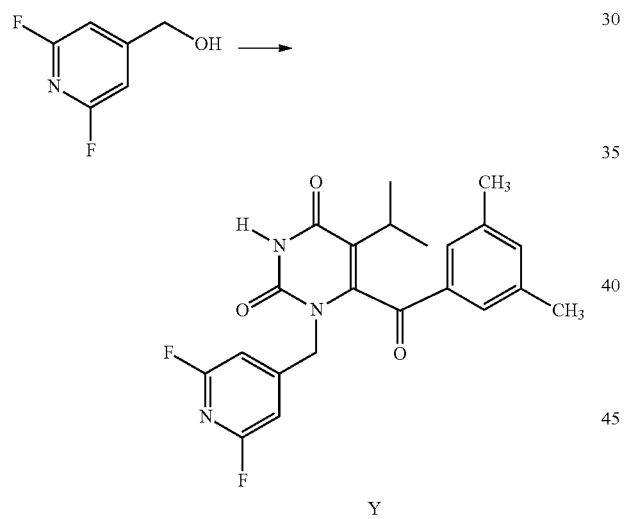
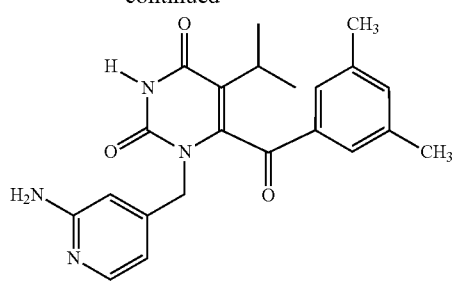
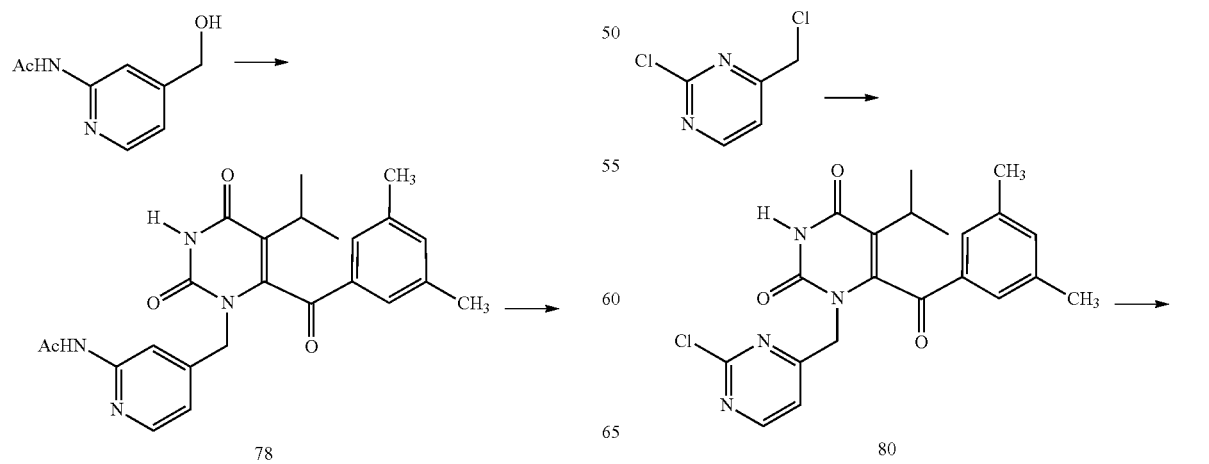

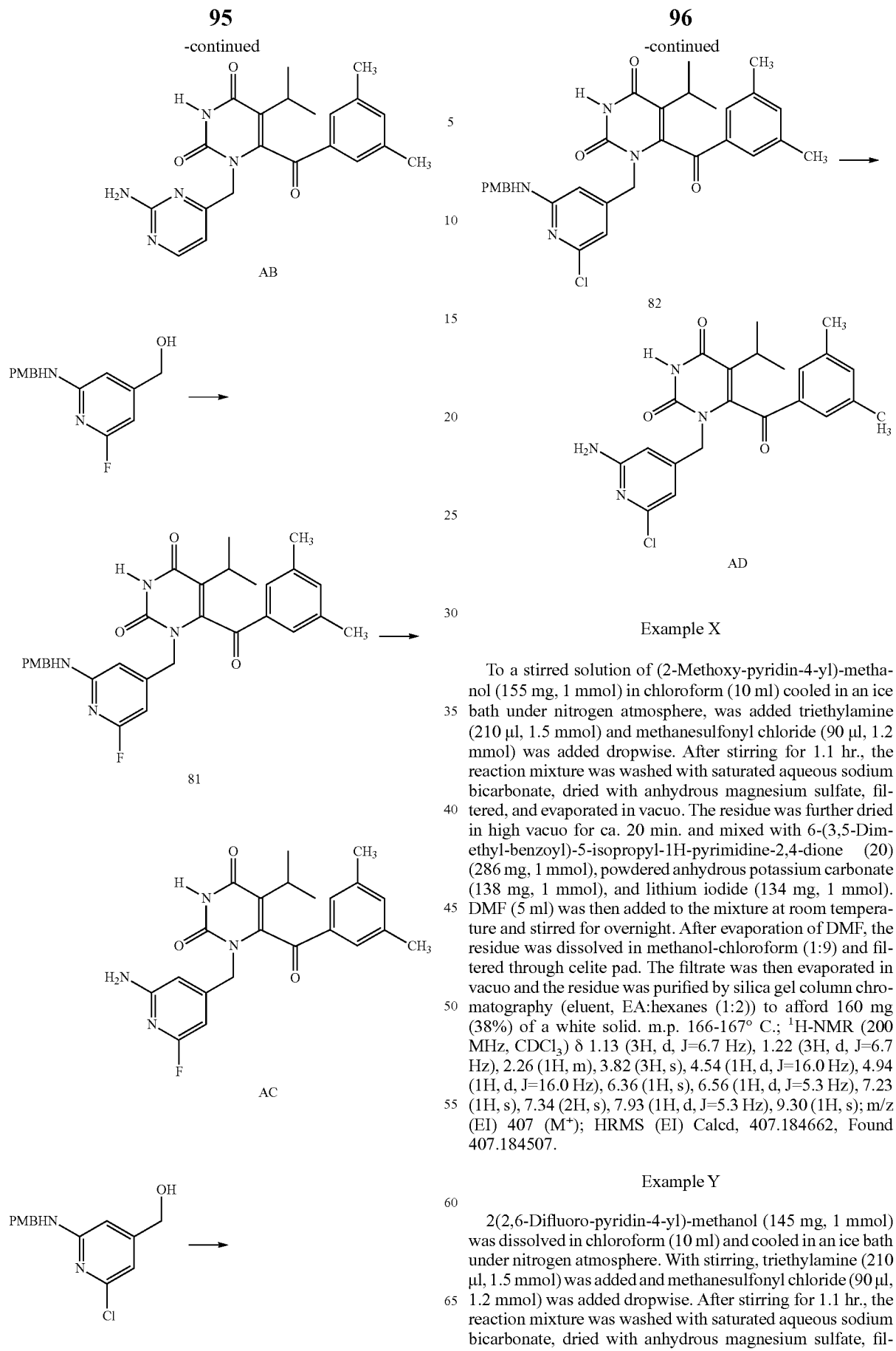

Example X

To a stirred solution of (2-Methoxy-pyridin-4-yl)-methanol (155 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3,5-Dimethyl-benzoyl)-5-isopropyl-1H-pyrimidine-2,4-dione (20) (286 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 160 mg (38%) of a white solid. m.p. 166-167° C.; $^1$H-NMR (200 MHz, CDCl$_3$) δ 1.13 (3H, d, J=6.7 Hz), 1.22 (3H, d, J=6.7 Hz), 2.26 (1H, m), 3.82 (3H, s), 4.54 (1H, d, J=16.0 Hz), 4.94 (1H, d, J=16.0 Hz), 6.36 (1H, s), 6.56 (1H, d, J=5.3 Hz), 7.23 (1H, s), 7.34 (2H, s), 7.93 (1H, d, J=5.3 Hz), 9.30 (1H, s); m/z (EI) 407 (M$^+$); HRMS (EI) Calcd, 407.184662, Found 407.184507.

Example Y

2(2,6-Difluoro-pyridin-4-yl)-methanol (145 mg, 1 mmol) was dissolved in chloroform (10 ml) and cooled in an ice bath under nitrogen atmosphere. With stirring, triethylamine (210 µl, 1.5 mmol) was added and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (20) (286 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 177 mg (43%) of a white solid. m.p. 242-243° C.; $^1$H-NMR (200 MHz, CDCl$_3$) δ 1.13 (3H, d, J=6.8 Hz), 1.22 (3H, d, J=6.8 Hz), 2.29-2.38 (7H, m), 4.45 (1H, d, J=16.2 Hz), 4.51 (2H, s), 4.85 (1H, d, J=16.2 Hz), 5.81 (2H, s), 6.05 (1H, s), 7.27 (1H, s), 7.39 (2H, s), 9.05 (1H, s); m/z (EI) 410 (M$^+$); HRMS (EI) Calcd, 410.175419, Found 410.177147.

N-{4-[6-(3,5-Dimethyl-benzoyl)-5-isopropyl-2,4-dioxo-3,4-dihydro-2H-pyrimidin-1-ylmethyl]-pyridin-2-yl}-acetamide (78): N-(4-Hydroxymethyl-pyridin-2-yl)-acetamide (166 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (20) (286 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (2:1)) to afford 165 mg (38%) a white solid. m.p. 244-245° C.; $^1$H NMR (200 MHz, CDCl$_3$) δ 1.17 (3H, d, J=6.7 Hz), 1.24 (3H, d, J=6.7 Hz), 2.20-2.40 (10H, m), 4.70 (1H, d, J=17.1 Hz), 4.88 (1H, d, J=17.1 Hz), 6.82 (1H, d, J=5.3 Hz), 7.24 (1H, s), 7.42 (2H, s), 7.99 (1H, s), 8.30 (1H, d, J=5.3 Hz), 10.01 (1H, s), 12.44 (1H, s); m/z (EI) 434 (M$^+$).

Example Z

Compound 78 (92 mg, 0.23 mmol) was refluxed with 4M NaOH (1 ml, 4 mmol) in ethanol (5 ml) for 6 hr. After cooling to room temperature, the mixture was evaporated in vacuo and the residue was purified by silica gel column chromatography (eluent, methanol:dichloromethane (1:9)) to afford 77 mg (86%) of a white solid. m.p. 277-280° C.; $^1$H-NMR (200 MHz, CDCl$_3$/CD$_3$OD) δ 1.12 (3H, d, J=6.7 Hz), 1.21 (3H, d, J=6.7 Hz), 2.25-2.40 (7H, m), 4.49 (1H, d, J=16.5 Hz), 4.82 (1H, d, J=16.5 Hz), 6.20 (1H, s), 6.27 (1H, d, J=5.3 Hz), 7.29 (1H, s), 7.41 (2H, s), 7.68 (1H, d, J=5.3 Hz); m/z (EI) 392 (M$^+$); HRMS (EI) Calcd, 392.184608, Found 392.184841.

2-{4-[6-(3,5-Dimethyl-benzoyl)-5-isopropyl-2,4-dioxo-3,4-dihydro-2 H-pyrimidin-1-ylmethyl]-6-methyl-pyridin-2-yl}-isoindole-1,3-dione (79): To a stirred solution of (20) (286 mg, 1 mmol), anhydrous powdered potassium carbonate (134 mg, 1 mmol), and lithium iodide (134 mg, 1 mmol) in DMF (5 ml) at room temperature, was added 2-(4-Chloromethyl-6-methyl-pyridin-2-yl)-isoindole-1,3-dione (286 mg, 1 mmol). After stirring for overnight, the mixture was evaporated in vacuo and the residue was purified by silica gel column chromatography (eluent, EA:hexanes (1:1)) to afford 273 mg (51%) of a white solid. m.p. 310-311° C.; $^1$H NMR (200 MHz, CDCl$_3$) δ 1.14 (3H, d, J=6.9 Hz), 1.22 (3H, d, J=6.9 Hz), 2.27 (6H, s), 2.36 (1H, m), 2.43 (3H, s), 4.54 (1H, d, J=16.2 Hz), 5.04 (1H, d, J=16.2 Hz), 6.82 (1H, s), 6.94 (1H, s), 7.21 (1H, s), 7.39 (2H, s), 7.77-7.82 (2H, m), 7.91-7.95 (2H, m), 8.96 (1H, s).

m/z (EI) 536 (M$^+$).

Example AA

Compound 79 (134 mg, 0.25 mmol) was refluxed with 4M NaOH (1 ml, 4 mmol) in ethanol (5 ml) for 7 hr. After cooling to room temperature, the mixture was evaporated in vacuo and the residue was purified by silica gel column chromatography (eluent, methanol:chloroform (1:9)) to afford 98 mg (97%) a white solid. m.p. 227-228° C.; $^1$H-NMR (200 MHz, CDCl$_3$) δ 1.12 (3H, d, J=6.7 Hz), 1.22 (3H, d, J=6.7 Hz), 2.18 (3H, s), 2.22-2.40 (7H, m), 4.34 (1H, d, J=15.8 Hz), 4.47 (2H, s), 4.93 (1H, d, J=15.8 Hz), 6.04 (2H, s), 7.24 (1H, s), 7.35 (2H, s); m/z (EI) 406 (M$^+$); HRMS (EI) Calcd, 406.200600, Found 406.200491.

1-(2-Chloro-pyrimidin-4-ylmethyl)-6-(3,5-dimethyl-benzoyl)-5-isopropyl-1H-pyrimidine-2,4-dione (80): To a stirred solution of (20) (286 mg, 1 mmol), anhydrous powdered potassium carbonate (134 mg, 1 mmol), and lithium iodide (134 mg, 1 mmol) in DMF (5 ml) at room temperature, was added 2-Chloro-4-chloromethyl-pyrimidine (164 mg, 1 mmol). After stirring for overnight, the mixture was evaporated in vacuo and the residue was purified by silica gel column chromatography (eluent, EA:hexanes (1:1)) to afford 210 mg (51%) of a white solid. m.p. 197-198° C.; $^1$H NMR (300 MHz, CDCl$_3$) δ 1.17 (3H, d, J=6.9 Hz), 1.21 (3H, d, J=6.9 Hz), 2.29-2.39 (7H, m), 4.73 (1H, d, J=17.4 Hz), 4.95 (1H, d, J=17.4 Hz), 7.07 (1H, d, J=5.1 Hz), 7.28 (1H, s), 7.48 (2H, s), 8.46 (1H, d, J=5.1 Hz), 9.41 (1H, s); m/z (EI) 412 (M$^+$).

Example AB

Compound 80 (300 mg, 0.725 mmol) and saturated ammonia in methanol (15 ml) were placed into a steel bomb and heated for 22 hr. in an oil bath (100° C.). After cooling to room temperature, the mixture was evaporated in vacuo and the residue was purified by silica gel column chromatography (eluent, methanol:chloroform (1:9)) to afford 225 mg (79%) of a white solid. m.p. 142-143° C.; $^1$H-NMR (200 MHz, CDCl$_3$) δ 1.15 (3H, d, J=6.7 Hz), 1.20 (3H, d, J=6.7 Hz), 2.25-2.40 (7H, m), 4.52 (1H, d, J=17.5 Hz), 4.90 (1H, d, J=17.5 Hz), 5.57 (2H, s), 6.31 (1H, d, J=5.1 Hz), 7.24 (1H, s), 7.46 (2H, s), 8.16 (1H, d, J=5.1 Hz); m/z (EI). 393 (M$^+$); HRMS (EI) Calcd, 393.180250, Found 393.180090.

6-(3,5-Dimethyl-benzoyl)-1-[2-fluoro-6-(4-methoxy-benzylamino)-pyridin-4-ylmethyl]-5-isopropyl-1H-pyrimidine-2,4-dione (81): [2-Fluoro-6-(4-methoxy-benzylamino)-pyridin-4-yl]-methanol (262 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (20) (286 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 298 mg (56%) of a white solid. m.p. 120-122° C.; $^1$H-NMR (200 MHz, CDCl$_3$) δ 1.11 (3H, d, J=6.9 Hz), 1.23 (3H, d, J=6.9 Hz), 2.31-2.33 (7H, m), 3.79 (3H, s), 4.25-4.27 (2H, m), 4.38 (1H, d, J=16.2 Hz), 4.85 (1H, d, J=16.2 Hz), 4.94 (1H, t, J=5.4 Hz), 5.76 (1H, s), 5.89 (1H, s), 6.84-6.87 (2H, m), 7.19-7.26 (3H, m), 7.34 (2H, s), 9.34 (1H, s).

Example AC

To a stirred solution of (81) (100 mg, 0.188 mmol) in acetonitrile (2 ml), was added ceric ammonium nitrate (207 mg, 0.377 mmol) and distilled water (1 ml) in this order. After 20 min., the mixture was diluted with ethyl acetate, washed with water, dried with anhydrous magnesium sulfate, filtered, and evaporated in vacuo. The residue was purified by silica gel column chromatography (eluent, EA:hexanes (1:1)) to afford 61 mg (79%) of a white solid. m.p. 242-243° C.; $^1$H-NMR (200 MHz, CDCl$_3$) δ 1.13 (3H, d, J=6.8 Hz), 1.22 (3H, d, J=6.8 Hz), 2.29-2.38 (7H, m), 4.45 (1H, d, J=16.2 Hz), 4.51 (2H, s), 4.85 (1H, d, J=16.2 Hz), 5.81 (2H, s), 6.05 (1H, s), 7.27 (1H, s), 7.39 (2H, s), 9.05 (1H, s); m/z (EI) 410 (M$^+$); HRMS (EI) Calcd, 410.175419, Found 410.177147.

1-[2-Chloro-6-(4-methoxy-benzylamino)-pyridin-4-ylmethyl]-6-(3,5-dimethyl-benzoyl)-5-isopropyl-1H-pyrimidine-2,4-dione (82): [2-Chloro-6-(4-methoxy-benzylamino)-pyridin-4-yl]-methanol (278 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with (20) (286 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 363 mg (66%) of a white solid. m.p. 211-212° C.; $^1$H-NMR (300 MHz, CDCl$_3$) δ 1.12 (3H, d, J=6.9 Hz), 1.21 (3H, d, J=6.9 Hz), 2.29-2.32 (7H, m), 3.79 (3H, s), 4.24-4.29 (3H, m), 4.89-4.98 (2H, m), 5.94 (1H, s), 6.14 (1H, s), 6.84-6.87 (2H, m); 7.19-7.32 (5H, m), 9.22 (1H, s); HRMS (EI) Calcd, 546.203384, Found 546.204693.

Example AD

To a stirred solution of (82) (100 mg, 0.18 mmol) in acetonitrile (2 ml) and acetic acid (1 ml), was added ceric ammonium nitrate (201 mg, 0.36 mmol) and distilled water (1 ml) in this order. After 30 min., the mixture was diluted with ethyl acetate, washed with water, dried with anhydrous magnesium sulfate, filtered, and evaporated in vacuo. The residue was purified by silica gel column chromatography (eluent, EA:hexanes (1:1)) to afford 66 mg (85%) of a white solid. m.p. 273-274° C.; $^1$H-NMR (200 MHz, CDCl$_3$) δ 1.13 (3H, d, J=6.9 Hz), 1.24 (3H, d, J=6.9 Hz), 2.29-2.38 (7H, m), 4.32 (1H, d, J=16.5 Hz), 4.46 (2H, s), 4.92 (1H, d, J=16.5 Hz), 6.06 (1H, s), 6.22 (1H, s), 7.27 (2H, s), 7.37 (1H, s), 8.35 (1H, s); m/z (EI) 426 (M$^+$); HRMS (EI) Calcd, 426.145869, Found 426.147096.

Examples AE, AF, AG, AH, AI, and AJ

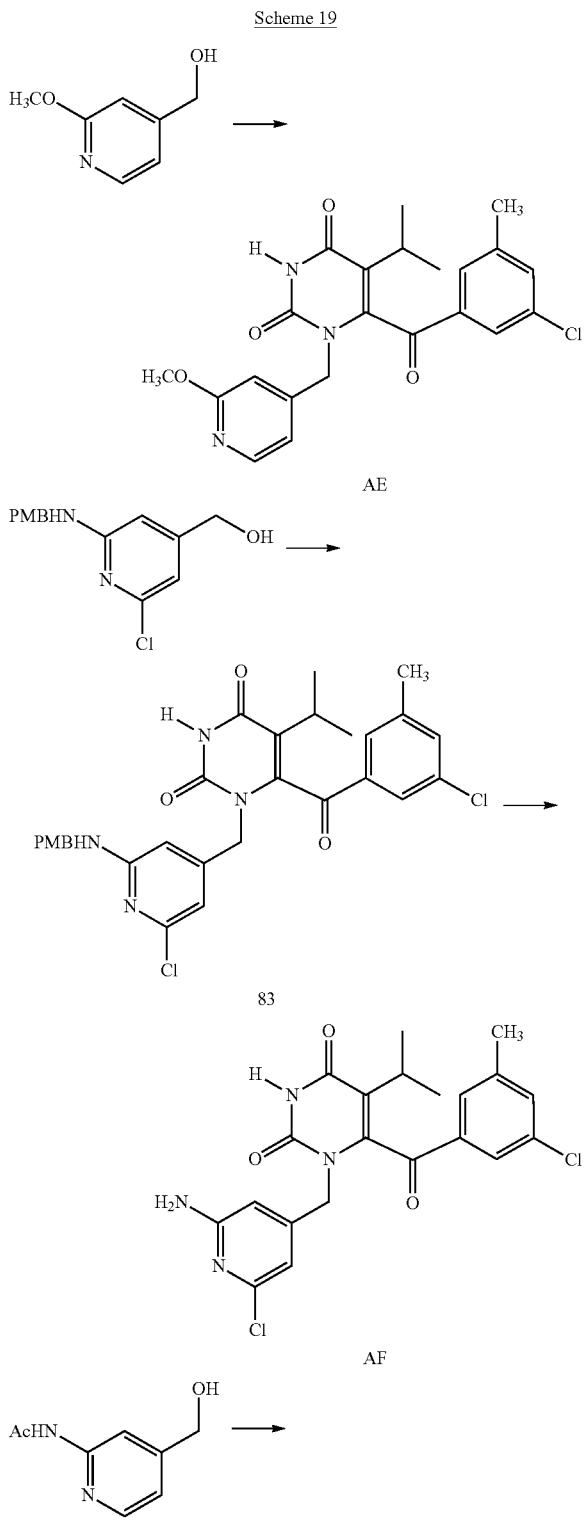

Scheme 19

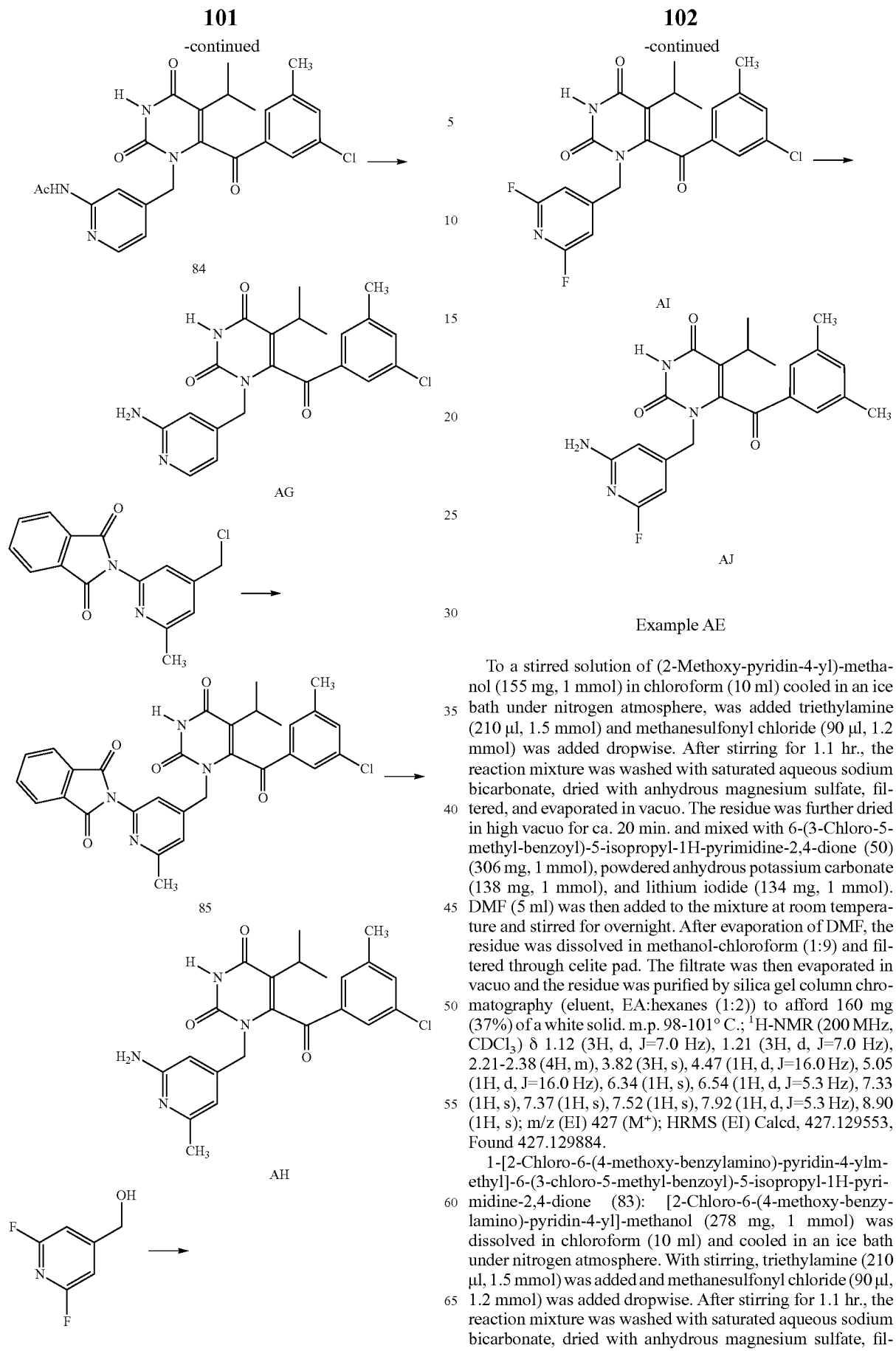

Example AE

To a stirred solution of (2-Methoxy-pyridin-4-yl)-methanol (155 mg, 1 mmol) in chloroform (10 ml) cooled in an ice bath under nitrogen atmosphere, was added triethylamine (210 μl, 1.5 mmol) and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Chloro-5-methyl-benzoyl)-5-isopropyl-1H-pyrimidine-2,4-dione (50) (306 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 160 mg (37%) of a white solid. m.p. 98-101° C.; $^1$H-NMR (200 MHz, CDCl$_3$) δ 1.12 (3H, d, J=7.0 Hz), 1.21 (3H, d, J=7.0 Hz), 2.21-2.38 (4H, m), 3.82 (3H, s), 4.47 (1H, d, J=16.0 Hz), 5.05 (1H, d, J=16.0 Hz), 6.34 (1H, s), 6.54 (1H, d, J=5.3 Hz), 7.33 (1H, s), 7.37 (1H, s), 7.52 (1H, s), 7.92 (1H, d, J=5.3 Hz), 8.90 (1H, s); m/z (EI) 427 (M$^+$); HRMS (EI) Calcd, 427.129553, Found 427.129884.

1-[2-Chloro-6-(4-methoxy-benzylamino)-pyridin-4-ylmethyl]-6-(3-chloro-5-methyl-benzoyl)-5-isopropyl-1H-pyrimidine-2,4-dione (83): [2-Chloro-6-(4-methoxy-benzylamino)-pyridin-4-yl]-methanol (278 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Chloro-5-methyl-benzoyl)-5-isopropyl-1H-pyrimidine-2,4-dione (306 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2); Rf~0.2 fraction was collected.) to afford 334 mg (59%) of a white solid.

Example AF

To a stirred solution of (83) (100 mg, 0.18 mmol) in acetonitrile (2 ml), was added ceric ammonium nitrate (201 mg, 0.36 mmol) and distilled water (1 ml) in this order. After 2 hr., the mixture was diluted with ethyl acetate, washed with water, dried with anhydrous magnesium sulfate, filtered, and evaporated in vacuo. The residue was purified by silica gel column chromatography (eluent, EA:hexanes (1:1)) to afford 34 mg (43%) of a white solid. m.p. 277-278° C.; $^1$H-NMR (200 MHz, CDCl$_3$) δ 1.14 (3H, d, J=6.8 Hz), 1.24 (3H, d, J=6.8 Hz), 2.26 (1H, m), 2.36 (3H, s), 4.26 (1H, d, J=16.2 Hz), 4.48 (2H, s), 5.02 (1H, d, J=16.2 Hz), 6.02 (1H, s), 6.32 (1H, s), 7.35 (1H, s), 7.42 (1H, s), 7.59 (1H, s), 8.36 (1H, s); m/z (EI) 446 (M$^+$); HRMS (EI) Calcd, 446.091246, Found 446.091835.

N-{4-[6-(3-Chloro-5-methyl-benzoyl)-5-isopropyl-2,4-dioxo-3,4-dihydro-2 H-pyrimidin-1-ylmethyl]-pyridin-2-yl}-acetamide (84): N-(4-Hydroxymethyl-pyridin-2-yl)-acetamide (166 mg, 1 mmol) was dissolved in chloroform (10 ml) and cooled in an ice bath under nitrogen atmosphere. With stirring, triethylamine (210 µl, 1.5 mmol) was added and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Chloro-5-methyl-benzoyl)-5-isopropyl-1H-pyrimidine-2,4-dione (306 mg, 1 mmol), powdered anhydrous potassium-carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (2:1)) to afford 145 mg (32%) of a white solid. m.p. 241-243° C.; $^1$H NMR (200 MHz, CDCl$_3$) δ 1.17 (3H, d, J=6.7 Hz), 1.23 (3H, d, J=6.7 Hz), 2.19-2.40 (7H, m), 4.63 (1H, d, J=16.7 Hz), 5.03 (1H, d, J=16.7 Hz), 6.83 (1H, d, J=5.3 Hz), 7.38 (1H, s), 7.46 (1H, s), 7.58 (1H, s), 7.99 (1H, s), 8.30 (1H, d, J=5.3 Hz), 9.89 (1H, s), 12.34 (1H, s).

Example AG

N-{4-[6-(3-Chloro-5-methyl-benzoyl)-5-isopropyl-2,4-dioxo-3,4-dihydro-2H-pyrimidin-1-ylmethyl]-pyridin-2-yl}-acetamide (90 mg, 0.20 mmol) was refluxed with 4M NaOH (1 ml, 4 mmol) in ethanol (5 ml) for 6 hr. After cooling to room temperature, the mixture was evaporated in vacuo and the residue was purified by silica gel column chromatography (eluent, EA) to afford 71 mg (88%) of a white solid. m.p. 261-264° C.; $^1$H-NMR (200 MHz, CDCl$_3$) δ 1.13 (3H, d, J=6.7 Hz), 1.23 (3H, d, J=6.7 Hz), 2.21-2.33 (4H, m), 4.39 (1H, d, J=15.6 Hz), 4.59 (2H, s), 4.97 (1H, d, J=15.6 Hz), 6.13 (1H, s), 6.26 (1H, d, J=5.3 Hz), 7.34 (1H, s), 7.39 (1H, s), 7.59 (1H, s), 7.87 (1H, d, J=5.3 Hz), 9.80 (1H, s); m/z (EI) 412 (M$^+$); HRMS (EI) Calcd, 412.129990, Found 412.130219.

2-{4-[6-(3-Chloro-5-methyl-benzoyl)-5-isopropyl-2,4-dioxo-3,4-dihydro-2H-pyrimidin-1-ylmethyl]-6-methyl-pyridin-2-yl}-isoindole-1,3-dione (85): To a stirred solution of 6-(3-Chloro-5-methyl-benzoyl)-5-isopropyl-1 H-pyrimidine-2,4-dione (306 mg, 1 mmol), anhydrous powdered potassium carbonate (134 mg, 1 mmol), and lithium iodide (134 mg, 1 mmol) in DMF (5 ml) at room temperature, was added 2-(4-Chloromethyl-6-methyl-pyridin-2-yl)-isoindole-1,3-dione (286 mg, 1 mmol). After stirring for overnight, the mixture was evaporated in vacuo and the residue was purified by silica gel column chromatography (eluent, EA:hexanes (1:1)) to afford 250 mg (45%) of a white solid. $^1$H NMR (200 MHz, CDCl$_3$) δ 1.14 (3H, d, J=6.8 Hz), 1.21 (3H, d, J=6.8 Hz), 2.25-2.32 (4H, m), 2.46 (3H, s), 4.51 (1H, d, J=16.0 Hz), 5.14 (1H, d, J=16.0 Hz), 6.84 (1H, s), 6.94 (1H, s), 7.33 (1H, s), 7.37 (1H, s), 7.64 (1H, s), 7.76-2.83 (2H, m), 7.90-7.96 (2H, m), 9.19 (1H, s).

Example AH

2-{4-[6-(3-Chloro-5-methyl-benzoyl)-5-isopropyl-2,4-dioxo-3,4-dihydro-2H-pyrimidin-1-ylmethyl]-6-methyl-pyridin-2-yl}-isoindole-1,3-dione (134 mg, 0.25 mmol) was refluxed with 4M NaOH (1 ml, 4 mmol) in ethanol (5 ml) for 7 hr. After cooling to room temperature, the mixture was evaporated in vacuo and the residue was purified by silica gel column chromatography (eluent, methanol:chloroform (1:9)) to afford 98 mg (97%) of a white solid. m.p. 254-255° C.; $^1$H-NMR (200 MHz, CDCl$_3$) δ 1.13 (3H, d, J=6.7 Hz), 1.22 (3H, d, J=6.7 Hz), 2.20-2.40 (7H, m), 4.24 (1H, d, J=16.0 Hz), 4.50 (2H, s), 5.08 (1H, d, J=16.0 Hz), 5.98 (1H, s), 6.05 (1H, s), 7.32 (1H, s), 7.38 (1H, s), 7.58 (1H, s); HRMS (EI) Calcd, 426.146431, Found 426.145869.

6-(3-Chloro-5-methyl-benzoyl)-1-(2,6-difluoro-pyridin-4-ylmethyl)-5-isopropyl-1H-pyrimidine-2,4-dione (AI): (2,6-Difluoro-pyridin-4-yl)-methanol (145 mg, 1 mmol) was dissolved in chloroform (10 ml) and cooled in an ice bath under nitrogen atmosphere. With stirring, triethylamine (210 µl, 1.5 mmol) was added and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Chloro-5-methyl-benzoyl)-5-isopropyl-1H-pyrimidine-2,4-dione (306 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 175 mg (40%) of a white solid. $^1$H-NMR (300 MHz, CDCl$_3$) δ 1.18 (3H, d, J=6.7 Hz), 1.25 (3H, d, J=6.8 Hz), 2.26 (1H, m), 4.76 (3H, s), 6.57 (2H, s), 7.67 (3H, s), 9.21 (1H, s); m/z (EI) 433 (M$^+$).

Example AJ

Example AI (130 mg, 0.3 mmol) and saturated ammonia in methanol (9 ml) were placed into a steel bomb and heated for 14 hr. in an oil bath (100-110° C.). After cooling to room temperature, the mixture was evaporated in vacuo and the residue was purified by silica gel column chromatography (eluent, EA:hexanes (1:1)) to afford 70 mg (54%) of a white solid. m.p. 252-253° C.; $^1$H-NMR (300 MHz, CDCl$_3$/CD$_3$OD) δ 1.13 (3H, d, J=6.8 Hz), 1.21 (3H, d, J=6.8 Hz), 2.28 (1H, m), 2.36 (3H, s), 4.39 (1H, d, J=16.5 Hz), 4.88 (1H, d, J=16.5 Hz), 5.82 (1H, s), 5.97 (1H, s), 7.40 (1H, s), 7.43 (1H, s), 7.60 (1H, s); HRMS (EI) Calcd, 430.120797, Found 430.120560.

Examples

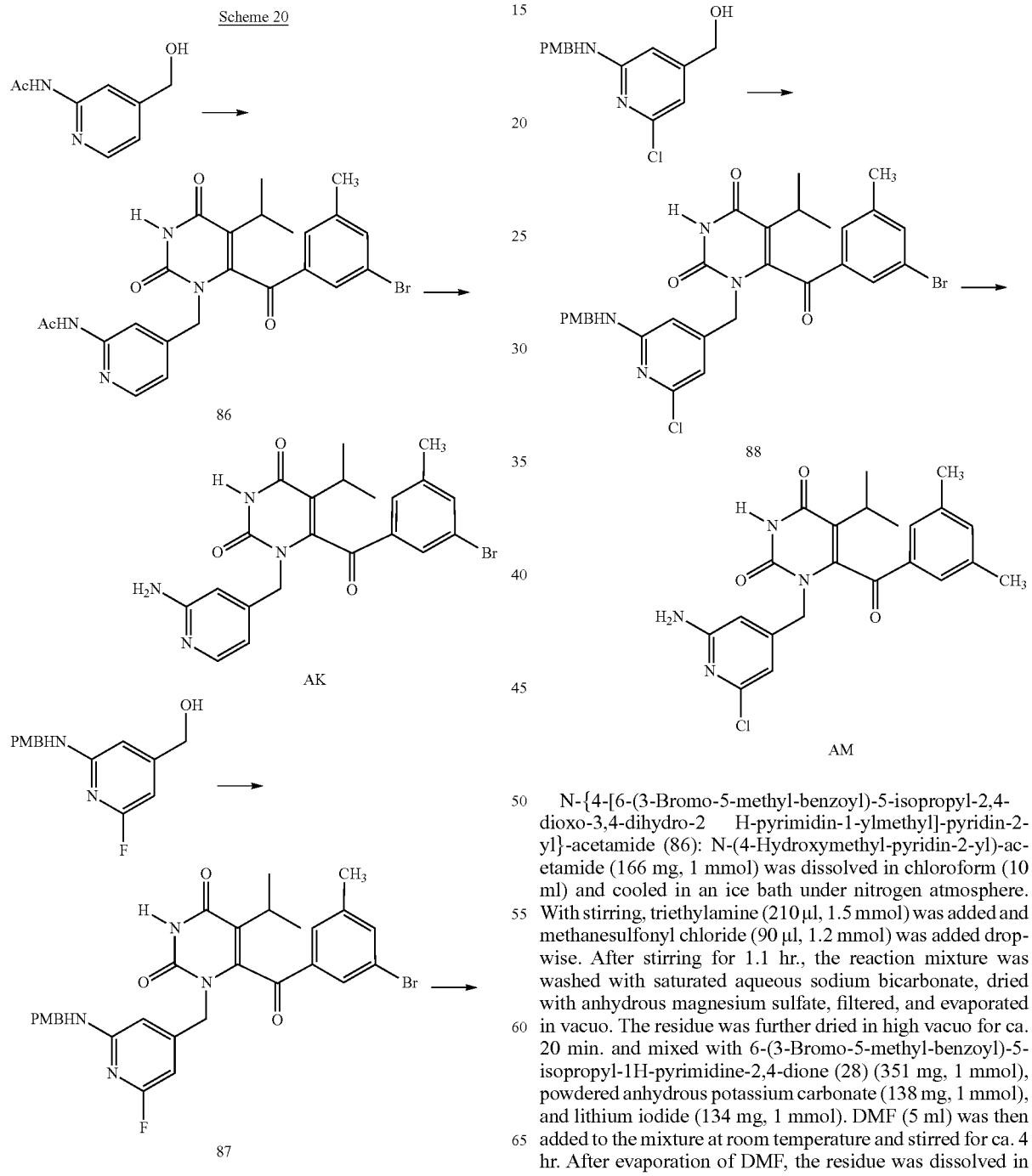

N-{4-[6-(3-Bromo-5-methyl-benzoyl)-5-isopropyl-2,4-dioxo-3,4-dihydro-2 H-pyrimidin-1-ylmethyl]-pyridin-2-yl}-acetamide (86): N-(4-Hydroxymethyl-pyridin-2-yl)-acetamide (166 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Bromo-5-methyl-benzoyl)-5-isopropyl-1H-pyrimidine-2,4-dione (28) (351 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad.

The filtrate was then evaporated in vacuo and the residue was purified by silica gel column chromatography (eluent, EA:hexanes (2:1); Rf~0.2 fraction was collected.) to afford 234 mg (47%) of a white solid.

Example AK

Compound 86 (205 mg, 0.41 mmol) was refluxed with 4M NaOH (1 ml, 4 mmol) in ethanol (5 ml) for 5 hr. After cooling to room temperature, the mixture was evaporated in vacuo and the residue was purified by silica gel column chromatography (eluent, methanol:dichloromethane (6:94)) to afford 141 mg (75%) of a white solid. m.p. 275-278° C.; $^1$H-NMR (200 MHz, CDCl$_3$/CD$_3$OD) δ 1.13 (3H, d, J=6.9 Hz), 1.21 (3H, d, J=6.9 Hz), 2.21-2.35 (4H, m), 4.41 (1H, d, J=16.4 Hz), 4.92 (1H, d, J=16.4 Hz), 6.17 (1H, s), 6.26 (1H, d, J=5.7 Hz), 7.45 (1H, s), 7.58 (1H, s), 7.71-7.73 (2H, m); m/z (EI) 458 (M$^+$); HRMS (EI) Calcd, 456.079086, Found 456.079702.

6-(3-Bromo-5-methyl-benzoyl)-1-[2-fluoro-6-(4-methoxy-benzylamino)-pyridin-4-ylmethyl]-5-isopropyl-1H-pyrimidine-2,4-dione (87): [2-Fluoro-6-(4-methoxy-benzylamino)-pyridin-4-yl]-methanol (262 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Bromo-5-methyl-benzoyl)-5-isopropyl-1 H-pyrimidine-2,4-dione (351 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:dichloromethane (1:9); Rf~0.2 fraction was collected.) to afford 340 mg (57%) of a white solid.

Example AL

To a stirred solution of Compound 87 (293 mg, 0.49 mmol) in acetonitrile (4 ml), was added ceric ammonium nitrate (540 mg, 0.98 mmol) and distilled water (2 ml) in this order. After 20 min., the mixture was diluted with ethyl acetate, washed with water, dried with anhydrous magnesium sulfate, filtered, and evaporated in vacuo. The residue was purified by silica gel column chromatography (eluent, EA:hexanes (1:2)) to afford 170 mg (73%) of a white solid. m.p. 235-236° C.; $^1$H-NMR (200 MHz, CDCl$_3$) δ 1.15 (3H, d, J=6.9 Hz), 1.22 (3H, d, J=6.9 Hz), 2.29 (1H, m), 2.35 (3H, s), 4.39 (1H, d, J=16.2 Hz), 4.60 (2H, s), 4.93 (1H, d, J=16.2 Hz), 5.82 (1H, s), 6.02 (1H, s), 7.44 (1H, s), 7.59 (2H, s), 7.76 (1H, s), 9.48 (1H, s); HRMS (EI) Calcd, 474.070280, Found 474.070707.

6-(3-Bromo-5-methyl-benzoyl)-1-[2-chloro-6-(4-methoxy-benzylamino)-pyridin-4-ylmethyl]-5-isopropyl-1H-pyrimidine-2,4-dione (88): [2-Chloro-6-(4-methoxy-benzylamino)-pyridin-4-yl]-methanol (278 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3-Bromo-5-methyl-benzoyl)-5-isopropyl-1 H-pyrimidine-2,4-dione (351 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2); Rf~0.2 fraction was collected.) to afford 275 mg (45%) of a white solid.

Example AM

To a stirred solution of (88) (220 mg, 0.36 mmol) in acetonitrile (4 ml) and acetic acid (2 ml), was added ceric ammonium nitrate (402 mg, 0.72 mmol) and distilled water (2 ml) in this order. After 2 hr., the mixture was diluted with ethyl acetate, washed with water, dried with anhydrous magnesium sulfate, filtered, and evaporated in vacuo. The residue was purified by silica gel column chromatography (eluent, methanol:chloroform (3:97)) to afford 118 mg (67%) of a white solid. m.p. 269-270° C.; $^1$H-NMR (200 MHz, CDCl$_3$) δ 1.14 (3H, d, J=6.9 Hz), 1.24 (3H, d, J=6.9 Hz), 2.28 (1H, m), 2.38 (3H, s), 4.32 (1H, d, J=16.5 Hz), 4.94 (1H, d, J=16.5 Hz), 6.09 (1H, s), 6.23 (1H, s), 7.45 (1H, s), 7.61 (1H, s), 7.75 (1H, s); HRMS (EI) Calcd, 490.040730, Found 490.041924.

Examples AN, AO, and AP

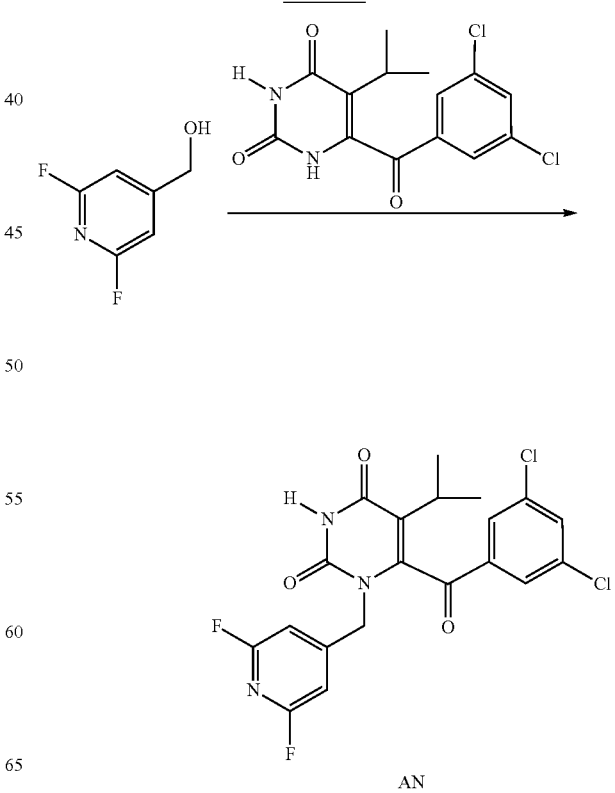

Scheme 21

AN

-continued

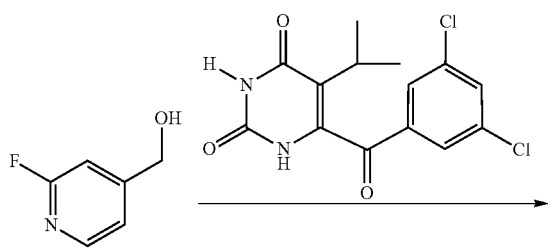

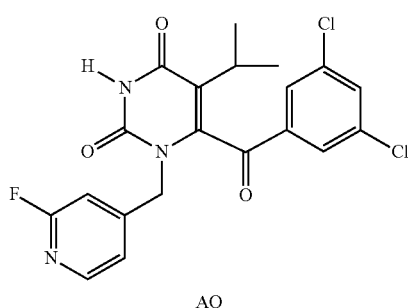

AO

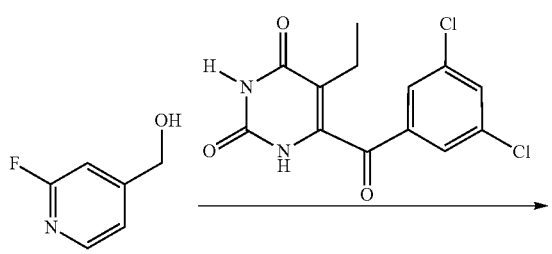

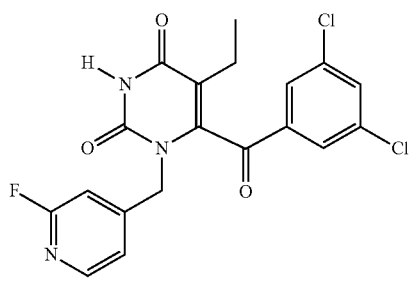

AP

Example AN (2,6-Difluoro-pyridin-4-yl)-methanol (145 mg, 1 mmol) was dissolved in chloroform (10 ml) and cooled in an ice bath under nitrogen atmosphere. With stirring, triethylamine (210 µl 1.5 mmol) was added and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3,5-Dichloro-benzoyl)-5-isopropyl-1H-pyrimidine-2,4-dione (327 mg, 1 mmol), powdered anhydrous potassium carbonate (138 mg, 1 mmol), and lithium iodide (134 mg, mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 185 mg (42%) of a white solid. $^1$H-NMR (300 MHz, CDCl$_3$) δ 1.18 (3H, d, J=6.7 Hz), 1.24 (3H, d, J=6.7 Hz), 2.26 (1H, m), 4.77 (2H, s), 6.57 (2H, s), 7.67 (3H, s), 9.56 (1H, s); m/z (EI) 453 (M$^+$); HRMS (EI) Calcd, 430.120797, Found 430.120560.

Example AO

To a stirred solution of (2-Fluoro-pyridin-4-yl)-methanol (127 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3,5-Dichloro-benzoyl)-5-isopropyl-1H-pyrimidine-2,4-dione (327 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 194 mg (44%) of a white solid.

m.p. 226-268° C.; $^1$H-NMR (200 MHz, CDCl$_3$) δ 1.16 (3H, d, J=6.8 Hz), 1.24 (3H, d, J=6.8 Hz), 2.25 (1H, m), 4.67 (1H, d, J=16.4 Hz), 4.91 (1H, d, J=16.4 Hz), 6.64 (1H, s), 6.90 (1H, d, J=5.0 Hz), 7.62 (3H, s), 8.07 (1H, d, J=5.0 Hz), 9.19 (1H, s); m/z (EI) 435 [M$^+$].

Example AP

To a stirred solution of (2-Fluoro-pyridin-4-yl)-methanol (127 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3,5-Dichloro-benzoyl)-5-ethyl-1H-pyrimidine-2,4-dione (313 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 120 mg (28%) of a white solid. m.p. 162-163° C.; $^1$H-NMR (200 MHz, CDCl$_3$/CD$_3$OD) δ 0.98 (3H, t, J=7.4 Hz), 2.06 (1H, m), 2.19 (1H, m), 4.79 (2H, s), 6.71 (1H, s), 6.96 (1H, d, J=5.4 Hz), 7.65 (3H, s), 8.07 (1H, d, J=5.4 Hz); m/z (EI) 421 [M$^+$].

Examples AQ and AR

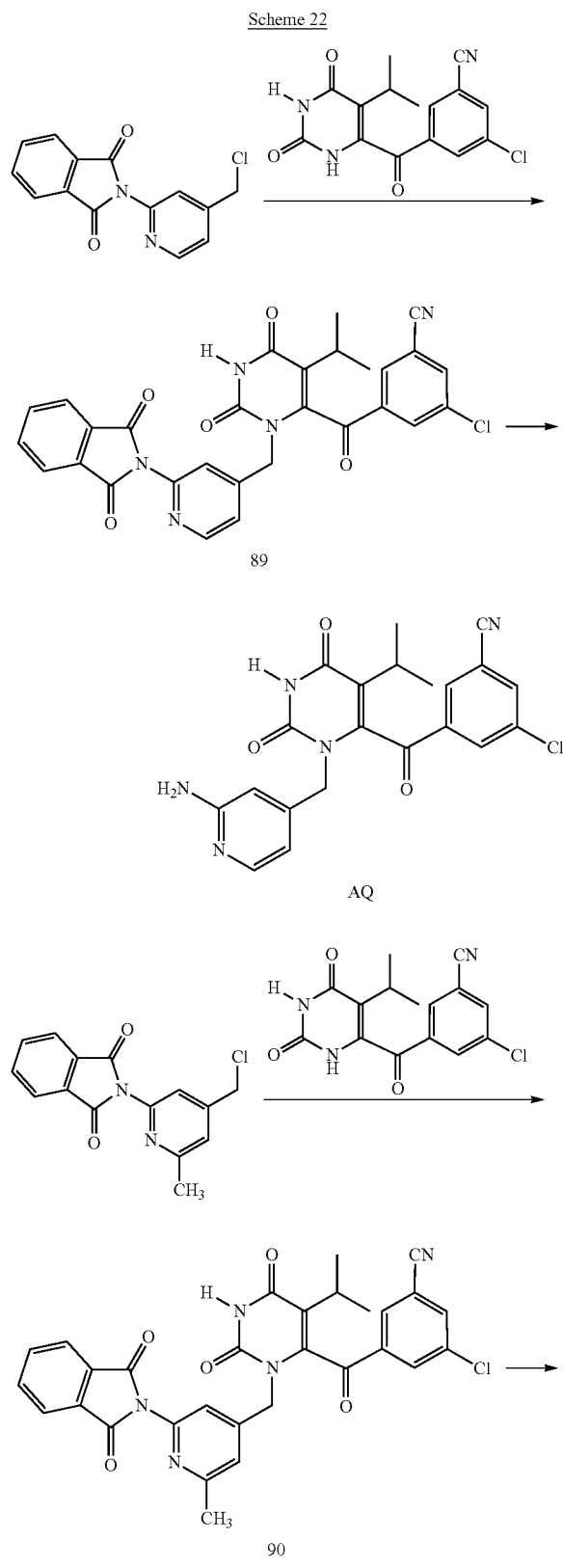

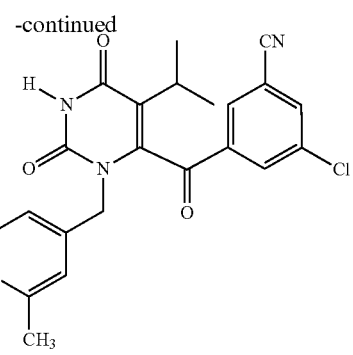

AR

3-Chloro-5-{3-[2-(1,3-dioxo-1,3-dihydro-isoindol-2-yl)-pyridin-4-ylmethyl]-5-isopropyl-2,6-dioxo-1,2,3,6-tetrahydro-pyrimidine-4-carbonyl}-benzonitrile (89): To a stirred solution of 3-Chloro-5-(5-isopropyl-2,6-dioxo-1,2,3,6-tetrahydro-pyrimidine-4-carbonyl)-benzonitrile (317 mgmg, 1 mmol), anhydrous powdered potassium carbonate (134 mg, 1 mmol), and lithium iodide (134 mg, 1 mmol) in DMF (5 ml) at room temperature, was added 2-(4-Chloromethyl-pyridin-2-yl)-isoindole-1,3-dione (272 mg, 1 mmol). After stirring for overnight, the mixture was evaporated in vacuo and the residue was purified by silica gel column chromatography (eluent, EA:hexanes (1:1); Rf~ⓔ0.3 fraction was collected.) to afford 160 mg (29%) of a white solid.

Example AQ

Compound 89 (160 mg, 0.29 mmol) was refluxed with hydrazine monohydrate (28 μl, 0.58 mmol) in ethanol (8 ml) for 3 hr. After cooling to room temperature, the mixture was evaporated in vacuo and the residue was purified by silica gel column chromatography (eluent, methanol:chloroform (5:95)) to afford 98 mg (80%) of a pale yellow solid. m.p. 243-244° C.; 1H-NMR (200 MHz, DMSO-$d_6$) δ 1.03 (3H, d, J=7.4 Hz), 1.10 (3H, d, J=7.0 Hz), 2.10 (1H, m), 4.49 (2H, s), 5.80 (2H, s), 6.08 (1H, s), 6.19 (1H, d, J=5.4 Hz), 7.67 (1H, d, J=5.4 Hz), 8.28 (1H, s), 8.38 (1H, s), 8.50 (1H, s), 11.67 (1H, s); m/z (EI) 423 ($M^+$).

3-Chloro-5-{3-[2-(1,3-dioxo-1,3-dihydro-isoindol-2-yl)-6-methyl-pyridin-4-ylmethyl]-5-isopropyl-2,6-dioxo-1,2,3,6-tetrahydro-pyrimidine-4-carbonyl}-benzonitrile (90): To a stirred solution of 3-Chloro-5-(5-isopropyl-2,6-dioxo-1,2,3,6-tetrahydro-pyrimidine-4-carbonyl)-benzonitrile (317 mg, 1 mmol), anhydrous powdered potassium carbonate (134 mg, 1 mmol), and lithium iodide (134 mg, 1 mmol) in DMF (5 ml) at room temperature, was added 2-(4-Chloromethyl-6-methyl-pyridin-2-yl)-isoindole-1,3-dione (286 mg, 1 mmol). After stirring for overnight, the mixture was evaporated in vacuo and the residue was purified by silica gel column chromatography (eluent, EA:hexanes (1:1); Rf~0.3 fraction was collected.) to afford 280 mg (49%) a yellow solid.

Example AR

Compound 90 (280 mg, 0.49 mmol) was refluxed with hydrazine monohydrate (97 μl, 2 mmol) in ethanol (10 ml) for 3 hr. After cooling to room temperature, the mixture was evaporated in vacuo and the residue was purified by silica gel column chromatography (eluent, methanol:chloroform (1:9)) to afford 100 mg (46%) of a pale yellow solid. m.p. 294-295° C.; 1H-NMR (200 MHz, DMSO-$d_6$) δ 1.04 (3H, d, J=7.0 Hz), 1.10 (3H, d, J=7.4 Hz), 2.04-2.09 (4H, m), 4.25 (1H, d, J=17.0

Hz), 4.71 (1H, d, J=17.0 Hz), 5.68 (2H, s), 5.84 (1H, s), 6.10 (1H, s), 8.24 (1H, m), 8.34 (1H, m), 8.44 (1H, s), 11.64 (1H, s); m/z (EI) 437 (M+).

Examples AS and AT

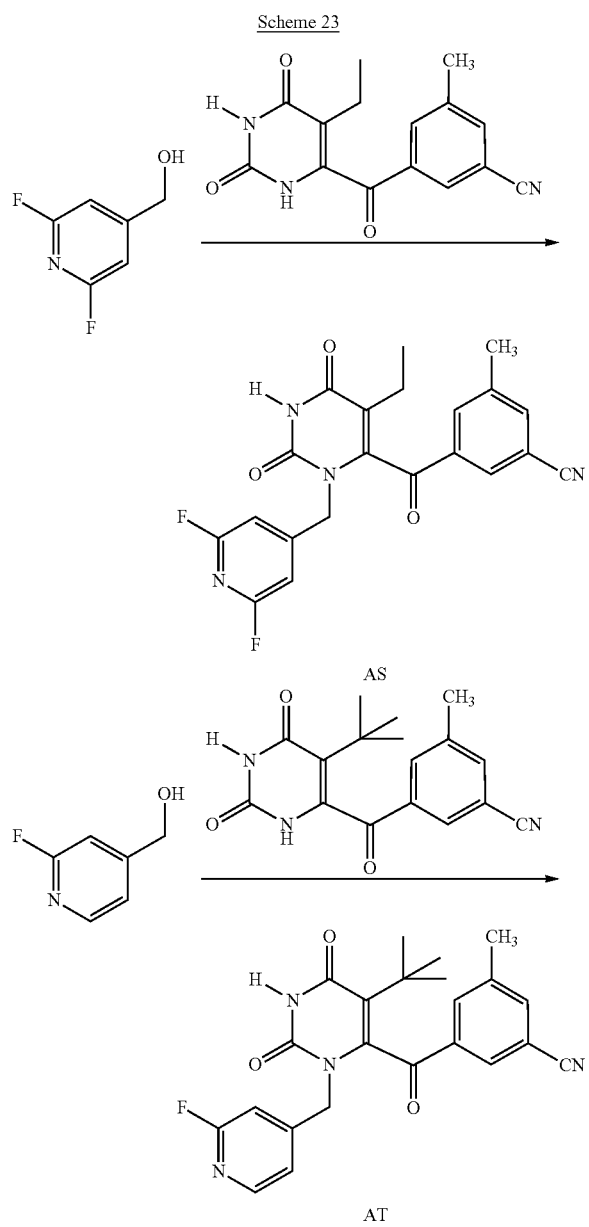

Example AS

To a stirred solution of (2,6-Difluoro-pyridin-4-yl)-methanol (145 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 3-(5-Ethyl-2,6-dioxo-1,2,3,6-tetrahydro-pyrimidine-4-carbonyl)-5-methyl-benzonitrile (283 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:1)) to afford 123 mg (30%) of a white solid. m.p. 186-187° C.; 1H-NMR (200 MHz, DMSO-$d_6$) δ 0.84 (3H, t, J=7.4 Hz), 1.80-2.07 (2H, m) 2.35 (3H, s), 4.60-4.90 (2H, m), 6.95 (2H, s), 7.98 (1H, s), 8.10 (1H, s), 8.34 (1H, s), 11.78 (1H, s); m/z (EI) 410 (M+).

Example AT

To a stirred solution of (2-Fluoro-pyridin-4-yl)-methanol (127 mg, 1 mmol) in chloroform (10 ml) cooled in an ice bath under nitrogen atmosphere, was added triethylamine (210 µl, 1.5 mmol) and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 3-(5-tert-Butyl-2,6-dioxo-1,2,3,6-tetrahydro-pyrimidine-4-carbonyl)-5-methyl-benzonitrile (311 mg, 1 mmol), powdered anhydrous potassium carbonate (138 mg, 1 mmol), and lithium iodide (134 mg, 1 mmol). DMF (5 ml) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 110 mg (26%) of a white solid. m.p. 247-248° C.; $^1$H-NMR (200 MHz, DMSO-$d_6$) δ 1.13 (9H, s), 2.35 (3H, s), 4.63 (2H, s), 6.87 (1H, s), 6.97 (1H, d, J=5.0 Hz), 7.93 (1H, s), 7.98 (1H, d, J=5.0 Hz), 8.08 (1H, s), 8.42 (1H, br. s), 11.69 (1H, s); m/z (EI) 420 [M+].

Examples AU and AV

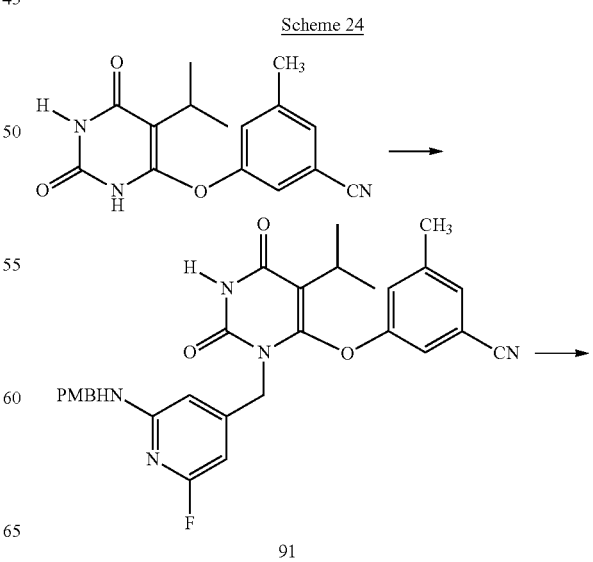

91

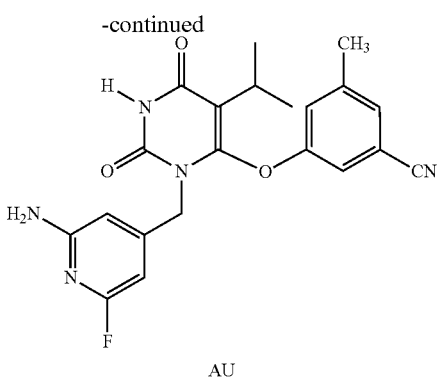

AU

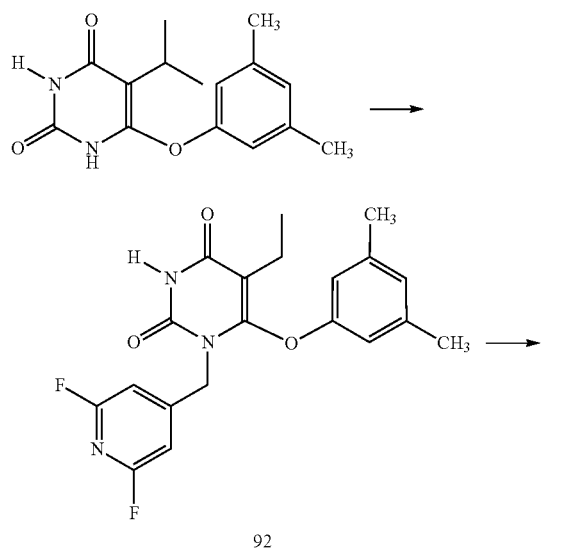

92

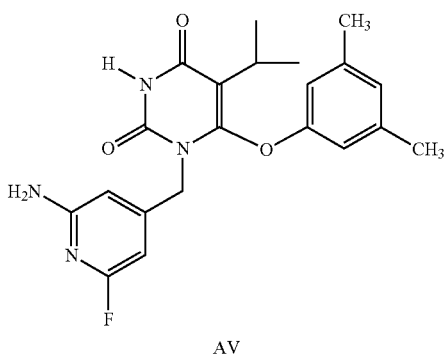

AV

3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-benzonitrile (91): [2-Fluoro-6-(4-methoxy-benzylamino)-pyridin-4-yl]-methanol (262 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 3-(5-Isopropyl-2,6-dioxo-1,2,3,6-tetrahydro-pyrimidin-4-yloxy)-5-methyl-benzonitrile (285 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:1)) to afford 253 mg (47%) of a colorless syrup. $^1$H NMR (200 MHz, CDCl$_3$/CD$_3$OD) δ 1.09 (6H, d, J=6.8 Hz), 2.32 (3H, s), 2.62 (1H, m), 3.80 (3H, s), 4.32 (2H, s), 4.70 (2H, s), 5.97 (1H, s), 6.24 (1H, s), 6.74-6.92 (3H, m), 7.18-7.32 (4H, m).

Example AU

To a stirred solution of 91 (253 mg, 0.478 mmol) in acetonitrile (4 ml), was added ceric ammonium nitrate (524 mg, 0.956 mmol) and distilled water (2 ml) in this order. After 30 min., EA and water was added to the reaction mixture. Organic layer was taken, dried with anhydrous magnesium sulfate, filtered, and evaporated in vacuo. The residue was purified by silica gel column chromatography (eluent, EA:hexanes (1:1)) to afford 92 mg (47%) of KRV-2169 as a pale brown syrup. Recrystallization from chloroform/ether/hexane resulted a white solid. m.p. 256-258° C.; $^1$H-NMR (200 MHz, CDCl$_3$) δ 1.11 (6H, d, J=6.8 Hz), 2.36 (3H, s) 2.64 (1H, m), 4.77 (2H, s), 4.80 (2H, s), 5.89 (1H, s), 6.16 (1H, s), 6.87 (1H, s), 7.00 (1H, s), 7.22 (1H, s), 9.87 (1H, s); m/z (EI) 409 [M$^+$].

1-(2,6-Difluoro-pyridin-4-ylmethyl)-6-(3,5-dimethyl-phenoxy)-5-isopropyl-1H-pyrimidine-2,4-dione (92): (2,6-Difluoro-pyridin-4-yl)-methanol (145 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 6-(3,5-Dimethyl-phenoxy)-5-isopropyl-1H-pyrimidine-2,4-dione (274 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexanes (1:2)) to afford 200 mg (50%) of a white solid. $^1$H-NMR (300 MHz, CDCl$_3$) δ 1.14 (6H, d, J=6.7 Hz), 2.27 (6H, s), 2.78 (1H, m), 4.90 (2H, s), 6.44 (2H, s), 6.61 (2H, s), 6.76 (1H, s), 8.81 (1H, s); m/z (EI) 401 (M$^+$).

Example AV

Compound 92 (220 mg, 0.548 mmol) and saturated ammonia in methanol (10 ml) were placed into a steel bomb and heated for 18 hr. in an oil bath (100-110° C.). After cooling to room temperature, the mixture was evaporated in vacuo and the residue was purified by silica gel column chromatography (eluent, EA:hexanes (1:1)) to afford 144 mg (66%) of a white solid. m.p. 213-215° C.; $^1$H-NMR (200 MHz, CDCl$_3$) δ 1.10 (6H, d, J=7.0 Hz), 2.29 (6H, s), 2.76 (1H, m), 4.68 (2H, s), 4.74 (2H, s), 5.99 (1H, s), 6.21 (1H, s), 6.47 (2H, s), 6.76 (1H, s), 9.53 (1H, s); m/z (EI) 398 (M⁺); HRMS (EI) Calcd, 398.175419, Found 398.177132.
Example AW
Scheme 25
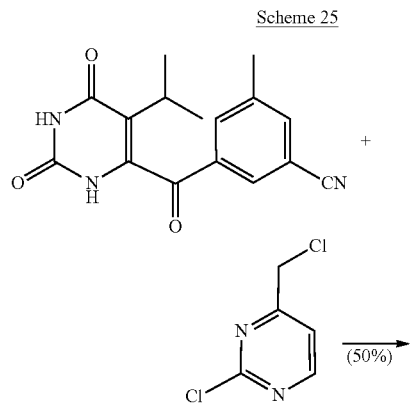
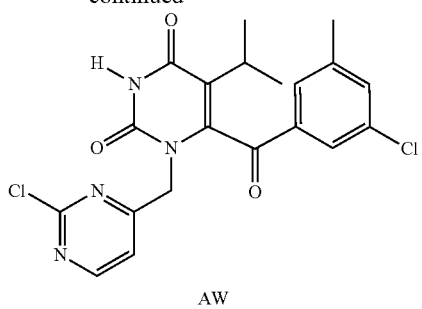
AW
Example AW
Example AW was prepared in a manner similar to Example L except that 3-(5-Isopropyl-2,6-dioxo-1,2,3,6-tetrahydro-pyrimidine-4-carbonyl)-5-methyl-benzonitrile was reacted with 2-Chloro-4-chloromethyl-pyrimidine to give Example AW with 50% yield.
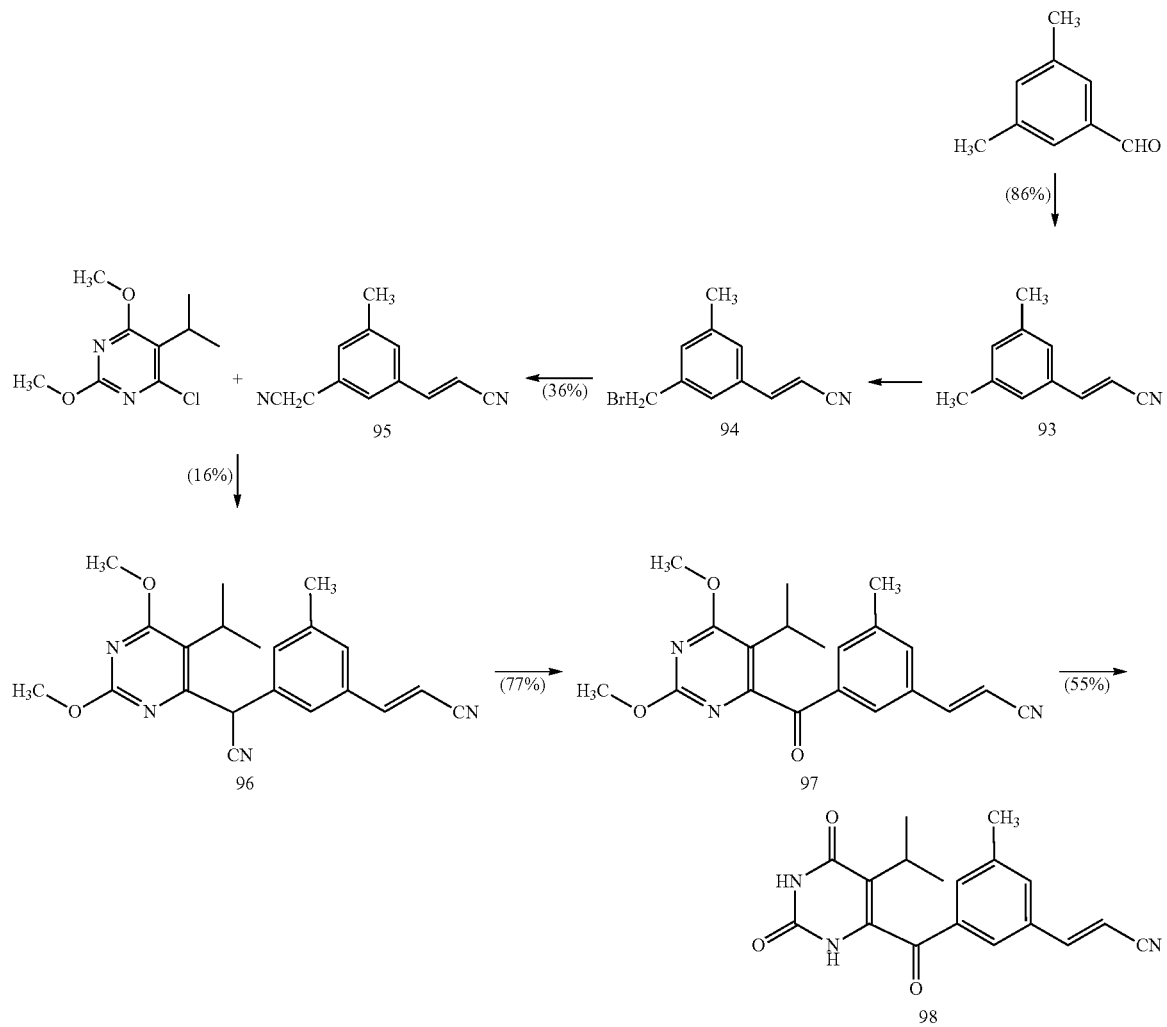
Scheme 26

3-(3,5-Dimethyl-phenyl)-acrylonitrile (93): To a stirred mixture of 3,5-dimethyl benzaldehyde (13.4 g, 0.1M), diethyl cyanomethylphosphonate (19.4 g, 0.11M) in anhydrous THF (200 ml) under nitrogen at 0° C. (ice bath), was added potassium t-butoxide (12.3 g, 0.11M). After stirring for 1 hr., the mixture was stirred for overnight at room temperature. The mixture was then partitioned between ether and water. The ether layer was taken, dried with anhydrous magnesium sulfate, filtered, evaporated in vacuo, and the residue was purified by silica gel column chromatography (eluent, ether:hexanes (1:20)) to afford 14.8 g (86%) of a white solid. m.p. 67-68° C.; $^1$H NMR (200 MHz, CDCl$_3$) δ 2.33 (6H, s), 5.83 (1H, d, J=16.6 Hz), 7.05 (3H, s), 7.28 (1H, d, J=16.6 Hz).

3-(3-Cyanomethyl-5-methyl-phenyl)-acrylonitrile (95): A mixture of 3-(3,5-Dimethyl-phenyl)-acrylonitrile (93) (15.7 g, 0.1M), NBS (18.58 g, 0.11M) and benzoyl peroxide (2.42 g, 10 mmol) in carbon tetrachloride (120 ml) was refluxed for 3 hr. under a light of 500 W tungsten lamp. After cooling to room temperature, the mixture was filtered and the filterate was evaporated in vacuo. The residue was dissolved in ether, washed with aqueous saturated sodium bicarbonate solution, dried with anhydrous magnesium sulfate, filtered, and evaporated in vacuo to give a crude product as a light yellow solid (94). A mixture of the crude product (94) and potassium cyanide (9.75 g, 0.15M) in ethanol (60 ml) and distilled water (30 ml) was refluxed for 2 hr. After cooling to room temperature, the mixture was evaporated in vacuo and the residue was partitioned between EA-ether (1:1) and water. The organic layer was taken, dried with anhydrous magnesium sulfate, filtered, and evaporated in vacuo. The residue was purified by silica gel column chromatography (eluent, ether: hexanes (from 1:1 to 2:1)) to afford 6.68 g (36%) of a pale yellow oil. $^1$H NMR (300 MHz, CDCl$_3$) δ 2.39 (3H, s), 3.74 (2H, s), 5.91 (1H, d, J=16.5 Hz), 7.21 (3H, s), 7.34 (1H, d, J=16.5 Hz).

3-{3-[Cyano-(5-isopropyl-2,6-dimethoxy-pyrimidin-4-yl)-methyl]-5-methyl-phenyl}-acrylonitrile (96): To a stirred mixture of 4-chloro-5-isopropyl-2,6-dimethoxy-pyrimidine (7.12 g, 32.88 mmol) and 3-(3-bromomethyl-5-methyl-phenyl)-acrylonitrile (5.7 g, 31.21 mmol) in anhydrous DMF (60 ml) at 0° C. (ice bath) under nitrogen atmosphere, was portionwise added 60% sodium hydride (2.76 g, 68.88 mmol). After stirring for 1 hr., the mixture was further stirred at room temperature for overnight. The mixture was then neutralized with aqueous saturated ammonium chloride solution and the crude product was extracted with ether and purified by silica gel column chromatography (eluent, EA: hexanes (from 1:4 to 1:2)) to afford 1.8 g (16%) of a pale yellow foam. $^1$H NMR (300 MHz, CDCl$_3$) δ 1.12 (3H, d, J=6.9 Hz), 1.15 (3H, d, J=6.9 Hz), 2.37 (3H, s), 3.02 (1H, m), 4.01 (6H, s), 5.39 (1H, s), 5.87 (1H, d, J=16.5 Hz), 7.23 (1H, s), 7.25 (1H, s), 7.27 (1H, s), 7.33 (1H, d, J=16.5 Hz).

3-[3-(5-Isopropyl-2,6-dimethoxy-pyrimidine-4-carbonyl)-5-methyl-phenyl]-acrylonitrile (97): To a stirred solution of 3-{3-[Cyano-(5-isopropyl-2,6-dimethoxy-pyrimidin-4-yl)-methyl]-5-methyl-phenyl}-acrylonitrile (96) (1.8 g, 4.97 mmol) in anhydrous DMF (20 ml) under nitrogen atmosphere, was added 60% sodium hydride (238 mg, 5.96 mmol). After 20 min., oxygen was bubbled into the reaction mixture for 3 hr. The mixture was partitioned between ether and aqueous saturated ammonium chloride solution. The organic layer was taken, washed with water twice, dried with anhydrous magnesium sulfate, filtered, and evaporated in vacuo. The residue was then purified by silica gel column chromatography (eluent, EA:hexanes (1:4)) to afford 1.34 g (77%) of a white solid. m.p. 144-145° C.; $^1$H NMR (300 MHz, CDCl$_3$) δ 1.19 (6H, d, J=6.9 Hz), 2.42 (3H, s), 2.83 (1H, m), 3.94 (3H, s), 4.08 (3H, s), 5.92 (1H, d, J=16.8 Hz), 3.39 (1H, d, J=16.8 Hz), 7.49 (1H, s), 7.69 (1H, s), 7.75 (1H, s).

3-[3-(5-Isopropyl-2,6-dioxo-1,2,3,6-tetrahydro-pyrimidine-4-carbonyl)-5-methyl-phenyl]-acrylonitrile (98): To a stirred solution of 3-[3-(5-Isopropyl-2,6-dimethoxy-pyrimidine-4-carbonyl)-5-methyl-phenyl]-acrylonitrile (5.36 g, 15.27 mmol) in anhydrous THF (50 ml), oxalyl chloride (25 ml) was added. The mixture was then refluxed with vigorous stirring for overnight. After cooling to room temperature, the mixture was evaporated in vacuo and the residue was purified by silica gel column chromatography (eluent, EA: hexanes (from 1:1 to 4:1)) to afford 2.7 g (55%) of a white solid. m.p. 233-235° C.; $^1$H NMR (300 MHz, CD$_3$OD/CDCl$_3$) δ 1.16 (6H, d, J=6.9 Hz), 2.39-2.56 (4H, m), 6.12 (1H, d, J=16.6 Hz), 7.49 (1H, d, J=16.6 Hz), 7.66 (1H, s), 7.83 (1H, s), 7.87 (1H, s); m/z (LC/Mass, EI) 324 (M+H$^+$).

Alternative Preparation Method of 3-[3-(5-Isopropyl-2,6-dioxo-1,2,3,6-tetrahydro-pyrimidine-4-carbonyl)-5-methyl-phenyl]-acrylonitrile Scheme 27

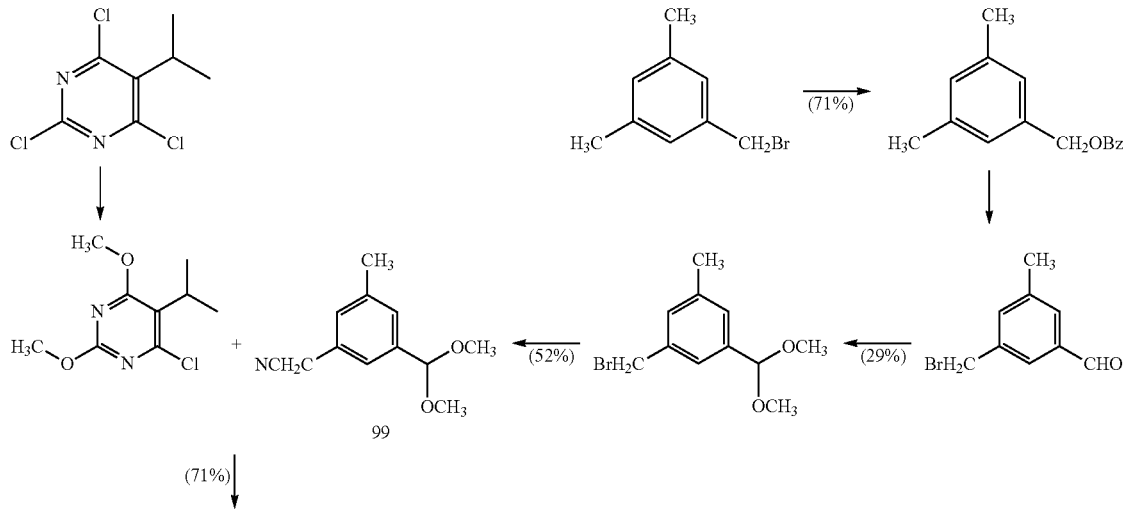

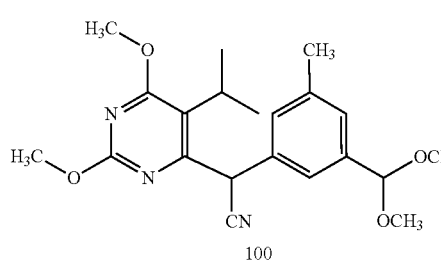

100

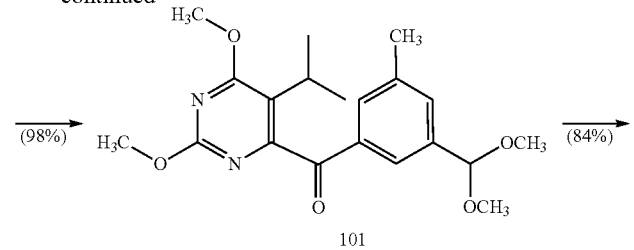

101

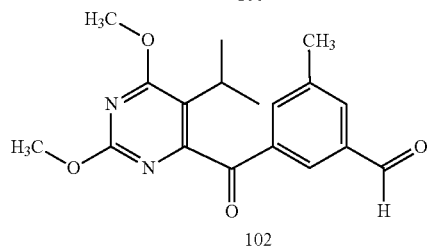

102

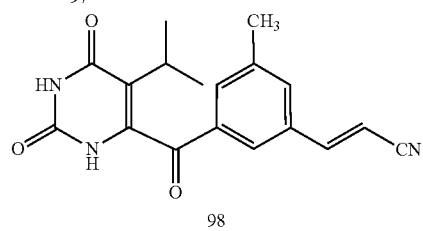

97

98

Benzoic acid 3,5-dimethyl-benzyl ester: A mixture of 3,5-dimethylbenzyl bromide (2, 39.8, 0.2M) and sodium benzoate (34.56 g, 0.24M) in anhydrous DMF (400 ml) was stirred at room temperature for overnight. The mixture was then partitioned between ether and water. The organic layer was taken, washed with water twice, dried with anhydrous magnesium sulfate, filtered, and evaporated in vacuo to give a pale yellow oil. The crude product was purified by silica gel column chromatography (eluent, hexane) to afford 32 g (71%) of a colorless oil. $^1$H NMR (200 MHz, CDCl$_3$) δ 2.33 (6H, s), 5.29 (2H, s), 6.98 (1H, s), 7.05 (2H, s), 7.38-7.59 (3H, m), 8.05-8.11 (2H, m).

1-Bromomethyl-3-dimethoxymethyl-5-methyl-benzene: A mixture of benzoic acid 3,5-dimethyl-benzyl ester (24 g, 0.1M) and NBS (39.16 g, 0.22M) in carbon tetrachloride (200 ml) was refluxed for 3 hr. under a light of 500 W tungsten lamp. After cooling to room temperature, the mixture was filtered and the filtrate was evaporated in vacuo. The residue was dissolved in ether, washed with aqueous saturated sodium bicarbonate solution, dried with anhydrous magnesium sulfate, filtered, and evaporated in vacuo to give 21 g of crude 3-bromomethyl-5-methyl-benzaldehyde.

A mixture of crude 3-bromomethyl-5-methyl-benzaldehyde (21 g, 98.51 mmol), trimethyl orthoformate (21.88 ml), and p-toluenesulfonic acid monohydrate (1.9 g) in anhydrous methanol (100 ml) was refluxed for 2 hr. After cooling to room temperature, the mixture was evaporated in vacuo. The residue was dissolved in ether, washed with aqueous sodium bicarbonate solution, dried with anhydrous magnesium sulfate, filtered, and evaporated in vacuo to give a crude product as a pale brown oil. The crude product was purified by silica gel column chromatography (eluent, ether:hexanes (1:9)) to afford 7.6 g (29% for 2 steps) of a colorless oil. $^1$H NMR (300 MHz, CDCl$_3$) δ 2.35 (3H, s), 3.33 (6H, s), 4.47 (2H, s), 5.32 (1H, s), 7.17 (1H, s), 7.19 (1H, s), 7.27 (1H, s).

(3-Dimethoxymethyl-5-methyl-phenyl)-acetonitrile (99): A mixture of 1-bromomethyl-3-dimethoxymethyl-5-methyl-benzene (6 g, 23 mmol) and sodium cyanide (1.7 g, 34 mmol) in methanol (30 ml) and distilled water (15 ml) was refluxed for 1.5 hr. After cooling to room temperature, the mixture was evaporated in vacuo and the residue was dissolved in ether, washed with water, dried with anhydrous magnesium sulfate, filtered, and evaporated in vacuo. The residue was then purified by silica gel column chromatography (eluent, ether:hexanes (1:3)) to afford 2.46 g (52%) of a colorless oil $^1$H NMR (300 MHz, CDCl$_3$) δ 2.37 (3H, s), 3.33 (6H, s), 3.71 (2H, s), 5.33 (1H, s), 7.12 (1H, s), 7.20 (1H, s), 7.22 (1H, s).

(3-Dimethoxymethyl-5-methyl-phenyl)-(5-isopropyl-2,6-dimethoxy-pyrimidin-4-yl)-acetonitrile (100): To a stirred mixture of 4-chloro-5-isopropyl-2,6-dimethoxy-pyrimidine (2.72 g, 12.5 mmol) and compound 6 (2.45 g, 11.9 mmol) in anhydrous DMF (20 ml) at 0° C. (ice bath) under nitrogen atmosphere, was added 60% sodium hydride (0.955 g, 23.8 mmol). After 1 hr., the mixture was further stirred for overnight at room temperature. The reaction mixture was then neutralized with aqueous saturated ammonium chloride solution and partitioned between ether and water. The ether layer was taken, washed with water twice, dried with anhydrous magnesium sulfate, filtered, and evaporated in vacuo to give an orange residue. The crude product was purified by silica gel column chromatography (eluent, EA:hexanes (1:9)) to afford 3.4 g (71%) a colorless syrup. $^1$H NMR (300 MHz, CDCl$_3$) δ 1.09 (3H, d, J=6.9 Hz), 1.11 (3H, d, J=6.9 Hz), 2.34 (3H, s), 3.04 (1H, m), 3.28 (3H, s), 3.29 (3H, s), 3.98 (3H, s), 4.02 (3H, s), 5.32 (1H, s), 5.38 (1H, s), 7.18 (1H, s), 7.22 (1H, s), 7.25 (1H, s).

(3-Dimethoxymethyl-5-methyl-phenyl)-(5-isopropyl-2,6-dimethoxy-pyrimidin-4-yl)-methanone (101): To a stirred solution of (3-dimethoxymethyl-5-methyl-phenyl)-(5-isopropyl-2,6-dimethoxy-pyrimidin-4-yl)-acetonitrile (3.4 g, 8.8 mmol) in anhydrous DMF (36 ml) at room temperature under nitrogen atmosphere, was added 60% sodium hydride (0.423 g, 10.6 mmol). After 20 min., oxygen was bubbled into the mixture for 3 hr. The mixture was then partitioned between ether and water, The ether layer was taken, washed with water twice, dried with anhydrous magnesium sulfate, filtered, and evaporated in vacuo. The residue was purified by silica gel column chromatography (eluent, EA:hexanes (1:4)) to afford 3.26 g (98%) of a pale yellow solid. m.p. 86-88° C.; $^1$H NMR (300 MHz, CDCl$_3$) δ 1.22 (6H, d, J=6.3 Hz), 2.41 (3H, s), 2.81 (1H, m), 3.31 (6H, s), 3.93 (3H, s), 4.06 (3H, s), 5.36 (1H, s), 7.53 (1H, s), 7.64 (1H, s), 7.71 (1H, s).

3-(5-Isopropyl-2,6-dimethoxy-pyrimidine-4-carbonyl)-5-methyl-benzaldehyde (102): To a stirred solution of (3-dimethoxymethyl-5-methyl-phenyl)-(5-isopropyl-2,6-dimethoxy-pyrimidin-4-yl)-methanone (3.13 g, 8.36 mmol) in chloroform (30 ml) at room temperature, was added hydrogen chloride in methanol solution [prepared from methanol (30 ml) and acetyl chloride (4 ml)]. After stirring for 2 hr., the mixture was evaporated in vacuo. The residue was dissolved in ether, washed with aqueous saturated sodium bicarbonate solution, dried with anhydrous magnesium sulfate, filtered, and evaporated in vacuo. The residue was purified by silica gel column chromatography (eluent, i) MC, ii) MC:EA (9:1)) to afford 2.3 g (84%) of a white solid. m.p. 111-113° C.; $^1$H NMR (300 MHz, CDCl$_3$) δ 1.20 (6H, d, J=7.2 Hz), 2.50 (3H, s), 2.85 (1H, m), 3.93 (3H, s), 4.08 (3H, s), 7.94 (1H, s), 7.99 (1H, s), 8.08 (1H, s), 10.02 (1H, s).

3-[3-(5-Isopropyl-2,6-dimethoxy-pyrimidine-4-carbonyl)-5-methyl-phenyl]-acrylonitrile (97): To a stirred mixture of 3-(5-isopropyl-2,6-dimethoxy-pyrimidine-4-carbonyl)-5-methyl-benzaldehyde (2.26 g, 6.89 mmol) and diethyl cyanomethylphosphonate (1.14 ml, 7.03 mmol) in anhydrous THF (15 ml) at 0° C. (ice bath) under nitrogen atmosphere, was added potassium t-butoxide (0.85 g, 7.58 mmol). After stirring for 1 hr., the mixture was further stirred for 4 hr. at room temperature. The reaction mixture was diluted with ether, washed with water, dried with anhydrous magnesium sulfate, filtered, and evaporated in vacuo. The residue was purified by silica gel column chromatography (eluent, EA:hexanes (1:4)) to afford 1.56 g (65%) of a white solid. m.p. 144-145° C.; $^1$H NMR (300 MHz, CDCl$_3$) δ 1.19 (6H, d, J=6.9 Hz), 2.42 (3H, s), 2.83 (1H, m), 3.94 (3H, s), 4.08 (3H, s), 5.92 (1H, d, J=16.8 Hz), 3.39 (1H, d, J=16.8 Hz), 7.49 (1H, s), 7.69 (1H, s), 7.75 (1H, s).

3-[3-(5-Isopropyl-2,6-dioxo-1,2,3,6-tetrahydro-pyrimidine-4-carbonyl)-5-methyl-phenyl]-acrylonitrile (98): To a stirred solution of 3-[3-(5-isopropyl-2,6-dimethoxy-pyrimidine-4-carbonyl)-5-methyl-phenyl]-acrylonitrile (5.36 g, 15.27 mmol) in anhydrous THF (50 ml), oxalyl chloride (25 ml) was added. The mixture was then refluxed with vigorous stirring for overnight. After cooling to room temperature, the mixture was evaporated in vacuo and the residue was purified by silica gel column chromatography (eluent, EA:hexanes (from 1:1 to 4:1)) to afford 2.7 g (55%) of a white solid. m.p. 233-235° C.; $^1$H NMR (300 MHz, CD$_3$OD/CDCl$_3$) δ 1.16 (6H, d, J=6.9 Hz), 2.39-2.56 (4H, m), 6.12 (1H, d, J=16.6 Hz), 7.49 (1H, d, J=16.6 Hz), 7.66 (1H, s), 7.83 (1H, s), 7.87 (1H, s); m/z (LC/Mass, EI) 324 (M+H$^+$).

Alternative Preparation Method of Intermediate 3-[3-(5-Isopropyl-2,6-dioxo-1,2,3,6-tetrahydro-pyrimidine-4-carbonyl)-5-methyl-phenyl]-acrylonitrile Scheme 28

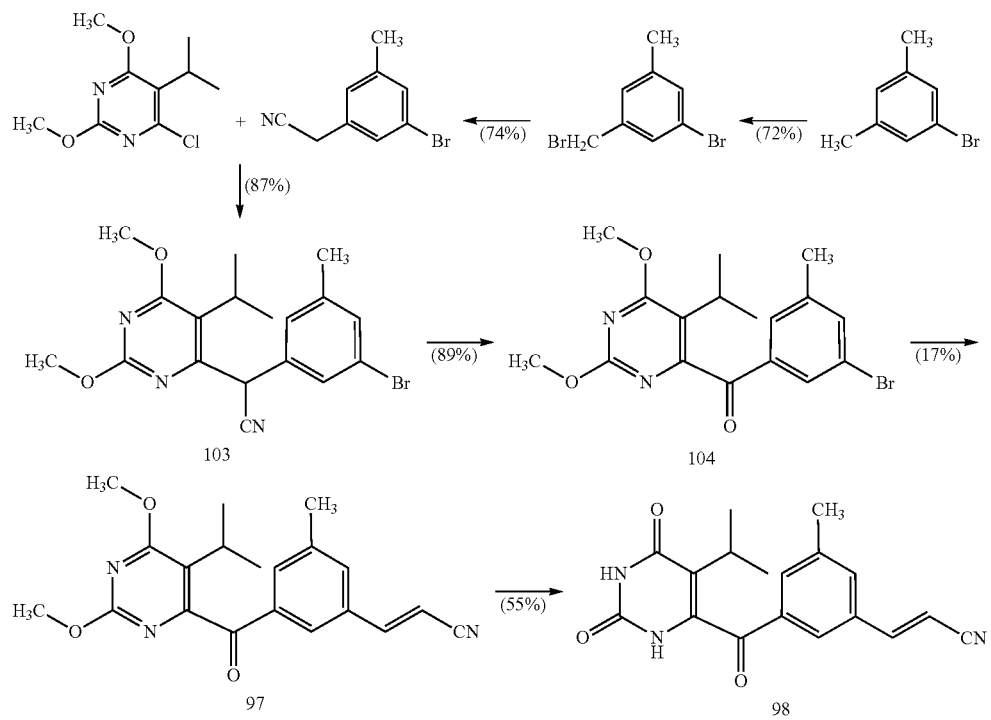

1-Bromo-3-bromomethyl-5-methyl-benzene: A mixture of 3,5-dimethylbromobenzene (80.25 g, 0.43M), NBS (77 g, 0.43M), and benzoyl peroxide (5.2 g, 0.021M) in carbon tetrachloride (400 ml) was refluxed for 3 hr. under a light of 500 W tungsten light. After cooling to room temperature, the mixture was filtered and the filtrate was evaporated in vacuo to give a white solid, which was purified by silica gel column chromatography (eluent, hexane) to afford 82 g (72%) of a white solid. m.p. 46-47° C.; $^1$H NMR (200 MHz, CDCl$_3$) δ 2.32 (3H, s), 4.38 (2H, s), 7.12 (1H, s), 7.25 (1H, s), 7.33 (1H, s).

(3-Bromo-5-methyl-phenyl)-acetonitrile: To a flask equipped with additional funnel, was placed potassium cyanide (29.6 g, 0.45M) and distilled water (30 ml). The mixture, with stirring, was heated up to 70° C. in an oil bath and 1-bromo-3-bromomethyl-5-methyl-benzene (80 g, 0.3M) in ethanol (150 ml) was dropwise added for 1 hr. through the addition funnel. After completion of addition, the mixture was refluxed for 2 hr. After cooling to room temperature, the mixture was evaporated in vacuo and the residue was partitioned between ether and water. The ether layer was taken, washed with water, dried with anhydrous magnesium sulfate, filtered, and evaporated in vacuo to give a brown residue, which was purified by silica gel column chromatography (eluent, ether:hexanes (1:3)) to afford 47 g (74%) of a light brown oil. $^1$H NMR (200 MHz, CDCl$_3$) δ 2.33 (3H, s), 3.68 (2H, s), 7.08 (1H, s), 7.28 (1H, s), 7.29 (1H, s).

(3-Bromo-5-methyl-phenyl)-(5-isopropyl-2,6-dimethoxy-pyrimidin-4-yl)-acetonitrile (103): To a stirred mixture of 4-chloro-5-isopropyl-2,6-dimethoxy-pyrimidine (47.63 g, 0.22M) and (3-bromo-5-methyl-phenyl)-acetonitrile (42 g, 0.2M) in anhydrous DMF (220 ml) in an ice-water bath under an atmosphere of nitrogen, was portionwise added 60% sodium hydride (16 g, 0.4M). After stirring for 1 hr., the mixture was stirred at room temperature for overnight. The mixture was neutralized with aqueous saturated ammonium chloride solution. The crude product was extracted with ether and purified by silica gel column chromatography (eluent, ether:hexanes (1:7)) to afford 68 g (87%) of a white solid. m.p. 123-124° C.; $^1$H NMR (200 MHz, CDCl$_3$) δ 1.11 (3H, d, J=6.9 Hz), 1.15 (3H, D, J=6.9 Hz), 2.32 (3H, s), 2.97 (1H, m), 4.00 (3H, s), 4.01 (3H, s), 5.34 (1H, s), 7.14 (1H, s), 7.28 (1H, s), 7.31 (1H, s).

(3-Bromo-5-methyl-phenyl)-(5-isopropyl-2,6-dimethoxy-pyrimidin-4-yl)-methanone (104): To a stirred solution of (3-bromo-5-methyl-phenyl)-(5-isopropyl-2,6-dimethoxy-pyrimidin-4-yl)-acetonitrile (40 g, 0.1M) in anhydrous DMF (300 ml) in a water bath under an atmosphere of nitrogen, was portionwise added 60% sodium hydride (4.92 g, 0.12M). After 30 min., oxygen gas was bubbled into the reaction mixture for 2 hr. The mixture was neutralized with aqueous saturated ammonium chloride solution. The crude product was extracted with ether and purified by silica gel column chromatography (eluent, ether:hexanes (1:9)) to afford 34.6 g (89%) of a white solid. m.p. 122-123° C.; $^1$H NMR (200 MHz, CDCl$_3$) δ 1.17 (6H, d, J=7.1 Hz), 2.36 (3H, s), 2.77 (1H, m), 3.92 (3H, s), 4.05 (3H, s), 7.54-7.56 (2H, m), 7.75 (1H, m).

3-[3-(5-Isopropyl-2,6-dimethoxy-pyrimidine-4-carbonyl)-5-methyl-phenyl]-acrylonitrile (97): To a stirred solution of (3-bromo-5-methyl-phenyl)-(5-isopropyl-2,6-dimethoxy-pyrimidin-4-yl)-methanone (3.79 g, 10 mmol) in anhydrous DMF (10 ml), was added sodium acetate (902 mg, 1 mmol), palladium acetate (224 mg, 1 mmol), tetrakis(triphenylphosphine)palladium(0) (1.049 g, 4 mmol), and acrylonitrile in this order. The mixture was then stirred at 90-132° C. (oil bath) for ca. 23 hr. After cooling to room temperature, ether and EA (2:1) was added to the reaction mixture. The mixture was then washed with aqueous saturated sodium bicarbonate solution, washed with water twice, dried with anhydrous magnesium sulfate, filtered, and evaporated in vacuo. The residue was purified by silica gel column chromatography (eluent, EA:hexanes (1:4)) to afford 595 mg (17%) of a white solid. Z-isomer (275 mg, 8%) was also obtained as a white solid. m.p. 144-145° C.; $^1$H NMR (300 MHz, CDCl$_3$) δ 1.19 (6H, d, J=6.9 Hz), 2.42 (3H, s), 2.83 (1H, m), 3.94 (3H, s), 4.08 (3H, s), 5.92 (1H, d, J=16.8 Hz), 7.39 (1H, d, J=16.8 Hz), 7.49 (1H, s), 7.69 (1H, s), 7.75 (1H, s). Z isomer: $^1$H NMR (300 MHz, CDCl$_3$) δ 1.19 (6H, d, J=7.2 Hz), 2.45 (3H, s), 2.84 (1H, m), 3.93 (3H, s), 4.06 (3H, s), 5.49 (1H, d, J=12.0 Hz), 7.11 (1H, d, J=12.0 Hz), 7.75 (1H, s), 7.90 (1H, s), 7.97 (1H, s).

3-[3-(5-Isopropyl-2,6-dioxo-1,2,3,6-tetrahydro-pyrimidine-4-carbonyl)-5-methyl-phenyl]-acrylonitrile (98): To a stirred solution of 3-[3-(5-isopropyl-2,6-dimethoxy-pyrimidine-4-carbonyl)-5-methyl-phenyl]-acrylonitrile (5.36 g, 15.27 mmol) in anhydrous THF (50 ml), oxalyl chloride (25 ml) was added. The mixture was then refluxed with vigorous stirring for overnight. After cooling to room temperature, the mixture was evaporated in vacuo and the residue was purified by silica gel column chromatography (eluent, EA: hexanes (from 1:1 to 4:1)) to afford 2.7 g (55%) of the a white solid. m.p. 233-235° C.; $^1$H NMR (300 MHz, CD$_3$OD/CDCl$_3$) δ 1.16 (6H, d, J=6.9 Hz), 2.39-2.56 (4H, m), 6.12 (1H, d, J=16.6 Hz), 7.49 (1H, d, J=16.6 Hz), 7.66 (1H, s), 7.83 (1H, s), 7.87 (1H, s); m/z (LC/Mass, EI) 324 (M+H$^+$).

Preparation Method of Intermediate 3-[3-(5-Ethyl-2,6-dioxo-1,2,3,6-tetrahydro-pyrimidine-4-carbonyl)-5-methyl-phenyl]-acrylonitrile Scheme 29

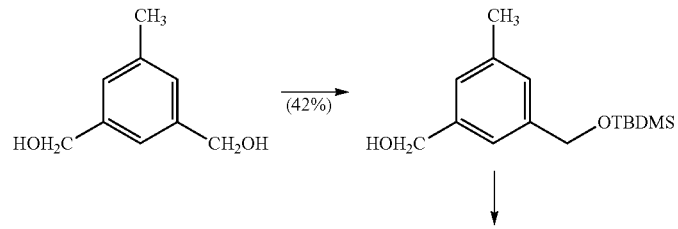

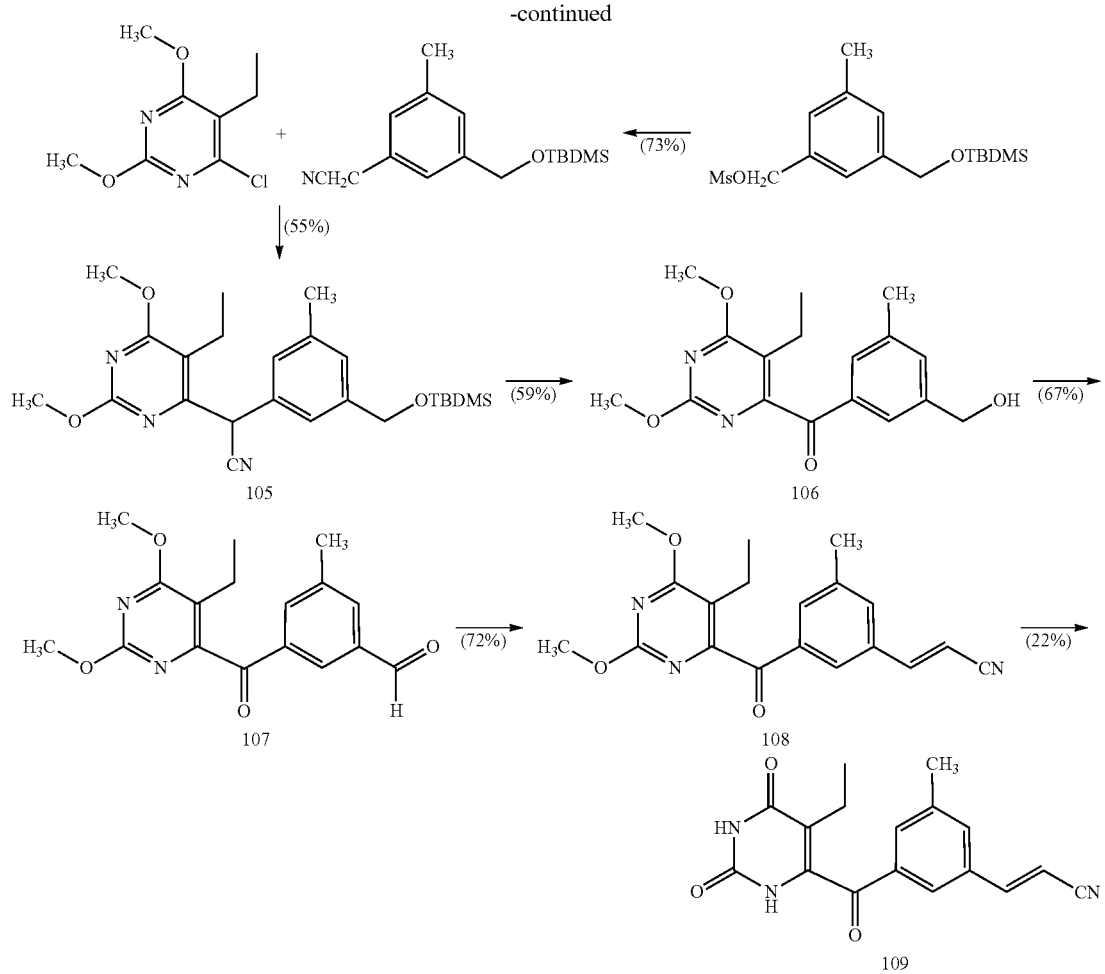

[3-(tert-Butyl-dimethyl-silanyloxymethyl)-5-methyl-phenyl]-methanol: To a stirred mixture of (3-hydroxymethyl-5-methyl-phenyl)-methanol (11.35 g, 74.67 mmol) and imidazole (7.62 g, 112 mmol) in anhydrous DMF (150 ml) at 0° C. (ice bath), was added t-butyldimethylsilyl chloride (11.25 g, 74.67 mmol). After stirring for overnight, the reaction mixture was evaporated in vacuo and the residue was purified by silica gel column chromatography (eluent, EA: hexanes (from 1:10 to 1:5)) to afford 8.3 g (42%) of a colorless oil. $^1$H NMR (200 MHz, CDCl$_3$) δ 0.11 (6H, s), 0.95 (9H, s), 2.35 (3H, s), 4.69 (2H, br. s), 4.75 (2H, s), 7.26-7.38 (4H, m).

[3-(tert-Butyl-dimethyl-silanyloxymethyl)-5-methyl-phenyl]-acetonitrile: To a stirred solution of [3-(tert-butyl-dimethyl-silanyloxymethyl)-5-methyl-phenyl]-methanol (11.1 g, 41.67 mmol) in dichloromethane (80 ml) at 0° C. (ice bath), was added triethylamine (8.78 ml, 62.5 mmol) followed by methanesulfonyl chloride (3.87 ml, 50 mmol). After stirring for 2 hr, the reaction mixture was washed with aqueous saturated sodium bicarbonate solution, dried with anhydrous magnesium sulfate, filtered, and evaporated in vacuo. The crude product was then dissolved in anhydrous DMF (80 ml) and sodium cyanide (6.28 g, 128 mmol) was added into the mixture. The mixture was stirred in an oil bath (60° C.) for 2 hr. After cooling to room temperature, the mixture was partitioned between ether and water. The ether layer was taken, washed with water twice, dried with anhydrous magnesium sulfate, filtered, and evaporated in vacuo. The residue was purified by silica gel column chromatography (eluent, EA: hexanes (from 1:20 to 1:10)) to afford 8.36 g (73%) of a white solid. m.p. 52-54° C.; $^1$H NMR (200 MHz, CDCl$_3$) δ 0.12 (6H, s), 0.95 (9H, s), 4.2.35 (3H, s), 3.71 (2H, s), 4.71 (2H, s), 7.03 (1H, s), 7.08 (2H, s).

[3-(tert-Butyl-dimethyl-silanyloxymethyl)-5-methyl-phenyl]-(5-ethyl-2,6-dimethoxy-pyrimidin-4-yl)-acetonitrile (105): To a stirred mixture of compound 1 (2.34 g, 16.5 mmol) and [3-(tert-butyl-dimethyl-silanyloxymethyl)-5-methyl-phenyl]-acetonitrile (4.33 g, 15.7 mmol) in anhydrous DMF (30 ml) at 0° C. (ice bath) under nitrogen atmosphere, was portionwise added 60% sodium hydride (1.26 g, 31.4 mmol). After stirring for 1 hr., the mixture was then stirred for overnight at room temperature. The mixture was neutralized with aqueous saturated ammonium chloride solution. The mixture was then partitioned between ether and water. The ether layer was taken, washed with water twice, dried with anhydrous magnesium sulfate, filtered, and evaporated in vacuo to give a crude product as a pale brown syrup. The crude product was purified by silica gel column chromatography (eluent, ether:hexanes (1:9)) to afford 3.8 g (55%) of a pale yellow syrup. $^1$H NMR (200 MHz, CDCl$_3$) δ 0.01 (6H, s), 0.83 (9H, s), 0.89 (3H, t, J=7.4 Hz), 2.26 (3H, s), 2.45 (2H, q, J=7.4 Hz), 3.91 (3H, s), 3.95 (3H, s), 4.60 (2H, s), 5.20 (1H, s), 6.99 (1H, s), 7.08 (2H, s).

(5-Ethyl-2,6-dimethoxy-pyrimidin-4-yl)-(3-hydroxymethyl-5-methyl-phenyl)-methanone (106): To a stirred solution of [3-(tert-butyl-dimethyl-silanyloxymethyl)-5-methyl-phenyl]-(5-ethyl-2,6-dimethoxy-pyrimidin-4-yl)-acetonitrile (3.74 g, 8.47 mmol) in anhydrous DMF (40 ml), was added 60% sodium hydride (373 mg, 9.32 mmol). After 20 min., oxygen was bubbled into the reaction mixture for 3 hr. The mixture was partitioned between ether and aqueous saturated ammonium chloride solution. The ether layer was taken, washed with water twice, dried with anhydrous magnesium sulfate, filtered, and evaporated in vacuo. The residue was stirred with p-toluenesulfonic acid monohydrate (152 mg, 0.8 mmol) in methanol (10 ml) for 2 hr. at room temperature. The mixture was evaporated in vacuo and the residue was purified by silica gel column chromatography (eluent, ether: hexanes (from 1:1 to 3:2)) to afford 1.59 g (59%) of a white solid. m.p. 101-103° C.; $^1$H NMR (200 MHz, CDCl$_3$) δ 1.05 (3H, t, J=7.4 Hz), 2.35-2.48 (5H, m), 3.93 (3H, s), 4.06 (3H, s), 4.63 (2H, br. S), 7.40 (1H, s), 7.56 (1H, s), 7.60 (1H, s).

3-(5-Ethyl-2,6-dimethoxy-pyrimidine-4-carbonyl)-5-methyl-benzaldehyde (107): A mixture of (5-ethyl-2,6-dimethoxy-pyrimidin-4-yl)-(3-hydroxymethyl-5-methyl-phenyl)-methanone (4.8 g, 15.2 mmol) and manganese dioxide (13.2 g, 152 mmol) in dichloromethane (110 ml) was stirred for 48 hr. at room temperature. The mixture was filtered through celite pad and the pad was washed with dichloromethane. The combined filtrate was evaporated in vacuo and the residue was purified by silica gel column chromatography (eluent, EA:hexanes (1:4)) to afford 3.22 g (67%) a white solid. m.p. 89-91° C.; $^1$H NMR (200 MHz, CDCl$_3$) δ 1.07 (3H, t, J=7.4 Hz), 2.41-2.52 (5H, m), 3.92 (3H, s), 4.06 (3H, s), 7.91 (1H, s), 7.99 (1H, s), 8.10 (1H, s), 10.01 (1H, s).

3-[3-(5-Ethyl-2,6-dimethoxy-pyrimidine-4-carbonyl)-5-methyl-phenyl]-acrylonitrile (108): To a stirred mixture of 3-(5-ethyl-2,6-dimethoxy-pyrimidine-4-carbonyl)-5-methyl-benzaldehyde (3.11 g, 9.9 mmol) and diethyl cyanomethyl-phosphonate (1.6 ml, 10 mmol) in anhydrous THF (20 ml) at 0° C. (ice bath) under nitrogen atmosphere, was added potassium t-butoxide (1.26 g, 11.2 mmol). After 1 hr., the mixture was stirred at room temperature for 5 hr. The mixture was then partitioned between ether and water. The ether layer was taken, dried with anhydrous magnesium sulfate, filtered, and evaporated in vacuo to give a pale yellow syrup. The crude product was purified by silica gel column chromatography (eluent, EA:hexanes (1:4)) to afford 2.39 g (72%) of a white solid. m.p. 165-166° C.; $^1$H NMR (200 MHz, CDCl$_3$) δ 1.09 (3H, t, J=7.8 Hz), 2.42-2.53 (5H, m), 3.96 (3H, s), 4.09 (3H, s), 5.93 (1H, d, J=16.8 Hz), 7.40 (1H, s, J=16.8 Hz), 7.50 (1H, s), 7.73 (1H, s), 7.79 (1H, s).

3-[3-(5-Ethyl-2,6-dioxo-1,2,3,6-tetrahydro-pyrimidine-4-carbonyl)-5-methyl-phenyl]-acrylonitrile (109): A mixture of 3-[3-(5-ethyl-2,6-dimethoxy-pyrimidine-4-carbonyl)-5-methyl-phenyl]-acrylonitrile (2.3 g, 6.82 mmol) and oxalyl chloride (10 ml) in anhydrous THF (30 ml) was refluxed for 4 hr. After cooling to room temperature, the mixture was evaporated in vacuo and the residue was purified by silica gel column chromatography (eluent, EA:hexanes (1:1)) to afford 460 mg (22%) of a white solid. m.p. 305-306° C.; $^1$H NMR (200 MHz, DMSO-d$_6$) δ 0.83 (3H, t, J=7.4 Hz), 1.94 (2H, q, J=7.4 Hz), 2.42 (3H, s), 6.65 (1H, d, J=16.8 Hz), 7.72 (1H, d, J=16.8 Hz), 7.80 (1H, s), 7.87 (1H, s), 8.01 (1H, s), 11.08 (1H, s), 11.29 (1H, s); m/z (LC/Mass, EI) 310 (M+H$^+$).

Preparation Method of Intermediate 3-[3-(5-Isopropyl-2,6-dioxo-1,2,3,6-tetrahydro-pyrimidine-4-carbonyl)-phenyl]-acrylonitrile Scheme 30

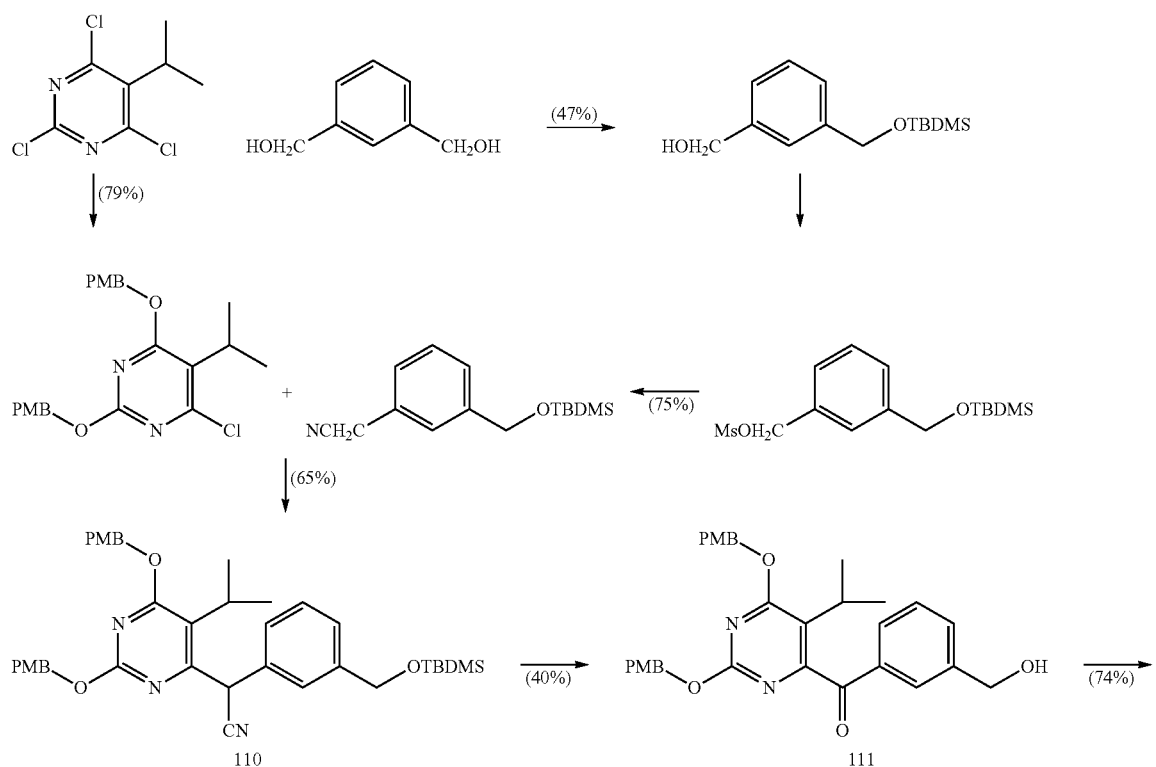

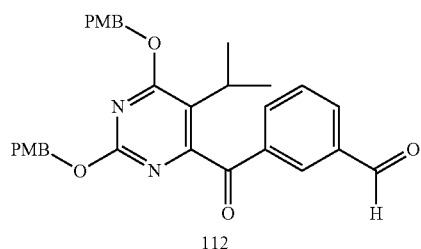

112

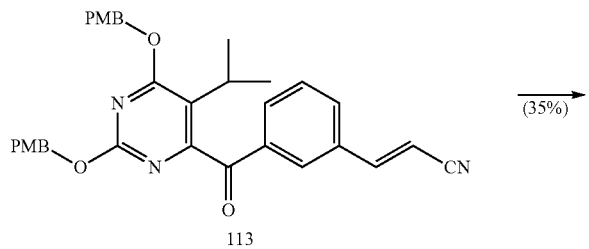

113

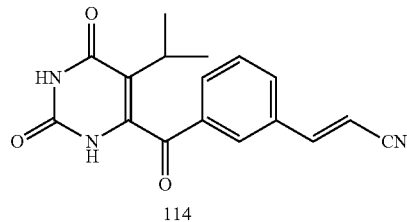

114

4-Chloro-5-isopropyl-2,6-bis-(4-methoxy-benzyloxy)-pyrimidine: To a stirred solution of p-methoxybenzyl alcohol (110 ml) in anhydrous DMF (50 ml) in a water bath under nitrogen atmosphere, was portionwise added 60% sodium hydride (4 g, 100 mmol). After complete reaction of sodium hydride, the mixture was cooled in an ice-water bath and 5-isopropyl-2,4,6-trichloropyrimidine (11.275 g, 50 mmol) was added. After 1 hr., the mixture was stirred for overnight at room temperature. The excess p-methoxybenzyl alcohol and DMF were distilled off in high vacuo and the residue was partitioned between ether and water. The ether layer was taken, washed with water, dried with anhydrous magnesium sulfate, filtered, and evaporated in vacuo to give a crude product as a colorless syrup. The crude product was purified by silica gel column chromatography (eluent, ether:hexanes (1:9)) to afford 17 g (79%) of a white solid. m.p. 69-70° C.; $^1$H NMR (200 MHz, CDCl$_3$) δ 1.23 (6H, d, J=7.0 Hz), 3.42 (1H, m), 3.81 (3H, s), 3.82 (3H, s), 5.31 (2H, s), 5.35 (2H, s), 6.87-6.92 (4H, m), 7.30-7.43 (4H, m).

[3-(tert-Butyl-dimethyl-silanyloxymethyl)-phenyl]-methanol: To a stirred mixture of 1,3-benzenedimethanol (18.5 g, 0.134M) and imidazole (13.66 g, 0.2M) in anhydrous DMF (150 ml) at 0° C. (ice bath) under a nitrogen atmosphere, was added t-butyldimethylsilyl chloride (20 g, 0.134M). After stirring for 4 hr., the mixture was evaporated in vacuo and the residue was purified by silica gel column chromatography (eluent, EA: hexanes (from 1:9 to 1:4)) to afford 16 g (47%) of a colorless oil. $^1$H NMR (200 MHz, CDCl$_3$) δ 0.11 (6H, s), 0.95 (9H, s), 1.63 (1H, t, J=6 Hz), 4.69 (2H, d, J=6 Hz), 4.75 (2H, s), 7.26-7.34 (4H, m).

[3-(tert-Butyl-dimethyl-silanyloxymethyl)-phenyl]-acetonitrile: To a stirred solution of [3-(tert-butyl-dimethyl-silanyloxymethyl)-phenyl]-methanol (10.52 g, 41.67 mmol) in dichloromethane (80 ml) at 0° C. (ice bath), was added triethylamine (8.78 ml, 62.5 mmol) followed by methanesulfonyl chloride (3.87 ml, 50 mmol). After stirring for 2 hr, the reaction mixture was washed with aqueous saturated sodium bicarbonate solution, dried with anhydrous magnesium sulfate, filtered, and evaporated in vacuo to give a pale yellow oil. The crude product was then dissolved in anhydrous DMF (80 ml) and sodium cyanide (6.28 g, 128 mmol) was added into the mixture. The mixture was stirred in an oil bath (60° C.) for 2 hr. After cooling to room temperature, the mixture was partitioned between ether and water. The ether layer was taken, washed with water twice, dried with anhydrous magnesium sulfate, filtered, and evaporated in vacuo. The residue was purified by silica gel column chromatography (eluent, EA: hexanes (from 1:20 to 1:10)) to afford 8.2 g (75%) of a pale yellow oil. $^1$H NMR (200 MHz, CDCl$_3$) δ 0.11 (6H, s), 0.95 (9H, s), 3.75 (2H, s), 4.75 (2H, s), 7.27-7.35 (4H, m).

[3-(tert-Butyl-dimethyl-silanyloxymethyl)-phenyl]-[5-isopropyl-2,6-bis-(4-methoxy-benzyloxy)-pyrimidin-4-yl]-acetonitrile (110): To a stirred mixture of 4-chloro-5-isopropyl-2,6-bis-(4-methoxy-benzyloxy)-pyrimidine (5.65 g, 13.17 mmol) and [3-(tert-butyl-dimethyl-silanyloxymethyl)-phenyl]-acetonitrile (3.27 g, 12.54 mmol) in anhydrous DMF (25 ml) in a water bath under a nitrogen atmosphere, was added 60% sodium hydride (1.0 g, 25.09 mmol). After 30 min., water bath was removed and the mixture was stirred for overnight at room temperature. The reaction mixture was neutralized with aqueous saturated ammonium chloride solution. The mixture was then partitioned between ether and water. The ether layer was taken, washed with water twice, dried with anhydrous magnesium sulfate, filtered, and evaporated in vacuo to give a crude product as a yellow oil. The crude product was purified by silica gel column chromatography (eluent, EA:hexanes (1:15)) to afford 5.34 g (65%) of a pale yellow syrup. $^1$H NMR (200 MHz, CDCl$_3$) δ 0.06 (6H, s), 0.90 (9H, s), 1.06 (6H, d, J=7.0 Hz), 3.01 (1H, m), 3.81 (6H, s), 4.71 (2H, s), 5.32 (2H, s), 5.35 (2H, s), 5.41 (3H, s), 6.86-6.91 (4H, m), 7.20-7.35 (6H, m), 7.41-7.49 (2H, m).

(3-Hydroxymethyl-phenyl)-[5-isopropyl-2,6-bis-(4-methoxy-benzyloxy)-pyrimidin-4-yl]-methanone (111): To a stirred solution of [3-(tert-butyl-dimethyl-silanyloxymethyl)-phenyl]-[5-isopropyl-2,6-bis-(4-methoxy-benzyloxy)-pyrimidin-4-yl]-acetonitrile (5.06 g, 7.75 mmol) in anhydrous DMF (30 ml), was added 60% sodium hydride (325 mg, 8.14 mmol). After 20 min., oxygen gas was bubbled into the reaction mixture for 3 hr. The mixture was partitioned between ether and aqueous saturated ammonium chloride solution. The ether layer was taken, washed with water twice, dried with anhydrous magnesium sulfate, filtered, and evaporated in vacuo. The residue was stirred with p-toluenesulfonic acid monohydrate (133 mg, 0.7 mmol) in methanol (10 ml) for 2 hr. at room temperature. The mixture was then evaporated in vacuo and the residue was purified by silica gel column chromatography (eluent, ether: hexanes (from 1:1 to 2:1)) to afford 1.67 g (40%) of a white foam. $^1$H NMR (200 MHz, CDCl$_3$) δ 1.15 (6H, d, J=6.8 Hz), 1.96 (1H, t, J=5.6 Hz), 2.82 (1H, m), 3.78 (3H, s), 3.82 (3H, s), 4.70 (2H, d, J=5.6 Hz), 5.28 (2H, s), 5.42 (2H, s), 6.78-6.98 (4H, m), 7.30-7.52 (5H, m), 7.61-7.79 (3H, m).

3-[5-Isopropyl-2,6-bis-(4-methoxy-benzyloxy)-pyrimidine-4-carbonyl]-benzaldehyde (112): A mixture of (3-hydroxymethyl-phenyl)-[5-isopropyl-2,6-bis-(4-methoxy-benzyloxy)-pyrimidin-4-yl]-methanone (1.9 g, 3.52 mmol), pyridinium chlorochromate (1.14 g, 5.28 mmol), and dried celite (1 g) in dichloromethane (20 ml) was stirred for 1 hr. at room temperature. The mixture was then filtered through a short silica gel pad and the pad was washed with EA. The combined filtrate was evaporated in vacuo and the residue was purified by silica gel column chromatography (eluent, EA:hexanes (1:4)) to afford 1.75 g (74%) of a pale yellow syrup. $^1$H NMR (200 MHz, CDCl$_3$) δ 1.19 (6H, d, J=7.4 Hz), 2.88 (1H, m), 3.79 (3H, s), 3.83 (3H, s), 5.29 (2H, s), 5.45 (2H, s), 6.77-6.95 (4H, m), 7.28-7.42 (4H, m), 7.65 (1H, m), 8.11-8.28 (3H, m), 10.03 (1H, s).

3-{3-[5-Isopropyl-2,6-bis-(4-methoxy-benzyloxy)-pyrimidine-4-carbonyl]-phenyl}-acrylonitrile (113): To a stirred mixture of 3-[5-isopropyl-2,6-bis-(4-methoxy-benzyloxy)-pyrimidine-4-carbonyl]-benzaldehyde (1.73 g, 3.22 mmol) and diethyl cyanomethylphosphonate (0.52 ml, 3.22 mmol) in anhydrous THF (10 ml) at 0° C. (ice bath) under nitrogen atmosphere, was added potassium t-butoxide (397 mg, 3.54 mmol). After 1 hr., the mixture was stirred for overnight at room temperature. The mixture was then partitioned between ether and water. The ether layer was taken, dried with anhydrous magnesium sulfate, filtered, and evaporated in vacuo to give a pale yellow syrup. The crude product was purified by silica gel column chromatography (eluent, EA:hexanes (2:7)) to afford 1.46 g (81%) of a pale yellow syrup. $^1$H NMR (200 MHz, CDCl$_3$) δ 1.19 (6H, d, J=7.0 Hz), 2.86 (1H, m), 3.82 (3H, s), 3.85 (3H, s), 5.31 (2H, s), 5.46 (2H, s), 5.93 (1H, d J=16.8 Hz), 6.81-6.97 (4H, m), 7.28-7.93 (8H, m).

3-[3-(5-Isopropyl-2,6-dioxo-1,2,3,6-tetrahydro-pyrimidine-4-carbonyl)-phenyl]-acrylonitrile (114): To a stirred solution of 3-{3-[5-isopropyl-2,6-bis-(4-methoxy-benzyloxy)-pyrimidine-4-carbonyl]-phenyl}-acrylonitrile (1.25 g, 2.23 mmol) in acetonitrile (10 ml) at room temperature, was added ceric ammonium nitrate (3.67 g, 6.70 mmol) followed by distilled water (5 ml). After 3 hr., the reaction mixture was diluted with EA, washed with water, dried with anhydrous magnesium sulfate, filtered, and evaporated in vacuo to give a crude product as a white solid. The crude product was purified by silica gel column chromatography (eluent, EA:hexanes (4:1)) to afford 240 mg (35%) of a white solid. m.p. 210-211° C.; $^1$H NMR (200 MHz, CD$_3$OD/CDCl$_3$) δ 1.10 (6H, d, J=6.8 Hz), 2.39 (1H, m), 6.03 (1H, d, J=16.8 Hz), 7.45 (1H, d, J=16.8 Hz), 7.58 (3H, m), 8.01 (1H, s); m/z (LC/Mass, EI) 310 (M+H$^+$).

Preparation Method of 3-[3-(5-Isopropyl-2,6-dioxo-1,2,3,6-tetrahydro-pyrimidin-4-yloxy)-5-methyl-phenyl]-acrylonitrile Scheme 31

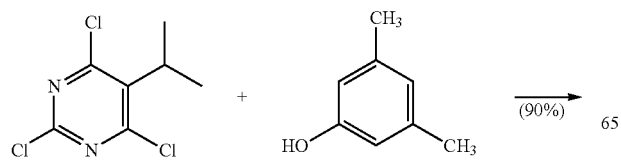

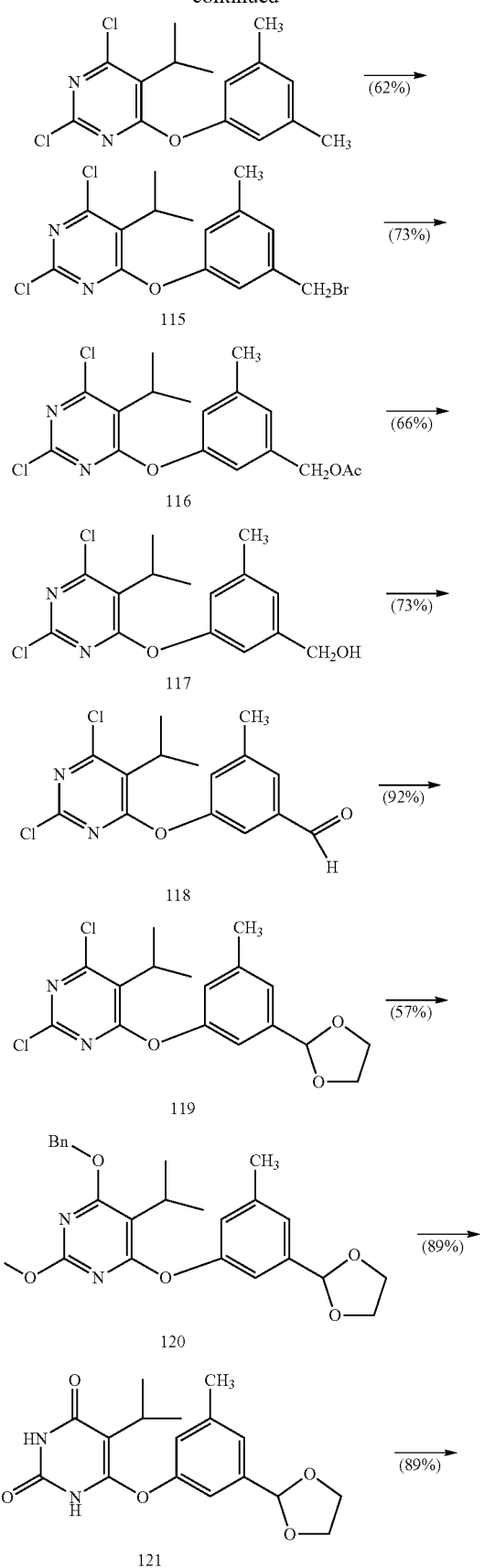

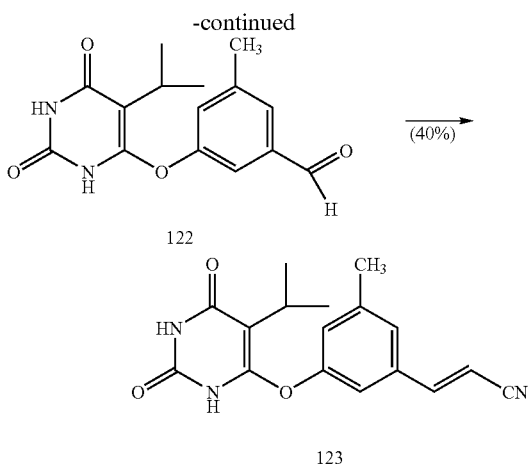

2,4-Dichloro-6-(3,5-dimethyl-phenoxy)-5-isopropyl-pyrimidine: To a stirred mixture of 5-isopropyl-2,4,6-trichloro-pyrimidine (23.68 g, 0.105M), 3,5-dimethylphenol (12.2 g, 0.2M) in anhydrous DMF (200 ml) cooled in a dry ice-acetone bath (−40° C.) under nitrogen atmosphere, was portionwise added 60% sodium hydride (4.2 g, 0.105M). The reaction temperature was then slowly raised to room temperature during 3 hr. The reaction mixture was then diluted with ether, washed with water twice, dried with anhydrous magnesium sulfate, filtered, and evaporated in vacuo to give a crude product as a pale yellow solid. The crude product was purified by silica gel column chromatography (eluent, ether: hexanes (1:9)) to afford 28 g (90%) of a white solid. m.p. 107-108° C.; $^1$H NMR (200 MHz, CDCl$_3$) δ 1.40 (6H, d, J=7.0 Hz), 2.35 (6H, s), 3.58 (1H, m), 6.72 (2H, s), 6.91 (1H, s).

4-(3-Bromomethyl-5-methyl-phenoxy)-2,6-dichloro-5-isopropyl-pyrimidine (115): A mixture of 2,4-dichloro-6-(3,5-dimethyl-phenoxy)-5-isopropyl-pyrimidine (9.72 g, 31 mmol), NBS (5.56 g, 31 mmol), and benzoyl peroxide (0.756 g, 3.1 mmol) in carbon tetrachloride (60 ml) was refluxed for 3 hr. under a light of 500 W tungsten lamp. After cooling to room temperature, the reaction mixture was filtered and evaporated in vacuo. The residue was purified by silica gel column chromatography (eluent, ether:hexanes (1:19)) to afford 8 g (62%) of a white solid. m.p. 98-101° C.; $^1$H NMR (200 MHz, CDCl$_3$) δ 1.41 (6H, d, J=7.2 Hz), 2.38 (3H, s), 3.59 (1H, m), 4.47 (2H, s), 6.86 (1H, s), 6.97 (1H, s), 7.13 (1H, s).

Acetic acid 3-(2,6-dichloro-5-isopropyl-pyrimidin-4-yloxy)-5-methyl-benzyl ester (116): To a stirred solution of 4-(3-bromomethyl-5-methyl-phenoxy)-2,6-dichloro-5-isopropyl-pyrimidine (14.4 g, 36.9 mmol) in anhydrous DMF (50 ml), was added sodium acetate (6.05 g, 73.8 mmol) and the mixture was stirred in an oil bath (90~100° C.) for overnight. After cooling to room temperature, the mixture was partitioned between ether and water. The ether layer was taken, washed with water twice, dried with anhydrous magnesium sulfate, filtered, and evaporated in vacuo. The residue was purified by silica gel column chromatography (eluent, ether: hexanes (from 1:9 to 1:4)) to afford 10 g (73%) of a white solid. m.p. 76-77° C.; $^1$H NMR (200 MHz, CDCl$_3$) δ 1.41 (6H, d, J=7.2 Hz), 2.12 (3H, s), 2.39 (3H, s), 3.58 (1H, m), 5.09 (2H, s), 6.88 (1H, s), 6.93 (1H, s), 7.08 (1H, s).

[3-(2,6-Dichloro-5-isopropyl-pyrimidin-4-yloxy)-5-methyl-phenyl]-methanol (117): To a stirred solution of acetic acid 3-(2,6-dichloro-5-isopropyl-pyrimidin-4-yloxy)-5-methyl-benzyl ester (5 g, 13.54 mmol) in THF (20 ml) at room temperature, was added lithium hydroxide (649 mg, 27 mmol) followed by distilled water (20 ml). After stirring for 23 hr., THF was removed in vacuo and the residue was partitioned between dichloromethane and water. The organic layer was taken, dried with anhydrous magnesium sulfate, filtered, and evaporated in vacuo. The residue was purified by silica gel column chromatography (eluent, ether: hexanes (from 1:4 to 1:1)) to afford 2.92 g (66%) of a white solid. m.p. 140-141° C.; $^1$H NMR (200 MHz, CDCl$_3$) δ 1.40 (6H, d, J=7.4 Hz), 1.76 (1H, t, J=5.6 Hz), 2.39 (3H, s), 3.58 (1H, m), 4.69 (2H, d, J=5.6 Hz), 6.84 (1H, s), 6.95 (1H, s), 7.09 (1H, s).

3-(2,6-Dichloro-5-isopropyl-pyrimidin-4-yloxy)-5-methyl-benzaldehyde (118): A mixture of [3-(2,6-dichloro-5-isopropyl-pyrimidin-4-yloxy)-5-methyl-phenyl]-methanol (2.36 g, 7.22 mmol), PCC (1.56 g, 7.22 mmol), and dried celite (2 g) was stirred in dichloromethane (20 ml) for 2 hr. at room temperature. The mixture was then filtered through a short silica gel pad and washed with EA. The combined filtrate was evaporated in vacuo and the residue was purified by silica gel column chromatography (eluent, EA:hexanes (1:15)) to afford 1.71 g (73%) of a pale yellow syrup. $^1$H NMR (200 MHz, CDCl$_3$) δ 1.42 (6H, d, J=7.2 Hz), 2.49 (3H, s), 3.61 (1H, m), 7.20 (1H, s), 7.44 (1H, s), 7.62 (1H, s), 10.01 (1H, s).

2,4-Dichloro-6-(3-[1,3]dioxolan-2-yl-5-methyl-phenoxy)-5-isopropyl-pyrimidine (119): A mixture of 3-(2,6-dichloro-5-isopropyl-pyrimidin-4-yloxy)-5-methyl-benzaldehyde (1.71 g, 5.25 mmol), ethylene glycol (0.88 ml, 15.75 mmol), and p-toluenesulfonic acid (263 mg, 0.26 mmol) in toluene (20 ml) was refluxed for 3 hr., using a reflux condenser equipped with a Dean-Stark trap. After cooling to room temperature, the mixture was diluted with EA, washed with aqueous saturated sodium bicarbonate solution, dried with anhydrous magnesium sulfate, filtered, and evaporated in vacuo. The residue was purified by silica gel column chromatography (eluent, EA:hexanes (1:15)) to afford 1.79 g (92%) of a colorless syrup. $^1$H NMR (200 MHz, CDCl$_3$) δ 1.40 (6H, d, J=7.0 Hz), 2.40 (3H, s), 3.58 (1H, m), 3.99-4.16 (4H, m), 5.82 (1H, s), 6.92 (1H, s), 7.03 (1H, s), 7.21 (1H, s).

2,4-Bis-benzyloxy-6-(3-[1,3]dioxolan-2-yl-5-methyl-phenoxy)-5-isopropyl-pyrimidine (120): To a stirred anhydrous benzyl alcohol (10 ml) under nitrogen atmosphere at room temperature, was added sodium metal (285 mg, 12.41 mmol). After 1 hr., 2,4-dichloro-6-(3-[1,3]dioxolan-2-yl-5-methyl-phenoxy)-5-isopropyl-pyrimidine (1.91 g, 5.17 mmol) in anhydrous benzyl alcohol (7 ml) was added. After stirring for overnight at room temperature, the mixture was evaporated in vacuo. The residue was dissolved in dichloromethane, filtered through a celite pad and the pad was washed with dichloromethane. The combined filtrate was then evaporated in vacuo and the residue was purified by silica gel column chromatography (eluent, EA:hexanes (1:10)) to afford 1.52 g (57%) of a colorless syrup. $^1$H NMR (200 MHz, CDCl$_3$) δ 1.30 (6H, d, J=7.2 Hz), 2.39 (3H, s), 3.43 (1H, m), 4.02-4.13 (4H, m), 5.12 (2H, s), 5.42 (2H, s), 5.81 (1H, s), 6.92 (1H, s), 7.07 (1H, s), 7.16 (1H, s), 7.20-7.43 (10H, m).

6-(3-[1,3]Dioxolan-2-yl-5-methyl-phenoxy)-5-isopropyl-1H-pyrimidine-2,4-dione (121): 2,4-Bis-benzyloxy-6-(3-[1,3]dioxolan-2-yl-5-methyl-phenoxy)-5-isopropyl-pyrimidine (1.56 g, 3.04 mmol) in anhydrous THF (20 ml) was stirred in the presence of 10% palladium on carbon (58 mg) under an atmosphere of hydrogen. After 3 hr., the mixture was filtered through a celite pad and the pad was washed with methanol. The combined filtrate was evaporated in vacuo and the residue was purified by silica gel column chromatography (eluent, EA:hexanes (4:1)) to afford 889 mg (89%) of a white solid. m.p. 201-203° C.; ¹H NMR (200 MHz, CDCl₃) δ 1.20 (6H, d, J=7.2 Hz), 2.37 (3H, s), 3.09 (1H, m), 4.02-4.15 (4H, m), 5.73 (1H, s), 6.80 (1H, s), 6.99 (1H, s), 7.16 (1H, s), 8.80 (1H, s), 9.19 (1H, s); m/z (LC/Mass, EI) 333 (M+H⁺).

3-(5-Isopropyl-2,6-dioxo-1,2,3,6-tetrahydro-pyrimidin-4-yloxy)-5-methyl-benzaldehyde (122): A mixture of 6-(3-[1,3]dioxolan-2-yl-5-methyl-phenoxy)-5-isopropyl-1H-pyrimidine-2,4-dione (1.33 g, 4 mmol), PPTS (201 mg, 0.8 mmol), and water (10 drops) in acetone (20 ml) was heated under reflux for 4 hr. After cooling to room temperature, the mixture was evaporated in vacuo and the residue was purified by silica gel column chromatography (eluent, CHCl₃: methanol (95:5)) to afford 1.03 g (89%) of a white solid. m.p. 241-242° C.; ¹H NMR (200 MHz, CD₃OD/CDCl₃) δ 1.03 (6H, d, J=7.2 Hz), 2.34 (3H, s), 2.84 (1H, m), 6.99 (1H, s), 7.17 (1H, s), 7.38 (1H, s), 9.81 (1H, s).

3-[3-(5-Isopropyl-2,6-dioxo-1,2,3,6-tetrahydro-pyrimidin-4-yloxy)-5-methyl-phenyl]-acrylonitrile (123): To a stirred mixture of 3-(5-isopropyl-2,6-dioxo-1,2,3,6-tetrahydro-pyrimidin-4-yloxy)-5-methyl-benzaldehyde (788 mg, 2.73 mmol) and diethyl cyanomethyl-phosphonate (451 μl, 2.79 mmol) in THF (15 ml) at 0° C. (ice bath) under nitrogen atmosphere, was added potassium t-butoxide (920 mg, 8.2 mmol). After stirring for 1 hr., the mixture was stirred for overnight at room temperature. The mixture was then diluted with EA, washed with aqueous saturated ammonium chloride solution, dried with anhydrous magnesium sulfate, filtered, and evaporated in vacuo. The residue was purified by silica gel column chromatography (eluent, EA: hexanes (from 2:3 to 1:1)) to afford 340 mg (40%) of a white solid. m.p. 279-280° C.; ¹H NMR (200 MHz, DMSO-d₆) δ 1.05 (6H, d, J=7.0 Hz), 2.33 (3H, s), 2.78 (1H, m), 6.55 (1H, d, J=16.8 Hz), 7.03 (1H, s), 7.21 (1H, s), 7.25 (1H, s), 7.62 (1H, d, J=16.8 Hz), 11.05 (1H, s), 11.31 (1H, s); m/z (LC/Mass, EI) 312 (M+H⁺).

Example AX

Scheme 32

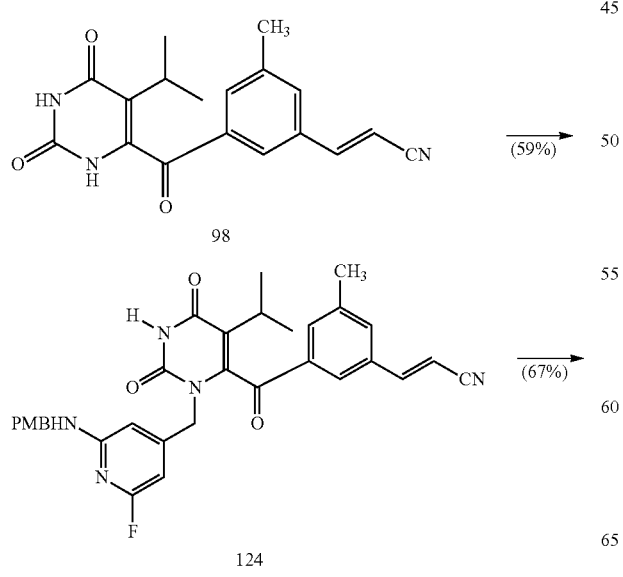

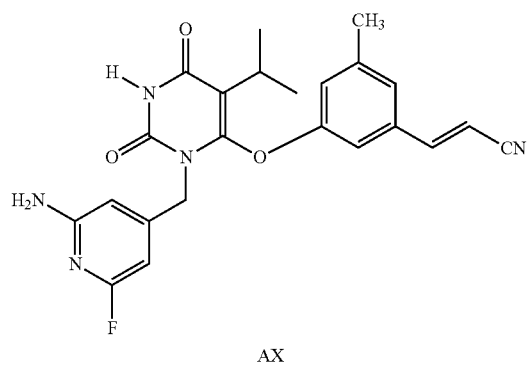

AX 3-(3-{3-[2-Fluoro-6-(4-methoxy-benzylamino)-pyridin-4-ylmethyl]-5-isopropyl-2,6-dioxo-1,2,3,6-tetrahydro-pyrimidine-4-carbonyl}-5-methyl-phenyl)-acrylonitrile (124): To a stirred solution of 2-fluoro-6-(p-methoxybenzylamino)-4-pyridine-methanol (262 mg, 1 mmol) in chloroform (10 ml) at 0° C. (ice bath), was added triethylamine (210 μl, 1.5 mmol) followed by methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (98) (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and evaporated in vacuo to give a light yellow foam. The crude product was purified by silica gel column chromatography (eluent, EA:hexanes (1:2); The fraction of Rf=0.16 was collected.) to afford 309 mg (59%) of a pale yellow foam.

Example AX

To a stirred solution of 3-(3-{3-[2-fluoro-6-(4-methoxy-benzylamino)-pyridin-4-ylmethyl]-5-isopropyl-2,6-dioxo-1,2,3,6-tetrahydro-pyrimidine-4-carbonyl}-5-methyl-phenyl)-acrylonitrile (124) (300 mg, 0.529 mmol) in acetonitrile (4 ml) at room temperature, was added CAN (580 mg, 1.058 mmol) followed by distilled water (2 ml). After 30 min., the mixture was diluted with EA, washed with water, dried with anhydrous magnesium sulfate, filtered, and evaporated in vacuo to give a light orange-colored syrup. The crude product was purified by silica gel column chromatography (eluent, EA:hexanes (1:1)) to afford 158 mg (67%) of a pale yellow solid. ¹H NMR (300 MHz, CDCl₃) δ 1.12 (3H, d, J=6.9 Hz), 1.22 (3H, d, J=6.9 Hz), 2.31 (1H, m), 2.40 (3H, s), 4.28 (1H, d, J=16.5 Hz), 4.73 (2H, s), 5.09 (1H, d, J=16.5 Hz), 5.67 (1H, s), 5.96 (1H, d, J=16.8 Hz), 6.10 (1H, s), 7.37 (1H, d, J=16.8 Hz), 7.49 (1H, s), 7.63 (2H, br. s), 9.82 (1H, s); m/z (LC/Mass, EI) 448 (M+H⁺).

Example AY

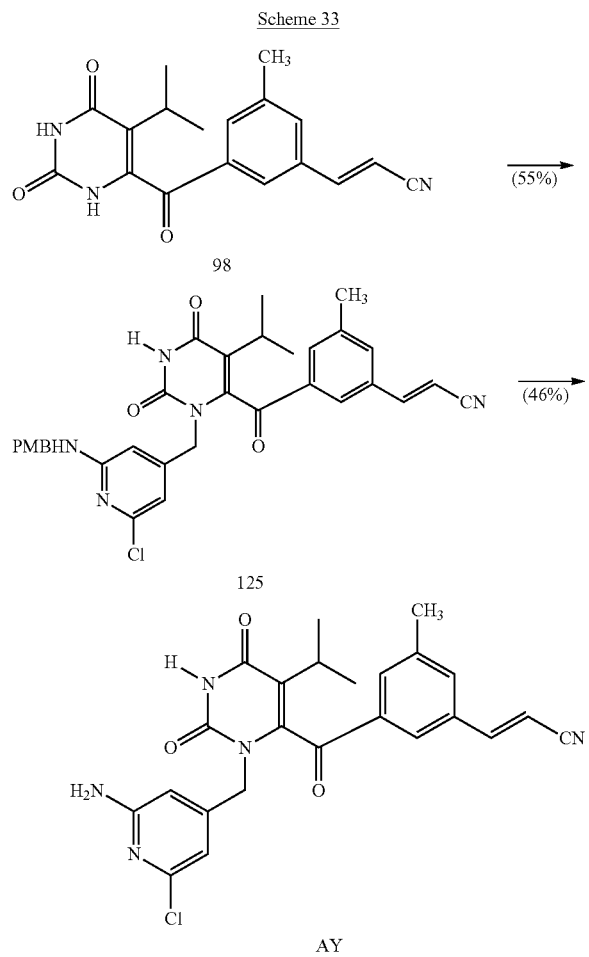

3-(3-{3-[2-Chloro-6-(4-methoxy-benzylamino)-pyridin-4-ylmethyl]-5-isopropyl-2,6-dioxo-1,2,3,6-tetrahydro-pyrimidine-4-carbonyl}-5-methyl-phenyl)-acrylonitrile (125): To a stirred solution of 2-chloro-6-(p-methoxybenzylamino)-4-pyridine-methanol (278 mg, 1 mmol) in chloroform (10 ml) at 0° C. (ice bath), was added triethylamine (210 µl, 1.5 mmol) followed by methanesulfonyl chloride (90 µl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (98) (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and evaporated in vacuo to give a light yellow foam. The crude product was purified by silica gel column chromatography (eluent, EA:hexanes (1:2); The fraction of $R_f$=0.19 was collected.) to afford 323 mg (55%) of a pale yellow foam.

Example AY

To a stirred solution of 3-(3-{3-[2-chloro-6-(4-methoxy-benzylamino)-pyridin-4-ylmethyl]-5-isopropyl-2,6-dioxo-1,2,3,6-tetrahydro-pyrimidine-4-carbonyl}-5-methyl-phenyl)-acrylonitrile (125) (323 mg, 0.529 mmol) in acetonitrile (4 ml) at room temperature, was added CAN (606 mg, 1.106 mmol) followed by distilled water (2 ml). After 45 min., the mixture was diluted with EA, washed with water, dried with anhydrous magnesium sulfate, filtered, and evaporated in vacuo to give the light orange-colored syrup. The crude product was purified by silica gel column chromatography (eluent, EA:hexanes (from 1:2 to 2:1)) to afford 120 mg (46%) of a pale yellow solid. $^1$H NMR (300 MHZ, CD$_3$OD/CDCl$_3$) δ 1.12 (3H, d, J=6.9 Hz), 1.21 (3H, d, J=6.9 Hz), 2.27 (1H, m), 2.41 (3H, s), 4.21 (1H, d, J=16.5 Hz), 5.06 (1H, d, J=16.5 Hz), 6.01 (1H, d, J=16.8 Hz), 6.04 (1H, s), 6.13 (1H, s), 7.39 (1H, d, J=16.8 Hz), 7.53 (2H, s), 7.67 (1H, s); m/z (LC/Mass, EI) 464 (M+H$^+$).

Example AZ

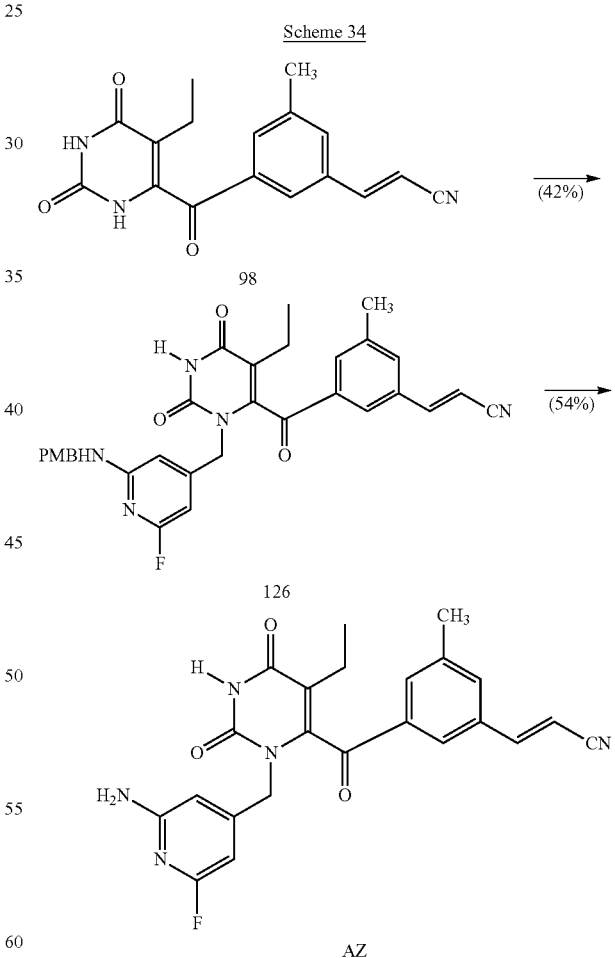

3-(3-{5-Ethyl-3-[2-fluoro-6-(4-methoxy-benzylamino)-pyridin-4-ylmethyl]-2,6-dioxo-1,2,3,6-tetrahydro-pyrimidine-4-carbonyl}-5-methyl-phenyl)-acrylonitrile (126): To a stirred solution of 2-fluoro-6-(p-methoxybenzylamino)-4-pyridine-methanol (262 mg, 1 mmol) in chloroform (10 ml) at 0° C. (ice bath), was added triethylamine (210 μl, 1.5 mmol) followed by methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-ethyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and evaporated in vacuo to give a light yellow foam. The crude product was purified by silica gel column chromatography (eluent, EA:hexanes (1:2); The fraction of $R_f$=0.11 was collected.) to afford 232 mg (42%) of a pale yellow solid.

Example AZ

To a stirred solution of 3-(3-{5-ethyl-3-[2-fluoro-6-(4-methoxy-benzylamino)-pyridin-4-ylmethyl]-2,6-dioxo-1,2,3,6-tetrahydro-pyrimidine-4-carbonyl}-5-methyl-phenyl)-acrylonitrile (126) (216 mg, 0.39 mmol) in acetonitrile (4 ml) at room temperature, was added CAN (428 mg, 0.78 mmol) followed by distilled water (2 ml). After 30 min., the mixture was diluted with EA, washed with water, dried with anhydrous magnesium sulfate, filtered, and evaporated in vacuo to give the light orange-colored syrup. The crude product was purified by silica gel column chromatography (eluent, EA:hexanes (1:1)) to afford 91 mg (54%) of a white solid. $^1$H NMR (200 MHz, DMSO-$d_6$) δ 0.82 (3H, t, J=7.4 Hz), 1.88-2.02 (2H, m), 2.37 (3H, s), 4.52 (2H, s), 5.84 (1H, s), 5.94 (1H, s), 6.24 (2H, s), 6.61 (1H, d, J=16.8 Hz), 7.67 (1H, d, J=16.8 Hz), 7.83 (1H, s), 7.85 (1H, s), 7.99 (1H, s), 11.80 (1H, s); m/z (LC/Mass, EI) 434 (M+H$^+$).

Example BA

Scheme 35

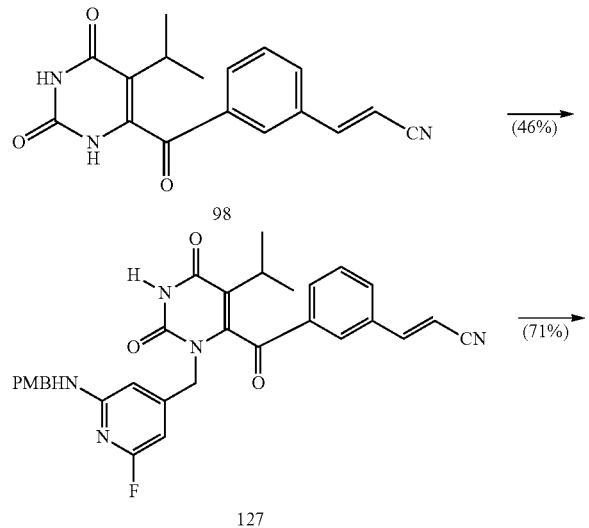

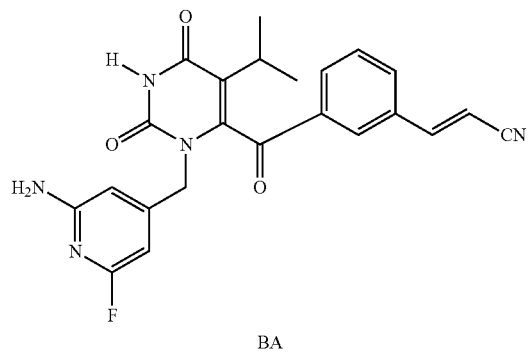

BA 3-(3-{3-[2-Fluoro-6-(4-methoxy-benzylamino)-pyridin-4-ylmethyl]-5-isopropyl-2,6-dioxo-1,2,3,6-tetrahydro-pyrimidine-4-carbonyl}-phenyl)-acrylonitrile (127): To a stirred solution of 2-fluoro-6-(p-methoxybenzylamino)-4-pyridinemethanol (186 mg, 0.712 mmol) in chloroform (7 ml) at 0° C. (ice bath), was added triethylamine (150 μl, 1.07 mmol) followed by methanesulfonyl chloride (64 μl, 0.85 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-phenyl]-acrylonitrile (309 mg, 0.712 mmol), anhydrous powdered potassium carbonate (110 mg, 0.8 mmol), lithium iodide (107 mg, 0.8 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and evaporated in vacuo to give a pale yellow foam. The crude product was purified by silica gel column chromatography (eluent, EA:hexanes (1:2); The fraction of $R_f$=0.14 was collected.) to afford 182 mg (46%) of a pale yellow syrup.

Example BA

To a stirred solution of 3-(3-{3-[2-fluoro-6-(4-methoxy-benzylamino)-pyridin-4-ylmethyl]-5-isopropyl-2,6-dioxo-1,2,3,6-tetrahydro-pyrimidine-4-carbonyl}-phenyl)-acrylonitrile (127) (170 mg, 0.307 mmol) in acetonitrile (4 ml) at room temperature, was added CAN (580 mg, 1.058 mmol) followed by distilled water (2 ml). After 30 min., the mixture was diluted with EA, washed with water, dried with anhydrous magnesium sulfate, filtered, and evaporated in vacuo to give the orange-colored syrup. The crude product was purified by silica gel column chromatography (eluent, EA:hexanes (1:1)) to afford 95 mg (71%) of a white solid. $^1$H NMR (500 MHz, DMSO-$d_6$) δ 1.01 (3H, d, J=6.8 Hz), 1.10 (3H, d, J=6.8 Hz), 2.11 (1H, m), 2.48 (3H, s), 4.49 (2H, s), 5.83 (1H, s), 5.92 (1H, s), 6.22 (2H, s), 6.65 (1H, d, J=16.8 Hz), 7.61 (1H, t, J=7.8 Hz), 7.01 (1H, d, J=16.8 Hz), 7.98 (1H, d, J=7.8 Hz), 8.04 (1H, d, J=7.8 Hz), 8.18 (1H, s), 11.70 (1H, s); m/z (LC/Mass, EI) 434 (M+H$^+$).

Example BB

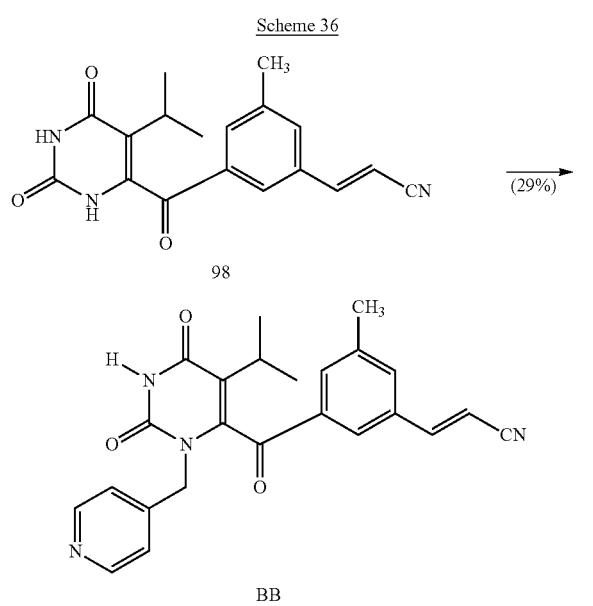

Scheme 36

Example BB

To a mixture of 3-[3-(5-isopropyl-2,6-dioxo-1,2,3,6-tetrahydro-pyrimidine-4-carbonyl)-5-methyl-phenyl]-acrylonitrile (98) (241 mg, 0.745 mmol), 4-chloromethylpyridine hydrochloride (134 mg, 0.816 mmol), anhydrous powdered potassium carbonate (103 mg, 0.745 mmol), and lithium iodide (100 mg, 0.745 mmol), was added anhydrous DMF (5 ml). The mixture was then stirred for overnight at room temperature. After evaporation of the mixture in vacuo, the residue was purified by silica gel column chromatography (eluent, EA:hexanes (from 1:1 to EA)) to afford 90 mg (29%) of a yellow solid. Recrystallization from chloroform/ether resulted a pale yellow solid. $^1$H NMR (200 MHz, CDCl$_3$) δ 1.12 (3H, d, J=6.6 Hz), 1.23 (3H, d, J=6.6 Hz), 2.28 (1H, m), 2.36 (3H, s), 4.59 (1H, d, J=16.8 Hz), 5.00 (1H, d, J=16.8 Hz), 5.94 (1H, 16.8 Hz), 6.98 (2H, d, J=4.8 Hz), 7.33 (1H, d J=16.8 Hz), 7.48 (1H, s), 7.52 (1H, s), 7.64 (1H, s), 8.40 (2H, d, J=4.8 Hz), 10.35 (1H, s); m/z (LC/Mass, EI) 415 (M+H$^+$).

Example BC

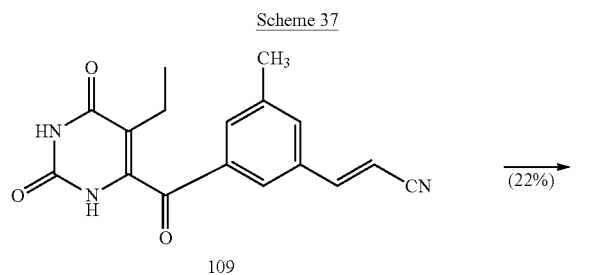

Scheme 37

Example BC

To a mixture of 3-[3-(5-ethyl-2,6-dioxo-1,2,3,6-tetrahydro-pyrimidine-4-carbonyl)-5-methyl-phenyl]-acrylonitrile (109) (263 mg, 0.851 mmol), 4-chloromethylpyridine hydrochloride (140 mg, 0.851 mmol), anhydrous powdered potassium carbonate (117 mg, 0.851 mmol), and lithium iodide (114 mg, 0.851 mmol), was added anhydrous DMF (5 ml). The mixture was then stirred for overnight at room temperature. After evaporation of the mixture in vacuo, the residue was purified by silica gel column chromatography (eluent, EA:hexanes (from 2:1 to EA)) to afford 75 mg (22%) of compound 55 as a light brown foam. Recrystallization from chloroform/ether resulted a pale brown solid. $^1$H NMR (500 MHz, CD$_3$OD/CDCl$_3$) δ 0.95 (3H, t, J=7.3 Hz), 1.98 (1H, m), 2.20 (1H, m), 2.37 (3H, s), 4.67 (1H, d, J=15.1 Hz), 4.91 (1H, d, J=15.1 Hz), 5.98 (1H, d, J=16.6 Hz), 7.01 (2H, d, J=6.0 Hz), 7.36 (1H, d, J=16.6 Hz), 7.49 (1H, s), 7.50 (1H, s), 7.68 (1H, s), 8.37 (2H, d, J=6.0 Hz); m/z (LC/Mass, EI) 401 (M+H$^+$).

Example BD

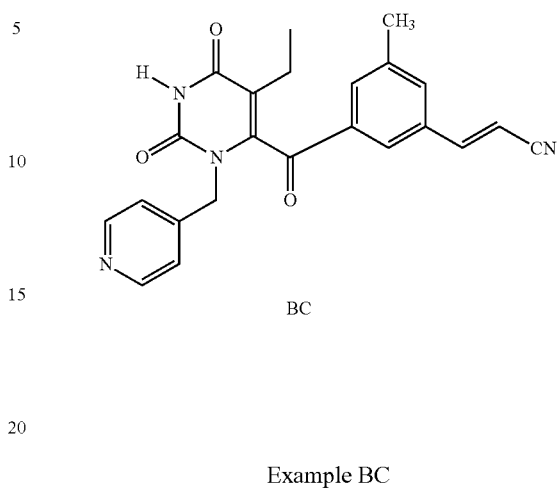

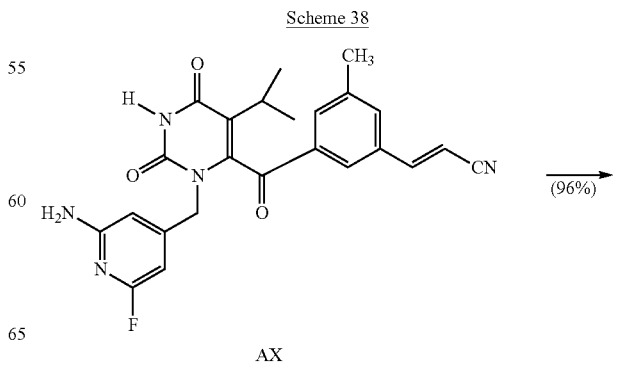

Scheme 38

145
-continued

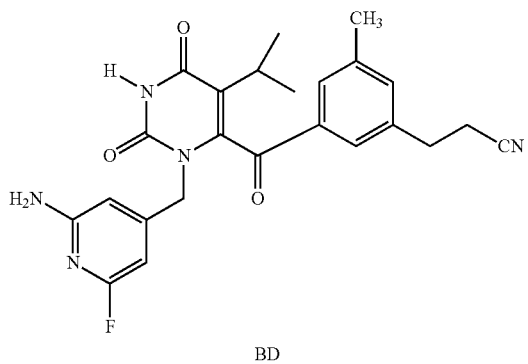

Example BD

Example BD

Example AX (90 mg, 0.2 mmol) was stirred with 10% palladium on carbon (10 mg) in anhydrous ethanol (20 ml) at room temperature under an atmosphere of hydrogen. After 18 hr., the reaction mixture was filtered through celite pad and the pad was washed with ethanol and chloroform. The combined filtrate was evaporated in vacuo and the residue was purified by silica gel column chromatography (eluent, EA:hexanes (2:1)) to afford 87 mg (96%) of a colorless syrup. Recrystallization of the syrup from chloroform/ether/hexane resulted a white solid. $^1$H NMR (200 MHz, CDCl$_3$) δ 1.14 (3H, d, J=7.0 Hz), 1.22 (3H, d, J=7.0 Hz), 2.29-2.35 (4H, m), 2.65 (2H, t, J=7.2 Hz), 2.95 (2H, t, J=7.2 Hz), 4.38 (1H, d, J=16.2 Hz), 4.78 (2H, s), 4.97 (1H, d, J=16.2 Hz), 5.79 (1H, s), 6.05 (1H, s), 7.32 (1H, s), 7.45 (1H, s), 7.54 (1H, s), 9.95 (1H, s). m/z (LC/Mass, EI) 450 (M+H$^+$).

Example BE

Scheme 39

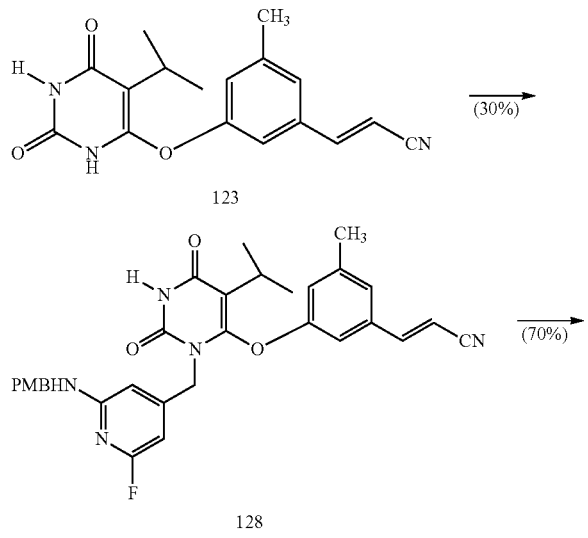

146
-continued

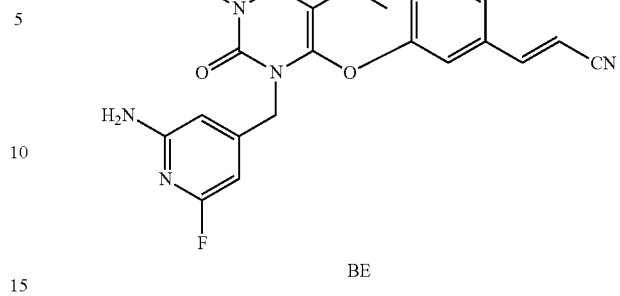

BE 3-(3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (128): To a stirred solution of 2-fluoro-6-(p-methoxybenzylamino)-4-pyridinemethanol (262 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidin-4-yloxy)-5-methyl-phenyl]-acrylonitrile (123) (311 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo to give a pale yellow foam. The crude product was purified by silica gel column chromatography (eluent, EA:hexanes (1:2); The fraction of R$_f$=0.19 was collected.) to afford 255 mg (46%) of a white foam. $^1$H NMR (300 MHz, CDCl$_3$) δ 1.10 (6H, d, J=6.9 Hz), 2.32 (3H, s), 2.68 (1H, m), 3.79 (3H, s), 4.31 (2H, d, J=5.5 Hz), 4.73 (2H, s), 5.02 (1H, t, J=5.5 Hz), 5.81 (1H, d, J=16.6 Hz), 5.85 (1H, s), 5.98 (1H, s), 6.64 (2H, s), 6.86-6.89 (2H, m), 6.98 (1H, s), 7.20-7.24 (3H, m), 8.98 (1H, s).

Example BE

To a stirred solution of 3-(3-{3-[2-fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (128) (166 mg, 0.2987 mmol) in acetonitrile (4 ml) at room temperature, was added CAN (327 mg, 0.5975 mmol) followed by distilled water (2 ml). After 30 min., the mixture was diluted with EA, washed with water, dried with anhydrous magnesium sulfate, filtered, and evaporated in vacuo to give the brown syrup. The crude product was purified by silica gel column chromatography (eluent, EA:hexanes (1:1)) to afford 91 mg (70%) of a pale yellow solid. $^1$H NMR (200 MHz, CD$_3$OD/CDCl$_3$) δ 1.12 (6H, d, J=7.0 Hz), 2.35 (3H, s), 2.71 (1H, s), 4.76 (2H, s), 5.90 (1H, s), 5.94 (1H, d, J=16.8 Hz), 6.10 (1H, s), 6.73 (1H, s), 6.78 (1H, s), 7.04 (1H, s), 7.33 (1H, d, J=16.8 Hz); m/z (LC/Mass, EI) 436 (M+H$^+$).

Alternative Preparation Method for Example BE

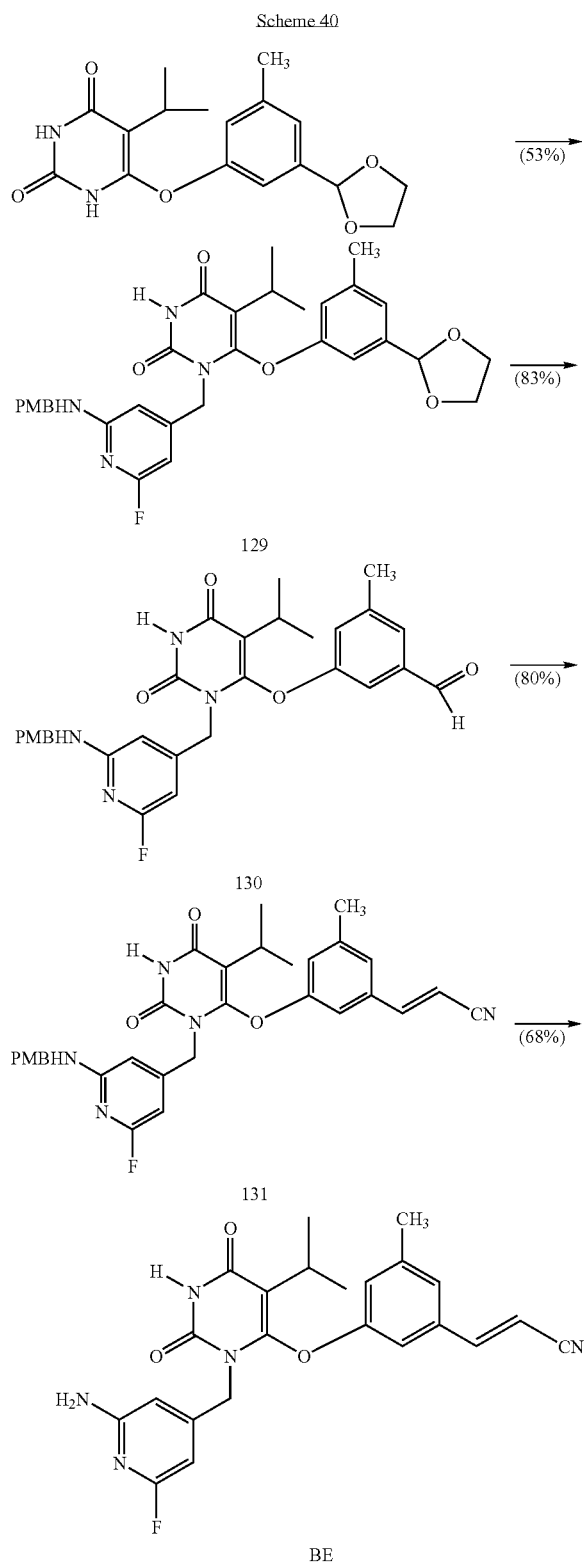

Scheme 40

6-(3-[1,3]Dioxolan-2-yl-5-methyl-phenoxy)-1-[2-fluoro-6-(4-methoxy-benzylamino)-pyridin-4-ylmethyl]-5-isopropyl-1H-pyrimidine-2,4-dione (129): To a stirred solution of 2-fluoro-6-(p-methoxybenzylamino)-4-pyridine-methanol (664 mg, 2.53 mmol) in chloroform (25 ml) at 0° C. (ice bat), was added triethylamine (532 μl, 3.8 mmol) followed by methanesulfonyl chloride (228 μl, 3.0 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 6-(3-[1,3]dioxolan-2-yl-5-methyl-phenoxy)-5-isopropyl-1H-pyrimidine-2,4-dione (842 mg, 2.53 mmol), anhydrous powdered potassium carbonate (349 mg, 2.53 mmol), and lithium iodide (339 mg, 2.53 mmol). Anhydrous DMF (25 ml) was then added into the mixture and stirred for overnight at room temperature. The mixture was evaporated in vacuo. The residue was dissolved in methanol-dichloromethane (1:9), filtered through a celite pad, and the pad was washed with dichloromethane. The combined filtrate was evaporated in vacuo and the residue was purified by silica gel column chromatography (eluent, EA:hexanes (1:2)) to afford 771 mg (53%) of a white foam. $^1$H NMR (200 MHz, CDCl$_3$) δ 1.12 (6H, d, J=7.2 Hz), 2.30 (3H, s), 2.73 (1H, m), 3.79 (3H, s), 3.94-4.14 (4H, m), 4.32 (2H, d, J=5.4 Hz), 4.71 (2H, s), 5.00 (1H, t, J=5.4 Hz), 5.67 (1H, s), 5.95 (2H, s), 6.59 (1H, s), 6.81-6.91 (3H, m), 7.02 (1H, s), 7.21-7.29 (2H, m), 9.06 (1H, s).

3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-benzaldehyde (130): A mixture of 6-(3-[1,3]dioxolan-2-yl-5-methyl-phenoxy)-1-[2-fluoro-6-(4-methoxy-benzylamino)-pyridin-4-ylmethyl]-5-isopropyl-1H-pyrimidine-2,4-dione (714 mg, 1.24 mmol), PPTS (62 mg, 0.25 mmol), and water (5 drops) in acetone (10 ml) was heated under reflux for 3 hr. After cooling to room temperature, the mixture was evaporated in vacuo and the residue was purified by silica gel column chromatography (eluent, EA: hexanes (from 1:1 to 2:3)) to afford 548 mg (83%) of a white solid. $^1$H NMR (200 MHz, CD$_3$OD/CDCl$_3$) δ 1.00 (6H, d, J=7.4 Hz), 2.30 (3H, s), 2.58 (1H, m), 3.71 (3H, s), 4.19 (2H, s), 4.65 (2H, s), 5.78 (1H, s), 5.86 (1H, s), 6.76-6.80 (3H, m), 7.02 (1H, s), 7.11-7.16 (2H, s), 7.32 (1H, s), 9.78 (1H, s).

3-(3-{3-[2-Fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (131): To a stirred solution of 3-{3-[2-fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-benzaldehyde (533 mg, 1 mmol) and diethyl cyanomethyl-phosphonate (162 μl, 1 mmol) in THF (10 ml) at 0° C. (ice bath) under nitrogen atmosphere, was added potassium t-butoxide (224 mg, 2 mmol). After stirring for 1 hr., the mixture was stirred for overnight at room temperature. The mixture was then diluted with EA, washed with aqueous saturated ammonium chloride solution, dried with anhydrous magnesium sulfate, filtered, and evaporated in vacuo. The residue was purified by silica gel column chromatography (eluent, EA:hexanes (1:2); The fraction of R$_f$=0.19 was collected.) to afford 445 mg (80%) of a white foam. $^1$H NMR (300 MHz, CDCl$_3$) δ 1.10 (6H, d, J=6.9 Hz), 2.32 (3H, s), 2.68 (1H, m), 3.79 (3H, s), 4.31 (2H, d, J=5.5 Hz), 4.73 (2H, s), 5.02 (1H, t, J=5.5 Hz), 5.81 (1H, d, J=16.6 Hz), 5.85 (1H, s), 5.98 (1H, s), 6.64 (2H, s), 6.86-6.89 (2H, m), 6.98 (1H, s), 7.20-7.24 (3H, m), 8.98 (1H, s).

Z isomer: (98 mg, 17%) was also obtained as a white foam. $^1$H NMR (200 MHz, CDCl$_3$) δ 1.12 (6H, d, J=7.0 Hz), 2.34 (3H, s), 2.72 (1H, m), 3.79 (3H, s), 4.33 (2H, d, J=5.6 Hz), 4.74 (2H, s), 5.17 (1H, t, J=5.6 Hz), 5.46 (1H, d, J=12.0 Hz), 5.92 (1H, s), 6.07 (1H, s), 6.67 (1H, s), 6.83-6.89 (2H, m), 7.01 (1H, d, J=12 Hz), 7.20-7.27 (4H, m), 9.18 (1H, s).

Example BE

To a stirred solution of 3-(3-{3-[2-fluoro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (384 mg, 0.69 mmol) in acetonitrile (6 ml) at room temperature, was added CAN (758 mg, 1.38 mmol) followed by distilled water (3 ml). After 30 min., the mixture was diluted with EA, washed with water, dried with anhydrous magnesium sulfate, filtered, and evaporated in vacuo to give the brown syrup. The crude product was purified by silica gel column chromatography (eluent, EA:hexanes (1:1)) to afford 205 mg (68%) as a pale yellow solid. $^1$H NMR (200 MHz, CD$_3$OD/CDCl$_3$) δ 1.12 (6H, d, J=7.0 Hz), 2.35 (3H, s), 2.71 (1H, s), 4.76 (2H, s), 5.90 (1H, s), 5.94 (1H, d, J=16.8 Hz), 6.10 (1H, s), 6.73 (1H, s), 6.78 (1H, s), 7.04 (1H, s), 7.33 (1H, d, J=16.8 Hz). m/z (LC/Mass, EI) 436 (M+H$^+$).

Example BF

Scheme 41

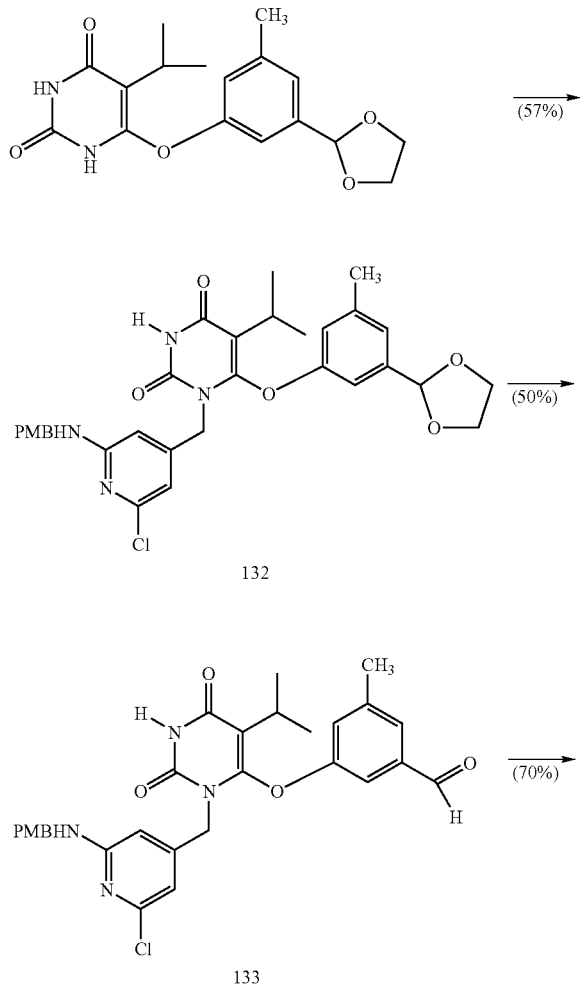

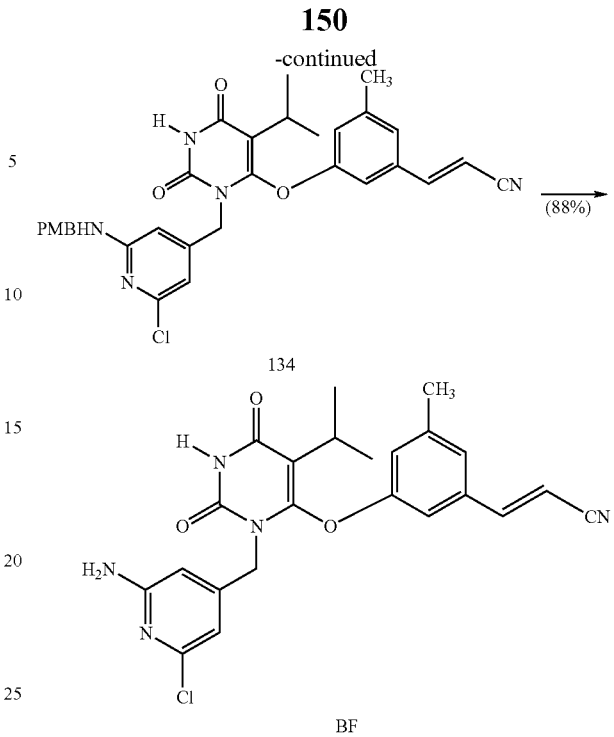

1-[2-Chloro-6-(4-methoxy-benzylamino)-pyridin-4-ylmethyl]-6-(3-[1,3]dioxolan-2-yl-5-methyl-phenoxy)-5-isopropyl-1H-pyrimidine-2,4-dione (132): To a stirred solution of 2-fluoro-6-(p-methoxybenzylamino)-4-pyridine-methanol (790 mg, 2.84 mmol) in chloroform (28 ml) at 0° C. (ice bat), was added triethylamine (597 μl, 4.26 mmol) followed by methanesulfonyl chloride (256 μl, 3.41 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with compound 8 (945 mg, 2.84 mmol), anhydrous powdered potassium carbonate (392 mg, 2.84 mmol), and lithium iodide (381 mg, 2.84 mmol). Anhydrous DMF (15 ml) was then added into the mixture and stirred for overnight at room temperature. The mixture was evaporated in vacuo. The residue was dissolved in methanol-dichloromethane (1:9), filtered through a celite pad, and the pad was washed with dichloromethane. The combined filtrate was evaporated in vacuo and the residue was purified by silica gel column chromatography (eluent, EA:hexanes (1:2)) to afford 963 mg (57%) of a white foam. $^1$H NMR (200 MHz, CDCl$_3$) δ 1.11 (6H, d, J=7.0 Hz), 2.30 (3H, s), 2.72 (1H, m), 3.79 (3H, s), 3.93-4.06 (4H, m), 4.30 (2H, d, J=5.4 Hz), 4.67 (2H, s), 5.04 (1H, t, J=5.4 Hz), 5.67 (1H, s), 5.96 (1H, s), 6.36 (1H, s), 6.57 (1H, s), 6.79 (1H, s), 6.85 (2H, d, J=8.4 Hz), 7.01 (1H, s), 7.22 (2H, d, J=8.4 Hz), 9.01 (1H, s).

3-{3-[2-Chloro-6-(4-methoxy-benzylamino)-pyridin-4-ylmethyl]-5-isopropyl-2,6-dioxo-1,2,3,6-tetrahydro-pyrimidin-4-yloxy}-5-methyl-benzaldehyde (133): A mixture of 1-[2-chloro-6-(4-methoxy-benzylamino)-pyridin-4-ylmethyl]-6-(3-[1,3]dioxolan-2-yl-5-methyl-phenoxy)-5-isopropyl-1 H-pyrimidine-2,4-dione (908 mg, 1.53 mmol), PPTS (77 mg, 0.31 mmol), and water (7 drops) in acetone (10 ml) was heated under reflux for 3 hr. After cooling to room temperature, the mixture was evaporated in vacuo and the residue was purified by silica gel column chromatography (eluent, EA:hexanes (1:2)) to afford 350 mg (50%) of a white foam. $^1$H NMR (200 MHz, CDCl$_3$) δ 1.11 (6H, d, J=6.8 Hz), 2.40 (3H, s), 2.68 (1H, m), 3.80 (3H, s), 4.29 (2H, d, J=5.4 Hz), 4.72 (2H, s), 5.02 (1H, t, J=5.4 Hz), 6.01 (1H, s), 6.26 (1H, s), 6.85-6.89 (3H, m), 7.09 (1H, s), 7.21-7.27 (2H, m), 7.40 (1H, s), 8.98 (1H, s), 9.89 (1H, s).

3-(3-{3-[2-Chloro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (134): To a stirred solution of 3-{3-[2-chloro-6-(4-methoxy-benzylamino)-pyridin-4-ylmethyl]-5-isopropyl-2,6-dioxo-1,2,3,6-tetrahydro-pyrimidin-4-yloxy}-5-methyl-benzaldehyde (335 mg, 0.611 mmol) and diethyl cyanomethyl-phosphonate (104 µl, 0.64 mmol) in THF (10 ml) at 0° C. (ice bath) under nitrogen atmosphere, was added potassium t-butoxide (151 mg, 1.34 mmol). After stirring for 1 hr., the mixture was stirred for overnight at room temperature. The mixture was then diluted with EA, washed with aqueous saturated ammonium chloride solution, dried with anhydrous magnesium sulfate, filtered, and evaporated in vacuo. The residue was purified by silica gel column chromatography (eluent, EA:hexanes (1:2)) to afford 243 mg (70%) of a white foam. $^1$H NMR (200 MHz, CDCl$_3$) δ 1.10 (6H, d, J=6.8 Hz), 2.32 (3H, s), 2.68 (1H, m), 3.78 (3H, s), 4.30 (2H, d, J=5.2 Hz), 4.68 (2H, s), 5.23 (1H, t, J=5.2 Hz), 5.82 (1H, d, J=16.6 Hz), 6.05 (1H, s), 6.21 (1H, s), 6.62 (2H, s), 6.84-6.90 (2H, m), 6.97 (1H, s), 7.18-7.27 (3H, m), 9.63 (1H, s).

Example BF

To a stirred solution of 3-(3-{3-[2-chloro-6-(4-methoxy-benzylamino)-pyridin-4-ylmethyl]-5-isopropyl-2,6-dioxo-1,2,3,6-tetrahydro-pyrimidin-4-yloxy}-5-methyl-phenyl)-acrylonitrile (220 mg, 0.38 mmol) in acetonitrile (4 ml) at room temperature, was added CAN (422 mg, 0.77 mmol) followed by distilled water (2 ml). After 25 min., the mixture was diluted with EA, washed with water, dried with anhydrous magnesium sulfate, filtered, and evaporated in vacuo to give the brown syrup. The crude product was purified by silica gel column chromatography (eluent, EA:hexanes (1:1)) to afford 154 mg (88%) of a pale yellow solid. $^1$H NMR (200 MHz, CD$_3$OD/CDCl$_3$) δ 1.11 (6H, d, J=7.0 Hz), 2.29 (3H, s), 4.73 (2H, s), 5.91 (1H, d, J=16.6 Hz), 6.16 (1H, s), 6.29 (1H, s), 6.70 (1H, s), 6.75 (1H, s), 7.02 (1H, s), 7.32 (1H, d, J=16.6 Hz).

Example BG and BH

Scheme 42

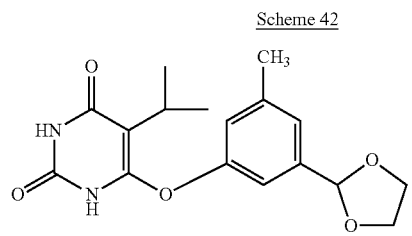

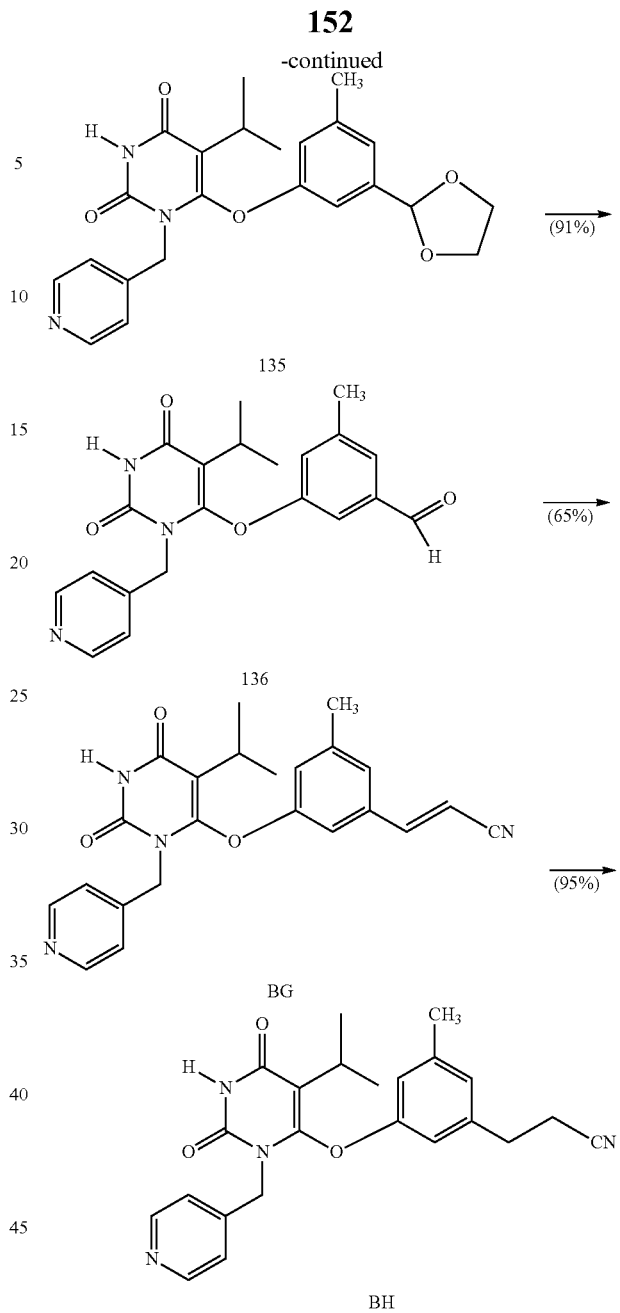

6-(3-[1,3]Dioxolan-2-yl-5-methyl-phenoxy)-5-isopropyl-1-pyridin-4-ylmethyl-1H-pyrimidine-2,4-dione (135): 6-(3-[1,3]Dioxolan-2-yl-5-methyl-phenoxy)-5-isopropyl-1H-pyrimidine-2,4-dione (2.66 g, 8 mmol) and anhydrous powdered potassium carbonate (1.31 g, 16 mmol) were dissolved in DMF (40 ml). With vigorous stirring, 4-chloromethylpyridine hydrochloride (2.21 g, 16 mmol) and lithium iodide (1 g, 8 mmol) were added in this order. The mixture was stirred for overnight at room temperature and evaporated in vacuo. The residue was dissolved in methanol-dichloromethane (1:9), filtered through a celite pad, and the filtrate was evaporated in vacuo. The residue was purified by silica gel column chromatography (eluent, EA:hexane (9:1)) to afford 1.36 g (40%) of 6-(3-[1,3]dioxolan-2-yl-5-methyl-phenoxy)-5-isopropyl-1-pyridin-4-ylmethyl-1H-pyrimidine-2,4-dione as a white foam. $^1$H NMR (200 MHz, CDCl$_3$)

δ 1.13 (6H, d, J=7.0 Hz), 2.32 (3H, s), 2.74 (1H, m), 3.98-4.17 (4H, m), 4.87 (2H, s), 5.71 (1H, s), 6.63 (1H, s), 6.79 (1H, s), 7.05 (1H, s), 7.08 (1H, s), 7.11 (1H, s), 7.53 (2H, dd, J=1.6 Hz, J=4.4 Hz), 9.37 (1H, s).

3-(5-Isopropyl-2,6-dioxo-3-pyridin-4-ylmethyl-1,2,3,6-tetrahydro-pyrimidin-4-yloxy)-5-methyl-benzaldehyde (136): A mixture of 6-(3-[1,3]dioxolan-2-yl-5-methyl-phenoxy)-5-isopropyl-1-pyridin-4-ylmethyl-1H-pyrimidine-2,4-dione (1.2 g, 2.83 mmol), p-toluenesulfonic acid monohydrate (538 mg, 2.83 mmol), and water (15 drops) in acetone (20 ml) was heated under reflux for 3 hr. After cooling to room temperature, excess sodium bicarbonate was added and the mixture was stirred for 1 hr. Then the mixture was evaporated in vacuo and the residue was purified by silica gel column chromatography (eluent, EA:hexane (9:1)) to afford 978 mg (91%) of 3-(5-Isopropyl-2,6-dioxo-3-pyridin-4-ylmethyl-1,2,3,6-tetrahydro-pyrimidin-4-yloxy)-5-methyl-benzaldehyde as a white solid. $^1$H NMR (200 MHz, CDCl$_3$) δ 1.12 (6H, d, J=7.0 Hz), 2.40 (3H, s), 2.70 (1H, m), 4.92 (2H, s), 6.90 (1H, s), 7.08 (1H, s), 7.11 (1H, s), 7.14 (1H, s), 7.43 (1H, s), 8.50 (2H, d, J=6.2 Hz), 9.73 (1H, s), 9.91 (1H, s). 6.85-6.89 (3H, m), 7.09 (1H, s), 7.21-7.27 (2H, m), 7.40 (1H, s), 8.98 (1H, s), 9.89 (1H, s).

Example BG

To a stirred solution of 3-(5-Isopropyl-2,6-dioxo-3-pyridin-4-ylmethyl-1,2,3,6-tetrahydro-pyrimidin-4-yloxy)-5-methyl-benzaldehyde (1.0 g, 2.63 mmol) and diethyl cyanomethyl-phosphonate (467 mg, 2.63 mmol) in THF (10 ml) at 0° C. (ice bath) under nitrogen atmosphere, was added potassium t-butoxide (650 mg, 5.8 mmol). After stirring for 1 hr., the mixture was stirred for overnight at room temperature. The mixture was then diluted with EA, washed with aqueous saturated ammonium chloride solution, dried with anhydrous magnesium sulfate, filtered, and evaporated in vacuo. The residue was purified by silica gel column chromatography (eluent, EA:hexane (9:1)) to afford 693 mg (65%) of compound A as a white solid. m.p. 268-269° C.; $^1$H-NMR (200 MHz, DMSO-d$_6$) δ 1.02 (6H, d, J=7.2 Hz), 2.25 (3H, s), 2.59 (1H, m), 4.80 (2H, s), 6.51 (1H, d, J=16.8 Hz), 7.02 (1H, s), 7.12 (1H, s), 7.15 (3H, s), 7.52 (1H, d, J=16.8 Hz), 8.40 (2H, d, J=1.8 Hz), 11.58 (1H, s); m/z (EI) 402 (M$^+$).

Example BH

Example BG (100 mg, 0.248 mmol) was stirred with 10% palladium on carbon (20 mg) in anhydrous ethanol (5 ml) and THF (5 ml) at room temperature under an atmosphere of hydrogen. After 18 hr., the reaction mixture was filtered through celite pad and the pad was washed with ethanol and chloroform. The combined filtrate was evaporated in vacuo and the residue was purified by silica gel column chromatography (eluent, EA:hexane (4:1)) to afford 95 mg (95%) of a white solid. m.p. 237-238° C.; $^1$H-NMR (200 MHz, CDCl$_3$) δ 1.12 (6H, d, J=7.2 Hz), 2.29 (3H, s), 2.31-2.89 (5H, m), 4.89 (2H, s), 6.53 (2H, s), 6.79 (1H, s), 7.09-7.12 (2H, m), 8.50-8.53 (2H, m), 10.13 (1H, s); m/z (EI) 404 (M$^+$).

Example BI

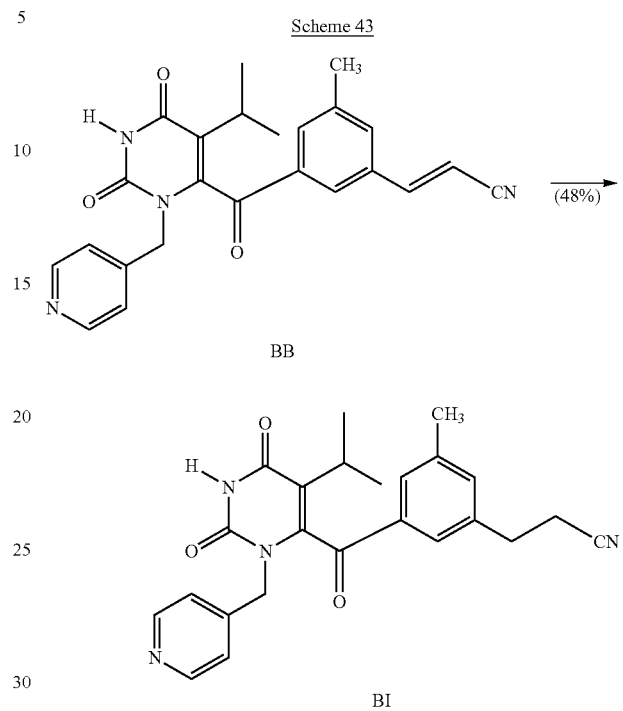

Scheme 43

Example BI

Example BB (181 mg, 0.4 mmol) was stirred with 10% palladium on carbon (32 mg) in anhydrous ethanol (10 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (2:1)) to afford 88 mg (48%) of a white solid. m.p. 125-126° C.; $^1$H-NMR (200 MHz, CDCl$_3$) δ 1.13 (3H, d, J=6.8 Hz), 1.23 (3H, d, J=6.8 Hz), 2.24-2.33 (4H, m), 2.62 (2H, t, J=7.0 Hz), 2.92 (2H, t, J=7.0 Hz), 4.62 (1H, d, J=16.4 Hz), 4.95 (1H, d, J=16.4 Hz), 6.97 (2H, dd, J=1.6 Hz, 4.2 Hz), 7.32 (1H, s), 7.39 (1H, s), 7.48 (1H, s), 8.40 (2H, dd, J=1.6 Hz, 4.2 Hz), 9.18 (1H, s); m/z (EI) 416 (M$^+$).

Example BJ

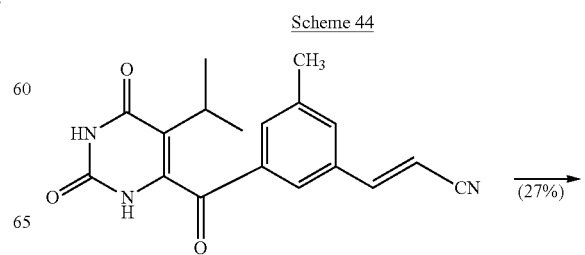

Scheme 44

155
-continued

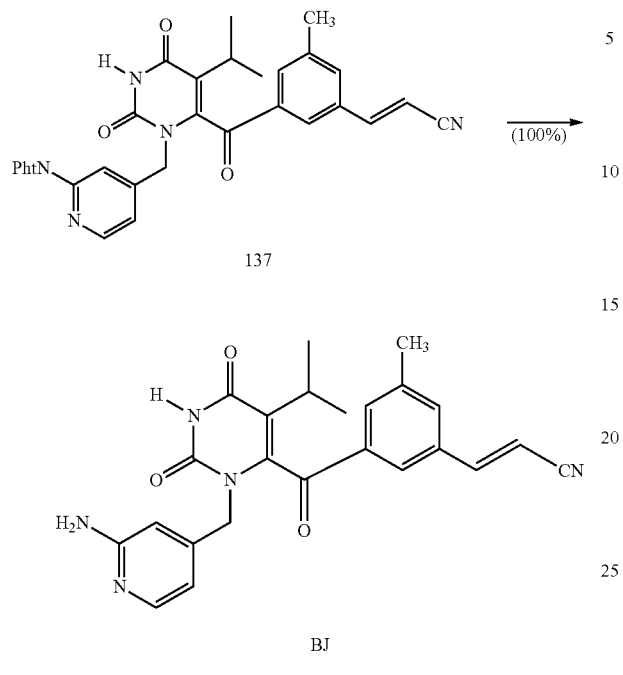

137

BJ 3-(3-{3-[2-(1,3-dioxo-1,3-dihydro-isoindol-2-yl)-pyridin-4-ylmethyl]-5-isopropyl-2,6-dioxo-1,2,3,6-tetrahydro-pyrimidine-4-carbonyl}-5-methyl-phenyl)-acrylonitrile (137): To a mixture of 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol), and 2-phthalimido-4-chloromethylpyridine, was added anhydrous DMF (5 ml) and the mixture was stirred for overnight at room temperature. The mixture was evaporated in vacuo and the residue was purified by silica gel column chromatography (eluent, EA:hexane (1:1)) to afford 152 mg (27%) of a white solid. $^1$H-NMR (200 MHz, DMSO-$d_6$) δ 1.01 (3H, d, J=6.8 Hz), 1.10 (3H, d, J=6.8 Hz), 2.12 (1H, m), 2.33 (3H, s), 4.76 (2H, s), 6.57 (1H, d, J=16.6 Hz), 7.25 (1H, d, J=5.2 Hz), 7.31 (1H, s), 7.61 (1H, d, J=16.6 Hz), 7.80 (1H, s), 7.88-8.02 (6H, m), 8.41 (1H, d, J=5.2 Hz), 11.72 (1H, s).

Example BJ 3-(3-{3-[2-(1,3-Dioxo-1,3-dihydro-isoindol-2-yl)-pyridin-4-ylmethyl]-5-isopropyl-2,6-dioxo-1,2,3,6-tetrahydro-pyrimidine-4-carbonyl}-5-methyl-phenyl)-acrylonitrile (145 mg, 0.259 mmol) was refluxed with hydrazine monohydrate (26 mg, 0.519 mmol) in ethanol (10 ml) After 3 hr., the mixture was evaporated in vacuo and the residue was purified by silica gel column chromatography (eluent, methanol:chloroform (5:95)) to afford 110 mg (100%) of as a white solid. m.p. 184-185° C.; $^1$H-NMR (200 MHz, CDCl$_3$/CD$_3$OD) δ 1.11 (3H, d, J=6.8 Hz), 1.21 (3H, d, J=6.8 Hz), 2.27 (1H, m), 2.39 (3H, s), 4.34 (1H, d, J=16.4 Hz), 4.99 (1H, d, J=16.4 Hz), 5.99 (1H, d, J=16.6 Hz), 6.15 (1H, s), 6.20 (1H, dd, J=1.4 Hz, 5.4 Hz), 7.33-7.70 (5H, m); m/z (EI) 429 (M$^+$).

156
Example BK

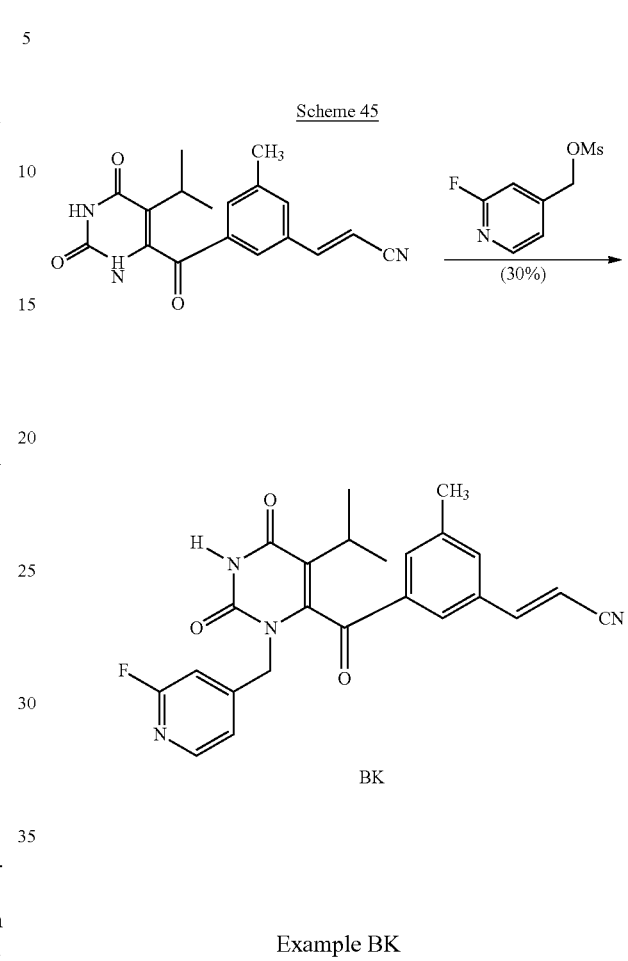

Scheme 45

BK

Example BK

To a stirred solution of 2-fluoro-4-pyridinemethanol (127 mg, 1 mmol) in chloroform (10 ml) at 0° C. (ice bath), was added triethylamine (210 µl, 1.5 mmol. and methanesulfonyl chloride (90 µl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, EA:hexane (1:2)) to afford 130 mg (30%) of a white solid.

M.p. 269-271° C.; $^1$H-NMR (200 MHz, CDCl$_3$/CD$_3$OD) δ 1.12 (3H, d, J=6.8 Hz), 1.22 (3H, d, J=6.8 Hz), 2.29 (1H, m), 2.41 (3H, s), 4.69 (1H, d, J=16.6 Hz), 4.86 (1H, d, J=16.6 Hz), 6.04 (1H, d, J=16.6 Hz), 6.66 (1H, s), 6.94 (1H, d, J=4.8 Hz), 7.40 (1H, d, J=16.6 Hz), 7.58 (2H, s), 7.75 (1H, s), 8.00 (1H, d, J=4.8 Hz); m/z (EI) 432 (M$^+$).

Example BL

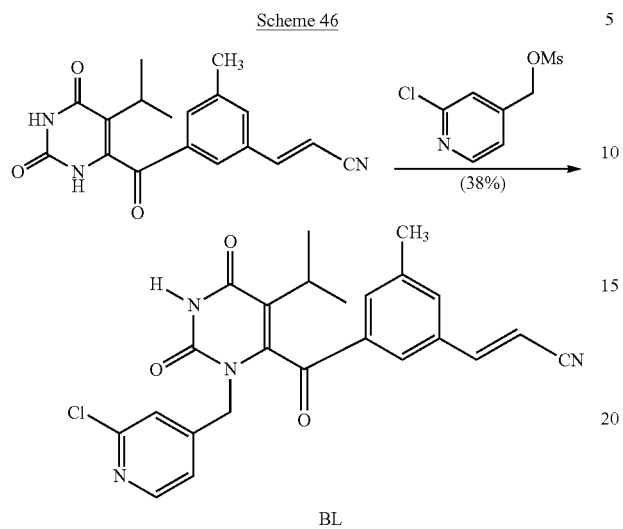

Scheme 46

BL

Example BL

To a stirred solution of 2-chloro-4-pyridinemethanol (144 mg, 1 mmol) in chloroform (10 ml) at 0° C. (ice bath), was added triethylamine (210 µl, 1.5 mmol) and methanesulfonyl chloride (90 µl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-Isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, methanol:chloroform (2:98)) to afford 174 mg (38%) of a white solid. m.p. 242-244° C.; $^1$H-NMR (200 MHz, CDCl$_3$/CD$_3$OD) δ 1.12 (3H, d, J=6.8 Hz), 1.22 (3H, d, J=6.8 Hz), 2.28 (1H, m), 2.40 (3H, s), 4.55 (1H, d, J=17.0 Hz), 4.97 (1H, d, J=17.0 Hz), 6.03 (1H, d, J=16.6 Hz), 6.97-6.99 (2H, m), 7.39 (1H, d, J=16.6 Hz), 7.55 (2H, s), 7.71 (1H, s), 8.15 (1H, d, J=5.8 Hz); m/z (EI) 448 (M$^+$).

Example BM

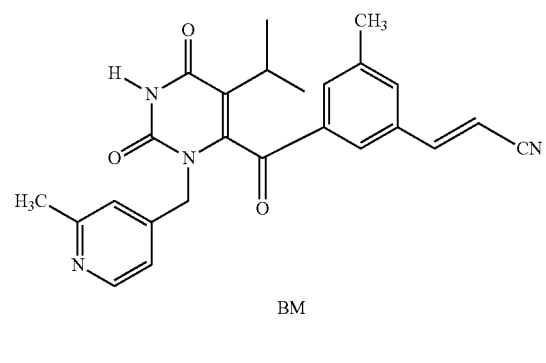

BM

Example BM

To a stirred solution of 2-chloro-4-pyridinemethanol (123 mg, 1 mmol) in chloroform (10 ml) at 0° C. (ice bath), was added triethylamine (210 µl, 1.5 mmol) and methanesulfonyl chloride (90 µl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, EA:hexane (1:1)) to afford 186 mg (43%) of a white solid. m.p. 173-174° C.; $^1$H-NMR (200 MHz, CDCl$_3$/CD$_3$OD) δ 1.09 (3H, d, J=6.8 Hz), 1.20 (3H, d, J=6.8 Hz), 2.26 (1H, m), 2.37 (6H, s), 4.54 (1H, d, J=16.6 Hz), 4.89 (1H, d, J=16.6 Hz), 6.02 (1H, d, J=16.6 Hz), 6.81-6.84 (2H, m), 7.38 (1H, d, J=16.6 Hz), 7.51 (1H, s), 7.54 (1H, s), 7.68 (1H, s), 8.18 (1H, dd, J=1.4 Hz, 3.4 Hz); m/z (EI) 428 (M$^+$).

Example BN

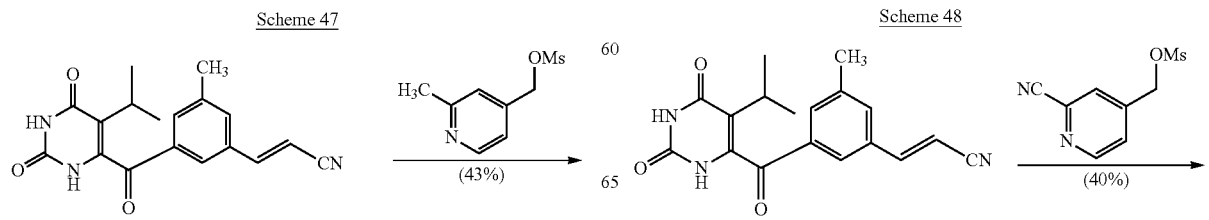

Scheme 47 / Scheme 48

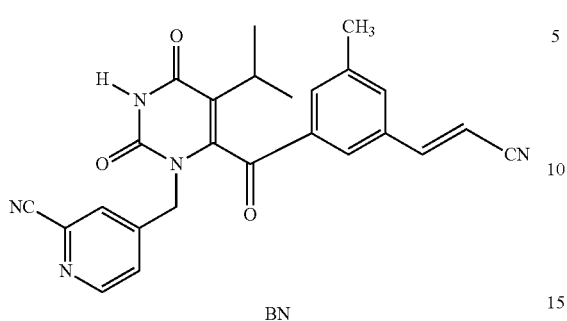

BN

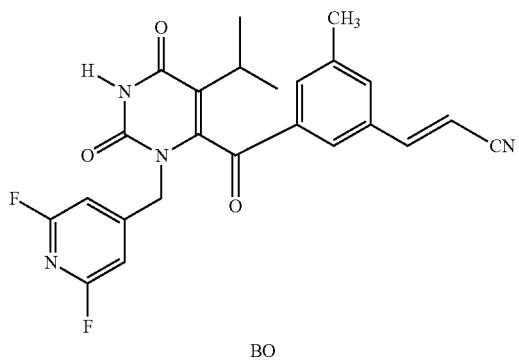

BO

Example BN

To a stirred solution of 2-chloro-4-pyridinemethanol (123 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, methanol:chloroform (2:98)) to afford 178 mg (40%) of a white solid. m.p. 269-271° C.; $^1$H-NMR (200 MHz, CDCl$_3$/CD$_3$OD) δ 1.13 (3H, d, J=6.8 Hz), 1.22 (3H, d, J=6.8 Hz), 2.29 (1H, m), 2.45 (3H, s), 4.72 (1H, d, J=16.4 Hz), 4.82 (1H, d, J=16.4 Hz), 6.09 (1H, d, J=16.6 Hz), 7.34-7.48 (3H, m), 7.63 (2H, s), 7.77 (1H, s), 8.54 (1H, d, J=5.2 Hz); m/z (EI) 439 (M$^+$).

Example BO

To a stirred solution of 2,6-difluoro-4-pyridinemethanol (145 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, methanol:chloroform (2:98)) to afford 120 mg (26%) of a white solid. m.p. 270-271° C.; $^1$H-NMR (200 MHz, CDCl$_3$/CD$_3$OD) δ 1.13 (3H, d, J=7.0 Hz), 1.22 (3H, d, J=7.0 Hz), 2.29 (1H, m), 2.43 (3H, s), 4.71 (1H, d, J=17.2 Hz), 4.83 (1H, d, J=17.2 Hz), 6.05 (1H, d, J=16.8 Hz), 6.58 (2H, s), 7.42 (1H, d, J=16.8 Hz), 7.59 (2H, s), 7.77 (1H, s); m/z (EI) 450 (M$^+$).

Example BP

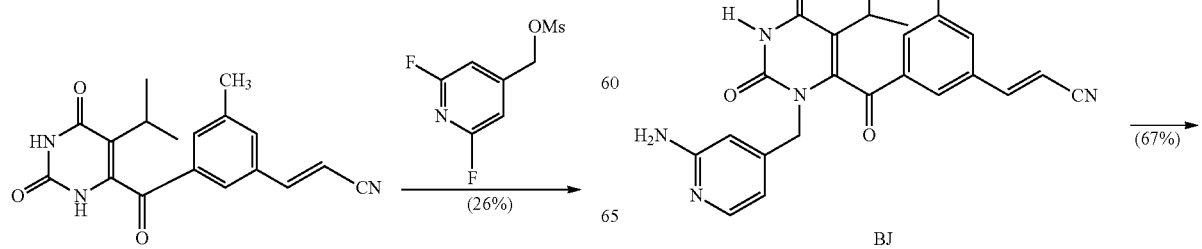

161

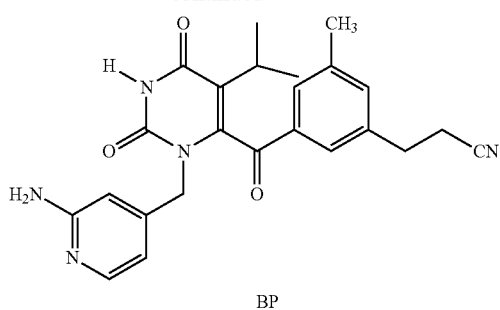

Example BP

Example BJ (124 mg, 0.289 mmol) was stirred with 10% palladium on carbon (20 mg) in anhydrous ethanol (10 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (4:1)) to afford 83 mg (67%) of a white solid. m.p. 243-245° C.; $^1$H-NMR (200 MHz, CDCl$_3$) δ 1.13 (3H, d, J=6.6 Hz), 1.23 (3H, d, J=6.6 Hz), 2.24-2.36 (4H, m), 2.62 (2H, t, J=6.8 Hz), 2.88 (2H, t, J=6.8 Hz), 4.37 (1H, d, J=16.2 Hz), 5.00-5.10 (3H, m), 6.17 (1H, s), 6.25 (1H, d, J=5.4 Hz), 7.27 (1H, s), 7.42 (1H, s), 7.49 (1H, s), 7.91 (1H, d, J=5.4 Hz), 12.09 (1H, s); m/z (EI) 431 (M$^+$).

Example BQ

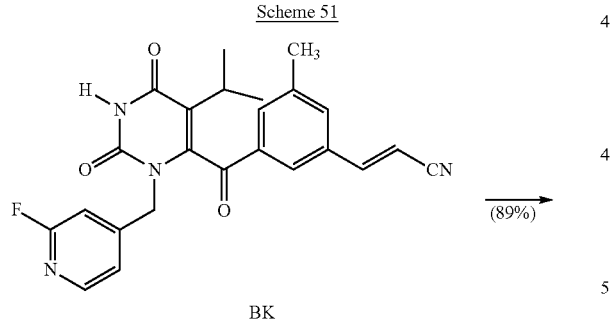

Scheme 51

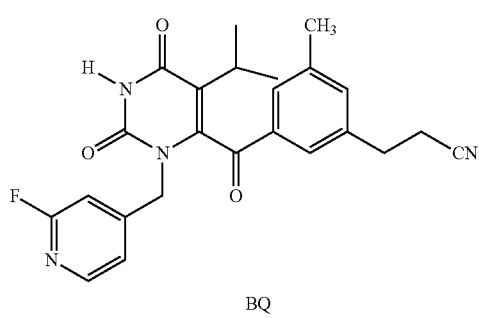

162

Example BQ

Example BK (84 mg, 0.194 mmol) was stirred with 10% palladium on carbon (20 mg) in anhydrous ethanol (10 ml) and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (1:1)) to afford 83 mg (67%) of a white solid. m.p. 230-231° C.; $^1$H-NMR (200 MHz, CDCl$_3$) δ 1.15 (3H, d, J=6.6 Hz), 1.24 (3H, d, J=6.6 Hz), 2.26-2.35 (4H, m), 2.64 (2H, t, J=7.0 Hz), 2.95 (2H, t, J=7.0 Hz), 4.65 (1H, d, J=16.6 Hz), 4.92 (1H, d, J=16.6 Hz), 6.61 (1H, s), 6.90 (1H, d, J=5.0 Hz), 7.34 (1H, s), 7.41 (1H, s), 7.53 (1H, s), 8.01 (1H, d, J=5.0 Hz), 9.13 (1H, s); m/z (EI) 434 (M$^+$).

Example BR

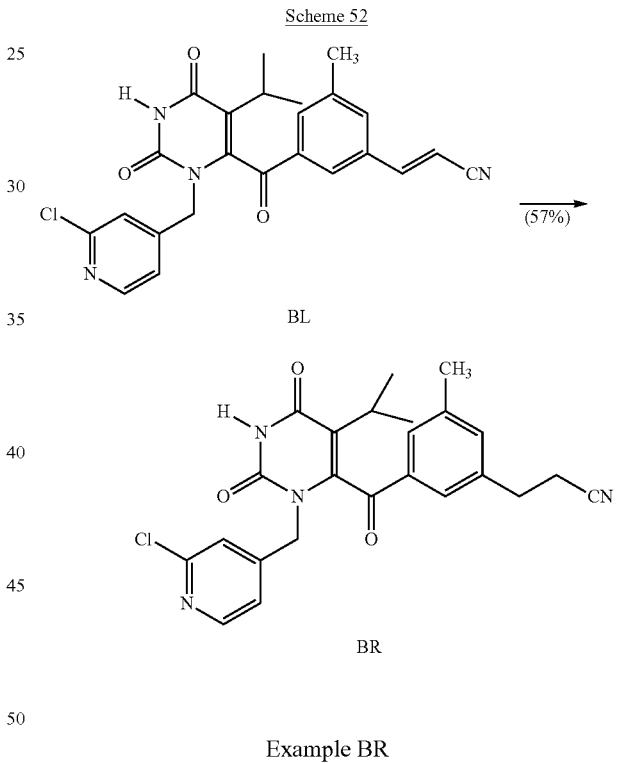

Example BR

Example BL (100 mg, 0.223 mmol) was stirred with 10% palladium on carbon (20 mg) in anhydrous ethanol (10 ml) and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (1:1)) to afford 57 mg (67%) of a white solid. m.p. 152-153° C.; 1H-NMR (200 MHz, CDCl$_3$) δ 1.15 (3H, d, J=6.8 Hz), 1.24 (3H, d, J=6.8 Hz), 2.26-2.35 (4H, m), 2.64 (2H, t, J=7.0 Hz), 2.95 (2H, t, J=7.0 Hz), 4.54 (1H, d, J=16.6 Hz), 4.99 (1H, d, J=16.6 Hz), 6.93-6.96 (2H, m), 7.34 (1H, s), 7.39 (1H, s), 7.50 (1H, s), 8.16 (1H, dd, J=1.4 Hz, 4.4 Hz), 9.06 (1H, s); m/z (EI) 450 (M$^+$).

Example BS

Scheme 53

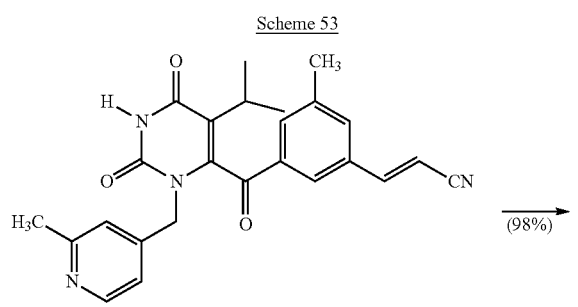

BM

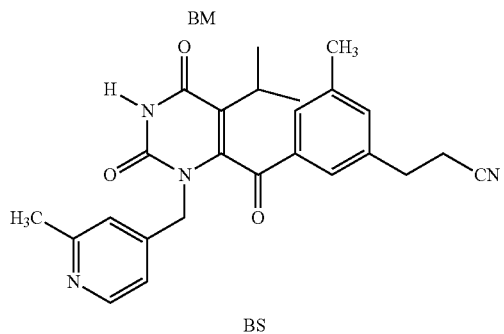

BS

Example BS

Example BM (100 mg, 0.233 mmol) was stirred with 10% palladium on carbon (20 mg) in anhydrous ethanol (10 ml) and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA) to afford 98 mg (98%) of a white solid. m.p. 115-116° C.; $^1$H-NMR (200 MHz, CDCl$_3$) δ 1.12 (3H, d, J=7.0 Hz), 1.22 (3H, d, J=7.0 Hz), 2.23-2.33 (4H, m), 2.40 (3H, s), 2.60 (2H, t, J=7.0 Hz), 2.90 (2H, t, J=7.0 Hz), 4.52 (1H, d, J=16.4 Hz), 4.98 (1H, d, J=16.4 Hz), 6.78-6.79 (2H, m), 7.30 (1H, s), 7.39 (1H, s), 7.42 (1H, s), 8.27 (1H, m), 10.00 (1H, s); m/z (EI) 430 (M$^+$).

Example BT

Scheme 54

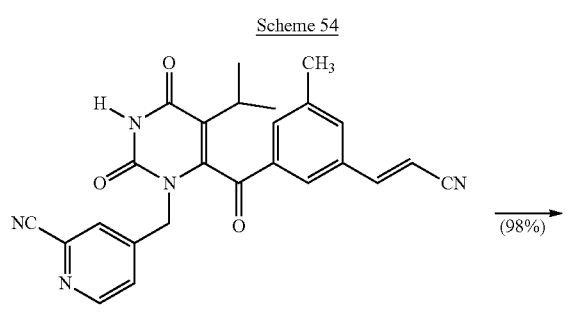

BN

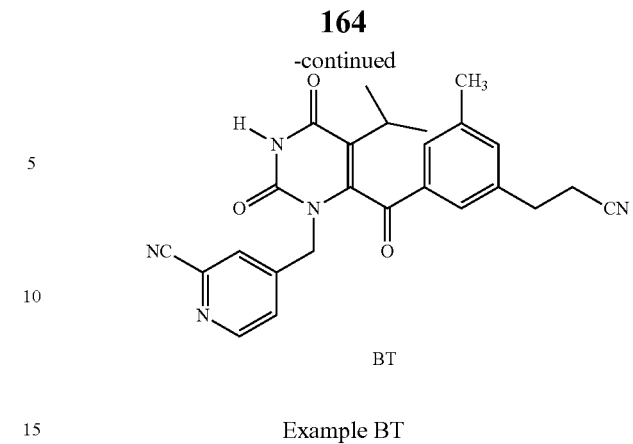

BT

Example BT

Example BN (100 mg, 0.227 mmol) was stirred with 10% palladium on carbon (20 mg) in anhydrous ethanol (10 ml) and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (1:1)) to afford 49 mg (49%) of a white solid. m.p. 230-231° C.; 1H-NMR (200 MHz, CDCl$_3$) δ 1.16 (3H, d, J=6.6 Hz), 1.23 (3H, d, J=6.6 Hz), 2.27-2.37 (4H, m), 2.69 (2H, t, J=7.2 Hz), 2.98 (2H, t, J=7.2 Hz), 4.72 (1H, d, J=16.8 Hz), 4.85 (1H, d, J=16.8 Hz), 7.30-7.39 (4H, m), 7.60 (1H, s), 8.54 (1H, d, J=5.2 Hz), 9.49 (1H, s); m/z (EI) 441 (M$^+$).

Example BU

Scheme 55

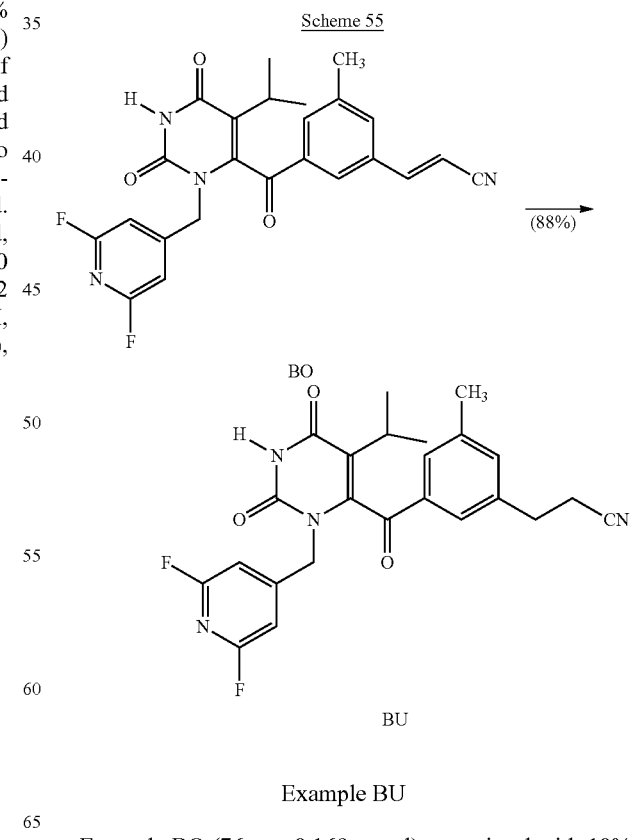

Example BU

Example BO (76 mg, 0.169 mmol) was stirred with 10% palladium on carbon (20 mg) in anhydrous ethanol (10 ml)

and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (1:1)) to afford 67 mg (88%) of a white solid. m.p. 223-225° C.; $^1$H-NMR (200 MHz, CDCl$_3$) δ 1.16 (3H, d, J=6.8 Hz), 1.24 (3H, d, J=6.8 Hz), 2.24-2.37 (4H, m), 2.65 (2H, t, J=7.4 Hz), 2.97 (2H, t, J=7.4 Hz), 4.70 (1H, d, J=16.8 Hz), 4.86 (1H, d, J=16.8 Hz), 6.55 (2H, s), 7.37 (1H, s), 7.45 (1H, s), 7.57 (1H, s), 9.44 (1H, s); m/z (EI) 452 (M$^+$).

Example BV

Scheme 56

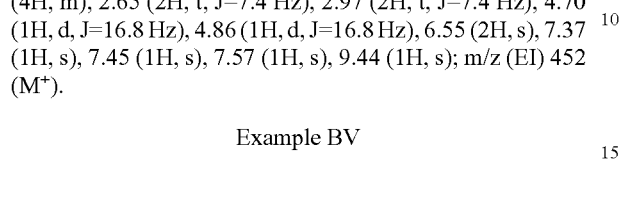

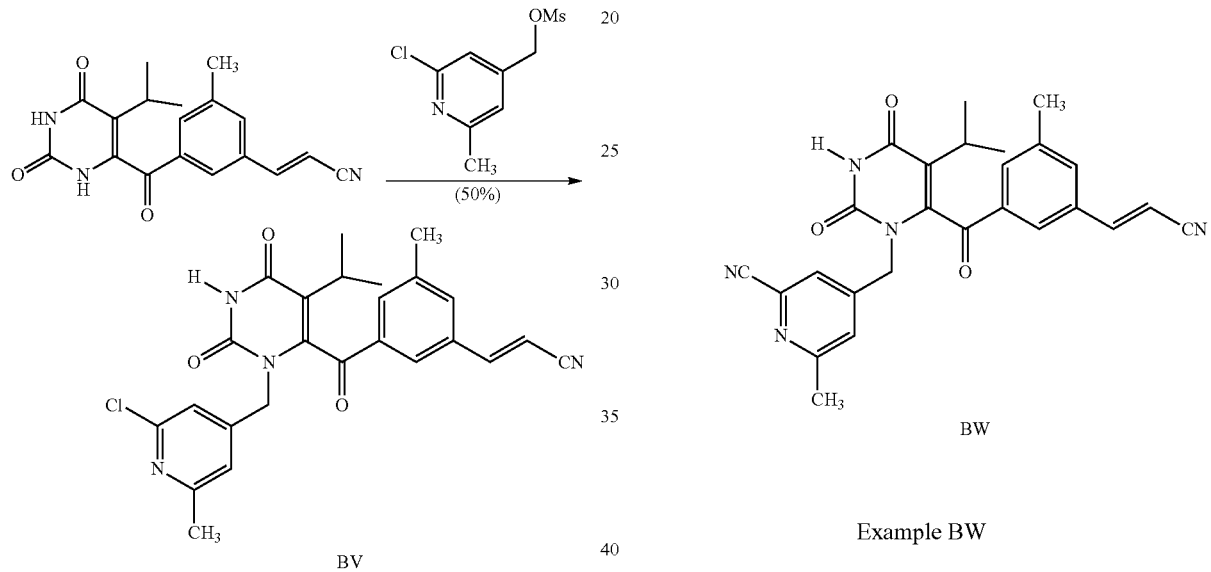

BV

Example BV

To a stirred solution of 2-chloro-6-methyl-4-pyridinemethanol (158 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, EA:hexane (1:2)) to afford 232 mg (50%) of as a white solid. m.p. 244-245° C.; $^1$H-NMR (200 MHz, CDCl$_3$) δ 1.13 (3H, d, J=7.0 Hz), 1.23 (3H, d, J=7.0 Hz), 2.21-2.35 (4H, m), 2.39 (3H, s), 4.37 (1H, t, J=16.4 Hz), 5.15 (1H, d, J=16.4 Hz), 5.94 (1H, d, J=16.8 Hz), 6.72 (2H, s), 7.35 (1H, d, J=16.8 Hz), 7.49 (2H, s), 7.64 (1H, s), 9.03 (1H, s); m/z (EI) 462 (M$^+$).

Example BW

Scheme 57

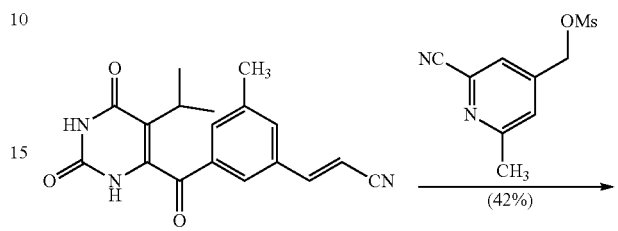

BW

Example BW

To a stirred solution of 2-cyano-6-methyl-4-pyridinemethanol (148 mg, 1 mmol) in chloroform (10 ml) at 0° C. (ice bath), was added triethylamine (210 μl, 1.5 mmol) and methanesulfonyl chloride (90 μl, 1.2 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-isopropyl-2,6-dioxo-1,2,3,6-tetrahydro-pyrimidine-4-carbonyl)-5-methyl-phenyl]-acrylonitrile (323 mg, 1 mmol), anhydrous powdered potassium carbonate (138 mg, 1 mmol), lithium iodide (134 mg, 1 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, EA:hexane (2:3)) to afford 194 mg (42%) of Example BW as a pale yellow syrup. $^1$H-NMR (200 MHz, CDCl$_3$) δ 1.13 (3H, d, J=7.0 Hz), 1.23 (3H, d, J=7.0 Hz), 2.28 (1H, m), 2.42 (3H, s) 2.47 (3H, s), 4.61 (1H, d, J=16.2 Hz), 4.89 (1H, d, J=16.2 Hz), 5.99 (1H, d, J=16.8 Hz), 7.09 (1H, s), 7.17 (1H, s), 7.38 (1H, d, J=16.8 Hz), 7.56 (2H, s), 7.70 (1H, s), 9.46 (1H, s); m/z (EI) 453 (M$^+$).

Example BX

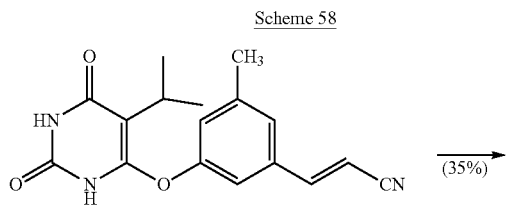

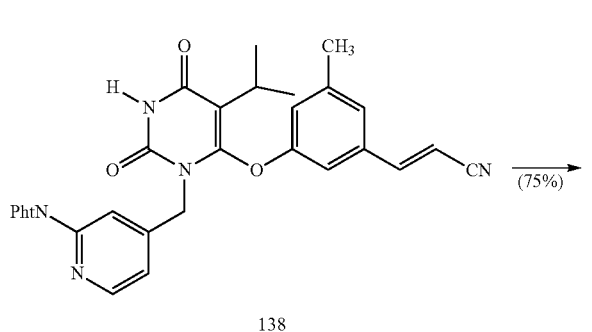

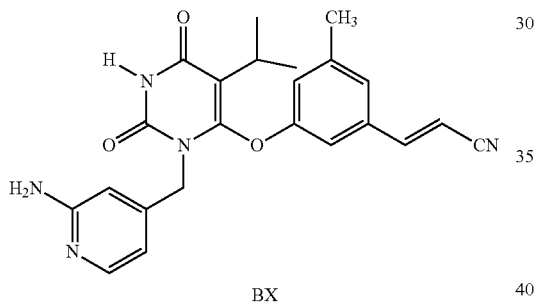

3-(3-{3-[2-(1,3-dioxo-1,3-dihydro-isoindol-2-yl)-pyridin-4-ylmethyl]-5-isopropyl-2,6-dioxo-1,2,3,6-tetrahydro-pyrimidin-4-yloxy}-5-methyl-phenyl)-acrylonitrile (138): To a mixture of 3-[3-(5-isopropyl-2,6-dioxo-1,2,3,6-tetrahydro-pyrimidine-4-carbonyl)-5-methyl-phenyl]-acrylonitrile (311 mg, 1 mmol), anhydrous powdered potassium carbonate (138 mg, 1 mmol), lithium iodide (134 mg, 1 mmol), and 2-phthalimido-4-chloromethylpyridine, was added anhydrous DMF (5 ml) and the mixture was stirred for overnight at room temperature. The mixture was evaporated in vacuo and the residue was purified by silica gel column chromatography (eluent, EA:hexane (3:2)) to afford 194 mg (35%) of as a white solid. $^1$H-NMR (200 MHz, DMSO-$d_6$) δ 1.01 (6H, d, J=7.0 Hz), 2.24 (3H, s), 2.56 (1H, m), 4.91 (2H, s), 6.46 (1H, d, J=14.2 Hz), 7.04 (1H, s), 7.15 (1H, s), 7.21 (1H, s), 7.24-7.34 (2H, m), 7.48 (1H, d, J=14.2 Hz), 7.90-8.01 (4H, m), 8.46 (1H, d, J=5.0 Hz), 11.59 (1H, s).

Example BX 3-(3-{3-[2-(1,3-dioxo-1,3-dihydro-isoindol-2-yl)-pyridin-4-ylmethyl]-5-isopropyl-2,6-dioxo-1,2,3,6-tetrahydro-pyrimidin-4-yloxy}-5-methyl-phenyl)-acrylonitrile (168 mg, 0.307 mmol) was refluxed with hydrazine monohydrate (31 mg, 0.614 mmol) in ethanol (10 ml) After 3 hr., the mixture was evaporated in vacuo and the residue was purified by silica gel column chromatography (eluent, EA:hexane (4:1)) to afford 97 mg (75%) of a pale yellow solid. m.p. 229-231° C.; $^1$H-NMR (200 MHz, CDCl$_3$) δ 1.12 (6H, d, J=7.0 Hz), 2.35 (3H, s), 2.72 (1H, m), 4.79 (2H, s), 5.08 (2H, br. s), 5.84 (1H, d, J=16.6 Hz), 6.29 (1H, s), 6.33 (1H, d, J=5.4 Hz), 6.66 (1H, s), 6.75 (1H, s), 6.99 (1H, s), 7.23 (1H, d, J=16.6 Hz), 7.99 (1H, d, J=5.4 Hz), 11.73 (1H, s); m/z (EI) 417 (M$^+$).

Example BY

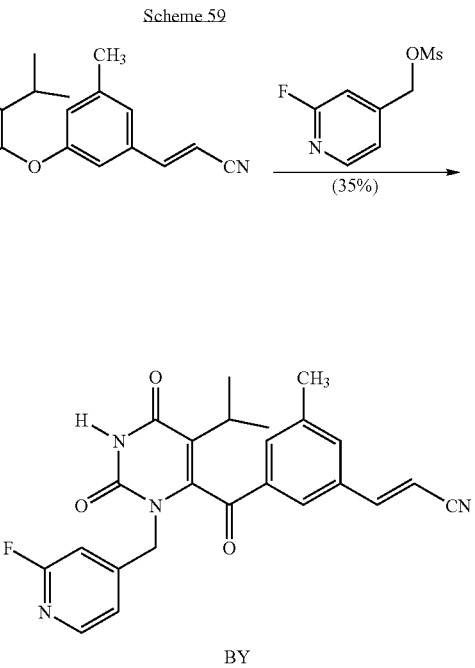

Example BY

To a stirred solution of 2-fluoro-4-pyridinemethanol (107 mg, 0.844 mmol) in chloroform (8 ml) at 0° C. (ice bath), was added triethylamine (177 μl, 1.26 mmol) and methanesulfonyl chloride (76 μl, 1 mmol). After stirring for 1.5 hr., the mixture was diluted with dichloromethane, washed with aqueous saturated sodium bicarbonate solution, dried with anhydrous magnesium sulfate, filtered, and evaporated in vacuo. The residue was further dried in high vacuo and mixed with 3-[3-(5-sopropyl-2,6-dioxo-1,2,3,6-tetrahydro-pyrimidine-4-carbonyl)-5-methyl-phenyl]-acrylonitrile (263 mg, 0.844 mmol), anhydrous powdered potassium carbonate (116 mg, 0.844 mmol), lithium iodide (113 mg, 0.844 mmol). Anhydrous DMF (5 ml) was then added into the mixture and stirred for overnight at room temperature. The mixture was evaporated in vacuo. The residue was dissolved in methanol-dichloromethane (1:9), filtered through celite pad, and the filtrate was evaporated in vacuo and the residue was purified by silica gel column chromatography (eluent, methanol:chloroform (2:98)) to afford 126 mg (35%) of a white solid. m.p. 259-260° C.; $^1$H-NMR (200 MHz, CDCl$_3$) δ 1.13 (6H, d, J=7.0 Hz), 2.33 (3H, s), 2.71 (1H, m), 4.92 (2H, s), 5.86 (1H, d, J=16.8 Hz), 6.66 (1H, s), 6.69 (1H, s), 6.74 (1H, s), 6.98-7.02 (2H, m), 7.28 (1H, d, J=16.8 Hz), 8.11 (1H, d, J=5.0 Hz), 9.12 (1H, s); m/z (EI) 420 (M$^+$).

Example BZ

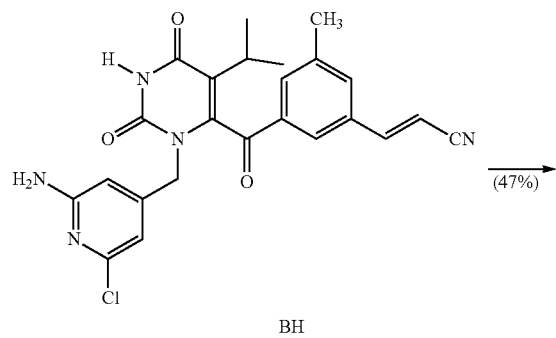

Scheme 60

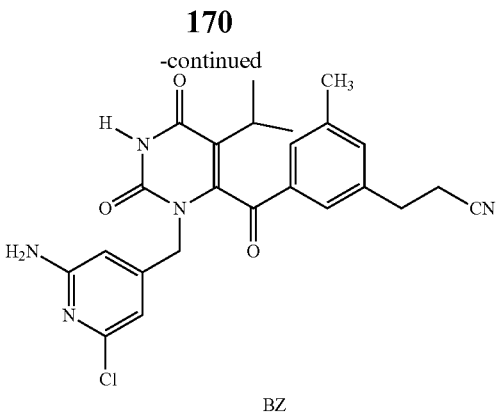

Example BZ

Example BH (120 mg, 0.258 mmol) was stirred with 10% palladium on carbon (32 mg) in anhydrous ethanol (10 ml) and THF (5 ml) at room temperature under an atmosphere of hydrogen. After 15 hr., the reaction mixture was filtered through celite pad and the pad was washed with ethanol and chloroform. The combined filtrate was evaporated in vacuo and the residue was purified by silica gel column chromatography (eluent, EA:hexane (2:1)) to afford 57 mg (47%) of a white solid. m.p. 251-252° C.; $^1$H-NMR (200 MHz, CDCl$_3$) δ 1.13 (3H, d, J=7.0 Hz), 1.21 (3H, d, J=7.0 Hz), 2.25-2.35 (4H, m), 2.64 (2H, t, J=7.0 Hz), 2.94 (2H, t, J=7.0 Hz), 4.25 (1H, d, J=15.8 Hz), 4.79 (2H, s), 5.03 (1H, d, J=15.8 Hz), 6.11 (1H, s), 6.14 (1H, s), 7.30 (1H, s), 7.43 (1H, s), 7.49 (1H, s), 9.86 (1H, s); m/z (EI) 465 (M$^+$).

Examples CA and CB

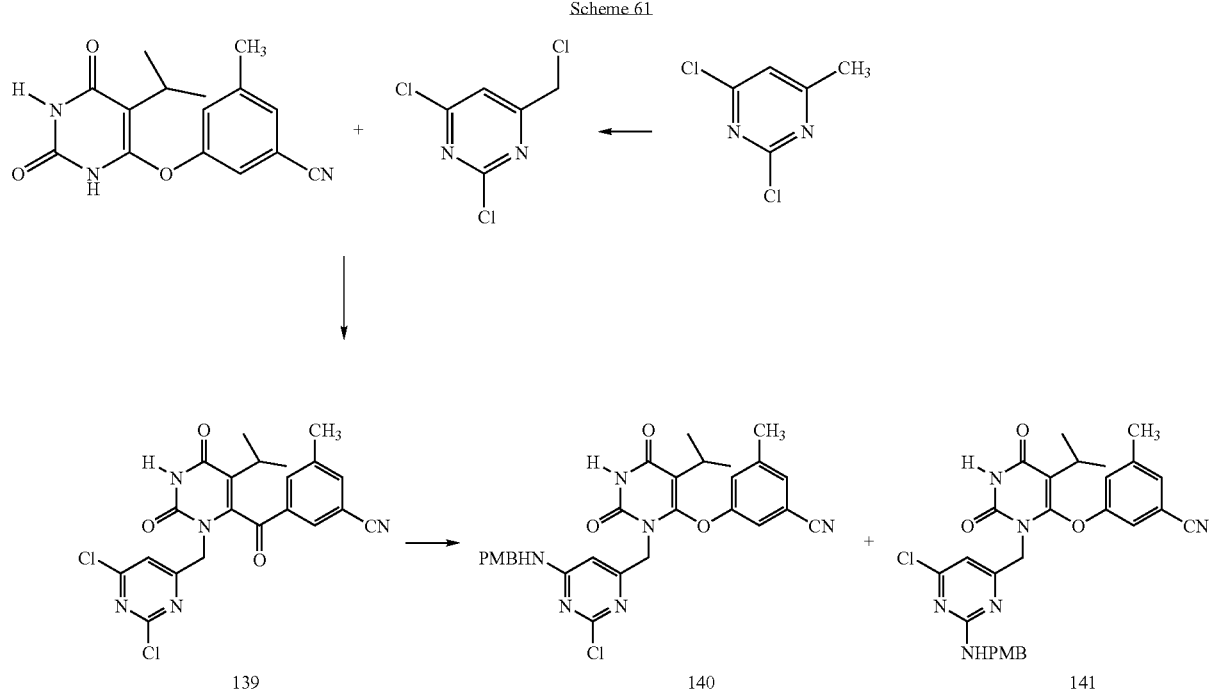

Scheme 61

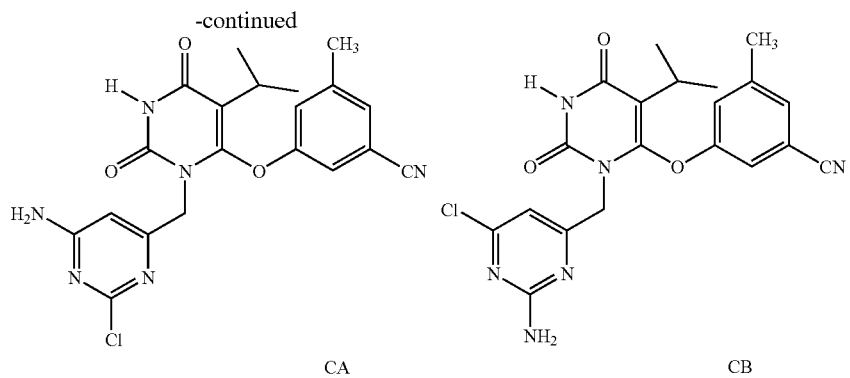

CA  CB 2,4-Dichloro-6-chloromethyl-pyrimidine: A mixture of 2,4-dichloro-6-methylpyrimidine (12.5 g, 76.65 mmol), N-chloro succinimide (12.28 g, 92 mmol), and benzoyl peroxide (2.78 g, 11.5 mmol) in carbon tetrachloride (150 ml) was refluxed for 24 hr. After cooling to room temperature, the mixture was filtered and evaporated in vacuo. The residue was purified by silica gel column chromatography (eluent, from hexane to 2% ether in hexane) to afford 6 g (40%) of 2,4-dichloro-6-chloromethyl-pyrimidine as a white solid. $^1$H NMR (200 MHz, CDCl$_3$) δ 4.58 (2H, s), 7.55 (1H, s).

3-[3-(2,6-Dichloro-pyrimidin-4-ylmethyl)-5-isopropyl-2,6-dioxo-1,2,3,6-tetrahydro-pyrimidine-4-carbonyl]-5-methyl-benzonitrile (139): To a mixture of 5-isopropyl-6-(3'-cyano-5'-methylbenzoyl)-2,4-pyrimidinedione (1.19 g, 4 mmol), 2,4-dichloro-6-chloromethyl-pyrimidine (790 mg, 4 mmol), anhydrous powdered potassium carbonate (552 mg, 4 mmol), and lithium iodide (536 mg, 4 mmol), was added DMF (20 ml). The mixture was stirred at room temperature for overnight and evaporated in vacuo. The residue was then purified by silica gel column chromatography (eluent, EA:hexane (1:2)) to afford 476 mg (26%) of 3-[3-(2,6-dichloro-pyrimidin-4-ylmethyl)-5-isopropyl-2,6-dioxo-1,2,3,6-tetrahydro-pyrimidine-4-carbonyl]-5-methyl-benzonitrile as a pale yellow foam.

$^1$H NMR (200 MHz, CDCl$_3$) δ 1.22 (3H, d, J=6.8 Hz), 1.25 (3H, d, J=6.8 Hz), 2.25 (1H, m), 2.52 (3H, s), 4.62 (1H, d, J=17.2 Hz), 4.98 (1H, d, J=17.2 Hz), 7.20 (1H, s), 7.77 (1H, s), 7.98 (1H, s), 8.10 (1H, s), 9.18 (1H, s).

3-{3-[2-Chloro-6-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (140) and 3-{3-[6-Chloro-2-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (141)

A mixture of 3-[3-(2,6-Dichloro-pyrimidin-4-ylmethyl)-5-isopropyl-2,6-dioxo-1,2,3,6-tetrahydro-pyrimidine-4-carbonyl]-5-methyl-benzonitrile (458 mg, 1 mmol) and p-methoxy benzylamine (262 µl, 2 mmol) in acetonitrile (10 ml) was refluxed for 2.5 hr. After cooling to room temperature, the mixture was evaporated in vacuo. The residue was dissolved in dichloromethane (20 ml), washed with water, dried with anhydrous magnesium sulfate, filtered, and evaporated in vacuo. The residue was purified by silica gel column chromatography (eluent, EA:hexane (1:2)) to afford 143 mg (25%) of 3-{3-[2-Chloro-6-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (R$_f$=0.14) and 302 mg (54%) of 3-{3-[6-Chloro-2-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (R$_f$=0.06) as a white solid, respectively.

3-{3-[2-Chloro-6-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (140)

m.p. 147-148° C.; $^1$H NMR (200 MHz, CDCl$_3$/CD$_3$OD) δ 1.07 (3H, d, J=7.0 Hz), 1.13 (3H, d, J=7.0 Hz), 2.14 (1H, m), 2.41 (3H, s), 3.74 (3H, s), 4.22 (1H, d, J=16.6 Hz), 4.32 (1H, br. s), 4.83 (1H, d, J=16.6 Hz), 6.00 (1H, s), 6.79 (2H, m), 7.20 (2H, m), 7.62 (1H, s), 7.88 (2H, s).

3-{3-[6-Chloro-2-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (141): m.p. 137-139° C.; $^1$H NMR (200 MHz, CDCl$_3$/CD$_3$OD) δ 1.12 (3H, d, J=6.6 Hz), 1.20 (3H, d, J=6.6 Hz), 2.20 (1H, m), 2.36 (3H, s), 3.80 (3H, s), 4.22-4.50 (2H, m), 5.01 (1H, d, J=17.0 Hz), 6.23 (1H, s), 6.84-6.91 (2H, m), 7.23-7.34 (2H, m), 7.62 (1H, br. s), 7.75 (2H, br. s), 7.90 (1H, br. s).

Example CA

To a stirred solution of 3-{3-[2-Chloro-6-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (143 mg, 0.256 mmol) in acetonitrile (3 ml) at room temperature, was added ceric ammonium nitrate (280 mg, 0.512 mmol) followed by distilled water (1.5 ml). After 30 mm., the mixture was diluted with EA, washed with water, dried with anhydrous magnesium sulfate, filtered, and evaporated in vacuo. The residue was purified by silica gel column chromatography (eluent, EA:hexane (1:1)) to afford 87 mg (77%) of white solid. m.p. 172-174° C.; $^1$H-NMR (200 MHz, DMSO-d$_6$) δ 1.04 (3H, d, J=6.8 Hz), 1.10 (3H, d, J=6.8 Hz), 2.12 (1H, m), 2.43 (3H, s), 4.43 (2H, s), 6.15 (1H, s), 7.36 (2H, s), 8.06 (1H, s), 8.08 (1H, s), 8.30 (1H, s), 11.71 (1H, s).

Example CB

To a stirred solution of 3-{3-[6-chloro-2-(4-methoxy-benzylamino)-pyrimidin-4-ylmethyl]-5-isopropyl-2,6-dioxo-1,2,3,6-tetrahydro-pyrimidine-4-carbonyl}-5-methyl-benzonitrile (287 mg, 0.513 mmol) in acetonitrile (6 ml) at room temperature, was added ceric ammonium nitrate (563 mg, 1.026 mmol) followed by distilled water (3 ml). After 1 hr., the mixture was diluted with EA, washed with water, dried with anhydrous magnesium sulfate, filtered, and evaporated in vacuo. The residue was purified by silica gel column chromatography (eluent, EA:hexane (1:1)) to afford 162 mg (72%) of a white solid. m.p. 337-338° C.; $^1$H-NMR (200 MHz, DMSO-$d_6$) δ 1.04 (3H, d, J=7.0 Hz), 1.07 (3H, d, J=7.0 Hz) 2.11 (1H, m), 2.38 (3H, s), 4.50 (1H, d, J=17.0 Hz), 4.74 (1H, d, J=17.0 Hz), 6.03 (1H, t, J=2.4 Hz), 6.46 (2H, s), 7.97 (1H, s), 8.09 (1H, s), 8.33 (1H, s), 11.65 (1H, s).

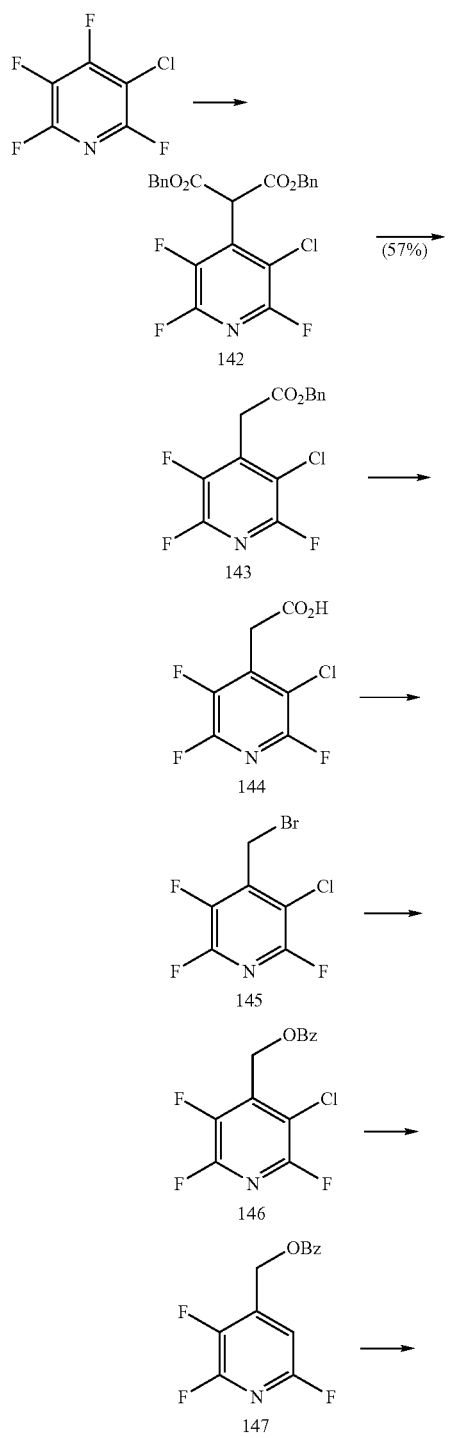

Scheme 62

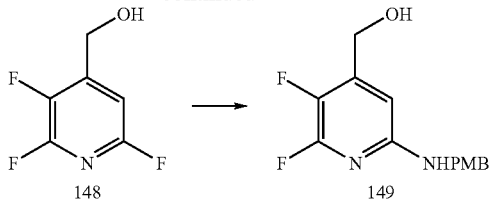

(3-Chloro-2,5,6-trifluoro-pyridin-4-yl)-acetic acid benzyl ester (143): 3-Chloro-2,4,5,6-tetrafluoropyridine (33.1 g, 178 mmol) and dibenzyl malonate (44.5 ml, 178 mmol) were dissolved in anhydrous DMF (360 ml) under nitrogen atmosphere. The mixture (142) was then cooled in an ice bath. To a stirred mixture, was portionwise added 60% sodium hydride (15.68 g, 392 mmol) during 2.5 hr. The mixture was then stirred in a water bath for ca. 15 hr. The mixture was neutralized with aqueous saturated ammonium chloride solution and the mixture was partitioned between ether and water. Ether layer was taken, washed with water twice, dried with anhydrous magnesium sulfate, filtered, and evaporated in vacuo to give a crude product as an yellow oil. The crude product was then dissolved in DMSO (200 ml) and stirred with water (3.2 ml) in an oil bath (130~140° C.) for 3 hr. After cooling to room temperature, water was added to the mixture and the product was extracted with ether. The ether layer was washed with water twice, dried with anhydrous magnesium sulfate, filtered, and evaporated in vacuo to give a light brown oil. The crude product was purified by silica gel column chromatography (eluent, ether:hexane (1:9)) to afford 41.9 g (74% for two steps) of (3-chloro-2,5,6-trifluoro-pyridin-4-yl)-acetic acid benzyl ester as a white solid. m.p. 87-92° C.; $^1$H NMR (200 MHz, CDCl$_3$) δδ 3.96 (2H, d, J=1.6 Hz), 5.19 (2H, s), 7.30-7.39 (5H, m).

(3-Chloro-2,5,6-trifluoro-pyridin-4-yl)-acetic acid (144): A mixture of (3-chloro-2,5,6-trifluoro-pyridin-4-yl)-acetic acid benzyl ester (29 g, 91.86 mmol), anhydrous THF (180 ml), and 10% palladium on carbon (1 g) was stirred for 4 hr. at room temperature under hydrogen atmosphere. The reaction mixture was then filtered through celite pad and the pad was washed with ethanol. The combined filtrate was evaporated in vacuo and the residue was recrystallized from dichloromethane to afford 16.2 g (78%) of (3-chloro-2,5,6-trifluoro-pyridin-4-yl)-acetic acid as a white solid. m.p. 127-129° C.: $^1$H NMR (200 MHz, CDCl$_3$) δ 3.97 (2H, d, J=1.6 Hz), 8.50 (1H, br. s).

4-Bromomethyl-3-chloro-2,5,6-trifluoro-pyridine (145): To a 1 L 3-neck flask equipped with addition funnel, was placed chlorobenzene (150 ml). (3-Chloro-2,5,6-trifluoro-pyridin-4-yl)-acetic acid (19.57 g, 86.77 mmol) and mercury oxide (20 g, 92.34 mmol) were added in this order. The mixture was heated up to 140~150° C. in an oil bath. Bromine (5.4 ml, 105 mmol) in chlorobenzene (90 ml) was then added dropwise through the addition funnel for 3 hr. After the addition of bromine solution, the reaction mixture was refluxed for further 1 hr. and cooled to room temperature. The mixture was filtered through celite pad and the pad was washed with chlorobenzene. The combined filtrate was evaporated in vacuo and the residue was purified by silica gel column chromatography (eluent, ether:hexane (1:15)) to give 17 g (75%) of 4-bromomethyl-3-chloro-2,5,6-trifluoro-pyridine as a colorless oil.

Benzoic acid 3-chloro-2,5,6-trifluoro-pyridin-4-ylmethyl ester (146): To a solution of the 4-bromomethyl-3-chloro-2,5,6-trifluoro-pyridine (15.6 g, 59.9 mmol) in DMF (90 ml)

cooled in an ice bath, sodium benzoate (12.9 g, 89.8 mmol) was added. After 1 hr., the mixture was stirred in a water bath for ca. 20 hr. The mixture was then diluted with ether, washed with water twice, dried with anhydrous magnesium sulfate, filtered, and evaporated in vacuo to give a light brown oil. The crude product was purified by silica gel column chromatography (eluent, ether:hexane (1:15) to afford 11.9 g (66%) of benzoic acid 3-chloro-2,5,6-trifluoro-pyridin-4-ylmethyl ester as a white solid. m.p. 60° C.; $^1$H NMR (200 MHz, CDCl$_3$) δ 5.54 (2H, d, J=1.6 Hz), 7.41-7.64 (3H, m), 8.00-8.05 (2H, m).

Benzoic acid 2,3,6-trifluoro-pyridin-4-ylmethyl ester (147): Benzoic acid 3-chloro-2,5,6-trifluoro-pyridin-4-ylmethyl ester (4.52 g, 15 mmol), anhydrous ethanol (50 ml), 10% palladium on carbon (500 mg), and triethylamine (2.5 ml, 18 mmol) were placed into a 500 ml bottle. The mixture was hydrogenated under hydrogen atmosphere (50 psi) for 1.5 hr. The reaction mixture was filtered through celite pad and the pad was washed with ethanol. The combined filtrate was evaporated in vacuo and the residue was purified by silica gel column chromatography (eluent, ether:hexane (1:15)) to afford 3.43 g (85%) of benzoic acid 2,3,6-trifluoro-pyridin-4-ylmethyl ester as a white solid. m.p. 73-76° C.; $^1$H NMR (200 MHz, CDCl$_3$) δ 5.52 (2H, s), 6.95 (1H, m), 7.30-7.70 (3H, m), 8.09-8.15 (2H, m).

(2,3,6-Trifluoro-pyridin-4-yl)-methanol (148): To a stirred solution of benzoic acid 2,3,6-trifluoro-pyridin-4-ylmethyl ester (3.43 g, 12.8 mmol) in anhydrous methanol (50 ml) at room temperature, was added sodium methoxide (693 mg, 12.8 mmol). After stirring for 20 min., excess ammonium chloride was added to the reaction mixture and stirring was continued for 30 min. The mixture was then evaporated in vacuo and the residue was dissolved in methanol-dichloromethane (1:9), filtered, and the filtrate was evaporated in vacuo. The residue was purified by silica gel column chromatography (eluent, EA:hexane (1:4) to EA) to afford 2.0 g (95%) of (2,3,6-trifluoro-pyridin-4-yl)-methanol as a white solid. m.p. 48-49° C.; $^1$H NMR (200 MHz, CDCl$_3$) δ 2.18 (1H, t, J=5.6 Hz), 4.88 (2H, d, J=5.6 Hz), 7.02 (1H, s).

[2,3-Difluoro-6-(4-methoxy-benzylamino)-pyridin-4-yl]-methanol (149): To a 100 ml round bottomed flask, were placed (2,3,6-trifluoro-pyridin-4-yl)-methanol (515 mg, 3.15 mmol) and p-methoxybenzyl amine (1.0 ml, 7.57 mmol). Nitrogen balloon was attached to the flask and the mixture was stirred in an oil bath (117~130° C.) for 2.5 hr. After cooling to room temperature, the mixture was purified by silica gel column chromatography (eluent, dichloromethane:methanol (95:5)) to afford 838 mg (94%) of [2,3-difluoro-6-(4-methoxy-benzylamino)-pyridin-4-yl]-methanol as a pale brown solid. $^1$H NMR (200 MHz, CDCl$_3$) δ 2.04 (1H, br. s), 3.79 (3H, s), 4.52 (2H, d, J=5.6 Hz), 4.70 (2H, br. s), 4.84 (1H, br. s), 6.22 (1H, m), 6.83-6.90 (2H, m), 7.24-7.31 (2H, m).

Example CC

Scheme 63

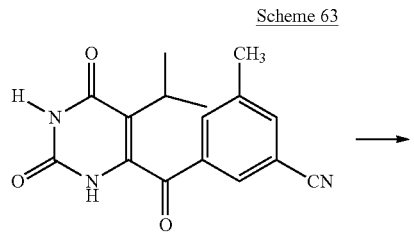

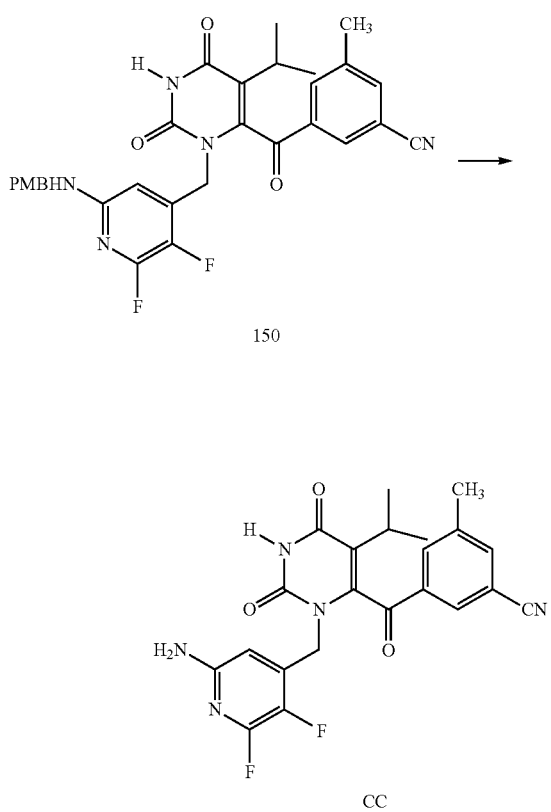

3-{3-[2,3-Difluoro-6-(4-methoxy-benzylamino)-pyridin-4-ylmethyl]-5-isopropyl-2,6-dioxo-1,2,3,6-tetrahydro-pyrimidine-4-carbonyl}-5-methyl-benzonitrile (150): 2,3-Difluoro-6-p-methoxybenzylamino-4-pyridinemethanol (280 mg, 1 mmol) was dissolved in chloroform (10 ml) and cooled in an ice bath under nitrogen atmosphere. With stirring, triethylamine (210 µl, 1.5 mmol) was added and methanesulfonyl chloride (90 µl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 5-isopropyl-6-(3'-cyano-5'-methylbenzoyl)-2,4-pyrimidinedione (285 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, EA:hexane (1:2)) to afford 309 mg (55%) of 3-[(3-[2,3-difluoro-6-(4-methoxy-benzylamino)-pyridin-4-ylmethyl]-5-isopropyl-2,6-dioxo-1,2,3,6-tetrahydro-pyrimidine-4-carbonyl]-5-methyl-benzonitrile as a yellow solid. $^1$H NMR (200 MHz, DMSO-d$_6$) δ 1.03 (3H, d, J=6.8 Hz), 1.09 (3H, d, J=6.8 Hz), 2.10 (1H, m), 2.31 (3H, s), 3.72 (3H, s), 4.24 (2H, d, J=3.8 Hz), 4.45 (1H, d, J=17.4 Hz), 4.80 (1H, d, J=17.4 Hz), 6.02 (1H, s), 6.87 (2H, d, J=8.0 Hz), 7.17 (2H, d, J=8.0 Hz), 7.41 (1H, t, J=3.8 Hz), 7.76 (1H, s), 8.05 (1H, s), 8.27 (1H, s), 11.66 (1H, s).

Example CC

To a stirred solution of 3-{3-[2,3-difluoro-6-(4-methoxybenzylamino)-pyridin-4-ylmethyl]-5-isopropyl-2,6-dioxo-1,2,3,6-tetrahydro-pyrimidine-4-carbonyl}-5-methyl-benzonitrile (287 mg, 0.513 mmol) in acetonitrile (10 ml) and acetic acid (3 ml), was added ceric ammonium nitrate (563 mg, 1.02 mmol) and distilled water (3 ml) in this order. After 40 min., ethyl acetate and water was added to the reaction mixture. Organic layer was taken, dried with anhydrous magnesium sulfate, filtered, and evaporated in vacuo. The residue was purified by silica gel column chromatography (eluent, EA:hexane (1:2)) to afford 191 mg (84%) of a pale yellow solid. m.p. 133-134° C.; $^1$H-NMR (200 MHz, CDCl$_3$) δ 1.17 (3H, d, J=6.4 Hz), 1.24 (3H, d, J=6.4 Hz) 2.26 (1H, m), 2.50 (3H, s), 4.65 (1H, d, J=17.8 Hz), 5.03 (1H, d, J=17.8 Hz), 6.73 (1H, t, J=3.0 Hz), 7.80 (1H, s), 7.85 (1H, s), 7.98 (1H, s), 9.28 (1H, s).

Example CD

Scheme 64

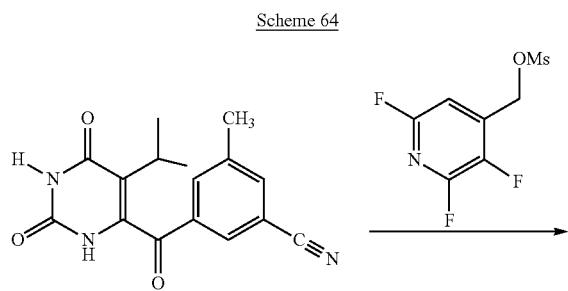

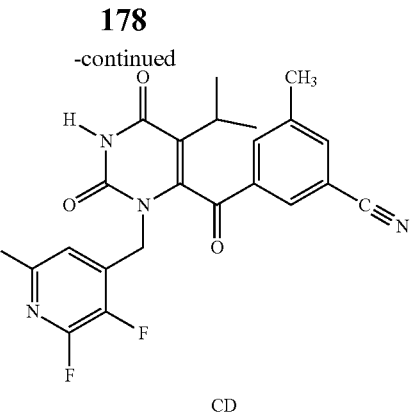

CD

Example CD 2,3,6-Trifluoro-4-pyridinemethanol (163 mg, 1 mmol) was dissolved in chloroform (10 ml) and cooled in an ice bath under nitrogen atmosphere. With stirring, triethylamine (210 μl, 1.5 mmol) was added and methanesulfonyl chloride (90 μl, 1.2 mmol) was added dropwise. After stirring for 1.1 hr., the reaction mixture was washed with saturated aqueous sodium bicarbonate, dried with anhydrous magnesium sulfate, filtered, and evaporated in vacuo. The residue was further dried in high vacuo for ca. 20 min. and mixed with 5-isopropyl-6-(3'-cyano-5'-methylbenzoyl)-2,4-pyrimidinedione (285 mg, 1 mmol), powdered anhydrous potassium carbonate (138 mg, 1 mmol), and lithium iodide (134 mg, 1 mmol). DMF (5 ml) was then added to the mixture at room temperature and stirred for ca. 4 hr. After evaporation of DMF, the residue was dissolved in methanol-chloroform (1:9) and filtered through celite pad. The filtrate was then evaporated in vacuo and the residue was purified by silica gel column chromatography (eluent, methanol:chloroform (2:98)) to afford 179 mg (40%) of a white solid. m.p. 133-134° C.; $^1$H-NMR (200 MHz, CDCl$_3$) δ 1.17 (3H, d, J=6.4 Hz), 1.24 (3H, d, J=6.4 Hz) 2.26 (1H, m), 2.50 (3H, s), 4.65 (1H, d, J=17.8 Hz), 5.03 (1H, d, J=17.8 Hz), 6.73 (1H, t, J=3.0 Hz), 7.80 (1H, s), 7.85 (1H, s), 7.98 (1H, s), 9.28 (1H, s); m/z (EI) 442 (M$^+$).

Example CE

Scheme 65

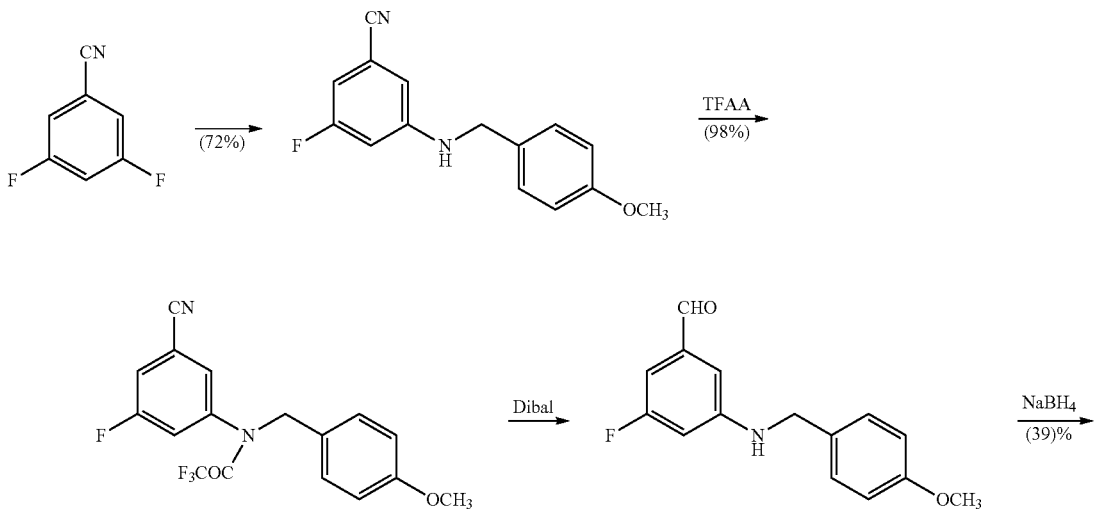

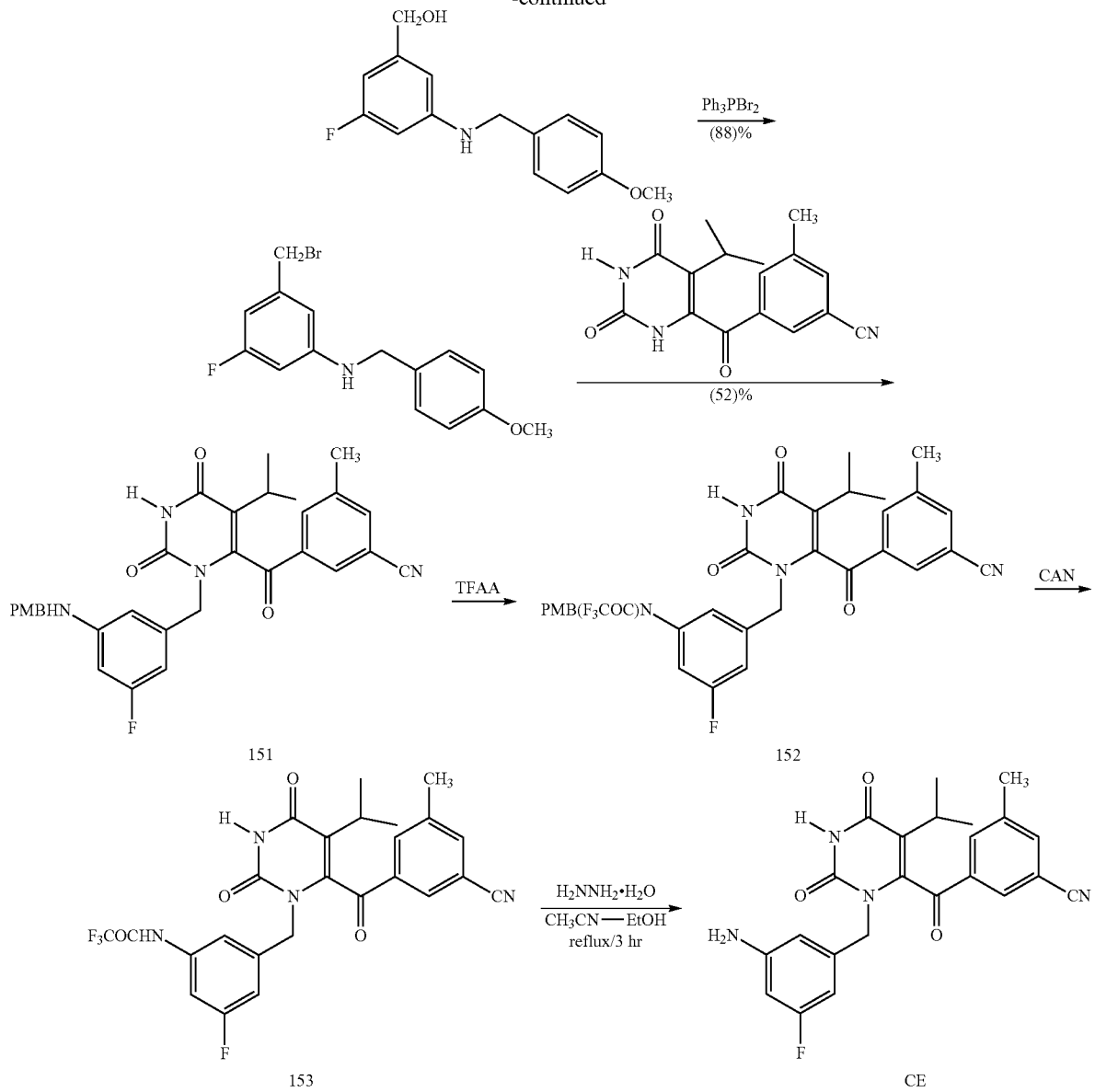

3-Fluoro-5-(4-methoxy-benzylamino)-benzonitrile: A mixture of 3,5-difluoro-benzonitrile (2.78 g, 20 mmol) and p-methoxybenzyl amine (5.74 ml, 44 mmol) in DMSO (20 ml) was stirred for 8 hr. in an oil bath (100-110° C.). After cooling to room temperature, the mixture was diluted with ether, washed with water, dried with anhydrous magnesium sulfate, filtered, and evaporated in vacuo. The residue was purified by silica gel column chromatography (eluent, EA: hexane (from 1:13 to 1:10)) to afford 3.92 g (76%) of a white solid. m.p. 93-94° C.; $^1$H NMR (200 MHz, CDCl$_3$) δ 3.61 (3H, s), 4.04 (2H, s); 4.16 (1H, br. s), 6.27 (1H, m), 6.42-6.47 (2H, m), 6.69 (2H, d, J=7.2 Hz), 7.06 (2H, d, J=7.2 Hz).

N-(3-Cyano-5-fluoro-phenyl)-2,2,2-trifluoro-N-(4-methoxy-benzyl)-acetamide

To a stirred solution of 3-fluoro-5-(4-methoxy-benzylamino)-benzonitrile (5.8 g, 22.65 mmol) in dichloromethane (50 ml) cooled in an ice bath, was added triethylamine (4.74 ml, 33.98 mmol) and trifluoroacetic anhydride (3.78 ml, 27.18 mmol). After 30 min., the mixture was stirred for 3 hr. at room temperature. The mixture was then washed with saturated aqueous sodium bicarbonate solution, dried with anhydrous magnesium sulfate, filtered, and evaporated in vacuo. The residue was purified by silica gel column chromatography (eluent, EA:hexane (1:6)) to afford 7.87 g (98%) of a white solid. m.p. 102-103° C.; $^1$H NMR (200 MHz, CDCl$_3$) δ3.80 (3H, s), 4.85 (2H, s), 6.82 (2H, d, J=7.0 Hz), 6.95-7.10 (4H, m), 7.39 (1H, d, J=7.2 Hz).

3-Fluoro-5-(4-methoxy-benzylamino)-benzaldehyde: To a stirred solution of N-(3-cyano-5-fluoro-phenyl)-2,2,2-trifluoro-N-(4-methoxy-benzyl)-acetamide (70.45 g, 21.148 mmol) in toluene (20 ml) cooled in an ice bath, was added 1.5M Dibal in toluene (14.8 ml, 22.2 mmol). After 2 hr., the mixture was stirred for overnight at room temperature. The mixture was diluted with toluene (50 ml), cooled in an ice bath, and acidified with 10% hydrochloric acid. The mixture was then extracted with ether, washed with saturated aqueous sodium bicarbonate solution, dried with anhydrous magnesium sulfate, filtered, and evaporated in vacuo to give 7.87 g of crude 3-fluoro-5-(4-methoxy-benzylamino)-benzaldehyde as a pale yellow syrup. The crude product was used for the next reaction without further purification.

[3-Fluoro-5-(4-methoxy-benzylamino)-phenyl]-methanol: 3-Fluoro-5-(4-methoxy-benzylamino)-benzaldehyde (crude product) was dissolved in anhydrous ethanol (40 ml) and cooled in an ice bath. Sodium borohydride (800 mg, 21 mmol) was then added with stirring. After 1 hr., the mixture was diluted with methanol and excess ammonium chloride was added. After stirring for 1 hr. at room temperature, the mixture was evaporated in vacuo and coevaporated with methanol several times. The residue was purified by silica gel column chromatography (eluent, EA: hexane (from 1:4 to 1:1)) to afford 2.16 g (39%) of [3-fluoro-5-(4-methoxy-benzylamino)-phenyl]-methanol as a white solid. m.p. 93° C.

$^1$H NMR (200 MHz, CDCl$_3$) δ 3.82 (3H, s), 4.24 (2H, s), 4.59 (2H, s), 6.26 (1H, m), 6.39-6.43 (2H, m), 6.88 (2H, d, J=5.2 Hz), 7.28 (2H, d, J=5.2 Hz).

(3-Bromomethyl-5-fluoro-phenyl)-(4-methoxy-benzyl)-amine: A mixture of [3-fluoro-5-(4-methoxy-benzylamino)-phenyl]-methanol (522 mg, 2 mmol) and triphenylphosphine dibromide (1.27 g, 3 mmol) in dichloromethane (6 ml) was stirred in an ice bath for 30 min. The mixture was then warmed up to room temperature, diluted with EA (20 ml), washed with saturated aqueous sodium bicarbonate solution followed by brine, dried with anhydrous magnesium sulfate, filtered, and evaporated in vacuo. The residue was purified by silica gel column chromatography (eluent, EA:hexane (1:10)) to afford 570 mg (88%) of a pale yellow syrup. $^1$H NMR (200 MHz, CDCl$_3$) δ 3.86 (3H, s), 4.30 (2H, s), 4.40 (2H, s), 6.41 (1H, m), 6.56-6.60 (2H, m), 6.90-6.96 (2H, m), 7.31-7.35 (2H, m).

N-{3-[6-(3-Cyano-5-methyl-benzoyl)-5-isopropyl-2,4-dioxo-3,4-dihydro-2 H-pyrimidin-1-ylmethyl]-5-fluoro-phenyl}-2,2,2-trifluoro-N-(4-methoxy-benzyl)-acetamide (152): To a mixture of (3-bromomethyl-5-fluoro-phenyl)-(4-methoxy-benzyl)-amine (570 mg, 1.758 mmol), 5-isopropyl-6-(3'-cyano-5'-methylbenzoyl)-2,4-pyrimidinedione (522 mg, 1.758 mmol), and anhydrous powdered potassium carbonate (243 mg, 1.758 mmol), was added DMF (10 ml). The mixture was then stirred for overnight at room temperature and evaporated in vacuo. The residue was dissolved in methanol-dichloromethane (1:9), filtered through celite pad, and evaporated in vacuo to give a light yellow syrup. The crude product was purified by silica gel column chromatography (eluent, EA:hexane (1:4)) to afford 531 mg of 3-{3-[3-fluoro-5-(4-methoxy-benzylamino)-benzyl]-5-isopropyl-2,6-dioxo-1,2,3,6-tetrahydro-pyrimidine-4-carbonyl}-5-methyl-benzonitrile (151) as a yellow solid.

To a stirred solution of 3-{3-[3-Fluoro-5-(4-methoxy-benzylamino)-benzyl]-5-isopropyl-2,6-dioxo-1,2,3,6-tetrahydro-pyrimidine-4-carbonyl}-5-methyl-benzonitrile (531 mg, ~0.98 mmol)) and triethyl amine (274 μl, 1.96 mmol) in dichloromethane (10 ml) cooled in an ice bath, was dropwise added trifluoroacetic anhydride (205 μl, 1.47 mmol). After 1 hr., the mixture was stirred at room temperature for overnight. The mixture was diluted with dichloromethane, washed with saturated aqueous sodium bicarbonate solution, dried with anhydrous magnesium sulfate, filtered, and evaporated in vacuo. The residue (741 mg, ~1 mmol) was dissolved in acetonitrile (10 ml). With stirring, ceric ammonium nitrate (1.27 g, 2.32 mmol) and distilled water (5 ml) were added in this order. After 30 min., the mixture was diluted with ethyl acetate, washed with water, dried with anhydrous magnesium sulfate, filtered, and evaporated in vacuo. The residue was purified by silica gel column chromatography (eluent, EA:hexane (1:4)) to afford 315 mg (26% for 3 steps) of a white solid (152). $^1$H NMR (200 MHz, CDCl$_3$) δ 1.11 (3H, d, J=6.4 Hz), 1.22 (3H, d, J=6.4 Hz), 2.20 (1H, m), 2.46 (3H, s), 3.80 (3H, s), 4.51-4.82 (3H, m), 4.93 (1H, d, J=13.8 Hz), 6.58-6.62 (2H, m), 6.79-6.84 (3H, m), 7.04 (2H, m), 7.74 (1H, s), 7.84 (2H, s), 9.00 (1H, s).

N-{3-[6-(3-Cyano-5-methyl-benzoyl)-5-isopropyl-2,4-dioxo-3,4-dihydro-2 H-pyrimidin-1-ylmethyl]-5-fluoro-phenyl}-2,2,2-trifluoro-acetamide (153): N-{3-[6-(3-Cyano-5-methyl-benzoyl)-5-isopropyl-2,4-dioxo-3,4-dihydro-2 H-pyrimidin-1-ylmethyl]-5-fluoro-phenyl}-2,2,2-trifluoro-N-(4-methoxy-benzyl)-acetamide (389 mg, 0.61 mmol) was dissolved in acetonitrile (6 ml). With stirring, ceric ammonium nitrate (669 mg, 1.2 mmol) and distilled water (3 ml) were added in this order. After 24 hr., the mixture was diluted with ethyl acetate, washed with water, dried with anhydrous magnesium sulfate, filtered, and evaporated in vacuo. The residue was purified by silica gel column chromatography (eluent, EA:hexane (1:2)) to afford 240 mg (76%) of a white solid. $^1$H NMR (200 MHz, DMSO-d$_6$) δ 1.03 (3H, d, J=6.8 Hz), 1.18 (3H, d, J=6.8 Hz), 2.09 (1H, m), 2.32 (3H, s), 4.42 (1H, d, J=16.8 Hz), 4.97 (1H, d, J=16.8 Hz), 6.80 (1H, m), 7.08 (1H, s), 7.31 (1H, m), 7.91 (1H, s), 7.96 (1H, s), 8.16 (1H, s), 11.28 (1H, s), 11.69 (1H, s).

Example CE

N-{3-[6-(3-Cyano-5-methyl-benzoyl)-5-isopropyl-2,4-dioxo-3,4-dihydro-2H-pyrimidin-1-ylmethyl]-5-fluoro-phenyl}-2,2,2-trifluoro-acetamide (180 mg, 0.35 mmol) was dissolved in acetonitrile (5 ml) and ethanol (5 ml). Hydrazine monohydrate (174 mg, 3.5 mmol) was then added and the mixture was refluxed for 3 hr. The mixture was evaporated in vacuo and the residue was purified by silica gel column chromatography (eluent, EA:hexane (1:1)) to afford 100 mg (68%) of a yellow solid. m.p. 263-264° C. $^1$H-NMR (200 MHz, DMSO-d$_6$) δ 1.02 (3H, d, J=6.8 Hz), 1.09 (3H, d, J=6.8 Hz), 2.08 (1H, m), 2.38 (3H, s), 4.32 (1H, d, J=16.6 Hz), 4.72 (1H, d, J=16.6 Hz), 5.31 (2H, s), 5.91-6.01 (3H, m), 7.95 (1H, s), 7.96 (1H, s), 8.21 (1H, s), 11.63 (1H, s).

Scheme 66

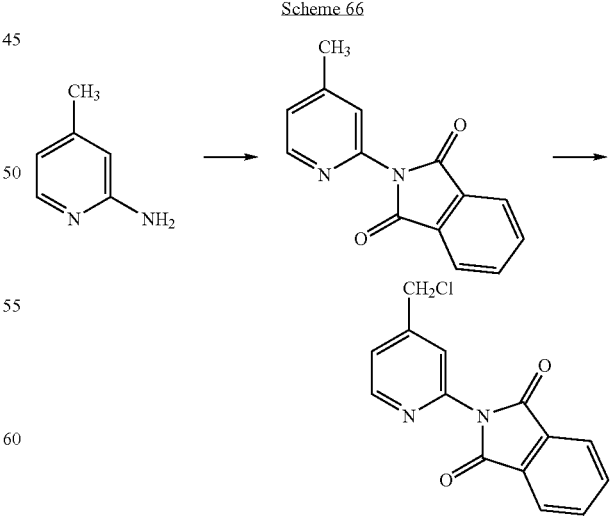

2-(4-Methyl-pyridin-2-yl)-isoindole-1,3-dione: To a mixture of 2-Amino-4-methylpyridine (21.6 g, 0.2 mol) and phthalic anhydride (29.6 g, 0.2 mol) in toluene (160 ml), was added triethylamine (2.8 ml, 0.02 mol). The mixture was refluxed for 5 hr. After cooling to room temperature, the mixture was evaporated in vacuo and the residue was suspended in acetic anhydride (250 ml). The mixture was then heated to reflux for 4 hr until the solid dissolves completely. After cooling to room temperature, white precipitate was collected by filtration and washed with acetic anhydride and hexane, and dried in high vacuo to give 26.6 g (56%) of 2-(4-methyl-pyridin-2-yl)-isoindole-1,3-dione as a white solid. $^1$H NMR (200 MHz, CDCl$_3$) δ 2.45 (3H, s), 7.18 (1H, d, J=5.0 Hz), 7.25 (1H, s), 7.76-7.99 (4H, m), 8.53 (1H, d, J=5.0 Hz). m/z (EI) 238 (M$^+$).

2-(4-Chloromethyl-pyridin-2-yl)-isoindole-1,3-dione: A mixture of 2-(4-methyl-pyridin-2-yl)-isoindole-1,3-dione (952 mg, 4 mmol)), N-chloro succinimide (640 mg, 4.8 mmol), and benzoyl peroxide (484 g, 2 mmol) in carbon tetrachloride (20 ml) was refluxed for 2 hr. After cooling to room temperature, the mixture was filtered and the filtrate was evaporated in vacuo. The residue was purified by silica gel column chromatography (eluent, dichloromethane:EA (95:5)) to afford 300 mg (28%) of 2-(4-chloromethyl-pyridin-2-yl)-isoindole-1,3-dione as a pale brown solid. m.p. 152-153° C. $^1$H NMR (200 MHz, CDCl$_3$) δ 4.64 (2H, s), 7.42 (1H, d, J=5.0 Hz), 7.49 (1H, s), 7.80-7.99 (4H, m), 8.68 (1H, d, J=5.0 Hz).

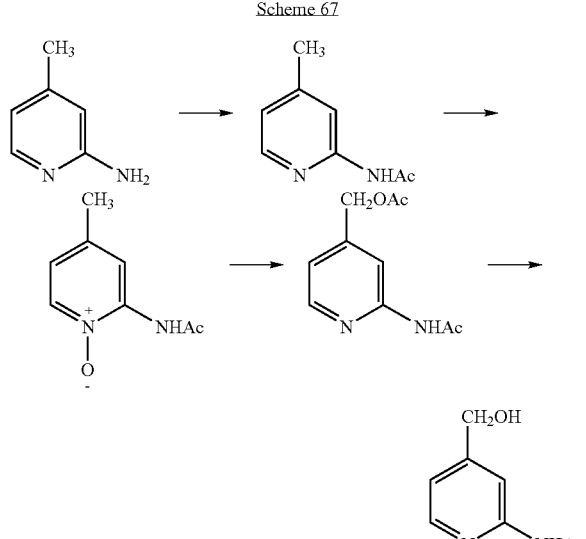

N-(4-Methyl-pyridin-2-yl)-acetamide

N-(4-Methyl-pyridin-2-yl)-acetamide was prepared according to the procedures described in JACS, 1957, 79, 3565.

N-(4-Methyl-1-oxy-pyridin-2-yl)-acetamide: 2-Acetamino-4-methylpyridine (30 g, 0.2 mol) was stirred with 57-80% m-CPBA (90 g, 0.3 mol) in dichloromethane (300 ml) in a water bath for 24 hr. The mixture was evaporated in vacuo and the residue was purified by silica gel column chromatography (eluent, 1) ether, 2) methanol:chloroform (5:95)) to afford 26 g (78%) of N-(4-methyl-1-oxy-pyridin-2-yl)-acetamide. $^1$H NMR (200 MHz, CDCl$_3$) δ 2.31 (3H, s), 2.37 (3H, s), 6.80 (1H, dd, J=2.4 Hz, 6.6 Hz), 8.11 (1H, d, J=6.6 Hz), 8.26 (1H, d, J=2.4 Hz), 10.02 (1H, s).

Acetic acid 2-acetylamino-pyridin-4-ylmethyl ester: N-(4-Methyl-1-oxy-pyridin-2-yl)-acetamide (17.6 g, 0.1 mol) was refluxed with sodium acetate (8.69 g, 0.1 mol) in acetic anhydride (150 ml). After 1.5 hr., the mixture was cooled to room temperature and evaporated in vacuo. The residue was purified by silica gel column chromatography (eluent, EA:hexane (1:1)) to afford 4.2 g (20%) of acetic acid 2-acetylamino-pyridin-4-ylmethyl ester. $^1$H NMR (200 MHz, CDCl$_3$) δ 2.16 (3H, s), 2.21 (3H, s), 5.13 (2H, s), 6.99 (1H, d, J=5.6 Hz), 8.11 (1H, br. s), 8.12 (1H, s), 8.23 (1H, d, J=5.6 Hz).

N-(4-Hydroxymethyl-pyridin-2-yl)-acetamide: Acetic acid 2-acetylamino-pyridin-4-ylmethyl ester (4.2 g, 20 mmol) was stirred with ammonium hydroxide (10 ml) in methanol (50 ml) at room temperature. After 24 hr., the mixture was evaporated in vacuo and the residue was purified by silica gel column chromatography (eluent, EA) to afford 3.36 g (quantitative) of N-(4-hydroxymethyl-pyridin-2-yl)-acetamide as a pale yellow solid. m.p. 145° C.; $^1$H NMR (200 MHz, CDCl$_3$/CD$_3$OD) δ 2.19 (3H, s), 4.67 (2H, s), 7.08 (1H, d, J=5.0 Hz), 8.10 (1H, s), 8.17 (1H, d, J=5.0 Hz).

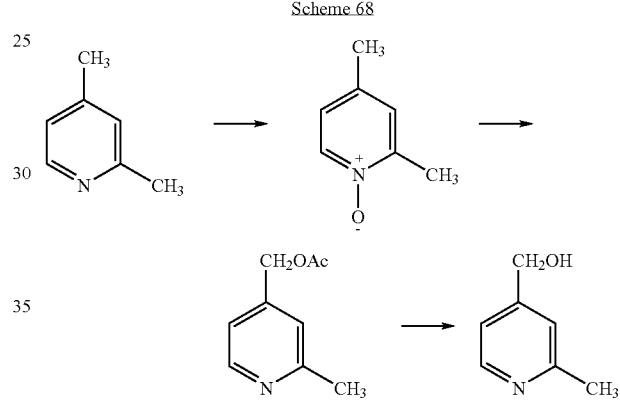

2,4-Dimethyl-pyridine 1-oxide: 2,4-Dimethylpyridine (40 g, 0.37 mol) was stirred with 30% hydrogen peroxide (170 ml) in glacial acetic acid (400 ml) in an oil bath (80-90° C.) for 24 hr. After cooling to room temperature, the mixture was evaporated in vacuo and the residue was purified by silica gel column chromatography (eluent, 1) ether, 2) methanol:chloroform (8:92)) to afford 45 g (98%) of 2,4-dimethyl-pyridine 1-oxide as an oil. $^1$H NMR (200 MHz, DMSO-d$_6$) δ 2.02 (3H, s), 2.18 (3H, s), 6.69 (1H, d, J=6.5 Hz), 6.82 (1H, s), 7.84 (1H, d, J=6.5 Hz).

Acetic acid 2-methyl-pyridin-4-ylmethyl ester: 2,4-Dimethyl-pyridine 1-oxide (24.6 g, 0.2 mol) was stirred in acetic anhydride (200 ml) in an oil bath (140-150° C.) for 4 hr. After cooling to room temperature, the mixture was evaporated in vacuo and the residue was purified by silica gel column chromatography (eluent, ether:hexane (2:1)) to afford 5.1 g (15%) of acetic acid 2-methyl-pyridin-4-ylmethyl ester as a colorless oil. $^1$H NMR (200 MHz, CDCl$_3$) δ 2.15 (3H, s), 2.56 (3H, s), 5.08 (2H, s), 7.05 (1H, d, J=5.0 Hz), 7.11 (1H, s), 8.48 (1H, d, J=5.0 Hz).

(2-Methyl-pyridin-4-yl)-methanol: Acetic acid 2-methyl-pyridin-4-ylmethyl ester (5.1 g, 31 mmol) was stirred with ammonium hydroxide (10 ml) in methanol (25 ml) at room temperature. After 24 hr., the mixture was evaporated in vacuo and the residue was purified by silica gel column chromatography (eluent, EA) to afford 3.56 g (94%) of (2-methyl-pyridin-4-yl)-methanol as a pale yellow solid. m.p. 58-59° C.

¹H NMR (200 MHz, CDCl₃) δ 2.45 (3H, s), 4.66 (2H, s), 7.06 (1H, d, J=5.2 Hz), 7.14 (1H, s), 8.25 (1H, d, J=5.2 Hz).

Scheme 69

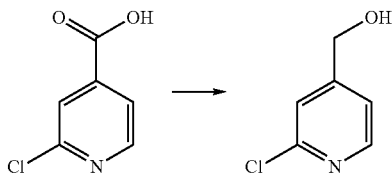

(2-Chloro-pyridin-4-yl)-methanol: To a stirred solution of 2-chloroisonicotinic acid (3.15 g, 20 mmol) in anhydrous THF (40 ml) cooled in an ice bath, was added borane-methyl sulfide complex (6 mL, 60 mmol). After 1 hr, the mixture was stirred for 48 hr at room temperature. The mixture was cooled in an ice bath and conc. HCl (30 ml) was added and stirred for 30 min. The mixture was then basified by addition of 50% aqueous NaOH (30 ml). The product was extracted with dichloromethane, dried with anhydrous potassium carbonate, filtered, and evaporated in vacuo. The crude product was purified by silica gel column chromatography (eluent, ether:hexane (5:1)) to afford 172 g (60%) of 2-chloro-4-pyridinemethanol as a white solid. m.p. 77-79° C.; ¹H NMR (200 MHz, CDCl₃) δ 2.97 (1H, br. s), 4.74 (2H, s), 7.20 (1H, d, J=5.7 Hz), 7.36 (1H, s), 8.28 (1H, d, J=5.7 Hz).

Scheme 70

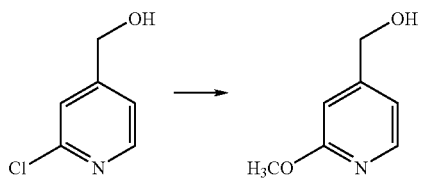

(2-Methoxy-pyridin-4-yl)-methanol: (2-Chloro-pyridin-4-yl)-methanol (2.82 g, 19.67 mmol) was refluxed with 25 wt. % sodium methoxide (25 ml) solution for 24 hr. After cooling to room temperature, the mixture was evaporated in vacuo and the residue was purified by silica gel column chromatography (eluent, EA:hexane (1:1)) to afford 1.8 g (60%) of (2-Methoxy-pyridin-4-yl)-methanol as a pale brown oil. ¹H NMR (200 MHz, CDCl₃) δ 2.16 (3H, s), 2.21 (3H, s), 5.13 (2H, s), 6.99 (1H, d, J=5.6 Hz), 8.11 (1H, br. s), 8.12 (1H, s), 8.23 (1H, d, J=5.6 Hz).

Scheme 71

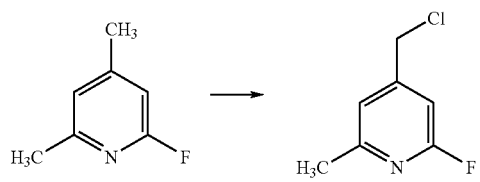

4-Chloromethyl-2-fluoro-6-methyl-pyridine: 2-Fluoro-4,6-dimethyl-pyridine (4.25 g, 34 mmol) was refluxed with N-chlorosuccinimide (4.99 g, 37.4 mmol) and benzoyl peroxide (822 mg, 3.4 mmol) in carbon tetrachloride (70 ml). After 3.5 hr., the mixture was cooled to room temperature and filtered. The filtrate was evaporated in vacuo and the residue was purified by silica gel column chromatography (eluent, ether:hexane (1:30)) to afford 740 mg (13%) of 4-chloromethyl-2-fluoro-6-methyl-pyridine as a yellow oil. ¹H NMR (200 MHz, CDCl₃) δ 2.51 (3H, s), 4.51 (2H, s), 6.77 (1H, s), 7.05 (1H, s).

Scheme 72

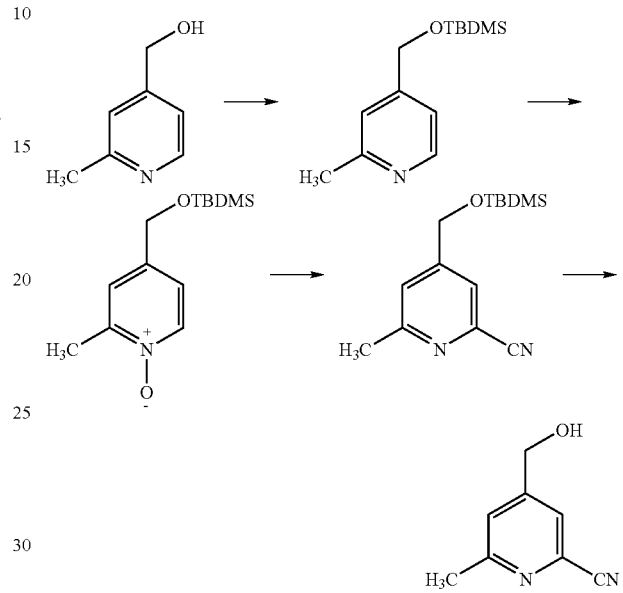

4-(tert-Butyl-dimethyl-silanyloxymethyl)-2-methyl-pyridine: 2-methylpyridine methanol (3.39 g, 27.56 mmol) was stirred with imidazole (6.12 g, 90 mmol), and tert-butyldimethylchlorosilane (6.78 g, 45 mmol) in DMF 960 ml) at room temperature for overnight. The mixture was diluted with ether, washed with aqueous saturated sodium bicarbonate, dried with anhydrous magnesium sulfate, filtered, and evaporated in vacuo. The residue was purified by silica gel column chromatography (eluent, ether:hexane (1:2)) to afford 5.9 g (90%) of 4-(tert-butyl-dimethyl-silanyloxymethyl)-2-methyl-pyridine as a colorless oil. ¹H NMR (200 MHz, CDCl₃) δ0.11 (6H, s), 0.94 (9H, s), (3H, s), 2.52 (3H, s), 4.67 (2H, s), 6.97 (1H, d, J=6.7 Hz), 7.08 (1H, s), 8.10 (1H, d, J=6.7 Hz).

4-(tert-Butyl-dimethyl-silanyloxymethyl)-2-methyl-pyridine 1-oxide: 4-(tert-Butyl-dimethyl-silanyloxymethyl)-2-methyl-pyridine (11.47 g, 0.248.4 mmol) was stirred with 57-80% m-CPBA (25.8 g) in dichloromethane (100 ml) in a water bath for 24 hr. The mixture was evaporated in vacuo and the residue was purified by silica gel column chromatography (eluent, ether:hexane (3:1)) to afford 11.3 g (93%) of 4-(tert-butyl-dimethyl-silanyloxymethyl)-2-methyl-pyridine 1-oxide as a white solid. ¹H NMR (200 MHz, CDCl₃) δ 0.11 (6H, s), 0.94 (9H, s), (3H, s), 2.52 (3H, s), 4.67 (2H, s), 6.97 (1H, d, J=6.7 Hz), 7.08 (1H, s), 8.10 (1H, d, J=6.7 Hz).

4-(tert-Butyl-dimethyl-silanyloxymethyl)-6-methyl-pyridine-2-carbonitrile: To a stirred solution of 4-(tert-butyl-dimethyl-silanyloxymethyl)-2-methyl-pyridine 1-oxide (11.2 g, 44 mmol) in dichloromethane (100 ml) at room temperature, was added trimethylsilyl cyanide (7.1 ml, 53.2 mmol). After 15 min., dimethylcarbamyl chloride (4.8 ml, 53.2 mmol) was added and the stirring was continued for 24 hr. The mixture was then cooled in an ice bath and saturated aqueous sodium bicarbonate solution (100 ml) was added. After 1 hr., organic layer was separated, dried with anhydrous magnesium sulfate, filtered, and evaporated in vacuo. The residue was purified by silica gel column chromatography (eluent, ether:hexane (1:1)) to afford 8.8 g (76%) of 4-(tert-butyl-dimethyl-silanyloxymethyl)-6-methyl-pyridine-2-carbonitrile as a white solid. $^1$H NMR (200 MHz, CDCl$_3$) δ 0.11 (6H, s), 0.94 (9H, s), (3H, s), 2.52 (3H, s), 4.67 (2H, s), 6.97 (1H, d, J=6.7 Hz), 7.08 (1H, s), 8.10 (1H, d, J=6.7 Hz).

4-Hydroxymethyl-6-methyl-pyridine-2-carbonitrile: 4-(tert-Butyl-dimethyl-silanyloxymethyl)-6-methyl-pyridine-2-carbonitrile (8 g, 30.53 mmol) was stirred with 1M tetrabutylammonium fluoride in THF (32 ml, 32 mmol) in THF (30 ml) at room temperature. After 1 hr., the mixture was evaporated in vacuo and the residue was purified by silica gel column chromatography (eluent, ether:hexane (4:1)) to afford 4.07 g (90%) of 4-Hydroxymethyl-6-methyl-pyridine-2-carbonitrile as a white solid. m.p. 136-138° C.; $^1$H NMR (200 MHz, CDCl$_3$) δ 2.59 (3H, s), 4.78 (2H, s), 7.39 (1H, s), 7.53 (1H, s).

Scheme 73

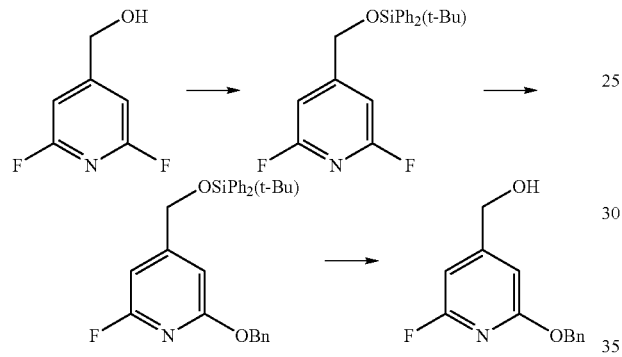

4-(tert-Butyl-diphenyl-silanyloxymethyl)-2,6-difluoro-pyridine: To a stirred solution of 2,6-difluoropyridine-4-methanol (2.9 g, 20 mmol) and imidazole (2.72 g, 40 mmol) in DMF (40 ml) at room temperature, was added tert-butyl (chloro)diphenylsilane (6.14 ml, 24 mmol). After stirring for overnight, the mixture was diluted with ether, washed with water, dried with anhydrous magnesium sulfate, filtered, and evaporated in vacuo. The residue was purified by silica gel column chromatography (eluent, ether:hexane (1:19)) to afford 7.98 g (100%) of 4-(tert-butyl-diphenyl-silanyloxymethyl)-2,6-difluoro-pyridine as a white solid. m.p. 83-84° C.; $^1$H NMR (200 MHz, CDCl$_3$) δ 1.11 (9H, s), 4.76 (2H, s), 6.79 (2H, s), 7.34-7.68 (10H, m).

(2-Benzyloxy-6-fluoro-pyridin-4-yl)-methanol: To a stirred solution of 4-(tert-butyl-diphenyl-silanyloxymethyl)-2,6-difluoro-pyridine (1.917 g, 5 mmol) and benzyl alcohol (543 µl, 5.25 mmol) in THF (20 ml) cooled in a dry ice-acetone bath (−50° C.) under nitrogen, was added 60% sodium hydride (240 mg, 6 mmol). The mixture was then slowly warmed up to room temperature during 2 hr. The mixture was diluted with ether, washed with water, dried with anhydrous magnesium sulfate, filtered, and evaporated in vacuo. The residue was then dissolved in THF (5 ml) and stirred with 1M tetrabutylammonium fluoride in THF (5.5 ml, 5.5 mmol) at room temperature for 1 hr. The mixture was evaporated in vacuo and the residue was purified by silica gel column chromatography (eluent, ether:hexane (1:3)) to afford 856 mg (73% for two steps) of (2-benzyloxy-6-fluoro-pyridin-4-yl)-methanol as a colorless oil. $^1$H NMR (200 MHz, CDCl$_3$) δ 1.99 (1H, br. s), 4.68 (2H, s), 5.32 (2H, s), 6.48 (1H, s), 6.64 (1H, s), 7.30-7.45 (5H, m).

(2-Fluoro-6-methoxy-pyridin-4-yl)-methanol: Prepared in a manner similar to (2-Benzyloxy-6-fluoro-pyridin-4-yl)-methanol; 384 mg as a white solid. m.p. 46-49° C.; $^1$H NMR (200 MHz, CDCl$_3$) δ 1.98 (1H, t, J=6.0 Hz), 3.90 (3H, s), 4.69 (2H, d, J=6.0 Hz), 6.46 (1H, s), 6.59 (1H, s).

Example CF

Scheme 74

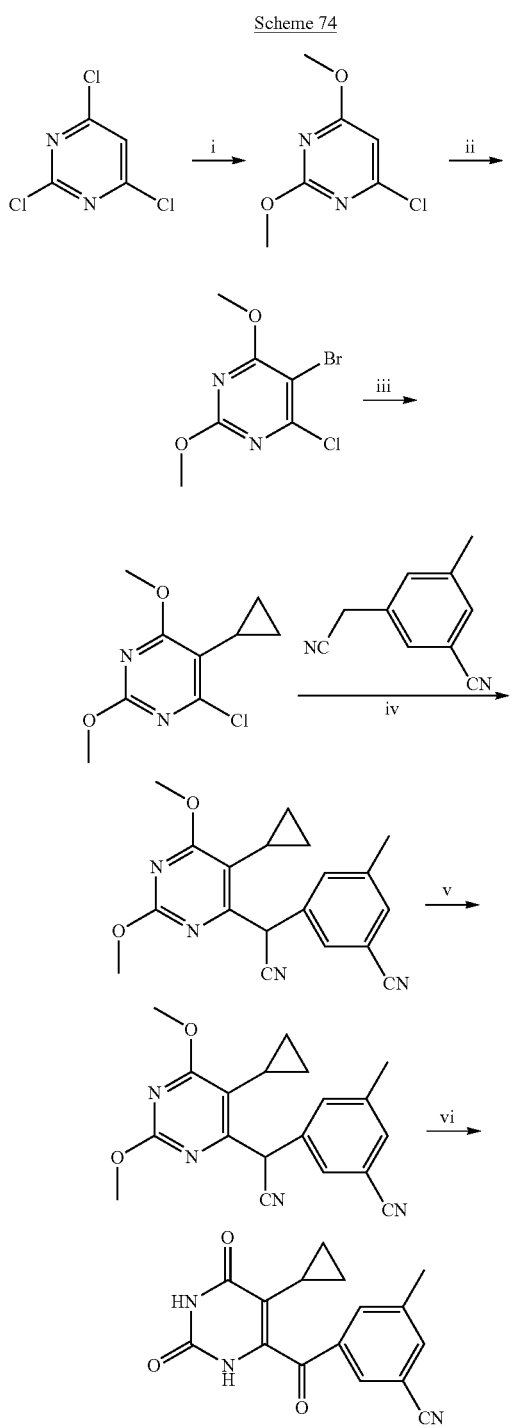

154

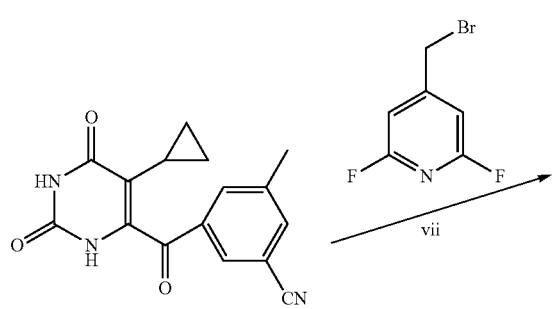

154

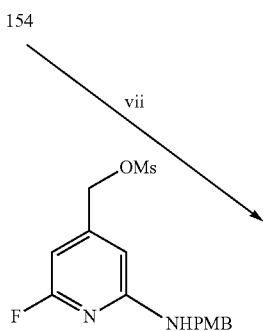

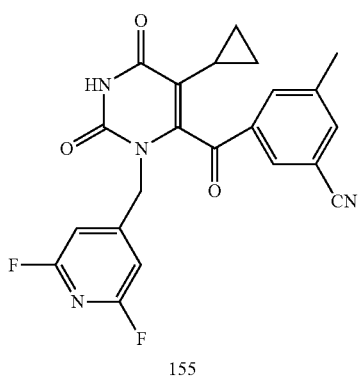

155

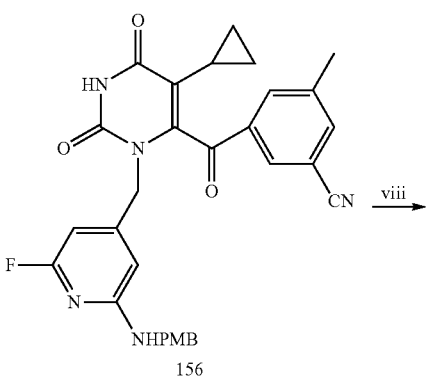

156

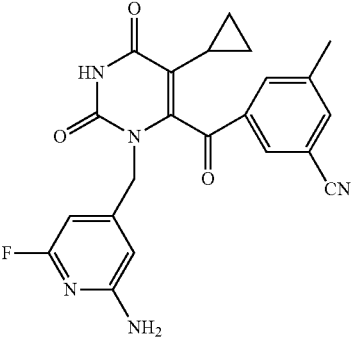

CG

Reagents and condition: i. NaOMe, MeOH, 0° C. -> r.t.; ii. Br₂, NaHCO₃, MeOH/H₂O; iii. cyclopropylboronic acid, Pd(dppf)Cl₂, DME, 2M Na₂CO₃; iv. NaH, DMF, 0° C. -> r.t.; v. NaH, DMF, O₂; vi. AcBr, 60° C.; vii. K₂CO₃, DMF, LiI; viii. TFA, 0° C. -> r.t..

4-Chloro-2,6-dimethoxy-pyrimidine: In a 250 mL round bottom flask, 2,4,6-trichloro-pyrimidine (11.41 g, 62.2 mmol) was dissolved in 140 mL MeOH. The flask was cooled to 0° C. NaOMe (25% in MeOH, 28.44 mL, 124.4 mmol) was added to the flask dropwise (in 30 minutes). The reaction was stirred at 0° C. for 2 hours, then was warmed up to room temperature for 1 hour. The reaction mixture was concentrated down. Ethyl acetate was added, followed by washing with water. The organic layer was concentrated down after drying over anhydrous sodium sulfate to give white solid (10.68 g, 98.4%). LC-MS shows 175.1 (M+1). $^1$H NMR (300 MHz, CDCl₃): δ 6.52 (s, 1H), 4.0 (s, 6H); $^{13}$C NMR (300 MHz, CDCl₃): δ 172.55, 164.96, 161.03, 99.94, 54.42, 53.76.

5-Bromo-4-chloro-2,6-dimethoxy-pyrimidine: In a 250 mL round bottom flask, 4-chloro-2,6-dimethoxy-pyrimidine (3.25 g, 18.65 mmol) and NaHCO₃ (3.6 g, 42.9 mmol) was charged with MeOH and water (1:1 ratio, 160 mL). Bromine (1.44 mL, 27.97 mmol) was added to the mixture dropwise (in 1 hour). The reaction was stirred at room temperature overnight. The reaction mixture was concentrated down. Ethyl acetate was added, followed by washing with brine. The organic layer was concentrated down and purified (silica gel, 0-50% EtOAC/hexane) to give white solid (4.06 g, 86%). LC-MS shows 255.1 (M+1). $^1$H NMR (300 MHz, CDCl₃): δ 4.07 (s, 3H), 3.98 (s, 3H); $^{13}$C NMR (300 MHz, CDCl₃): δ 168.27; 162.79; 160.38; 97.08; 55.78; 55.70.

4-Chloro-5-cyclopropyl-2,6-dimethoxy-pyrimidine: In a 5 mL microwave reaction tube, 5-bromo-4-chloro-2,6-dimethoxy-pyrimidine (116 mg, 0.457 mmol), cyclopropyl boronic acid (47 mg, 0.549 mmol, 1.2 eq.) and Pd(dppf(Cl₂ (38 mg, 0.1 eq.) was charged with DME (2.5 mL) and 2M Na2CO3 aqueous solution (0.91 mL, 4 eq.). The reaction was heated at 130° C. in the microwave reactor for 30 minutes. Ethyl acetate was added, followed by washing with brine. The organic layer was concentrated down and purified (silica gel, 0-50% EtOAC/hexane) to give white solid (64 mg, 65%). LC-MS shows 215.1 (M+1). $^1$H NMR (300 MHz, CDCl₃): δ 3.98 (dd, 6H), 1.62 (m, 1H), 0.99 (m, 2H), 0.78 (m, 2H).

(5-Cyclopropyl-2,6-dimethoxy-pyrimidin-4-yl)-(3,5-dimethyl-phenyl)-acetonitrile: 3-Cyanomethyl-5-methyl-benzonitrile (97 mg, 0.621 mmol) and 4-chloro-5-cyclopropyl-2,6-dimethoxy-pyrimidine (140 mg, 0.652 mmol, 1.05 eq.) were dissolved in 2 mL DMF. Cool the reaction flask to 0° C. NaH (60%, 51 mg, 1.24 mmol, 2 eq.) was added portionwise at 0° C. The reaction was stirred at 0° C., then warmed up to room temperature for 2 hours. Ethyl acetate was added to the reaction mixture, followed by washing with brine. The organic layer was concentrated down and purified (silica gel, 0-50% EtOAC/hexane) to give white solid (67 mg, 33%). LC-MS shows 335.2 (M+1). $^1$H NMR (300 MHz, CDCl$_3$): δ 7.58 (s, 1H), 7.50 (s, 1H), 7.43 (s, 1H), 5.82 (s, 1H), 4.0 (d, 6H), 2.4 (s, 3H), 1.43 (m, 1H), 1.09 (m, 2H), 0.64 (m, 2H).

3-(5-Cyclopropyl-2,6-dimethoxy-pyrimidine-4-carbonyl)-5-methyl-benzonitrile: At 0° C., NaH (60%, 9 mg, 0.4 mmol, 2 eq.) was added to (5-cyclopropyl-2,6-dimethoxy-pyrimidin-4-yl)-(3,5-dimethyl-phenyl)-acetonitrile (67 mg, 0.2 mmol) in 2 mL DMF solution. Oxygen balloon was applied. The reaction was stirred at 0° C. and warmed up to room temperature overnight. LC-MS shows the reaction complete. Ethyl acetate was added to the reaction mixture, followed by washing with brine. The organic layer was concentrated down and purified (silica gel, 0-50% EtOAc/hexane) to give white solid (31 mg, 48%). LC-MS shows 324.2 (M+1). $^1$H NMR (300 MHz, CDCl$_3$): δ 7.98 (s, 1H), 7.90 (s, 1H), 7.63 (s, 1H), 4.05 (s, 3H), 3.93 (s, 3H), 2.43 (s, 3H), 1.53 (m, 1H), 0.77 (m, 2H), 0.42 (m, 2H).

3-(5-Cyclopropyl-2,6-dioxo-1,2,3,6-tetrahydro-pyrimidine-4-carbonyl)-5-methyl-benzonitrile (154): Acetyl bromide (1 mL, excess) was added to 3-(5-cyclopropyl-2,6-dimethoxy-pyrimidine-4-carbonyl)-5-methyl-benzonitrile (31 mg, 0.096 mmol). The reaction was heated to 60° C. for 1 hour. The reaction was concentrated down and purified (silica gel, 20-80% EtOAc/hexane) to give white solid (22 mg, 77%). LC-MS shows 294.0 (M−1). $^1$H NMR (300 MHz, CDCl$_3$): δ 8.04 (s, 1H), 7.97 (s, 1H), 7.75 (s, 1H), 2.50 (s, 3H), 1.17 (m, 1H), 0.56 (m, 2H), 0.49 (m, 2H).

3-[5-Cyclopropyl-3-(2,6-difluoro-pyridin-4-ylmethyl)-2,6-dioxo 1,2,3,6tetrahydro-pyrimidine-4-carbonyl]-5-methyl-benzonitrile (155): 3-(5-Cyclopropyl-2,6-dioxo-1,2,3,6-tetrahydro-pyrimidine-4-carbonyl)-5-methyl-benzonitrile (10 mg, 0.034 mmol) was dissolved in 0.5 mL DMF. Potassium carbonate (4.7 mg, 1 eq.) and 4-bromomethyl-2,6-difluoro-pyridine (7 mg, 1 eq.) were added to the reaction, followed by lithium iodide (4.5 mg, 1 eq.) The reaction was stirred at room temperature overnight. Ethyl acetate was added to the reaction mixture, followed by washing with brine. The organic layer was concentrated down and purified by reversed phase HPLC (MeCN/water) to give white powder (1.2 mg, 9%). LC-MS shows 420.9 (M−1). $^1$H NMR (300 MHz, CD$_3$OD): δ 8.40 (s, 1H), 7.97 (s, 1H), 7.79 (s, 1H), 7.76 (s, 1H), 6.58 (s, 2H), 4.85 (s, 2H), 2.44 (s, 3H), 1.01 (m, 1H), 0.72 (m, 3H), 0.43 (m, 1H).

3-{5-Cyclopropyl-3-[2-fluoro-6-(4-methoxy-benzylamino)-pyridin-4-ylmethyl]-2,6-dioxo-1,2,3,6-tetrahydro-pyrimidine-4-carbonyl}-5-methyl-benzonitrile (156): 3-[5-Cyclopropyl-3-(2,6-difluoro-pyridin-4-ylmethyl)-2,6-dioxo-1,2,3,6tetrahydro-pyrimidine-4-carbonyl]-5-methyl-benzonitrile (16 mg, 0.054 mmol) was dissolved in 0.5 mL DMF. Potassium carbonate (7.5 mg, 1 eq.) and methanesulfonic acid 2-fluoro-6-(4-methoxy-benzylamino)-pyridin-4-ylmethyl ester (1 eq.) were added to the reaction, followed by lithium iodide (7.2 mg, 1 eq.) The reaction was stirred at room temperature overnight. Ethyl acetate was added to the reaction mixture, followed by washing with brine. The organic layer was concentrated down and purified (silica gel, 20-80% EtOAc/hexane) to give light yellow oil (10 mg, 34%). LC-MS shows 540.0 (M+1). $^1$H NMR (300 MHz, CDCl$_3$): δ 7.81 (s, 1H), 7.63 (s, 1H), 7.59 (s, 1H), 7.23 (s, 1H), 7.21 (s, 2H), 6.91 (s, 1H), 6.88 (s, 1H), 5.80 (s, 1H), 5.78 (s, 1H), 4.26 (d, 2H), 3.80 (s, 2H), 2.39 (s, 3H), 0.9 (m, 1H), 0.62 (m, 3H), 0.41 (m, 1H).

Example CF

TFA (1 mL, excess) was added to 3-{5-cyclopropyl-3-[2-fluoro-6-(4-methoxy-benzylamino)-pyridin-4-ylmethyl]-2,6-dioxo-1,2,3,6-tetrahydro-pyrimidine-4-carbonyl}-5-methyl-benzonitrile (10 mg, 0.018 mmol) at 0° C. The reaction was stirred at 0° C. and warmed up to room temperature for 5 hours. The reaction crude was concentrated down and purified by reversed phase HPLC (MeCN/water) to give white powder (4.0 mg, 52%). LC-MS shows 420.2 (M+1). $^1$H NMR (300 MHz, CD$_3$OD): δ 8.07 (s, 1H), 7.90 (s, 1H), 7.79 (s, 1H), 6.0 (s, 1H), 5.82 (s, 2H), 5.20 (d, 1H), 4.41 (d, 1H), 2.40 (s, 3H), 1.02 (m, 1H), 0.70 (m, 1H), 0.60 (m, 2H), 0.39 (m, 1H).

Examples CG, CH, and CI

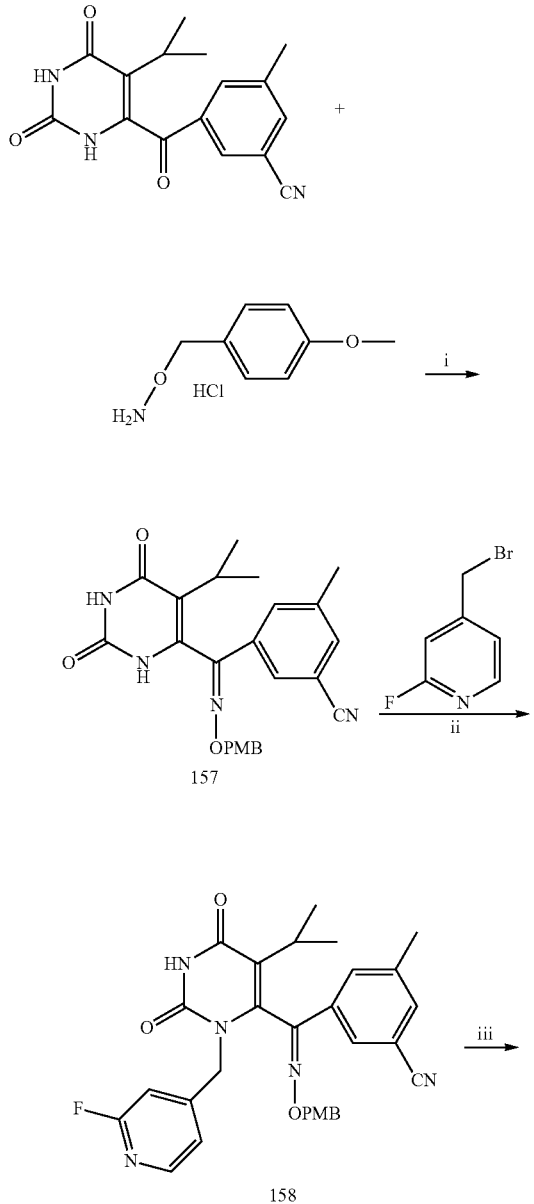

Scheme 75

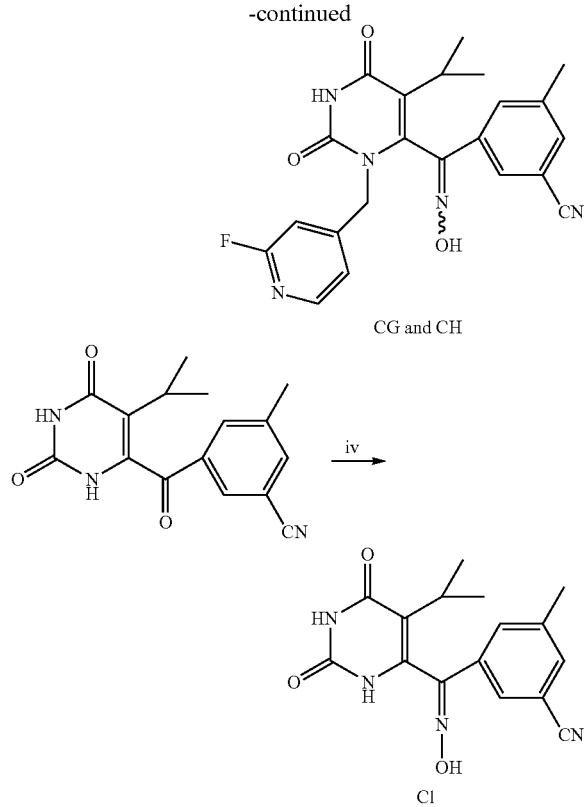

Reagents and conditions: i. EtOH, reflux; ii. K₂CO₃, DMF, LiI; iii. TFA, 0° C. -> r.t.; iv. NH₂OH•HCl, EtOH, reflux.

3-[(5-Isopropyl-2,6-dioxo-1,2,3,6-tetrahydro-pyrimidin-4-yl)-(4-methoxybenzyloxyimino)-methyl]-5-methyl-benzonitrile (157): Ethanol (5 mL) and o-(4-methoxy-benzyl)-hydroxylamine hydrochloride (427 mg, 2.25 mmol, 10 eq.) was added to 3-(5-isopropyl-2,6-dioxo-1,2,3,6-tetrahydro-pyrimidine-4-carbonyl)-5-methyl-benzonitrile (67 mg, 0.225 mmol). The reaction was heated to reflux for 4 days. The precipitate of the reaction crude was filtered off and the filtrate was concentrated down and purified (silica gel, 20-80% EtOAc/hexane) to give white solid (75 mg, 77%). LC-MS shows 433.1 (M+1). ¹H NMR (300 MHz, CDCl₃): δ 9.90 (br, 1H), 9.60 (br, 1H), 7.77 (s, 1H), 7.50 (m, 2H), 7.25 (m, 2H), 6.93 (m, 2H), 5.20 (s, 2H), 3.80 (s, 3H), 2.40 (s, 3H), 2.21 (m, 1H), 1.00 (d, 6H).

3-[[3-(2-Fluoro-pyridin-4-ylmethyl)-5-isopropyl-2,6-dioxo-1,2,3,6-tetrahydro-pyrimidin-4-yl]-(4-methoxy-benzyloxyimino)-methyl]-5-methyl-benzonitrile (158): 3-[(5-Isopropyl-2,6-dioxo-1,2,3,6-tetrahydro-pyrimidin-4-yl)-(4-methoxybenzyloxyimino)-methyl]-5-methyl-benzonitrile (71 mg, 0.164 mmol, 1.2 eq.) was dissolved in 2.0 mL DMF. Potassium carbonate (19 mg, 0.137 mmol, 1 eq.) and 4-bromomethyl-2-fluoro-pyridine (26 mg, 1 eq.) were added to the reaction, followed by lithium iodide (18 mg, 1 eq.) The reaction was stirred at room temperature overnight. Ethyl acetate was added to the reaction mixture, followed by washing with brine. The organic layer was concentrated down and purified (silica gel, 20-80% EtOAc/hexane) to white powder (32 mg, 36%). LC-MS shows 542.2 (M+1). ¹H NMR (300 MHz, CDCl₃): δ 8.80 (br, 1H), 7.93 (d, 1H), 7.62 (s, 1H), 7.42 (s, 1H), 7.32 (d, 2H), 7.21 (s, 1H), 6.92 (d, 2H), 6.72 (d, 1H), 6.40 (s, 1H), 5.08 (dd, 2H), 4.90 (d, 1H), 4.22 (d, 1H), 3.80 (s, 3H), 2.32 (s, 3H), 2.20 (m, 1H), 1.16 (d, 3H), 1.12 (d, 3H).

Examples CG and CH

TFA (1.5 mL, excess) was added to 3-[[3-(2-fluoro-pyridin-4-ylmethyl)-5-isopropyl-2,6-dioxo-1,2,3,6-tetrahydro-pyrimidin-4-yl]-(4-methoxy-benzyloxyimino)-methyl]-5-methyl-benzonitrile (30 mg, 0.055 mmol). The reaction was stirred at 50° C. overnight. The reaction crude was concentrated down and purified by reversed phase HPLC (MeCN/water) to give 2 products as white powder (8.2 mg, trans (CG) and 0.9 mg, cis (CH) based on NOE NMR) LC-MS shows 522.2 (M+1). ¹H NMR of the trans product (CG) (300 MHz, CDCl₃): δ 10.68 (br, 1H), 9.36 (br, 1H), 7.98 (d, 1H), 7.73 (s, 1H), 7.52 (s, 2H), 6.98 (d, 1H), 6.71 (s, 1H), 5.00 (dd, 1H), 4.63 (d, 1H), 2.42 (s, 3H), 2.37 (m, 1H), 1.36 (d, 3H), 1.17 (d, 3H).

Example CI

Hydroxylamine hydrochloride (262 mg, 3.77 mmol, 20 eq.) was added to 3-(5-isopropyl-2,6-dioxo-1,2,3,6-tetrahydro-pyrimidine-4-carbonyl)-5-methyl-benzonitrile (56 mg, 0.188 mmol) in 15 mL ethanol. The reaction was heated to reflux for 3 days. The precipitate of the reaction crude was filtered off and the filtrate was concentrated down and purified by reversed phase HPLC (MeCN/water) to give white solid (19 mg, 32%). LC-MS shows 313.1 (M+1). ¹H NMR (300 MHz, CD₃OD): c 7.81 (s, 1H), 7.70 (s, 1H), 7.61 (s, 1H), 2.44 (s, 3H), 2.38 (m, 1H), 1.71 (d, 6H).

Example CJ

Scheme 76

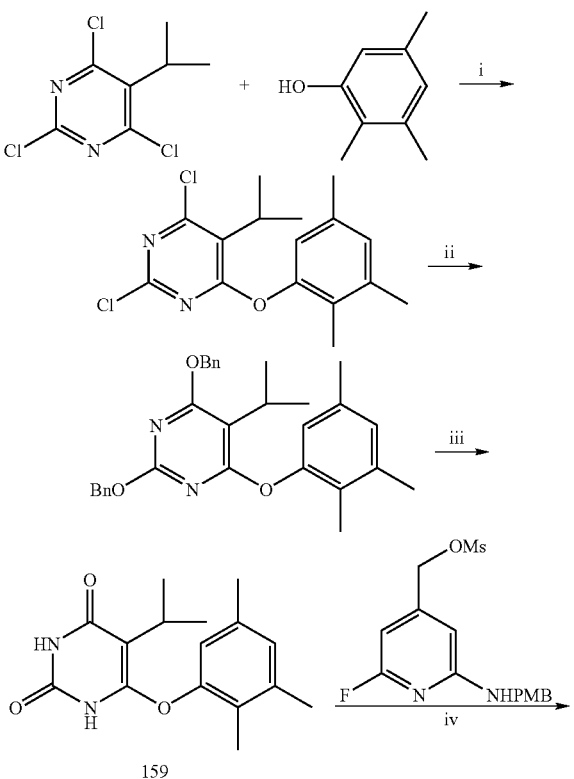

-continued

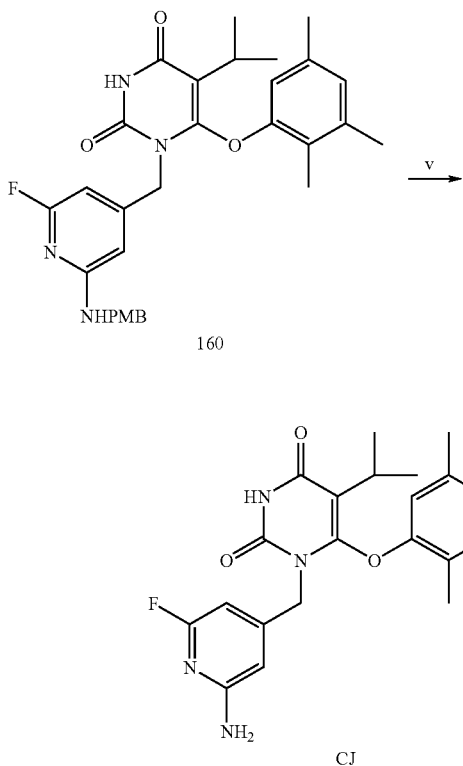

160

Reagents and conditions: i. NaH, DMF; ii. BnOH, NaH, DMF; iii. EtOH/EtOAc, H₂; iv. K₂CO₃, DMF, LiI; v. TFA, r.t.

2,4-Dichloro-5-isopropyl-6-(2,3,5-trimethyl-phenoxy)-pyrimidine: Sodium hydride (60%, 59 mg, 1.44 mmol. 1.1 eq.) was added to 2,3,5-trimethyl-phenol (179 mg, 1.31 mmol) in DMF (2 mL). The mixture was stirred at room temperature for 15 minutes and then added to 2,4,6-trichloro-5-isopropyl-pyrimidine (296 mg, 1.31 mmol) in 1 mL DMF. The reaction was stirred at room temperature for 4 hours. Ethyl acetate was added and washed with brine. The organic layer was concentrated down and purified (silica gel, 0-50% EtOAC/hexane) to give white solid (400 mg, 94%). LC-MS shows 325.2 (M+1). ¹H NMR (300 MHz, CDCl₃): δ 6.94 (s, 1H), 6.63 (s, 1H), 3.61 (m, 1H), 2.32 (s, 6H), 2.02 (s, 3H), 1.42 (d, 6H).

2,4-Bis-benzyloxy-5-isopropyl-6-(2,3,5-trimethyl-phenoxy)-pyrimidine: Sodium hydride (60%, 81 mg, 1.98 mmol. 3 eq.) was added to benzyl alcohol (205 μl, 1.98 mmol, 3 eq.) in 10 mL DMF. The mixture was stirred at room temperature for 15 minutes and then added to 2,4-dichloro-5-isopropyl-6-(2,3,5-trimethyl-phenoxy)-pyrimidine (320 mg, 0.66 mmol, 1 eq.). The reaction was heated to 70° C. for 1 hour. The reaction was cooled down to room temperature. Ethyl acetate was added and washed with brine. The organic layer was concentrated down and purified (silica gel, 0-50% EtOAC/hexane) to give white solid (260 mg, 84%). LC-MS shows 469.2 (M+1). ¹H NMR (300 MHz, CDCl₃): δ 7.3-7.5 (m, 10H), 6.91 (s, 1H), 6.72 (s, 1H), 5.41 (m, 4H), 3.48 (m, 1H), 2.38 (s, 6H), 2.0 (s, 3H), 1.36 (d, 6H).

5-Isopropyl-6-(2,3,5-trimethyl-phenoxy)-1H-pyrimidine-2,4-dione (159): 2,4-Bis-benzyloxy-5-isopropyl-6-(2,3,5-tri-methyl-phenoxy)-pyrimidine was dissolved in 6 mL ethyl acetate and 6 mL ethanol mixture. 10% Pd/C (52 mg) was added to the mixture. Then hydrogen balloon was applied. The reaction was stirred at room temperature for 40 minutes. The reaction crude was filtered through celite. The filtrate was concentrated down and purified (silica gel, 0-50% EtOAC/hexane) followed by reverse phase HPLC (MeCN/water) to give white solid (94 mg, 59%). LC-MS shows 289.1 (M+1). ¹H NMR (300 MHz, CDCl₃): δ 9.6 (br, 1H), 8.9 (br, 1H), 6.88 (s, 1H), 6.58 (s, 1H), 3.12 (m, 1H), 2.18 (s, 6H), 2.12 (s, 3H), 1.22 (d, 6H).

1-[2-Fluoro-6-(4-methoxy-benzylamino)-pyridin-4-ylmethyl]-5-isopropyl-6-(2,3,5-trimethyl-phenoxy)-1H-pyrimidine-2,4-dione (160): 5-Isopropyl-6-(2,3,5-trimethyl-phenoxy)-1H-pyrimidine-2,4-dione (39 mg, 0.135 mmol) was dissolved in 1.5 mL DMF. Potassium carbonate (31 mg, 2 eq.) was added and the reaction was stirred at room temperature for 10 minutes. Methanesulfonic acid 2-fluoro-6-(4-methoxy-benzylamino)-pyridin-4-ylmethyl ester (0.135 mmol) and lithium iodide (15 mg, 1 eq.) were added. The reaction was stirred at room temperature overnight. Ethyl acetate was added to the reaction mixture, followed by washing with brine. The organic layer was concentrated down and purified (silica gel, 0-80% EtOAC/hexane) to give white powder (25 mg, 42%). LC-MS shows 533.1 (M+1). ¹H NMR (300 MHz, CDCl₃): δ 8.68 (b, 1H), 7.22 (d, 2H), 6.86 (d, 2H), 6.75 (s, 1H), 6.18 (s, 1H), 5.95 (d, 2H), 4.94 (d, 1H), 4.45 (d, 1H), 4.37 (s, 2H), 3.80 (s, 3H), 2.68 (m, 1H), 2.23 (s, 3H), 2.19 (s, 3H), 2.06 (s, 3H), 1.15 (dd, 6H).

Example CJ

TFA (1.5 mL, excess) was added to 3-[[3-(2-Fluoro-pyridin-4-ylmethyl)-5-isopropyl-2,6-dioxo-1,2,3,6-tetrahydropyrimidin-4-yl]-(4-methoxy-benzyloxyimino)-methyl]-5-methyl-benzonitrile (30 mg, 0.055 mmol). The reaction was stirred at room temperature for 2 hours. The reaction crude was concentrated down and purified by reversed phase HPLC (MeCN/water) to give white powder (4.4 mg, 23%) LC-MS shows 413.2 (M+1). ¹H NMR (300 MHz, CDCl₃): δ 8.9 (br, 1H), 6.73 (s, 1H), 6.22 (s, 1H), 6.17 (s, 1H), 5.00 (d, 1H), 4.50 (d, 1H), 2.70 (m, 1H), 2.13 (s, 3H), 2.10 (s, 3H), 2.07 (s, 3H), 1.16 (dd, 6H).). ᶠNMR (300 MHz, CDCl₃): δ −70.83.

Example CK

Scheme 77

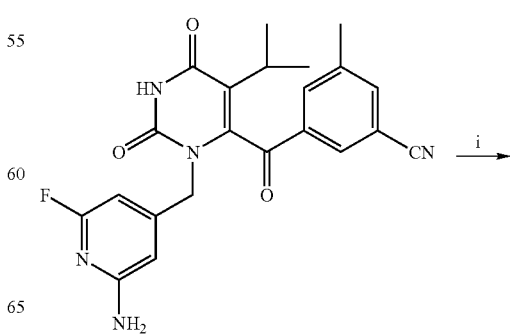

-continued

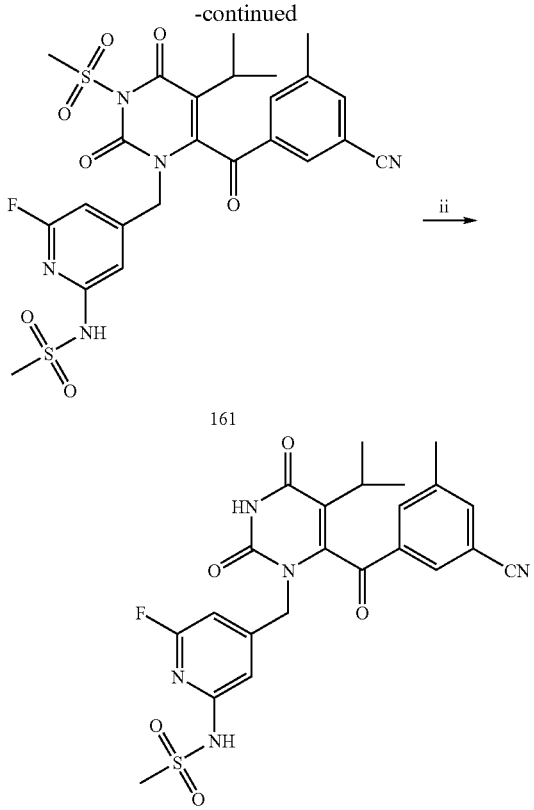

161

CK

Reagents and conditions: i. MsCl, TEA, THF 0° C.; ii. K₂CO₃, MeOH/THF.

N-{4-[6-(3-Cyano-5-methyl-benzoyl)-5-isopropyl-3-methanesulfonyl-2,4-dioxo-3,4-dihydro-2H-pyrimidin-1-yl-methyl]-6-fluoro-pyridin-2-yl}-methanesulfonamide (161): 3-[3-(2-Amino-6-fluoro-pyridin-4-ylmethyl)-5-isopropyl-2,6-dioxo-1,2,3,6-tetrahydro-pyrimidine-4-carbonyl]-5-methyl-benzonitrile (86 mg, 0.204 mmol) was dissolved in 5 mL THF. TEA (0.31 μl, 12 eq.) was added and the reaction was stirred at 0° C. for 10 minutes. MsCl (158 μl, 10 eq.) was added. The reaction was stirred at 0° C. for 40 minutes. The reaction crude was concentrated down and purified (silica gel, 0-80% EtOAC/hexane) to give white powder (89 mg, 75%). LC-MS shows 578.0 (M+1). ¹H NMR (300 MHz, CDCl₃): δ 9.6 (s, 1H), 7.98 (s, 1H), 7.83 (s, 1H), 7.76 (s, 1H), 7.07 (s, 1H), 6.83 (s, 1H), 4.82 (dd, 2H), 3.63 (s, 3H), 3.56 (s, 3H), 2.43 (s, 3H), 2.22 (m, 1H), 1.22 (dd, 6H).

Example CK

N-{4-[6-(3-Cyano-5-methyl-benzoyl)-5-isopropyl-3-methanesulfonyl-2,4-dioxo-3,4-dihydro-2H-pyrimidin-1-yl-methyl]-6-fluoro-pyridin-2-yl}-methanesulfonamide (107 mg, 0.186 mmol) was dissolved in THF (2 mL) and MeOH (2 mL) mixture. Potassium carbonate (34 mg, 1.5 eq.) was added and the reaction was stirred at room temperature for 50 minutes. The reaction crude was concentrated down and purified by reversed phase HPLC (MeCN/water) to give light brown powder (59 mg, 64%). LC-MS shows 500.1 (M+1). ¹H NMR (300 MHz, CDCl₃): δ 9.3 (s, 1H), 8.03 (b, 1H), 7.98 (s, 1H), 7.83 (s, 1H), 7.73 (s, 1H), 6.77 (s, 1H), 6.31 (s, 1H), 4.72 (dd, 2H), 3.52 (s, 3H), 2.43 (s, 3H), 2.22 (m, 1H), 1.22 (dd, 6H).

Examples CL, CM, CN, and CO

Scheme 78

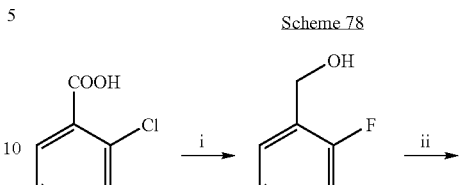

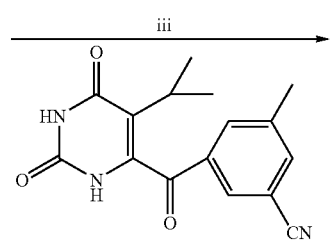

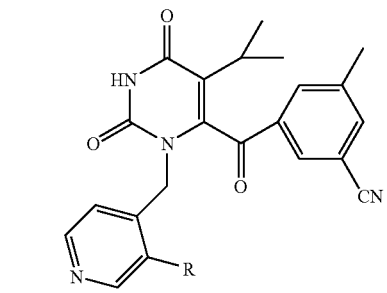

CL R = fluoro
CM R = methyl
CN R = Cl

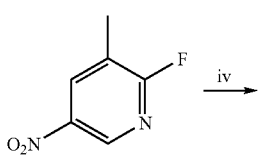

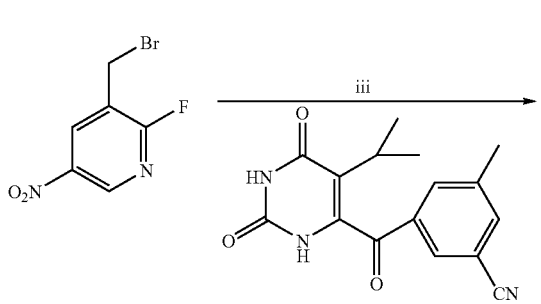

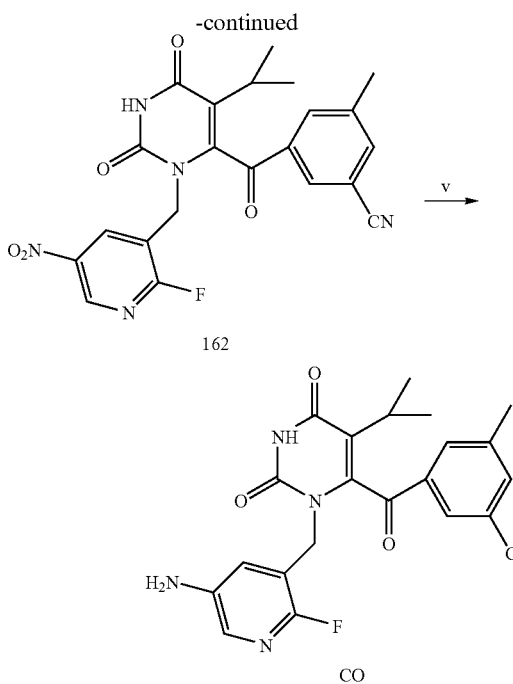

Reagents and conditions: i. LAH, THF, 0° C.; ii. MsCl, TEA, DCM, 0° C.; iii. K₂CO₃, LiI, DMF; iv. NBS, DCM; v. Fe, HOAc (3-Fluoro-pyridin-4-yl)-methanol: At 0° C. LAH (200 mg, 4 eq.) was added to 3-fluoro-isonicotinic acid (186 mg, 1.32 mmol, 1 eq.) suspension in 25 mL THF. The reaction was stirred at 0° C. for 1 hour. The reaction was quenched by adding 0.2 mL water, followed by 0.4 mL 10% NaOH aqueous solution and 0.6 mL water at 0° C. Ethyl acetate was added to the reaction crude and washed with brine. n-Butanol was used to extract back from the brine. The organic layers were combined and concentrated down and purified (silica gel, 0-15% MeOH/DCM) to give colorless oil (78 mg, 46%). $^1$H NMR (300 MHz, CD$_3$OD): δ 8.39 (m, 2H), 7.61 (m, 1H), 4.86 (s, 2H).

Methanesulfonic acid 3-fluoro-pyridin-4-ylmethyl ester: At 0° C. TEA (44 μl, 0.314 mmol, 2 eq.) was added to (3-fluoro-pyridin-4-yl)-methanol (20 mg, 0.157 mmol, 1 eq.) in 1 mL DCM, followed by MsCl (15 μl, 0.188 mmol, 1.2 eq.) The reaction was stirred at 0° C. for 30 minutes. HPLC and LC-MS showed reaction complete. The reaction crude was concentrated down. Ethyl acetate was added and washed with saturated NAHCO₃ aqueous solution. The Ethyl acetate layer was concentrated after dried over Na₂SO₄ to give color oil which was used directly in next step. LC-MS shows 206.1 (M+1).

Example CL 3-(5-Isopropyl-2,6-dioxo-1,2,3,6-tetrahydro-pyrimidine-4-carbonyl)-5-methyl-benzonitrile (56 mg, 0.188 mmol, 1.2 eq.) was dissolved in 2 mL DMF. Potassium carbonate (22 mg, 1 eq.) was added and the reaction was stirred at room temperature for 10 minutes. Methanesulfonic acid 3-fluoro-pyridin-4-ylmethyl ester (0.157 mmol, 1 eq.) and lithium iodide (21 mg, 1 eq.) were added. The reaction was stirred at room temperature for 3 hours. Ethyl acetate was added to the reaction mixture, followed by washing with brine. The organic layer was concentrated down and purified (silica gel, 0-80% EtOAC/hexane) followed by reverse phase HPLC (MeCN/water) to give white powder (8.0 mg, 13%). LC-MS shows 407.2 (M+1). $^1$H NMR (300 MHz, CDCl₃): δ 8.98 (s, 1H), 8.35 (d, 1H), 8.20 (s, 1H), 7.88 (s, 1H), 7.68 (m, 2H), 7.12 (m, 1H), 4.88 (s, 2H), 2.42 (s, 3H), 2.22 (m, 1H), 1.22 (dd, 6H).

Example CM

Followed the similar procedure as for compound 89 using 3-methyl-isonicotinic acid as starting material. LC-MS shows 403.2 (M+1). $^1$H NMR (300 MHz, CDCl₃): δ 9.08 (s, 1H), 8.38 (dd, 1H), 8.10 (s, 1H), 7.82 (s, 1H), 7.60 (d, 2H), 6.95 (m, 1H), 5.0 (s, 2H), 4.62 (d, 1H), 2.40 (s, 3H), 2.21 (m, 1H), 2.03 (s, 3H), 1.20 (dd, 6H).

Example CN

Followed the similar procedure as stated in Example 21 to 23 using 3-chloro-isonicotinic acid as starting material. LC-MS shows 423.2 (M+1). $^1$H NMR (300 MHz, CD$_3$OD): δ 8.42 (s, 1H), 8.37 (s, 1H), 8.12 (s, 1H), 8.0 (s, 1H), 7.82 (s, 1H), 4.90 (s, 2H), 2.41 (s, 3H), 2.28 (m, 1H), 1.20 (dd, 6H).

3-Bromomethyl-2-fluoro-5-nitro-pyridine: 2-Fluoro-3-methyl-5-nitro-pyridine (445 mg, 2.85 mmol) was dissolved in 20 mL DCM. NBS (1.01 g, 5.7 mmol, 2 eq.) was added. The reaction was stirred at room temperature for 2 days. HPLC showed 20% conversion. The reaction was concentrated down and purified (silica gel, 0-80% EtOAc/hexane) to give light yellow oil (100 mg, 15%). $^1$H NMR (300 MHz, CD$_3$OD): δ 8.39 (m, 2H), 7.61 (m, 1H), 4.86 (s, 2H).

3-[3-(2-Fluoro-5-nitro-pyridin-3-ylmethyl)-5-isopropyl-2,6-dioxo-1,2,3,6-tetrahydro-pyrimidine-4-carbonyl]-5-methyl-benzonitrile (162): 3-(5-Isopropyl-2,6-dioxo-1,2,3,6-tetrahydro-pyrimidine-4-carbonyl)-5-methyl-benzonitrile (37 mg, 0.124 mmol, 1.2 eq.) was dissolved in 1.5 mL DMF. Potassium carbonate (14 mg, 1 eq.) was added and the reaction was stirred at room temperature for 10 minutes. 3-Bromomethyl-2-fluoro-5-nitro-pyridine (27 mg, 0.103 mmol, 1 eq.) and lithium iodide (14 mg, 1 eq.) were added. The reaction was stirred at room temperature for 2 hours. Ethyl acetate was added to the reaction mixture, followed by washing with brine. The organic layer was concentrated down and purified (silica gel, 0-80% EtOAC/hexane) to give white powder (16 mg, 34%). LC-MS shows 449.9 (M−1). $^1$H NMR (300 MHz, CDCl₃): δ 8.98 (d, 2H), 8.48 (m, 1H), 7.98 (s, 1H), 7.93 (s, 1H), 7.78 (m, 2H), 5.08 (d, 1H), 4.56 (d, 1H), 2.50 (s, 3H), 2.22 (m, 1H), 1.22 (dd, 6H).

Example CO

3-[3-(2-Fluoro-5-nitro-pyridin-3-ylmethyl)-5-isopropyl-2,6-dioxo-1,2,3,6-tetrahydro-pyrimidine-4-carbonyl]-5-methyl-benzonitrile (16 mg, 0.035 mmol.) was dissolved in 1.5 mL acetic acid. Iron powder (80 mg, 40 eq.) was added and the reaction was stirred at room temperature for 2 hours. The reaction crude was filtered through celite after diluting with DCM. The filtrate was concentrated down and purified by reverse phase HPLC (MeCN/water) to give white powder (4.8 mg, 33%). LC-MS shows 422.2 (M+1). $^1$H NMR (300 MHz, CDCl₃): δ 9.0 (br, 1H), 7.83 (s, 1H), 7.68 (m, 2H), 7.37 (s, 1H), 7.00 (m, 1H), 5.08 (d, 1H), 4.56 (d, 1H), 2.42 (s, 3H), 2.16 (m, 1H), 1.20 (dd, 6H).

Example CP

Scheme 79

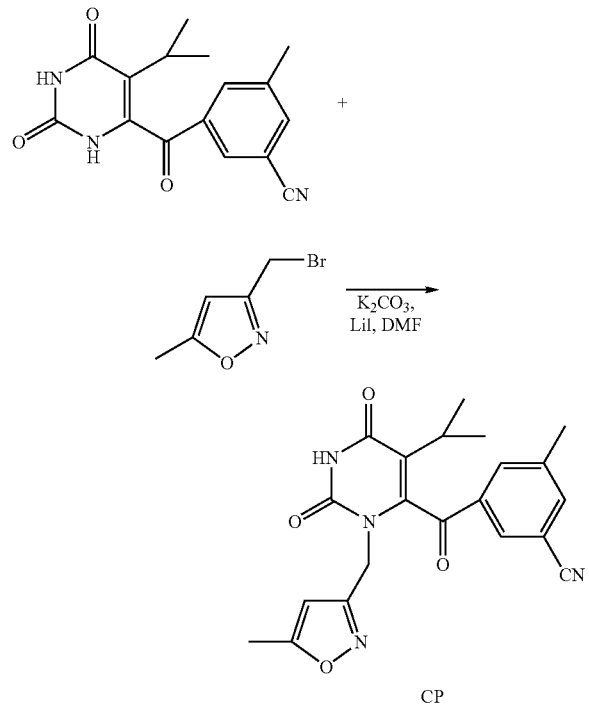

CP

Example CP 3-(5-Isopropyl-2,6-dioxo-1,2,3,6-tetrahydro-pyrimidine-4-carbonyl)-5-methyl-benzonitrile (43 mg, 0.144 mmol 1.2 eq.) was dissolved in 1 mL DMF. Potassium carbonate (17 mg, 1 eq.) was added and the reaction was stirred at room temperature for 10 minutes. 3-Bromomethyl-5-methyl-isoxazole (21 mg, 0.12 mmol, 1 eq.) and lithium iodide (16 mg, 1 eq.) were added. The reaction was stirred at room temperature for 1.5 hours. Ethyl acetate was added to the reaction mixture, followed by washing with brine. The organic layer was concentrated down and purified (silica gel, 0-80% EtOAC/hexane) followed by reverse phase HPLC (MeCN/water) to give white powder 11.20 mg, 24%). LC-MS shows 393.1 (M+1). $^1$H NMR (300 MHz, CDCl$_3$): δ 9.06 (s, 1H), 7.92 (s, 1H), 7.80 (s, 1H), 7.71 (s, 1H), 5.94 (s, 1H), 5.10 (m, 1H), 4.56 (m, 1H), 2.47 (s, 3H), 2.30 (s, 3H), 2.22 (m, 1H), 1.20 (dd, 6H).

Example CQ

Scheme 80

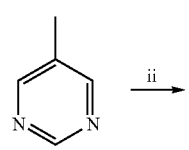

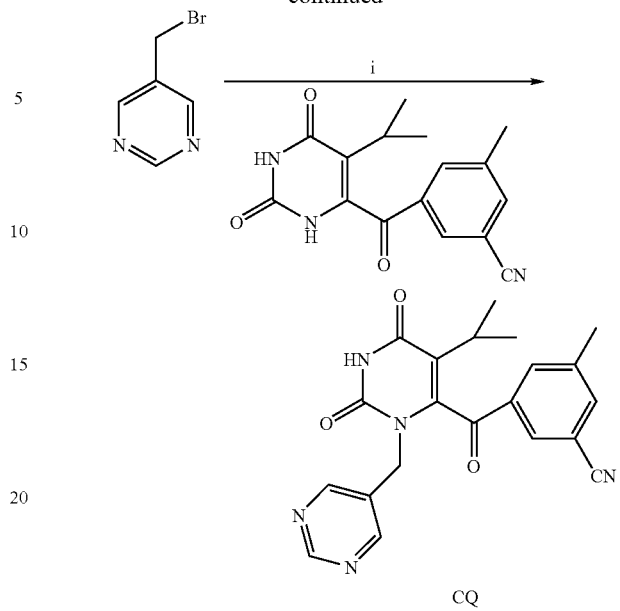

CQ

Reagents and conditions: i. K$_2$CO$_3$, LiI, DMF; ii. NBS, DCM.

5-Bromomethyl-pyrimidine: 5-Methyl-pyrimidine (340 mg, 3.61 mmol) was dissolved in 20 mL DCM. NBS (707 mg, 1.1 eq.) was added. The reaction was heated to 45° C. for 2 days. The reaction crude was filtered through celite. The filtrate was concentrated down and purified (silica gel, 0-80% EtOAc/hexane) to give light yellow oil (220 mg, 35%). $^1$H NMR (300 MHz, CD$_3$OD): δ 9.11 (s, 1H), 8.83 (s, 2H), 4.61 (s, 2H).

Example CQ 3-(5-Isopropyl-2,6-dioxo-1,2,3,6-tetrahydro-pyrimidine-4-carbonyl)-5-methyl-benzonitrile (55 mg, 0.204 mmol, 1.1 eq.) was dissolved in 2 mL DMF. Potassium carbonate (26 mg, 1 eq.) was added and the reaction was stirred at room temperature for 10 minutes. 5-Bromomethyl-pyrimidine (43 mg, 0.186 mmol, 1 eq.) and lithium iodide (25 mg, 1 eq.) were added. The reaction was stirred at room temperature for 2 hours. Ethyl acetate was added to the reaction mixture, followed by washing with brine. The organic layer was concentrated down and purified (silica gel, 0-80% EtOAC/hexane) followed by reverse phase HPLC (MeCN/water) to give white powder (6.8 mg, 9.4%). LC-MS shows 390.1 (M+1). $^1$H NMR (300 MHz, CDCl$_3$): δ 9.23 (s, 1H), 9.17 (s, 1H), 8.59 (s, 2H), 7.96 (s, 1H), 7.78 (m, 2H), 4.80 (s, 2H), 2.48 (s, 3H), 2.22 (m, 1H), 1.20 (dd, 6H).

Example CR

Scheme 81

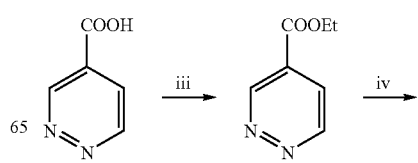

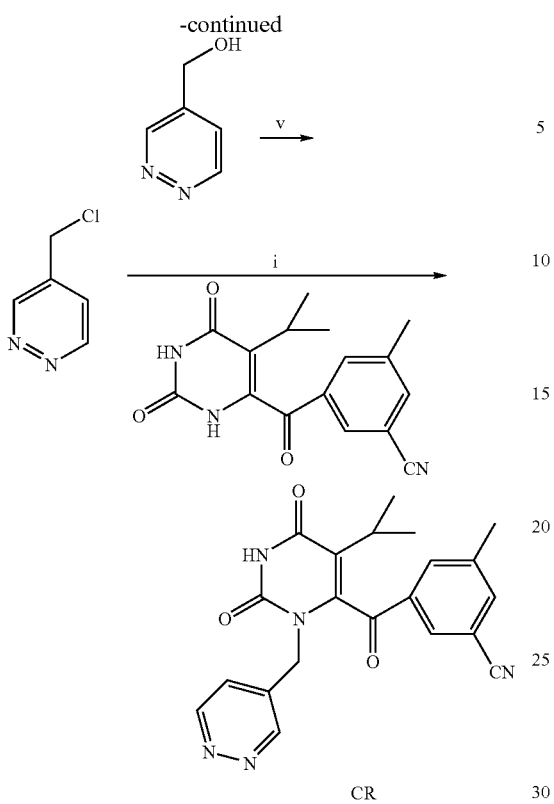

Reagents and conditions: i. K₂CO₃, LiI, DMF; ii. NBS, DCM; iii. EtOH, cat. HCl, reflux; iv. LAH, THF, 0° C.; v. SOCl₂, DCM, 0° C.

Pyridazine-4-carboxylic acid ethyl ester: In a 250 mL round bottom flask, 1 mL concentrated HCl and 70 mL ethanol was added to pyridazine-4-carboxylic acid (3.78 g, 30.4 mmol). The mixture was refluxed overnight. The reaction was 80% complete based on HPLC. The reaction mixture was concentrated down. The residue was purified (silica gel, 2-10% MeOH/DCM) to give light yellow oil (1.8 g, 49%). $^1$H NMR (300 MHz, CD₃OD): δ 9.62 (s, 1H), 9.43 (d, 1H), 8.08 (d, 1H), 4.52 (dd, 2H), 1.43 (t, 3H).

Pyridazin-4-yl-methanol: At 0° C., Lithium aluminum hydride (277 mg, 1.5 eq.) was added to pyridazine-4-carboxylic acid ethyl ester (740 mg, 4.86 mmol) in 30 mL THF. The reaction was stirred at 0° C. for 30 minutes. The completion of RXN was monitored by HPLC. 4 mL 1N NaOH aqueous solution was added to the reaction at 0° C. dropwise. The reaction mixture was filtered through celite pad and the filtrate was concentrated down. The crude was purified (silica gel, 2-10% MeOH/DCM) to give light yellow oil (110 mg, 20%). $^1$H NMR (300 MHz, CD₃OD): δ 9.19 (s, 1H), 9.17 (d, 1H), 7.72 (d, 1H), 4.76 (s, 2H).

4-Chloromethyl-pyridazine: At 0° C., pyridazine-4-yl-methanol (49.5 mg, 0.45 mmol) in 2 mL DCM suspension was added to thionyl chloride (164 µl, 2.25 mmol, 5 eq.) in 2 mL DCM solution. The reaction was stirred at 0° C. for 30 minutes. The reaction mixture was concentrated down to give the crude product which was used in next step reaction directly.

Example CR

In a 10 mL round bottom flask, potassium carbonate (62 mg, 0.45 mmol, 1 eq.) was added to 3-(5-isopropyl-2,6-dioxo-1,2,3,6-tetrahydro-pyrimidine-4-carbonyl)-5-methyl-benzonitrile (174 mg, 0.58 mmol, 1.3 eq.) in 2 mL DMF. In another 10 mL round bottom flask, potassium carbonate (62 mg, 0.45 mmol, 1 eq.) was added to crude 4-chloromethyl-pyridazine (0.45 mmol, 1.0 eq.) in 2 mL DMF. The mixture of 4-chloromethyl-pyridazine was added to the mixture of 3-(5-isopropyl-2,6-dioxo-1,2,3,6-tetrahydro-pyrimidine-4-carbonyl)-5-methyl-benzonitrile at room temperature, followed by adding lithium iodide (60 mg, 1 eq.). The reaction was stirred overnight. The reaction mixture was extracted using ethyl acetate and saturated bicarbonate aqueous solution. The organic layer was concentrated down and purified by silica gel (EtOAc/hexane, then MeOH/DCM), followed by reverse phase HPLC (MeCN/water) to give white powder (19 mg, 11%). LC-MS shows 390.4 (M+1). $^1$H NMR (300 MHz, CDCl₃): δ 9.17 (d, 1H), 9.03 (d, 1H), 8.02 (s, 1H), 7.83 (s, 1H), 7.76 (s, 1H), 7.46 (s, 1H), 4.80 (m, 2H), 2.44 (s, 3H), 2.22 (m, 1H), 1.20 (dd, 6H).

Example CS

Scheme 82

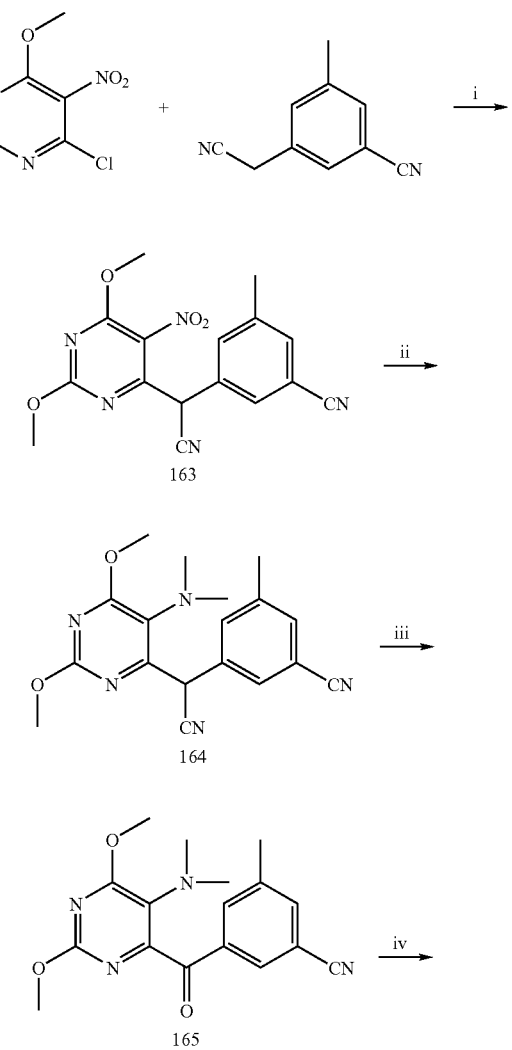

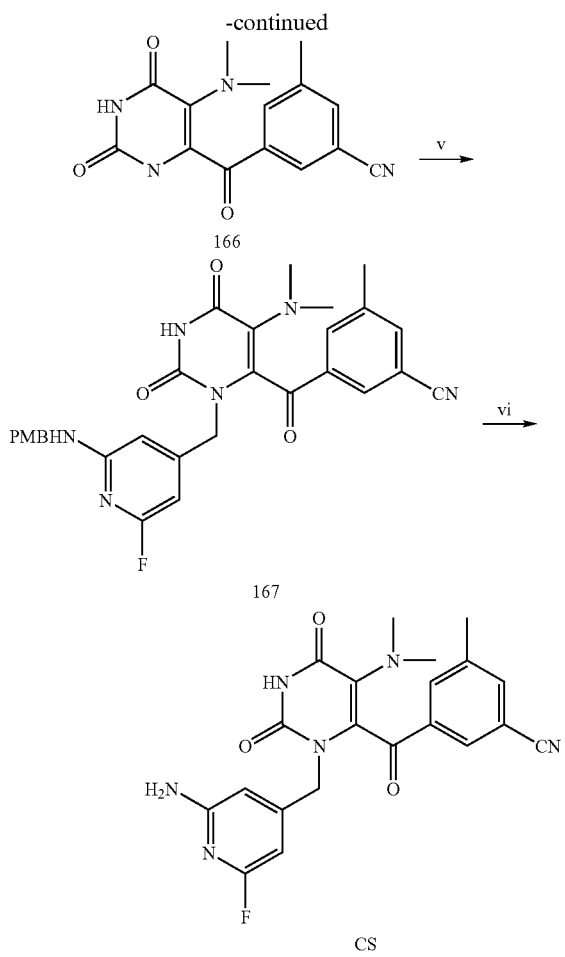

Reagents and conditions: i. NaH, DMF, 98%; ii. a. Pd/C, decaborane; b. HCHO, 25%; iii. NaH, O₂, DMF, 99%; iv. AcBr, 55%; v. methanesulfonic acid 2-fluoro-6-(4-methoxy-benzylamino)-pyridin-4-ylmethyl ester, K₂CO₃, LiI, DMF, 41%; vi. TFA 3-[Cyano-(2,6-dimethoxy-5-nitro-pyrimidin-4-yl)-methyl]-5-methyl-benzonitrile (163): 4-Chloro-2,6-dimethoxy-5-nitro-pyrimidine (0.45 g, 2.05 mmol, 1.05 eq., prepared according to Cushman et al. *J. Org. Chem.* 2004, 69, 601-612) and 3-cyanomethyl-5-methyl-benzonitrile (0.305 g, 1.95 mmol, 1.0 eq.) was dissolved in DMF (3.36 mL) and cooled to 0° C. 60% Sodium hydride (0.157 g, 3.92 mmol, 2.0 eq.) was added portionwise and the reaction was stirred at 0° C. for 1 h, then rt for 1 h. The reaction was cooled to 0° C. and quenched with saturated ammonium chloride solution. The pH was adjusted to ~6.0 with 1N HCl and mixture was extracted with ethyl ether. The organic layer was washed with water (2×), dried (MgSO₄) and concentrated. The resulting residue was purified by flash column chromatography (silica gel, 20 to 50% ethyl acetate/hexane) to give a yellow foam (0.6514 g, 98%). ¹H NMR (300 MHz, CDCl₃): δ 7.56 (s, 1H), 7.54 (s, 1H), 7.40 (s, 1H), 5.64 (s, 1H), 4.05 (s, 6H), 2.34 (s, 3H). Mass spectrum: 338.0 (M−H)⁻.

3-[Cyano-(5-dimethylamino-2,6-dimethoxy-pyrimidin-4-yl)-methyl]-5-methyl-benzonitrile (164): A mixture of 3-[cyano-(2,6-dimethoxy-5-nitro-pyrimidin-4-yl)-methyl]-5-methyl-benzonitrile (0.3796 g, 1.12 mmol), 10% palladium on carbon (0.065 g), acetic acid (9 drops) and decaborane (0.041 g, 0.336 mmol) in methanol (20 mL) was heated at 70° C. for 30 min. Reaction mixture was cooled to rt and 37% aqueous formaldehyde (272 μL, 3.36 mmol) and decaborane (0.027 g) were added and stirred overnight at rt. Mixture was filtered through a Celite pad, concentrated and purified by flash column chromatography (silica gel, 20 to 50% ethyl acetate/hexane) to give a yellow oil (0.0872 g, 23%). ¹H NMR (300 MHz, CDCl₃): δ 7.51 (s, 2H), 7.33 (s, 1H), 5.76 (s, 1H), 3.93 (s, 3H), 3.91 (s, 3H), 2.48 (s, 6H), 2.32 (s, 3H). Mass spectrum: 338.2 (M+H)⁺.

3-(5-Dimethylamino-2,6-dimethoxy-pyrimidine-4-carbonyl)-5-methyl-benzonitrile (165): To a solution of 3-[cyano-(5-dimethylamino-2,6-dimethoxy-pyrimidin-4-yl)-methyl]-5-methyl-benzonitrile (0.0872 g, 0.258 mmol) in DMF (1.0 mL) was added 60% sodium hydride (0.0114 g, 0.284 mmol) and stirred for 30 min. Oxygen was bubbled into reaction mixture overnight. The reaction was quenched with saturated ammonium chloride solution. The pH was adjusted to ~6.0 with 1N HCl and mixture was extracted with ethyl acetate. The organic layer was washed with water (2×), dried (MgSO₄) and concentrated to give a yellow solid (0.0834 g, 99%). ¹H NMR (300 MHz, CDCl₃): δ 7.91 (s, 1H), 7.85 (s, 1H), 7.64 (s, 1H), 4.08 (s, 3H), 3.93 (s, 3H), 2.53 (s, 6H), 2.44 (s, 3H). Mass spectrum: 327.2 (M+H)⁺.

3-(5-Dimethylamino-2,6-dioxo-1,2,3,6-tetrahydro-pyrimidine-4-carbonyl)-5-methyl-benzonitrile (166): A solution of 3-(5-dimethylamino-2,6-dimethoxy-pyrimidine-4-carbonyl)-5-methyl-benzonitrile (0.0834 g, 0.255 mmol) in acetyl bromide (3.0 mL) was heated at 70° C. for 12 h. Reaction mixture was concentrated and purified by reverse phase HPLC (Phenomenex Synergi® column, 5 to 100% acetonitrile/H₂O) to give an orange solid after lyophilization (0.030 g, 39%). ¹H NMR (300 MHz, CDCl₃): δ 9.55 (br s, 1H), 9.32 (br s, 1H), 7.85 (s, 1H), 7.79 (s, 1H), 7.64 (s, 1H), 2.45 (s, 9H). Mass spectrum: 299.1 (M+H)⁺.

3-{5-Dimethylamino-3-[2-fluoro-6-(4-methoxy-benzylamino)-pyridin-4-ylmethyl]-2,6-dioxo-1,2,3,6-tetrahydro-pyrimidine-4-carbonyl}-5-methyl-benzonitrile (167): A solution 3-(5-dimethylamino-2,6-dioxo-1,2,3,6-tetrahydro-pyrimidine-4-carbonyl)-5-methyl-benzonitrile (0.0087 g, 0.0292 mmol), methanesulfonic acid 2-fluoro-6-(4-methoxy-benzylamino)-pyridin-4-ylmethyl ester (0.0095 g, 0.0292 mmol), lithium iodide (0.002 g, 0.0146 mmol) and potassium carbonate (0.004 g, 0.0292 mmol) in DMF (3.0 mL) was stirred at 0° C. for 7 h. Reaction mixture was diluted with acetonitrile and purified by reverse phase HPLC (Phenomenex Synergi® column, 5 to 100% acetonitrile/H₂O) to give an yellow powder after lyophilization (0.0063 g, 40%). ¹H NMR (300 MHz, CDCl₃): δ 8.55 (br s, 1H), 7.62 (s, 1H), 7.52 (s, 1H), 7.49 (s, 1H), 7.22 (s, 1H), 7.19 (d, J=8.4 Hz, 2H), 6.85 (d, J=8.4 Hz, 2H), 5.77 (d, J=8.4 Hz, 1H), 4.22 (s, 2H), 3.77 (s, 3H), 2.39 (s, 6H). Mass spectrum: 543.1 (M+H)⁺.

Example CS

A solution 3-{5-dimethylamino-3-[2-fluoro-6-(4-methoxy-benzylamino)-pyridin-4-ylmethyl]-2,6-dioxo-1,2,3,6-tetrahydro-pyrimidine-4-carbonyl}-5-methyl-benzonitrile (0.0087 g, 0.016 mmol) in TFA (1.0 mL) was stirred at 0° C. for 1 h, then rt for 3 h. Reaction mixture was concentrated, co-evaporated with acetonitrile and purified by reverse phase HPLC (Phenomenex Synergi® column, 5 to 100% acetonitrile/H₂O) to give an yellow powder solid after lyophilization (0.0032 g, 47%). ¹H NMR (300 MHz, CD₃OD): δ 7.90 (s, 1H), 7.74 (s, 1H), 7.69 (s, 1H), 5.98 (s, 1H), 5.82 (s, 1H), 4.9 (2H+CD₃OH) 2.41 (s, 6H), 2.36 (s, 3H). Mass spectrum: 423.1 (M+H)⁺.

Example CT

Scheme 83

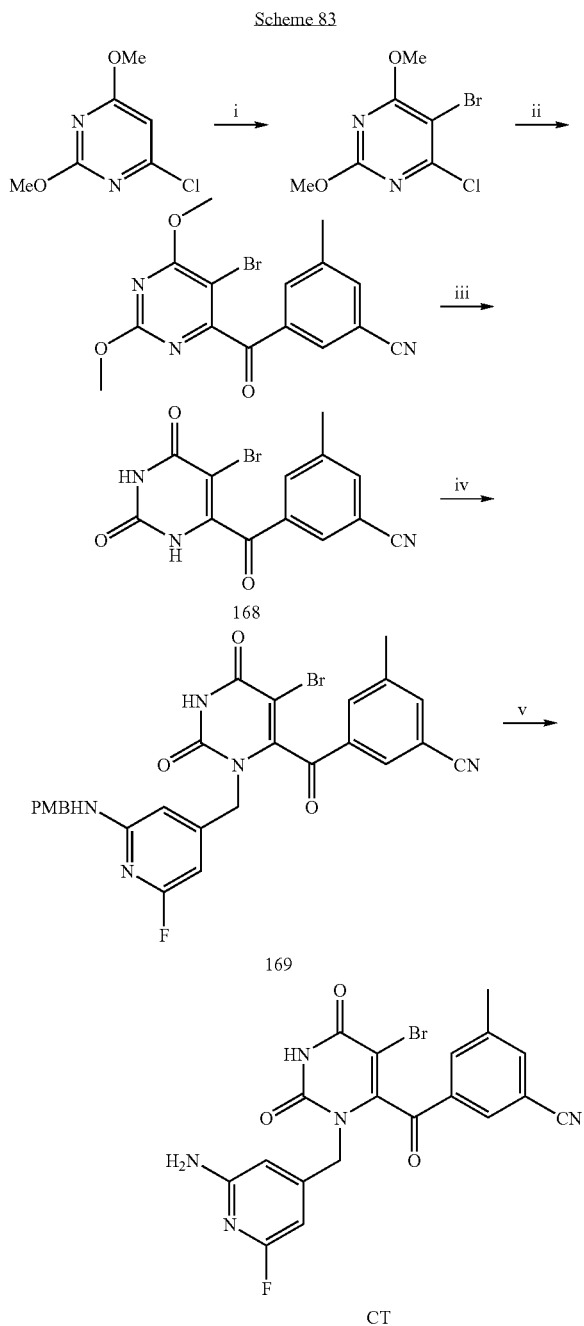

Reagents and Conditions: i. NaHCO₃, Br₂; ii. a. 3-cyanomethyl-5-methyl-benzonitrile, NaH, DMF; b. NaH, O₂, DMF; iii. AcBr; iv. methanesulfonic acid 2-fluoro-6-(4-methoxy-benzylamino)-pyridin-4-ylmethyl ester, K₂CO₃, LiI, DMF; v. TFA 5-Bromo-4-chloro-2,6-dimethoxy-pyrimidine: 4-Chloro-2,6-dimethoxy-pyrimidine (2.2 g, 12.6 mmol) and sodium bicarbonate (2.39 g, 28.4 mmol) were stirred in aqueous methanol (50%, 40 mL) at room temperature. Bromine (3.52 g, 22.0 mmol) was added dropwise over a period of 60 minutes. After the addition was complete, stirring was continued for additional 60 minutes. The solid was collected and was washed with water to yield 6.2 g of crude material. 3.1 g of the crude material were dissolved in hot methanol (40 mL) and water (10 mL) was added. The resultant precipitate was collected and dried in vacuo to yield the product (1.0 g, 3.95 mmol). $^1$H (CDCl₃): δ=4.05 (s, 3H), 3.99 (s, 3H) ppm.

3-(5-Bromo-2,6-dimethoxy-pyrimidine-4-carbonyl)-5-methyl-benzonitrile: 5-Bromo-2-chloro-2,4-dimethoxy-pyrimidine (980 mg, 3.87 mmol) and 3-cyanomethyl-5-methyl-benzonitrile (666.4 mg, 4.26 mmol) were dissolved in dimethyl formamide (10 mL) at room temperature. The solution was cooled to 0° C. Sodium hydride in mineral oil (60%, 170 mg, 4.26 mmol) was added, the reaction mixture was allowed to warm to room temperature and stirring was continued. After 18 hours, a second batch of sodium hydride suspension in mineral oil (60%, 170 mg, 4.26 mmol) was added and stirring was continued for 30 minutes. The reaction was placed under an atmosphere of oxygen and stirring at room temperature was continued. After 72 hours, the reaction was quenched with aqueous ammonium chloride solution and extracted with diethyl ether. The combined organic layers were dried over sodium sulfate. Filtration and evaporation of solvents yielded the crude material. The crude material was purified by flash chromatography on silica gel (eluent: ethyl acetate in hexanes) to yield the product (445 mg, 1.23 mmol). $^1$H (CDCl₃): δ=7.93 (s, 1H), 7.87 (s, 1H), 7.70 (s, 1H), 4.13 (s, 3H), 3.98 (s, 3H), 2.46 (s, 3H) ppm.

3-(5-Bromo-2,6-dioxo-1,2,3,6-tetrahydro-pyrimidine-4-carbonyl)-5-methyl-benzonitrile (168): To a solution of 3-(5-bromo-2,6-dimethoxy-pyrimidine-4-carbonyl)-5-methyl-benzonitrile (0.158 g, 0.436 mmol) in acetyl bromide (2.0 mL) was heated at 65° C. for 24 h. Reaction mixture was concentrated and flash column chromatography (silica gel, 0 to 80% ethyl acetate/hexane) to give a yellow film (0.0802 g, 55%). $^1$H NMR (300 MHz, CD₃OD): δ 8.18 (s, 1H), 8.09 (s, 1H), 7.90 (s, 1H), 2.46 (s, 3H). Mass spectrum: 335.3 (M+H)⁺.

3-{5-Bromo-3-[2-fluoro-6-(4-methoxy-benzylamino)-pyridin-4-ylmethyl]-2,6-dioxo-1,2,3,6-tetrahydro-pyrimidine-4-carbonyl}-5-methyl-benzonitrile (169): A solution 3-[(5-dimethylamino-3-[2-fluoro-6-(4-methoxy-benzylamino)-pyridin-4-ylmethyl]-2,6-dioxo-1,2,3,6-tetrahydro-pyrimidine-4-carbonyl]-5-methyl-benzonitrile (0.048 g, 0.144 mmol), methanesulfonic acid 2-fluoro-6-(4-methoxy-benzylamino)-pyridin-4-ylmethyl ester (0.0245 g, 0.072 mmol), lithium iodide (0.010 g, 0.072 mmol) and potassium carbonate (0.010 g, 0.072 mmol) in DMF (0.5 mL) was warmed to rt overnight. Reaction mixture was concentrated and purified by flash column chromatography (silica gel, 30 to 80% ethyl acetate) to give an yellow solid (0.0174 g, 42%). $^1$H NMR (300 MHz, CD₃OD): δ 7.96 (s, 1H), 7.79 (s, 1H), 7.67 (s, 1H), 7.25 (d, J=8.4 Hz, 2H), 6.89 (d, J=8.7 Hz, 2H), 5.89 (s, 1H), 5.79 (s, 1H), 5.26 (d, J=18.3 Hz, 1H), 4.35 (d, J=16.2 Hz, 1H), 4.23 (s, 2H), 3.79 (s, 3H), 2.33 (s, 3H). Mass spectrum: 578.0 (M+H)⁺.

Example CT

A solution 3-[3-(2-Amino-6-fluoro-pyridin-4-ylmethyl)-5-dimethylamino-2,6-dioxo-1,2,3,6-tetrahydro-pyrimidine-4-carbonyl]-5-methyl-benzonitrile (0.0222 g, 0.0384 mmol) in TFA (2.0 mL) was stirred at 0° C. for 1 h, then rt for 3 h. Reaction mixture was concentrated, co-evaporated with acetonitrile and purified by reverse phase HPLC (Phenomenex Synergi® column, 5 to 100% acetonitrile/H₂O) to give a yellow powder after lyophilization (0.0077 g, 34%). $^1$H NMR (300 MHz, d₆-acetone): δ 8.22 (s, 1H), 8.11 (s, 1H), 7.88 (s, 1H), 6.13 (s, 1H), 5.96 (s, 1H), 5.61 (br s, 1H), 5.00 (d, J=19.2 Hz, 1H), 4.57 (d, J=17.1 Hz, 1H), 2.42 (s, 3H). Mass spectrum: 458.2, 460.1 (M+H)+.

Example CU

Scheme 84

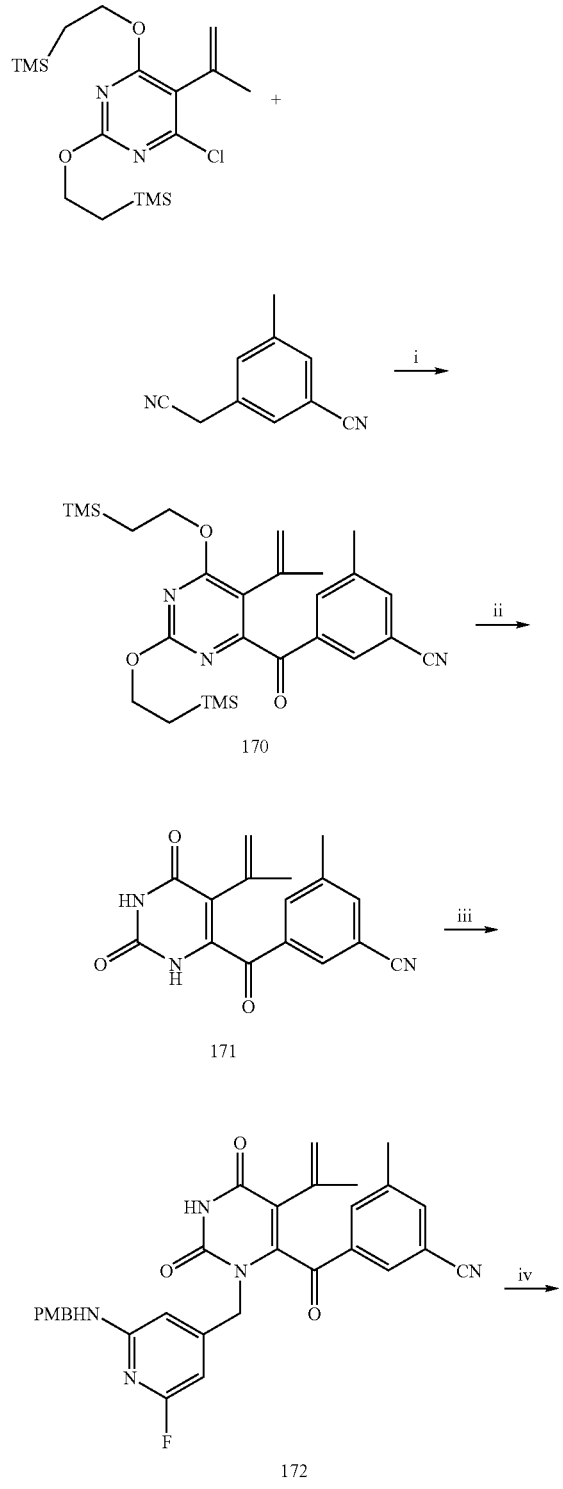

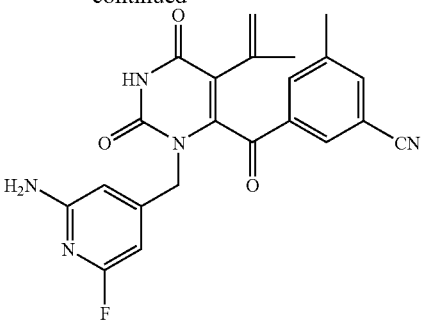

CU

Reagents and Conditions: i. a: NaH, DMF; b. O2, 58%; ii. TFA, CH2Cl2, 82%; iii. methanesulfonic acid 2-fluoro-6-(4-methoxy-benzylamino)-pyridin-4-ylmethyl ester, K2CO3, LiI, DMF, 49%; iv. DDQ, CH2Cl2/H2O, 60%.

3-[5-Isopropenyl-2,6-bis-(2-trimethylsilanyl-ethoxy)-pyrimidine-4-carbonyl]-5-methyl-benzonitrile (170): 4-Chloro-5-isopropenyl-2,6-bis-(2-trimethylsilanyl-ethoxy)-pyrimidine (2.12 g, 5.49 mmol, prepared according to Pews et al. *J. Fluorine. Chem.* 1989, 42, 179-186) and 3-cyanomethyl-5-methyl-benzonitrile (0.8166 g, 5.23 mmol) was dissolved in DMF (10 mL) and cooled to 0° C. 60% Sodium hydride (0.157 g, 3.92 mmol, 2.0 eq.) was added portionwise and the reaction was stirred at 0° C. for 6 h, then rt for 1 h. Oxygen was bubbled into reaction mixture overnight. The reaction was quenched with 1N HCl and saturated ammonium chloride solution was added. The mixture was extracted with ethyl acetate, the organic layer was dried (MgSO4), concentrated and purified by flash column chromatography (silica gel, 0 to 5% ethyl acetate/hexane) to give a yellow solid (1.568 g, 58%). 1H NMR (300 MHz, CDCl3): δ 7.87 (s, 1H), 7.84 (s, 1H), 7.60 (s, 1H), 4.96 (s, 1H), 4.96 (s, 1H), 4.66 (s, 1H), 4.6-4.4 (m, 2H), 4.4-4.3 (m, 1H) 2.39 (s, 3H), 1.91 (s, 1H), 1.20-1.00 (m, 4H), 0.03 (br s, 9H), 0.027 (br s, 9H). Mass spectrum: 495.9 (M+H)+.

3-(5-Isopropenyl-2,6-dioxo-1,2,3,6-tetrahydro-pyrimidine-4-carbonyl)-5-methyl-benzonitrile (171): To a solution of 3-[5-isopropenyl-2,6-bis-(2-trimethylsilanyl-ethoxy)-pyrimidine-4-carbonyl]-5-methyl-benzonitrile (0.636 g, 1.28 mmol) in dichloromethane (10 mL) at 0° C. was added TFA (2 mL). Reaction mixture was stirred at 0° C. for 30 min, concentrated and purified by flash column chromatography (silica gel, 0 to 10% methanol/dichloromethane) to give a yellow solid (0.311 g, 82%). 1H NMR (300 MHz, CD3OD): δ 8.11 (s, 1H), 8.03 (s, 1H), 7.88 (s, 1H), 4.91 (s, 1H), 4.75 (s, 1H), 2.49 (s, 3H), 1.82 (s, 3H). Mass spectrum: 296.1 (M+H)+.

3-{3-[2-Fluoro-6-(4-methoxy-benzylamino)-pyridin-4-ylmethyl]-5-isopropenyl-2,6-dioxo-1,2,3,6-tetrahydro-pyrimidine-4-carbonyl}-5-methyl-benzonitrile (172): A solution of 3-(5-isopropenyl-2,6-dioxo-1,2,3,6-tetrahydro-pyrimidine-4-carbonyl)-5-methyl-benzonitrile (0.0375 g, 0.127 mmol), methanesulfonic acid 2-fluoro-6-(4-methoxy-benzylamino)-pyridin-4-ylmethyl ester (0.024 g, 0.072 mmol), lithium iodide (0.0048 g, 0.036 mmol) and potassium carbonate (0.010 g, 0.072 mmol) in DMF (1.0 mL) was stirred at 0° C. for 2 h, then warmed to rt. After 6 h, reaction mixture was diluted with ethyl acetate, washed with water (2×), dried (MgSO4), concentrated and purified by flash column chromatography (silica gel, 10 to 50% ethyl acetate/hexane) to give a yellow solid (0.019 g, 49%). 1H NMR (300 MHz, CD3CN): δ 7.87 (s, 1H), 7.74 (s, 1H), 7.65 (s, 1H), 7.19 (d, J=8.7 Hz, 2H), 6.85 (d, J=8.7 Hz, 2H), 5.89 (s, 1H), 5.84 (s, 1H), 5.66 (br s, 1H), 5.2-4.95 (br s, 1 h), 4.92 (s, 1H), 4.70 (s, 1H), 4.5-4.2 (br s, 1H), 4.20 (d, J=5.7 Hz, 2H), 3.75 (s, 3H), 2.30 (s, 3H), 1.67 (s, 3H). Mass spectrum: 538.1 (M+H)+.

Example CU

To a mixture of 3-{3-[2-fluoro-6-(4-methoxy-benzylamino)-pyridin-4-ylmethyl]-5-isopropenyl-2,6-dioxo-1,2,3,6-tetrahydro-pyrimidine-4-carbonyl}-5-methyl-benzonitrile (0.0118 g, 0.022 mmol) in dichloromethane (1.4 mL) and water (0.7 mL) at 0° C. was added 2,3-dichloro-5,6-dicyano-1,4-benzoquinone (0.006 g, 0.026 mmol). After 1 h, reaction mixture was diluted with ethyl acetate, washed with water (3×), dried (MgSO4) and concentrated. The resulting residue was purified by reverse phase HPLC (Phenomenex Synergi® column, 5 to 100% acetonitrile/H2O), then by flash column chromatography (silica gel, 30 to 70% ethyl acetate/hexane) to give an off-white solid after lyophilization (0.019 g, 60%). 1H NMR (300 MHz, CD3OD): δ 7.90 (s, 1H), 7.73 (s, 1H), 7.72 (s, 1H), 5.99 (s, 1H), 5.82 (s, 1H), 4.93 (s, 1H) 4.74 (s, 1H), 2.35 (s, 3H), 1.69 (s, 3H). Mass spectrum: 420.2 (M+H)+.

Example CV

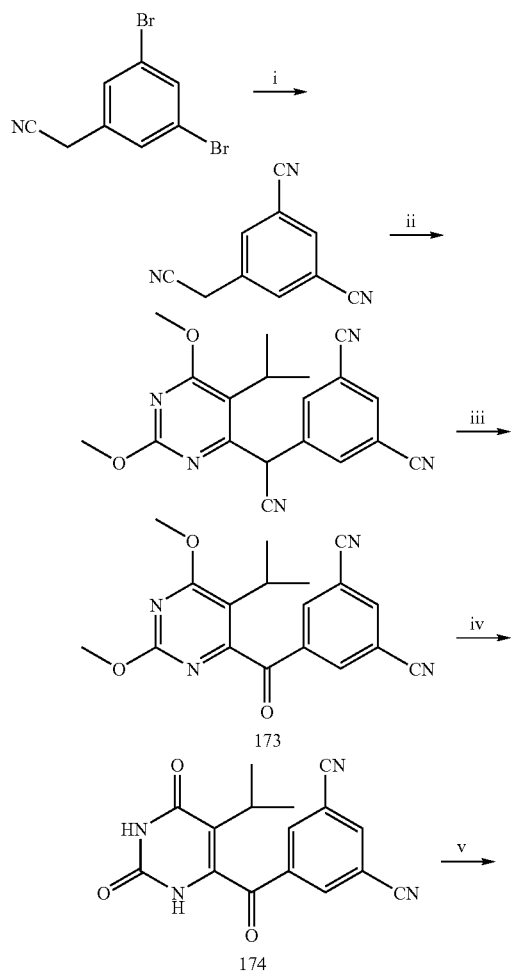

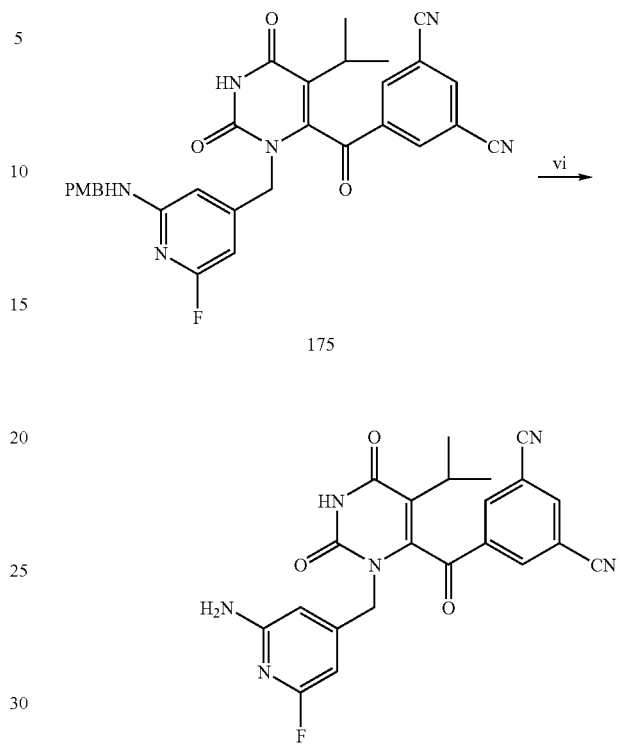

Reagents and conditions: i. Zn(CN)2, Pd(PPh3)4, DMF, 72%; ii. 4-chloro-5-isopropyl-2,6-dimethoxy-pyrimidine, NaH, DMF, 43%; iii. NaH, O2, DMF, 8%; iv. AcBr, 97%, v. methanesulfonic acid 2-fluoro-6-(4-methoxy-benzylamino)-pyridin-4-ylmethyl ester, K2CO3, LiI, DMF, 31%; vi. TFA, CH2Cl2, 62%.

5-Cyanomethyl-isophthalonitrile: A mixture of commercially available (3,5-dibromo-phenyl)-acetonitrile (0.65 g, 2.36 mmol) and zinc cyanide (0.832 g, 7.09 mmol) in DMF (10 mL) was heated at 90° C., evacuated and backfilled with argon (3×). Pd(PPh3)4 (0.272 g, 0.236 mmol) was added and reaction mixture stirred at 90° C. overnight. Reaction mixture was cooled, diluted with ethyl acetate, washed with water (3×), brine, dried (MgSO4) and concentrated. The resulting reside was flash column chromatography (silica gel, ethyl acetate/hexane) to give an off-white solid (0.285 g, 72%). 1H NMR (300 MHz, CDCl3): δ 7.91 (s, 1H), 7.86 (s, 1H), 3.85 (s, 2H).

5-[Cyano-(5-isopropyl-2,6-dimethoxy-pyrimidin-4-yl)-methyl]-isophthalonitrile: 5-Cyanomethyl-isophthalonitrile (0.285 g, 1.70 mmol) and 4-chloro-5-isopropyl-2,6-dimethoxy-pyrimidine (0.360 g, 1.66 mmol) was dissolved in DMF (8.0 mL) and cooled to 0° C. 60% Sodium hydride (0.136 g, 3.40 mmol) was added portionwise and the reaction was stirred at 0° C. for 2 h, then rt overnight. The reaction was quenched with saturated ammonium chloride solution and pH was adjusted to ~6.0 with 1N HCl. Mixture was extracted with ethyl acetate and organic layer was dried (MgSO4) and concentrated. The resulting residue was purified by flash column chromatography (silica gel, 10 to 50% ethyl acetate/hexane) to give a white solid (0.2457 g, 43%). 1H NMR (300 MHz, CDCl3): δ 7.90 (s, 3H), 5.46 (s, 1H), 3.96 (s, 3H), 3.89 (s, 3H), 3.05-2.9 (m, 1H), 1.16 (d, J=6.9 Hz, 3H), 1.15 (d, J=7.2 Hz, 3H).

5-(5-Isopropyl-2,6-dimethoxy-pyrimidine-4-carbonyl)-isophthalonitrile (173): To a solution of 5-[cyano-(5-isopropyl-2,6-dimethoxy-pyrimidin-4-yl)-methyl]-isophthalonitrile (0.2457 g, 0.707 mmol) in DMF (2.4 mL) was added 60% sodium hydride (0.031 g, 0.778 mmol) and stirred for 30 min. Oxygen was bubbled into reaction mixture for 4 h. The reaction was quenched with saturated ammonium chloride solution and pH was adjusted to ~6.0 with 1N HCl. Mixture was extracted with ethyl acetate and organic layer was washed with water (2×), dried ($MgSO_4$) and concentrated. The resulting residue was purified by flash column chromatography (silica gel, 10 to 50% ethyl acetate/hexane) to give a white foam (0.018 g, 8%). $^1$H NMR (300 MHz, $CDCl_3$): δ 8.32 (s, 2H); 8.08 (s, 1H), 4.05 (s, 3H), 3.89 (s, 3H), 3.0-2.8 (m, 1H), 1.19 (s, 3H), 1.42 (s, 3H). Mass spectrum: 337.2 $(M+H)^+$.

5-(5-Isopropyl-2,6-dioxo-1,2,3,6-tetrahydro-pyrimidine-4-carbonyl)-isophthalonitrile (174): A solution of 5-(5-isopropyl-2,6-dimethoxy-pyrimidine-4-carbonyl)-isophthalonitrile (0.018 g, 0.0535 mmol) in acetyl bromide (0.7 mL) was heated at 60° C. for 5 h. Reaction mixture was concentrated and purified by flash column chromatography (silica gel, 0 to 5% methanol/dichloromethane) to give a yellow film (0.017 g, 97%). $^1$H NMR (300 MHz, $CD_3OD$): δ 8.65 (s, 2H), 8.52 (s, 1H), 2.5-2.3 (m, 1H), 1.14 (s, 3H), 1.10 (s, 3H). Mass spectrum: 307.1 $(M+H)^+$.

5-{3-[2-Fluoro-6-(4-methoxy-benzylamino)-pyridin-4-ylmethyl]-5-isopropyl-2,6-dioxo-1,2,3,6-tetrahydro-pyrimidine-4-carbonyl}-isophthalonitrile (175): A solution 5-(5-isopropyl-2,6-dioxo-1,2,3,6-tetrahydro-pyrimidine-4-carbonyl)-isophthalonitrile (0.016 g, 0.0535 mmol), methanesulfonic acid 2-fluoro-6-(4-methoxy-benzylamino)-pyridin-4-ylmethyl ester (0.017 g, 0.0535 mmol), lithium iodide (0.0036 g, 0.0268 mmol) and potassium carbonate (0.0074 g, 0.0535 mmol) in DMF (0.5 mL) was stirred at 0° C. for 4 h, then warmed to rt overnight. Reaction mixture was diluted with ethyl acetate, washed with water (2×), dried ($MgSO_4$) and concentrated. The resulting residue was purified by flash column chromatography (silica gel, 10 to 50% ethyl acetate/hexane), then by reverse phase HPLC (Phenomenex Synergi® column, 5 to 100% acetonitrile/$H_2O$) to give an yellow solid (0.0091 g, 31%). $^1$H NMR (300 MHz, $CD_3OD$): δ 8.31 (s, 2H), 8.13 (s, 1H), 7.25 (d, J=8.7 Hz, 2H), 6.86 (d, J=8.4 Hz, 2H), 5.79 (s, 1H), 5.74 (s, 1H), 5.17 (d, J=16.8 Hz, 1H), 4.20 (s, 2H), 4.13 (d, J=16.8 Hz, 1H), 3.75 (s, 3H), 2.2-2.0 (m, 1H), 1.12 (d, J=6.6 Hz, 3H), 1.07 (d, J=6.6 Hz, 3H). Mass spectrum: 553.1 $(M+H)^+$.

Example CV

A solution 5-[(3-[2-fluoro-6-(4-methoxy-benzylamino)-pyridin-4-ylmethyl]-5-isopropyl-2,6-dioxo-1,2,3,6-tetrahydro-pyrimidine-4-carbonyl]-isophthalonitrile (0.00917 g, 0.0165 mmol) in TFA (1.0 mL) was stirred at 0° C. for 5 min, then rt for 2 h. Reaction mixture was concentrated, co-evaporated with acetonitrile and purified by reverse phase HPLC (Phenomenex Synergi® column, 5 to 100% acetonitrile/$H_2O$) to give a yellow powder after lyophilization (0.0044 g, 62%). $^1$H NMR (300 MHz, $CD_3OD$): δ 8.47 (s, 2H), 8.40 (s, 1H), 5.92 (s, 1H), 5.82 (s, 1H), 5.05 (d, J=16.8 Hz, 1H), 4.29 (d, J=17.7 Hz, 1H), 2.3-2.1 (m, 1H), 1.12 (d, J=6.6 Hz, 3H), 1.11 (d, J=6.3 Hz, 3H). Mass spectrum: 433.2 $(M+H)^+$.

Example CW

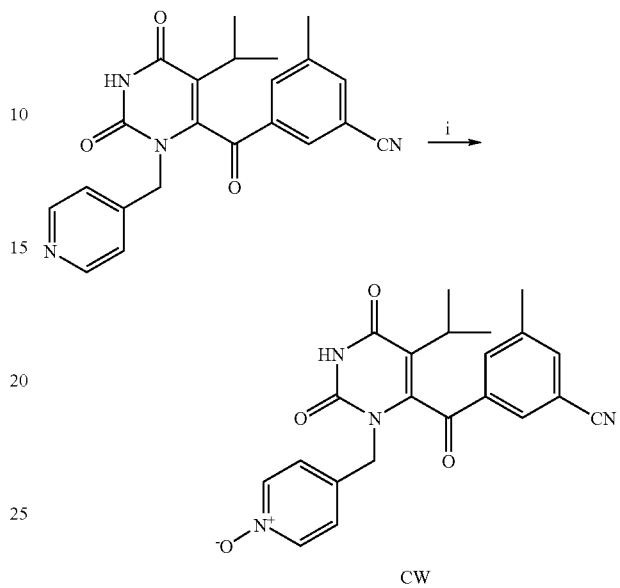

Reagents and conditions: i. mCPBA, $CH_2Cl_2$, 99%.

Example CW

A solution of 3-(5-isopropyl-2,6-dioxo-3-pyridin-4-ylmethyl-1,2,3,6-tetrahydro-pyrimidine-4-carbonyl)-5-methyl-benzonitrile (0.0089 g, 0.0229 mmol) and m-chloroperbenzoic acid (0.0077 g, 0.0344 mmol) in dichloromethane (0.5 mL) was stirred overnight at rt. Reaction mixture was concentrated and purified by flash column chromatography (silica gel, 1 to 5% methanol/dichloromethane) to give a white solid after lyophilization (0.011 g, 99%). $^1$H NMR (300 MHz, $CD_3OD$): δ 8.12 (s, 1H), 8.08 (d, J=6.9 Hz, 2H), 7.95 (s, 1H), 7.86 (s, 1H), 7.24 (d, J=6.9 Hz, 2H), 4.78 (s, 2H), 2.40 (s, 3H), 2.3-2.1 (m, 1H), 1.14 (d, j=6.0 Hz, 3H), 1.08 (d, j=6.0 Hz, 3H). Mass spectrum: 405.2 $(M+H)^+$.

Example CX

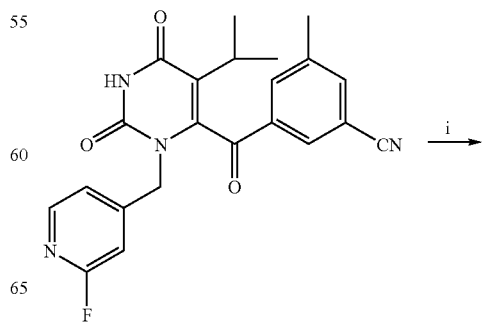

-continued

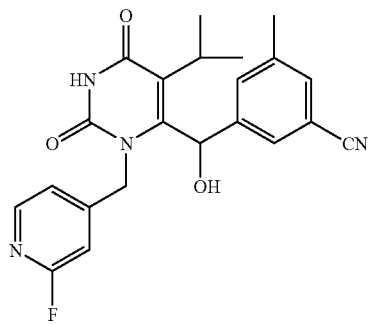

CX

Reagents and conditions: i. NaBH₄, ethanol, 51%.

Example CX

A solution of 3-[3-(2-Fluoro-pyridin-4-ylmethyl)-5-isopropyl-2,6-dioxo-1,2,3,6-tetrahydro-pyrimidine-4-carbonyl]-5-methyl-benzonitrile (0.0226 g, 0.0556 mmol) and sodium borohydride (0.0021 g, 0.0556 mmol) in ethanol (1.0 mL) was stirred at 0° C. for 2 h, then stirred at rt for 2 h. Reaction mixture was quenched with saturated ammonium chloride solution and pH was adjusted to ~6.0 with 1N HCl. Mixture was extracted with ethyl acetate and organic layer was dried (MgSO₄) and concentrated. The resulting residue was purified by reverse phase HPLC (Phenomenex Synergi® column, 5 to 100% acetonitrile/H₂O) to give white powder after lyophilization (0.0116 g, 51%). $^1$H NMR (300 MHz, CD₃OD): δ 7.88 (d, J=5.4 Hz, 1H), 7.43 (s, 1H), 7.27 (s, 1H), 7.21 (s, 1H), 6.72 (d, J=5.4 Hz, 1H), 6.39 (s, 1H), 6.27 (s, 1H), 5.24 (d, J=18.3 Hz, 1H), 5.01 (d, J=18.0 Hz, 1H), 3.3-3.2 (m, 1H), 2.23 (s, 3H), 1.40 (d, J=6.9 Hz, 3H), 1.30 (d, J=6.9 Hz, 3H). Mass spectrum: 409.2 (M+H)⁺.

Example CY

Scheme 88

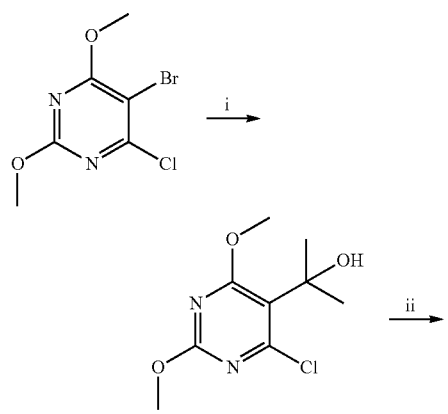

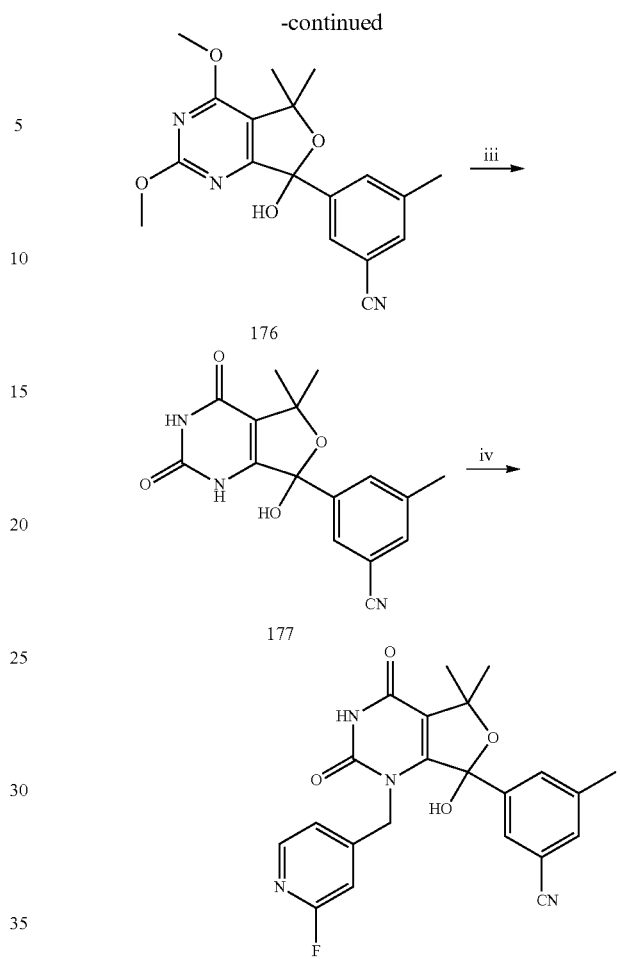

CY

Reagents and Conditions: i. nBuLi, acetone, THF, 55%; ii. 3-Cyanomethyl-5-methyl-benzonitrile, NaH, DMF, 18%; iii. AcBr, 25%; iv. 4-bromomethyl-2-fluoro-pyridine, K₂CO₃, LiI, DMF, 13%.

2-(4-Chloro-2,6-dimethoxy-pyrimidin-5-yl)-propan-2-ol: To a solution of 5-Bromo-4-chloro-2,6-dimethoxy-pyrimidine (0.546 g, 2.16 mmol) in THF (22 mL) at −78° C. was added n-butyllithium (1.6 M in hexanes, 1.48 mL, 2.37 mmol) over 2 min. Reaction mixture was stirred from 45 min at −78° C., then acetone (0.31 mL, 4.32 mmol) was added. Reaction mixture was stirred for 1 h at −78° C., then quenched with saturated ammonium chloride solution and extracted with ethyl acetate. Organic layer was washed with saturated ammonium chloride solution, dried (MgSO₄), concentrated and purified by flash column chromatography (silica gel, 10 to 30% ethyl acetate/hexane) to give a colorless oil (0.275 g, 55%). $^1$H NMR (300 MHz, CDCl₃): δ 3.97 (br s, 1H), 3.92 (s, 3H), 3.82 (s, 3H), 1.54 (s, 6H). Mass spectrum: 233.0, 235.0 (M+H)⁺.

3-(7-Hydroxy-2,4-dimethoxy-5,5-dimethyl-5,7-dihydro-furo[3,4-d]pyrimidin-7-yl)-5-methyl-benzonitrile (176): 3-Cyanomethyl-5-methyl-benzonitrile (0.067 g, 0.432 mmol) and 2-(4-Chloro-2,6-dimethoxy-pyrimidin-5-yl)-propan-2-ol (0.100 g, 0.432 mmol) was dissolved in DMF (1.5 mL) and cooled to 0° C. 60% Sodium hydride (0.035 g, 0.64 mmol) was added portionwise and the reaction was stirred at 0° C. for 1 h, then rt overnight. The reaction was quenched with 1N HCl, extracted with ethyl acetate and washed with saturated ammonium chloride solution. Organic layer was dried (MgSO$_4$) and concentrated and purified by flash column chromatography (silica gel, 0 to 40% ethyl acetate/hexane) to give a white solid (0.027 g, 18%). $^1$H NMR (300 MHz, CDCl$_3$): δ 7.80 (s, 2H), 7.39 (s, 1H), 4.01 (s, 3H), 3.93 (s, 3H), 2.37 (s, 3H), 1.66 (s, 3H), 1.63 (s, 3H). Mass spectrum: 342.3 (M+H)$^+$.

3-(7-Hydroxy-5,5-dimethyl-2,4-dioxo-1,2,3,4,5,7-hexahydro-furo[3,4-d]pyrimidin-7-yl)-5-methyl-benzonitrile (177): A solution of 3-(7-Hydroxy-2,4-dimethoxy-5,5-dimethyl-5,7-dihydro-furo[3,4-d]pyrimidin-7-yl)-5-methyl-benzonitrile (0.027 g, 0.080 mmol) in acetyl bromide (2.0 mL) was heated at 60° C. for 3 h. Reaction mixture was concentrated and purified by reverse phase HPLC (Phenomenex Synergi® column, 5 to 100% acetonitrile/H$_2$O) to give a desired product (0.0063 g, 25%). $^1$H NMR (300 MHz, CD$_3$OD): δ 7.76 (s, 1H), 7.70 (s, 1H), 7.51 (s, 1H), 2.38 (s, 1H), 1.60 (s, 3H), 1.59 (s, 3H). Mass spectrum: 314.0 (M+H)$^+$.

Example CY: A solution 3-(7-Hydroxy-5,5-dimethyl-2,4-dioxo-1,2,3,4,5,7-hexahydro-furo[3,4-d]pyrimidin-7-yl)-5-methyl-benzonitrile (0.0063 g, 0.020 mmol), 4-bromomethyl-2-fluoro-pyridine (0.0038 g, 0.020 mmol) and potassium carbonate (0.0028 g, 0.020 mmol) in DMF (0.4 mL) was stirred at 0° C. for 4 h, then warmed to rt overnight. Reaction mixture was diluted with ethyl acetate, neutralized with 1N HCl, washed with saturated ammonium chloride solution, dried (MgSO$_4$) and concentrated. The resulting residue was purified by reverse phase HPLC (Phenomenex Synergi® column, 5 to 100% acetonitrile/H$_2$O) to give a white powder after lyophilization (0.0011 g, 13%). $^1$H NMR (300 MHz, CD$_3$OD): δ 7.86 (d, J=5.4 Hz, 1H), 7.56 (s, 1H), 7.40 (s, 1H), 7.17 (s, 1H), 6.71 (d, J=5.4 Hz, 1H), 6.36 (s, 1H), 5.01 (d, J=18.0 Hz, 1H), 4.82 (d, J=18.0 Hz, 1H), 2.18 (s, 3H), 1.62 (s, 3H), 1.71 (s, 3H). Mass spectrum: 423.2 (M+H)$^+$.

Examples CZ and DA

Scheme 89

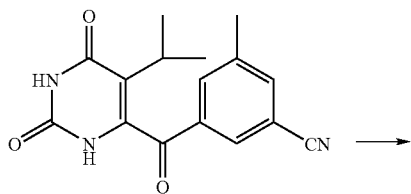

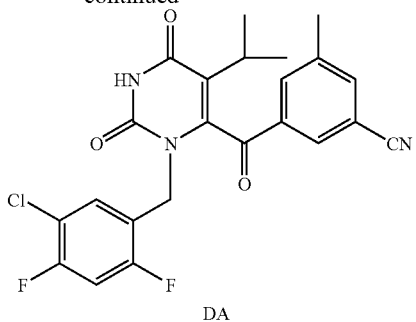

Example CZ 3-(5-Isopropyl-2,6-dioxo-1,2,3,6-tetrahydro-pyrimidine-4-carbonyl)-5-methyl-benzonitrile (25.1 mg, 0.0845 mmol), lithium iodide (12.0 mg, 0.0845 mmol), potassium carbonate (12.0 mg, 0.0845 mmol), and 2,4,6 trifluoro benzyl bromide (19.0 mg, 0.0845 mmol) were stirred in dimethyl formamide (2.0 mL) at room temperature. After 18 hours, all volatiles were removed in vacuo and the crude material was purified by flash chromatography on silica gel (eluent: ethyl acetate/hexanes). The product containing fractions were combined and the solvents were removed in vacuo to yield the product (15.3 mg, 0.0346 mmol). $^1$H (DMSO-d6): δ=11.62 (s, 1H), 8.17 (s, 1H), 8.02 (s, 1H), 7.91 (s, 1H), 6.59 (m, 2H), 4.90 (d, J=16.5 Hz, 1H), 4.68 (d, J=16.5 Hz, 1H), 2.36 (s, 3H), 2.06 (m, 1H), 1.05 (d, J=6.6 Hz, 3H), 0.98 (d, J=6.6 Hz, 3H) ppm.

Example DA 3-(5-Isopropyl-2,6-dioxo-1,2,3,6-tetrahydro-pyrimidine-4-carbonyl)-5-methyl-benzonitrile (52.3 mg, 0.176 mmol), lithium iodide (23.5 mg, 0.176 mmol), potassium carbonate (24.3 mg, 0.176 mmol), and 2,4, difluoro 5 chloro benzyl bromide (42.6 mg, 0.176 mmol) were stirred in dimethyl formamide (3.0 mL) at room temperature. After 18 hours, all volatiles were removed in vacuo and the crude material was purified by flash chromatography on silica gel (eluent: ethyl acetate/hexanes). The product containing fractions were combined and the solvents were removed in vacuo to yield the product (40.0 mg, 0.087 mmol). $^1$H (DMSO-d6): δ=11.65 (s, 1H), 8.25 (s, 1H), 8.02 (s, 1H), 7.95 (s, 1H), 7.54 (m, 1H), 7.18 (m, 1H), 4.95 (d, J=16.8 Hz, 1H), 4.45 (d, J=16.8 Hz, 1H), 2.34 (s, 3H), 2.06 (m, 1H), 1.09 (d, J=6.9 Hz, 3H), 1.02 (d, J=6.9 Hz, 3H) ppm.

Example DB

Scheme 90

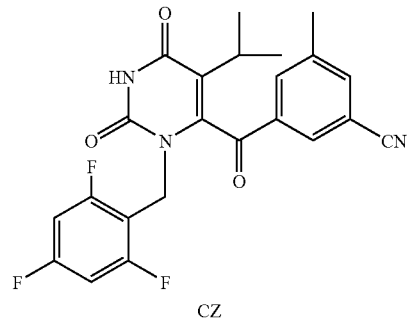

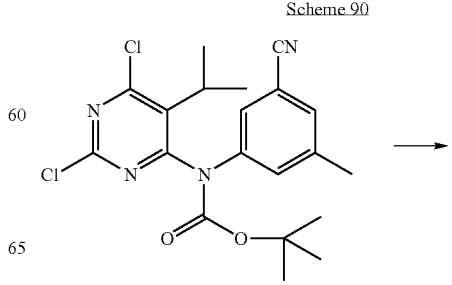

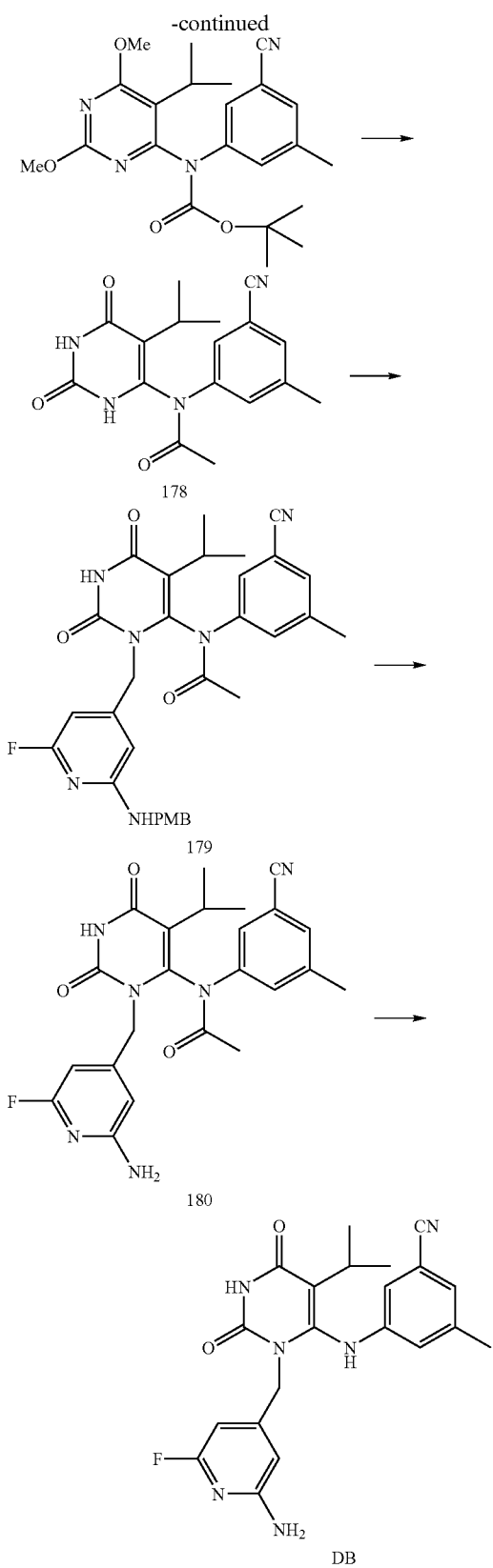

hydride (60% in mineral oil, 109 mg, 2.73 mmol) was added and stirring at room temperature was continued. After 10 minutes, 2,4,6 trichloro-5-isopropyl pyrimidine (514 mg, 2.28 mmol) was added. After 6 hours, the reaction was diluted with water and extracted with diethyl ether. The organic extracts were washed with water and dried over sodium sulfate. Filtration and evaporation of solvents yielded a crude material, which was purified via flash chromatography on silica gel (eluent: ethyl acetate in hexanes) to yield (3-Cyano-5-methyl-phenyl)-(2,6-dichloro-5-isopropyl-pyrimidin-4-yl)-carbamic acid tert-butyl ester (469.2 mg, 1.114 mmol). $^1$H (CDCl$_3$): δ=7.31 (s, 2H), 7.24 (s, 1H), 3.34 (m, 1H), 2.37 (s, 3H), 1.46 (s, 9H), 1.29-1.24 (m, 6H) ppm.

(3-Cyano-5-methyl-phenyl)-(2,6-dimethoxy-5-isopropyl-pyrimidin-4-yl)-carbamic acid tert-butyl ester: (3-Cyano-5-methyl-phenyl)-(2,6-dichloro-5-isopropyl-pyrimidin-4-yl)-carbamic acid tert-butyl ester (469 mg, 1.113 mmol) was dissolved in methanol (4 mL) at room temperature. Sodium methoxide solution (25% in methanol, 1.18 g, 5.56 mmol) was added and the reaction was heated at 75° C. After 4 hours, the reaction was stopped by the evaporation of solvents. The crude material was purified via flash chromatography on silica gel (eluent: ethyl acetate in hexanes) to yield (3-Cyano-5-methyl-phenyl)-(2,6-dimethoxy-5-isopropyl-pyrimidin-4-yl)-carbamic acid tert-butyl ester (336.8 mg, 0.816 mmol). $^1$H (CDCl$_3$): δ=7.36 (s, 1H), 7.31 (s, 1H), 7.20 (s, 1H), 4.02 (s, 3H), 3.92 (s, 3H), 3.01 (m, 1H), 2.32 (s, 3H), 1.41 (s, 9H), 1.20-1.10 (m, 6H) ppm.

(3-Cyano-5-methyl-phenyl)-(2,6-dimethoxy-5-isopropyl-pyrimidin-4-yl)-carbamic acid tert-butyl ester (178): (3-Cyano-5-methyl-phenyl)-(2,6-dimethoxy-5-isopropyl-pyrimidin-4-yl)-carbamic acid tert-butyl ester (168.0 mg, 0.407 mmol) was dissolved in acetyl bromide (1.5 mL) at room temperature and consecutively heated at 65° C. After 4 hours, the reaction was cooled to room temperature and all volatiles were removed in vacuo. The crude material was purified via flash chromatography on silica gel (eluent: ethyl acetate in hexanes) to yield (3-Cyano-5-methyl-phenyl)-(2,6-dimethoxy-5-isopropyl-pyrimidin-4-yl)-carbamic acid tert-butyl ester (29.7 mg, 0.091 mmol). $^1$H (CDCl$_3$): δ=7.57 (s, 1H), 7.42 (s, 2H), 2.79 (m, 1H), 2.39 (s, 3H), 2.18 (s, 3H), 1.26-1.15 (m, 6H) ppm.

N-(3-Cyano-5-methyl-phenyl)-N-{3-[2-fluoro-6-(4-methoxy-benzylamino)-pyridin-4-ylmethyl]-5-isopropyl-2,6-dioxo-1,2,3,6-tetrahydro-pyrimidin-4-yl}-acetamide (179): Potassium carbonate (25 mg, 0.18 mmol) and lithium chloride (24 mg, 0.18 mmol) were added to a solution of N-(3-cyano-5-methyl-phenyl)-N-(5-isopropyl-2,6-dioxo-1,2,3,6-tetrahydro-pyrimidin-4-yl)-acetamide (60 mg, 0.18 mmol) and (4-bromomethyl-6-fluoro-pyridin-2-yl)-(4-methoxy-benzyl)-amine (59 mg, 0.18 mmol) in dimethylformamide (1 mL). After 17 hours the solvent was removed and the residue was subjected to flash chromatography (eluant: 0-5% methanol/dichloromethane). The product containing fractions were combined and the solvent was removed in vacuo to yield the product (58 mg, 0.10 mmol). $C_{31}H_{31}FN_6O_4$ calculated 570.2, observed [M+1]$^+$ 571.1; rt=3.82 min.

N-[3-(2-Amino-6-fluoro-pyridin-4-ylmethyl)-5-isopropyl-2,6-dioxo-1,2,3,6-tetrahydro-pyrimidin-4-yl]-N-(3-cyano-5-methyl-phenyl)-acetamide (180): A solution of N-(3-cyano-5-methyl-phenyl)-N-{3-[2-fluoro-6-(4-methoxy-benzylamino)-pyridin-4-ylmethyl]-5-isopropyl-2,6-dioxo-1,2,3,6-tetrahydro-pyrimidin-4-yl}-acetamide (58 mg, 0.10 mmol) in acetonitrile (0.7 mL) was treated with glacial acetic acid (0.275 mL), cerric (IV) ammonium nitrate (111 mg, 0.20 mmol) and water (10 drops). After 30 min the mixture was partitioned between water (5 mL) and ethyl acetate (10 mL).

(3-Cyano-5-methyl-phenyl)-(2,6-dichloro-5-isopropyl-pyrimidin-4-yl)-carbamic acid tert-butyl ester: 3-Nitrilo-5-methyl-N-Boc-aniline (530 mg, 2.28 mmol) were dissolved in dimethyl formamide (5 mL) at room temperature. Sodium The solvent was removed from the organic phase in vacuo and the residue was subjected to flash chromatography (eluant: 0-70% ethyl acetate/hexanes). The product containing fractions were combined and the solvent was removed in vacuo to yield the product (23 mg, 0.051 mmol). $C_{23}H_{23}FN_6O_3$ calculated 450.2, observed [M+1]+451.1; rt=3.08 min.

Example DB

Sodium methoxide (8 mg, 0.15 mmol) was added to a solution of 3-[3-(2-amino-6-fluoro-pyridin-4-ylmethyl)-5-isopropyl-2,6-dioxo-1,2,3,6-tetrahydro-pyrimidin-4-ylamino]-5-methyl-benzonitrile (23 mg, 0.051 mmol) in methanol (0.5 mL). After 1.25 hours a saturated solution of ammonium chloride (0.2 mL) was added and all volatiles were removed in vacuo. The residue was subjected to flash chromatography (eluant: 20-100% ethyl acetate/hexanes). The product containing fractions were combined and the solvent was removed in vacuo to yield the product (11 mg, 0.027 mmol). $^1$H (MeOH-d4): δ=6.96 (s, 1H), 6.74 (s, 1H), 6.67 (s, 1H), 6.06 (s, 1H), 5.48 (s, 1H), 5.49 (s, 1H) 2.77 (p, J=7.2 Hz, 1H), 2.27 (s, 3H), 1.18 (d, J=6.9 Hz, 6H). $^{19}$F (MeOH-d4): δ=−74.85 (s, 1F); $C_{21}H_{21}FN_6O_2$ calculated 408.2, observed [M+1]$^+$ 409.1; rt=3.21 min.

Example DC syrup. The crude compound 44 was further dried in high vacuo for ca. 20 min. and mixed with compound 32 (5.94 g, 20 mmol), powdered anhydrous potassium carbonate (2.76 g, 20 mmol), and lithium iodide (20.68 g, 20 mmol). DMF (100 mL) was then added to the mixture at room temperature and stirred for ca. 4 hr. After evaporation of DMF, the residue was dissolved in 100 mL of methanol-chloroform (1:9) and filtered through celite pad. The celite pad was washed with 50 mL of methanol-chloroform (1:9). The filtrate was then evaporated in vacuo and the residue was purified by silica gel column chromatography (eluent, EA: hexane (1:2)) to afford 6 g (55%) of Compound 182 as a yellow solid. m.p. 200-201° C. $^1$H NMR (300 MHz, CDCl$_3$) δ 1.11 (3H, d, J=6.9 Hz), 1.22 (3H, d, J=6.9 Hz), 2.19 (1H, m), 2.38 (3H, s), 3.80 (3H, s), 4.19 (1H, d, J=16.2 Hz), 4.27 (2H, d, J=5.4 Hz), 5.05-5.17 (2H, m), 5.69 (1H, s), 5.83 (1H, s), 6.86-6.91 (2H, m), 7.23-7.26 (2H, m), 7.60 (1H, s), 7.63 (1H, s), 7.78 (1H, s), 9.35 (1H, s). HRMS (EI) Calc. 541.212533; Found 541.212860.

Example DC

Compound 182 (4 g, 7.39 mmol) was dissolved in acetonitrile (50 mL) and glacial acetic acid (20 mL) by heating with heat gun. The mixture was then cooled to room temperature. With vigorous stirring, Ceric Ammonium Nitrate (CAN) (8.1 g, 14.78 mmol) and distilled water was added in this order.

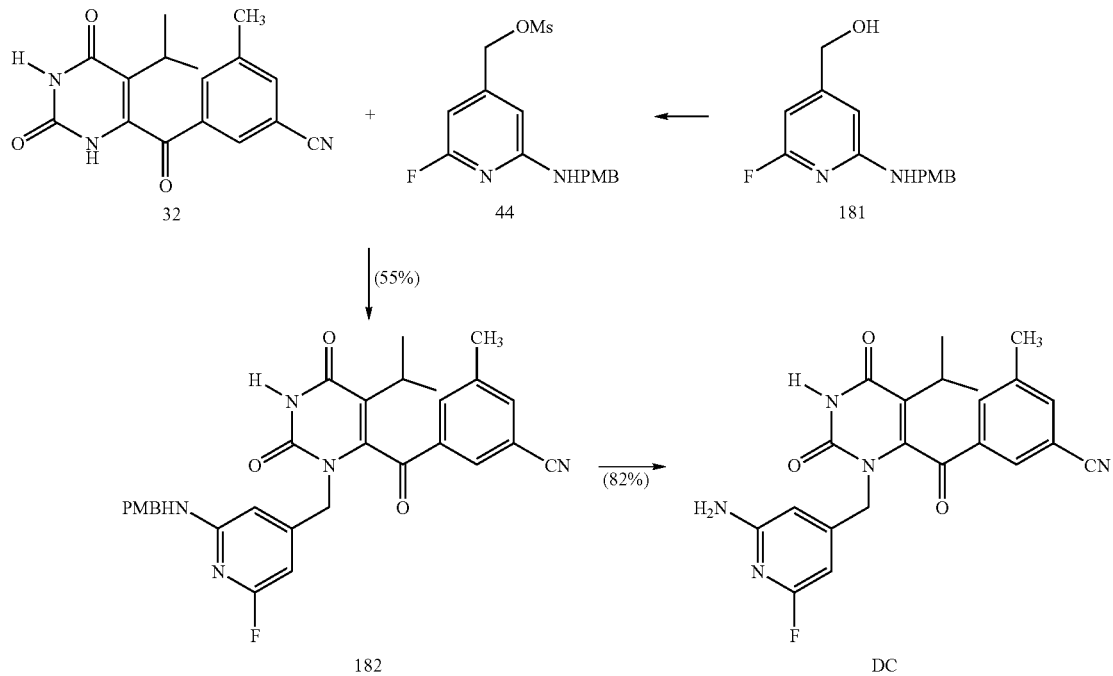

Scheme 91

Compound 182

Compound 181 (5.24 g, 20 mmol) was dissolved in chloroform (180 mL) and cooled in an ice bath under nitrogen atmosphere. With stirring, triethylamine (4.2 mL, 30 mmol) was added and methanesulfonyl chloride (1.8 mL, 24 mmol) was added dropwise. After stirring for 1.1 hr., the reaction mixture was washed with sat. aqueous sodium bicarbonate, dried with anhydrous magnesium sulfate, filtered, and evaporated in vacuo to afford a crude compound 44 as a light brown After 30 min., EA and water was added to the reaction mixture. Organic layer was taken, dried with anhydrous magnesium sulfate, filtered, and evaporated in vacuo to give a crude product as a light brown residue. The crude product was purified by silica gel column chromatography (eluent, EA:hexane, from 1:1 to 2:1)) to afford 2.55 g (82%) of Example DC as a yellow solid. m.p. 258-260° C. λ$_{max}$ (KBr): 2238 (CN) cm$^{-1}$, $^1$H NMR (300 MHz, CD$_3$OD/CDCl$_3$) δ 1.12 (3H, d, J=6.9 Hz), 1.20 (3H, d, J=6.9 Hz), 2.24 (1H, m), 2.43 (3H, s), 4.29 (1H, d, J=16.5 Hz), 4.80 (2H, s), 5.04 (1H, d, J=16.5 Hz), 5.76 (1H, s), 5.97 (1H, s), 7.71 (2H, s), 7.94 (1H, s). $^{13}$C NMR (125 MHz, CD$_3$OD/CDCl$_3$) ⓔ18.70, 19.67, 20.26, 28.72, 46.38, 93.80 (d, J=36.2 Hz), 103.04, 103.07, 112.87, 116.83, 117.39, 134.92, 138.28, 140.88, 144.52, 150.60 (d, J=8.7 Hz), 150.90, 158.02, 158.15, 162.17, 162.84 (d, J=237.5), 180.32 m/z (EI) 421 (M$^+$), HRMS (EI) Calcd. 421.155018; Found 421.155823.

Example DC can be further purified by dissolving in acetone, concentration, addition of methanol, and recrystallization.

Preparation of Compound 32 with sat. aqueous sodium bicarbonate solution, dried with anhydrous magnesium sulfate, filtered and evaporated in vacuo to afford the crude product as a yellow solid.

The yellow solid was dissolved in ether (100 mL) and methanol (100 mL) was added. The mixture was then concentrated and recrystallized to give a white precipitate. The precipitate was filtered, washed with methanol, and dried in vacuo to afford 87 g (88%) of 2,4,6-trichloro-5-isopropylpyrimidine as a white solid, after repeating this procedure 3 times. m.p. 70-71° C. $^1$H NMR (200 MHz, CDCl$_3$) δ 1.44 (6H, d, J=7.2 Hz), 3.76 (1H, m). $^{13}$C NMR (50 MHz, CDCl$_3$) δ 18.69, 29.49, 135.19, 155.99, 162.20, m/z (EI) 225 (M$^+$).

Scheme 92

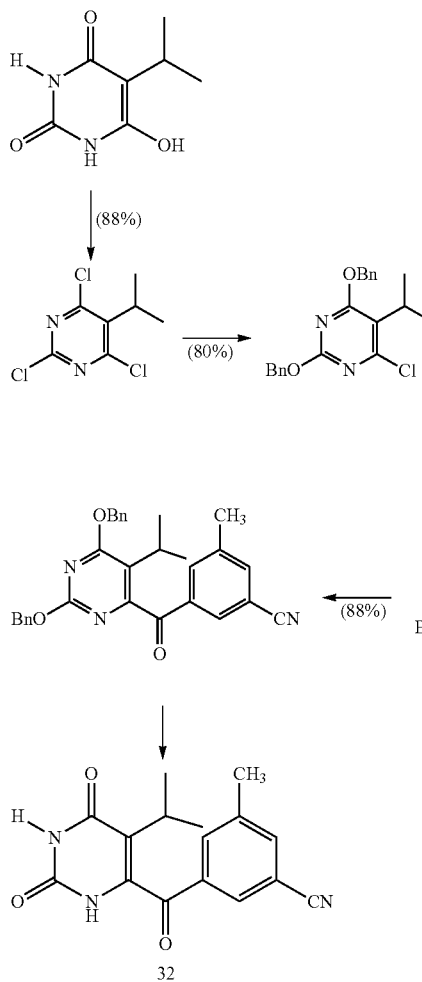
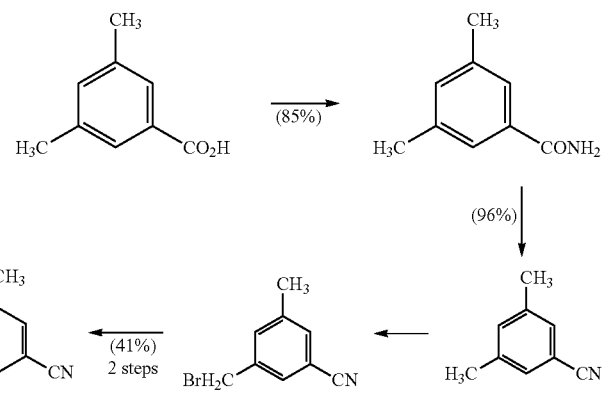
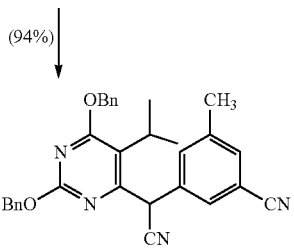

2,4,6-trichloro-5-isopropylpyrimidine

With vigorous stirring, 5-Isopropyl barbaric acid (Lancaster, 75 g, 0.44M) was added to phosphorus oxychloride (250 mL). N,N-diethylaniline (72 mL, 0.44M) was then added and the reaction mixture was refluxed in an oil bath (ca. 140° C.) for overnight. After cooling to room temperature, the excess phosphorus oxychloride was evaporated in vacuo and the residue was poured into crushed ice (exothermic reaction). Earth-like precipitate was formed immediately.

After stirring at room temperature for ca. 4 hr., the precipitate was filtered and washed with water several times. The precipitate was then dissolved in hexane (or ether), washed 2,4-bis(benzyloxy)-6-chloro-5-isopropylpyrimidine To a stirred solution of benzyl alcohol (600 mL) in water bath, was added sodium metal (12.24 g, 0.532 M) under nitrogen atmosphere.

After complete reaction of sodium metal, the mixture was cooled in an ice bath and 2,4,6-trichloro-5-isopropylpyrimidine (63 g, 0.28M) was added portionwise. After stirring for ca. 1 hr. in an ice bath, the reaction mixture was stirred at room temperature for overnight. Excess benzyl alcohol was evaporated in vacuo (water bath temp. ca. 80° C.), and the residue was dissolved in ether, washed with water, dried with anhydrous magnesium sulfate, filtered, and evaporated in vacuo to give a light yellow oil. The yellow oil was then recrystallized from ether/hexane to afford 41 g of 2,4-bis(benzyloxy)-6-chloro-5-isopropylpyrimidine as a white solid. The mother liquor was evaporated in vacuo and the residue was purified by silica gel column chromatography (eluent, ether:hexane (3:97)) to give 37 g of 2,4-bis(benzyloxy)-6-chloro-5-isopropylpyrimidine as a white solid. The combined yield was 78 g (80%). m.p. 77-78° C. $^1$H NMR (200 MHz, CDCl$_3$) δ 1.26 (6H, d, J=7.0 Hz), 3.45 (1H, m), 5.37 (2H, s), 5.42 (2H, s), 7.30-7.40 (10H, m). $^{13}$C NMR (50 MHz, CDCl$_3$) δ 19.80, 27.54, 69.11, 69.41, 117.69, 127.86, 128.07, 128.50, 135.86, 136.10, 159.19, 161.18, 169.59, m/z (EI) 368 (M$^+$).

3,5-dimethylbenzamide 3,5-Dimethylbenzoic acid (50 g, 0.33 M, Aldrich) was suspended in thionyl chloride (150 mL) and DMF (0.5 mL) was added. The mixture was then refluxed for 2.5 hr. Excess thionyl chloride was evaporated in vacuo and the residue was added dropwise to ammonium hydroxide solution (ACS, 250 ml) cooled in an ice bath. The mixture was stirred for further 30 min. The white precipitate was then filtered, washed with water several times, and dried by standing on air. The crude product was dissolved in MC, washed with water, dried with anhydrous magnesium sulfate, filtered, and evaporated in vacuo to afford 42 g (85%) of 3,5-dimethylbenzamide as a white solid. m.p. 148-149° C. $^1$H NMR (200 MHz, CDCl$_3$) δ 2.35 (6H, s), 6.01 (2H, br. s), 7.15 (1H, s), 7.42 (2H, s).

3,5-dimethylbenzonitrile 3,5-dimethylbenzamide (50 g, 0.3356M) was suspended in benzene (400 mL). Thionyl chloride (49 mL, 0.671M) and DMF (2 mL) were added and the mixture was refluxed for 2 hr. After cooling to room temperature, the mixture was poured into a crushed ice. After 1 hr., the solution was neutralized by the addition of 6N sodium hydroxide solution. The product was then extracted with ether, dried with anhydrous magnesium sulfate, filtered, and evaporated in vacuo to give a yellow solid. The crude product was then purified by silica gel column chromatography (eluent, EA:hexane (1:4)) to afford 42 g (95%) of 3,5-dimethylbenzonitrile as a yellow solid. m.p. 51-52° C. $^1$H NMR (300 MHz, CDCl$_3$) δ 2.34 (6H, s), 7.21 (1H, s), 7.26 (2H, s).

3-(bromomethyl)-5-methylbenzonitrile

To a stirred solution of carbon tetrachloride (270 mL), was added 3,5-dimethylbenzonitrile (37 g, 0.282M), N-bromo succinimide (NBS) (50 g, 0.282 M), and benzoyl peroxide (3.4 g, 14 mmol). The mixture was then refluxed for 3 hr. under a light of 500 W tungsten lamp. After cooling to room temperature, the mixture was filtered, evaporated, and the residue was purified by silica gel column chromatography (eluent, ether:hexane (1:10)) to give 48 g (81%) of 3-(bromomethyl)-5-methylbenzonitrile as a white solid. m.p. 80-81° C. $^1$H NMR (200 MHz, CDCl$_3$) δ 2.39 (3H, s), 4.43 (2H, s), 7.39 (1H, s), 7.43 (1H, s), 7.48 (1H, s).

3-(cyanomethyl)-5-methylbenzonitrile

To a stirred ethanol (150 mL), was added 3-(bromomethyl)-5-methylbenzonitrile (48 g, 0.228M), potassium cyanide (27 g, 0.42M), and distilled water (77 mL). The mixture was then refluxed for 3 hr. After cooling to room temperature, the reaction mixture was evaporated in vacuo and the residue was partitioned between ether and water. The ether layer was taken, dried with anhydrous magnesium sulfate, filtered, evaporated in vacuo and the residue was purified by silica gel column chromatography (eluent, ether:hexane (1:1)) to afford 18.3 g (51%) of 3-(cyanomethyl)-5-methylbenzonitrile as a pale yellow solid. m.p. 63-64° C. $^1$H NMR (300 MHz, CDCl$_3$) δ 2.42 (3H, s), 3.77 (2H; s), 7.42 (2H, s), 7.45 (1H, s).

3-((2,6-bis(benzyloxy)-5-isopropylpyrimidin-4-yl)(cyano)methyl)-5-methylbenzonitrile 2,4-bis(benzyloxy)-6-chloro-5-isopropylpyrimidine (45.4 g, 0.123M) and 3-(cyanomethyl)-5-methylbenzonitrile (18.3 g, 0.117M) were dissolved in anhydrous DMF (200 mL). After cooling the mixture in an ice bath under nitrogen atmosphere, 60% sodium hydride (9.38 g, 0.235M) was added portionwise (addition time ca. 1.5 hr.). The mixture was stirred for further 1 hr. in an ice bath and stirred for ca. 20 hr. at room temperature. The reaction mixture was then cooled in an ice bath and sat. aqueous ammonium chloride solution was added thoroughly. The crude product was extracted with ether, washed with water twice, dried with magnesium sulfate, filtered, and evaporated in vacuo to give a light brown syrup, which was purified by silica gel column chromatography (eluent, EA:hexane (1:9)) to afford 53.46 g (94%) of 3-((2,6-bis(benzyloxy)-5-isopropylpyrimidin-4-yl)(cyano)methyl)-5-methylbenzonitrile as a light brown syrup. $\lambda_{max}$ (film) 2236 (nitrile) cm$^{-1}$, $^1$H NMR (200 MHz, CDCl$_3$) δ 1.10 (3H, d, J=6.9 Hz), 1.12 (3H, d, J=6.9 Hz), 2.36 (3H, s), 2.96 (1H, m), 5.37 (1H, s), 5.44 (4H, s), 7.32-7.55 (13H, m).

3-(2,6-bis(benzyloxy)-5-isopropylpyrimidine-4-carbonyl)-5-methylbenzonitrile To a stirred solution of 3-((2,6-bis(benzyloxy)-5-isopropylpyrimidin-4-yl)(cyano)methyl)-5-methylbenzonitrile (53.46 g, 0.0195M) in anhydrous DMF (400 mL) in a water bath under nitrogen atmosphere, was added 60% sodium hydride (4.87 g, 0.1205M) portionwise. After 30 min., oxygen gas was bubbled into the reaction mixture using oxygen balloon. After 3 hr., sat. aqueous ammonium chloride solution was added and the product was extracted with ether. Ether layer was washed with water twice, dried with anhydrous magnesium sulfate, filtered, and evaporated in vacuo to give a crude product as a light yellow solid. The crude product was purified by silica gel column chromatography (eluent, EA:hexane (1:9)) to afford 45.7 g (88%) of 3-(2,6-bis(benzyloxy)-5-isopropylpyrimidine-4-carbonyl)-5-methylbenzonitrile as a light yellow solid. m.p. 129-130° C. $^1$H NMR (300 MHz, CDCl$_3$) δ 1.20 (3H, d, J=7.0 Hz), 1.22 (3H, d, J=7.0 Hz), 2.43 (3H, s), 2.84 (1H, m), 5.34 (2H, s), 5.51 (2H, s), 7.29-7.46 (10H, m), 7.66 (1H, s), 7.83 (1H, s), 7.90 (1H, s).
Compound 32
3-(2,6-bis(benzyloxy)-5-isopropylpyrimidine-4-carbonyl)-5-methylbenzonitrile (22 g, 46 mmol), anhydrous ethanol (150 ml), 10 drops of glacial acetic acid, and 10% palladium on carbon (3 g) was placed into a 500 mL bottle. The mixture was then hydrogenated using Parr Hydrogenator under hydrogen atmosphere (20 psi) for ca. 1 hr. The mixture was then filtered through celite pad and the pad was washed with chloroform and ethanol. The combined filtrate was evaporated in vacuo to give a crude product as a yellow solid.

The crude product was filtered through short silica gel column (eluent, methanol:chloroform (1:5)) to give a product contaminated with side product (more polar than product). To get rid of the side product, the mixture was dissolved in methanol (225 mL) and ethanol (200 mL). The solution was then concentrated as much as possible and the precipitate was filtered, washed with ethanol, and dried in high vacuo to afford a pure product. After repeating this process 3 times, 10.5 g (76.6%) of compound was obtained as a white solid. m.p. 262-263° C., $\lambda_{max}$ (film) 2236 (nitrile, weak) cm$^{-1}$. $^1$H NMR (200 MHz, CD$_3$ODCDCl$_3$). 1.16 (6H, d, J=6.9 Hz), 2.41 (1H, m), 2.52 (3H, s), 7.79 (1H, s), 7.94 (1H, s), 8.04 (1H, s). $^{13}$C NMR (50 MHz, DMSO-d$_6$) δ 20.11, 20.28, 27.35, 112.50; 114.11, 117.78, 130.92, 133.87, 135.13, 138.65, 140.95, 144.00, 150.44, 163.61, 189.47. m/z (EI) 308 (M$^+$).

Preparation of Compound 181

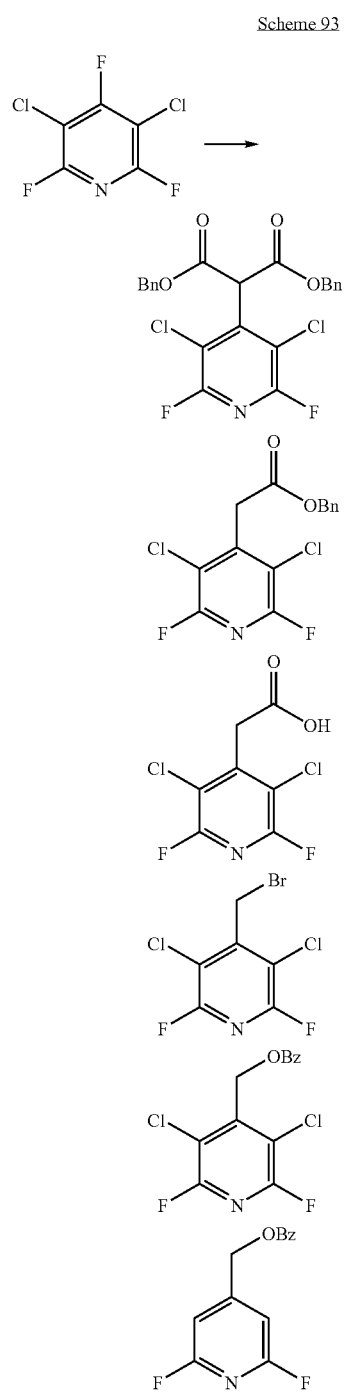

Scheme 93

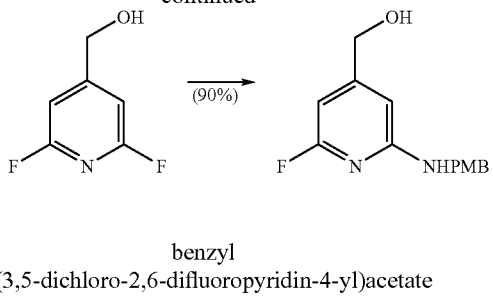

benzyl 2-(3,5-dichloro-2,6-difluoropyridin-4-yl)acetate 3,5-dichloro-2,4,6-trifluoropyridine (25 g, 15.4 mL, 123.7 mmol) and dibenzyl malonate (35.8 g, 31.5 mL, 126 mmol, Aldrich) were dissolved in anhydrous DMF (240 mL) under nitrogen atmosphere. The mixture was then cooled in an ice bath. To a stirred mixture, was added 60% sodium hydride (10 g, 250 mmol) portionwise (2 g) for 2 hr. The mixture was then stirred in a water bath for ca. 17 hr. Glacial acetic acid was added and the mixture was partitioned between ether and water. Ether layer was taken, washed with water twice, dried with anhydrous magnesium sulfate, filtered, and dried in vacuo to give 62 g of dibenzyl 2-(3,5-dichloro-2,6-difluoropyridin-4-yl)malonate as a yellow oil. dibenzyl 2-(3,5-dichloro-2,6-difluoropyridin-4-yl)malonate (62 g) was then dissolved in dimethyl sulfoxide (DMSO) (120 mL) and stirred with water (10 mL) in an oil bath (130-140° C.) for 3 hr. After cooling to room temperature, water was added to the mixture and the product was extracted with ether (Sometimes addition of EA is necessary to dissolve product completely). The ether layer was washed with water twice, dried with anhydrous magnesium sulfate, filtered, and evaporated in vacuo to give a light yellow solid. The crude product was recrystallized from MC/Hexane three times to afford 30.9 g (75% for two steps) of benzyl 2-(3,5-dichloro-2,6-difluoropyridin-4-yl)acetate as a white solid. m.p. 98-101° C. $^1$H NMR (200 MHz, CDCl$_3$) δ 4.11 (2H, s), 5.19 (2H, s), 7.30-7.38 (5H, m).

2-(3,5-dichloro-2,6-difluoropyridin-4-yl)acetic acid

Benzyl 2-(3,5-dichloro-2,6-difluoropyridin-4-yl)acetate (30.9 g, 93 mmol), anhydrous ethanol, and 10% palladium on carbon were placed into a 500 mL bottle. The mixture was then hydrogenated using Parr Hydrogenator under hydrogen atmosphere (20 psi) for 30 min. The reaction mixture was then filtered through celite pad and the pad was washed with ethanol. The filtrate was evaporated in vacuo and the residue was recrystallized from MC to afford 21 g (89%) of 2-(3,5-dichloro-2,6-difluoropyridin-4-yl)acetic acid as a white solid. m.p. 157-159° C. $^1$H NMR (200 MHz, CDCl$_3$) δ 4.13 (2H, s).

4-(bromomethyl)-3,5-dichloro-2,6-difluoropyridine

To a 1 L 3-neck flask equipped with addition funnel, was placed chlorobenzene (150 ml). 2-(3,5-dichloro-2,6-difluoropyridin-4-yl)acetic acid (21 g, 86.77 mmol) and mercury oxide (20 g, 92.34 mmol) were added in this order. The mixture was heated up to 140-150° C. in an oil bath. Bromine (5.4 mL, 105 mmol) in chlorobenzene (90 ml) was then added dropwise through the addition funnel for 2~2.5 hr. After the addition of bromine solution, the reaction mixture was refluxed for further 1 hr. and cooled to room temperature. The mixture was filtered through celite pad and the pad was washed with chlorobenzene. The combined filterate was evaporated in vacuo and the residue was purified by silica gel column chromatography (eluent, ether:hexane (1:10)) to give 20 g (80%) of 4-(bromomethyl)-3,5-dichloro-2,6-difluoropyridine as a colorless oil. ¹H NMR (300 MHz, CDCl₃) δ 4.66 (2H, s). m/z (EI) 277 (M⁺).

(3,5-dichloro-2,6-difluoropyridin-4-yl)methyl benzoate

To a stirred DMF (90 ml) in an ice bath, 4-(bromomethyl)-3,5-dichloro-2,6-difluoropyridine (20 g, 72 mmol) and sodium benzoate (15 g, 104 mmol) were added. After 1 hr., the mixture was stirred in a water bath for ca. 20 hr. The product was then extracted with ether, washed with water twice, dried with anhydrous magnesium sulfate, filtered, and evaporated in vacuo to give a light brown oil. The light brown oil was purified by silica gel column chromatography (eluent, ether:hexane (1:15) to afford 18.6 g (81%) of (3,5-dichloro-2,6-difluoropyridin-4-yl)methyl benzoate as a colorless oil. ¹H NMR (200 MHz, CDCl₃) δ 5.61 (2H, s), 7.40-7.64 (3H, m), 8.00-8.05 (2H, m).

(2,6-difluoropyridin-4-yl)methyl benzoate (3,5-dichloro-2,6-difluoropyridin-4-yl)methyl benzoate (19.6 g, 61.6 mmol), anhydrous ethanol (150 ml), and 10% palladium on carbon (3 g) were placed into a 500 mL bottle. The mixture was hydrogenated under hydrogen atmosphere (50 psi) for 1.5 hr. The reaction mixture was filtered through celite pad and the pad was washed with ethanol. The combined filtrate was evaporated in vacuo and the residue was purified by silica gel column chromatography (eluent, ether:hexane (1:4)) to afford 9.15 g (61%) of (2,6-difluoropyridin-4-yl)methyl benzoate as a white solid. m.p. 83-84° C. ¹H NMR (200 MHz, CDCl₃) δ 5.42 (2H, s), 6.87 (2H, s), 7.45-7.67 (3H, m), 8.08-8.13 (2H, m).

(2,6-difluoropyridin-4-yl)methanol

To a stirred solution of (2,6-difluoropyridin-4-yl)methyl benzoate (10.29 g, 41.325 mmol) in anhydrous methanol (80 mL) at room temperature, was added sodium methoxide (2.23 g, 41.325 mmol). After stirring for 20 min., excess ammonium chloride was added to the reaction mixture and stirring was continued for 30 min. The mixture was then evaporated in vacuo and the residue was dissolved in methanol-MC (1:9), filtered, and the filtrate was evaporated in vacuo to give a crude product. The crude product was purified by silica gel column chromatography (eluent, EA:hexane (1:2 to 2:1)) to afford 5.9 g (98%) of (2,6-difluoropyridin-4-yl)methanol as a white solid. m.p. 66-67° C. ¹H NMR (200 MHz, CDCl₃) δ 2.19 (1H, t, J=5.8 Hz), 4.81 (2H, d, J=5.8 Hz), 6.84 (2H, s).

Compound 181

To a 100 mL round bottomed flask, were placed (2,6-difluoropyridin-4-yl)methanol (4.08 g, 28 mmol) and p-methoxybenzyl amine (7.35 mL, 56 mmol). Nitrogen balloon was attached to the flask and the mixture was stirred in an oil bath (117~130° C.) for 2 hr. After cooling to room temperature, the mixture was filtered through silica gel column (eluent, MC:methanol (5:95)) to give a crude product, which was then purified further by silica gel column chromatography (eluent, ether:hexane (3:2 to 3:1)) to afford 6.66 g (90%) of compound 181 as a white solid. m.p. 98-99° C. ¹H NMR (300 MHz, CDCl₃) δ 1.78 (1H, t, J=5.7 Hz), 3.80 (3H, s), 4.40 (2H, d, J=5.7 Hz), 4.61 (2H, d, J=5.7 Hz), 4.85 (1H, br. s), 6.14 (1H, s), 6.21 (1H, s), 6.84-6.89 (2H, m), 7.23-7.27 (2H, m). ¹³C NMR (50 MHz, DMSO-d₆) δ 43.67, 55.01, 61.67 (d, J=3.4 Hz), 90.85 (d, 37.5 Hz), 101.17, 113.69, 128.46, 131.84, 157.80 (d, J=8.3 Hz), 158.17, 158.18 (d, J=17.8 Hz), 163.09 (d, J=229.5 Hz). m/z (EI) 262 (M⁺).

Examples DD, DE, DF, DG, DH, and DI

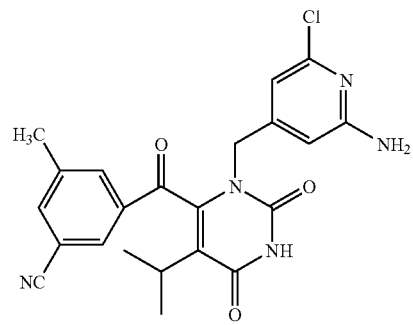

DD

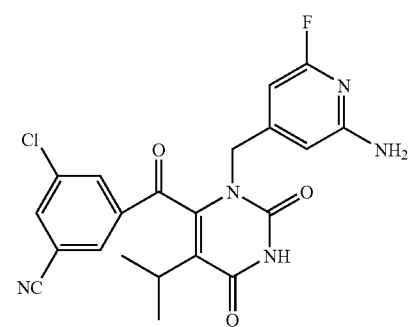

DE

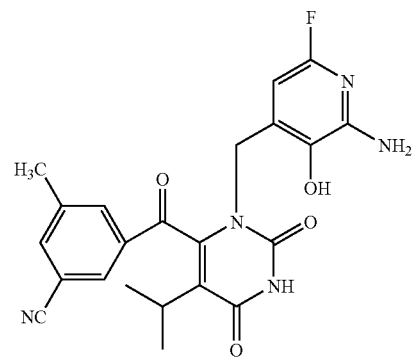

DF

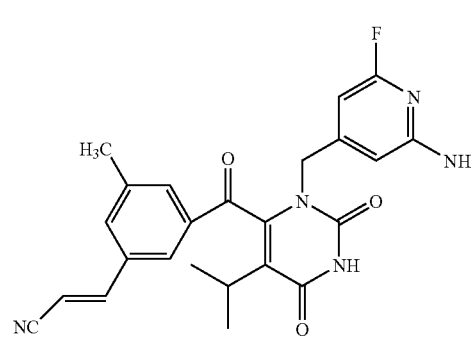

DG

DH

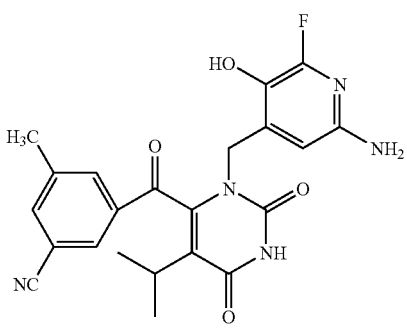

DI

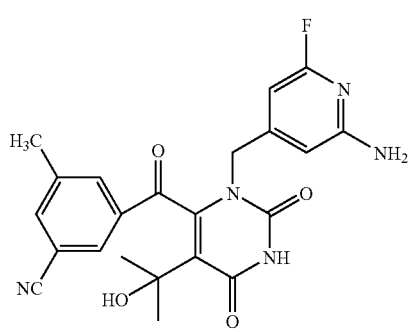

Examples DD, DE, DF, DG, DH, and DI can be prepared using procedures similar to those used to prepare Example DC. For example, compound DD can be prepared by reacting compound 32 with a protected (2-amino-6-chloropyridin-4-yl)methanol, rather than with compound 44; compound DE can be prepared by reacting compound 44 with 3-chloro-5-(5-isopropyl-2,6-dioxo-1,2,3,6-tetrahydropyrimidine-4-carbonyl)benzonitrile (e.g., prepared as in Scheme 2 using 3-chloro-5-(cyanomethyl)benzonitrile rather than compound 12) rather than compound 32; Examples DF and DH can be prepared by reacting compound 32 with a protected 2-amino-6-fluoro-4-(hydroxymethyl)pyridin-3-ol or 6-amino-2-fluoro-4-(hydroxymethyl) pyridin-3-ol, respectively, rather than with compound 44; Example DG can be prepared by reacting compound 44 with 3-(3-chloro-5-(5-isopropyl-2,6-dioxo-1,2,3,6-tetrahydropyrimidine-4-carbonyl)phenyl) acrylonitrile (e.g., prepared in Scheme 2 using 3-(3-chloro-5-(cyanomethyl)phenyl)acrylonitrile rather than 3-(cyanomethyl)-5-methylbenzonitrile) rather than compound 32; and compound DI can be prepared by oxidation of Example DC, including but not limited to, by incubation of Example DC with S9 human microsomal fraction.

Biological Assay

The compounds of the present invention are tested for the antiviral activity by utilizing MT-2 cells, 50 µl of 2× test concentration of 5-fold serially diluted compound in culture medium with 10% FBS was added to each well of a 96-well plate (9 concentrations) in triplicate. MT-2 cells were infected with HIV-IIIb at a multiplicity of infection (m.o.i) of 0.01 for 3 hours. Fifty microliters of infected cell suspension in culture medium with 10% FBS (~1.5×10$^4$ cells) was then added to each well containing 50 µl of diluted compound. The plates were then incubated at 37° C. for 5 days. For the antiviral assay utilizing MT-4 cells, 20 µl of 2× test concentration of 5-fold serially diluted compound in culture medium with 10% FBS was added to each well of a 384-well plate (7 concentrations) in triplicate. MT-4 cells were next mixed with HIV-IIIb at an m.o.i. of 0.1 and 20 µl of virus/cell mixture (~2000 cells) was immediately added to each well containing 20 µl of diluted compound. The plates were then incubated at 37° C. for 5 days. After 5 days of incubation, 100 µl of CellTiter-Glo™ Reagent (catalog #G7571, Promega Biosciences, Inc., Madison, Wis.) was added to each well containing MT-2 cells and 40 µl to each well containing MT-4 cells. Cell lysis was carried out by incubation at room temperature for 10 min and chemiluminescence was read.

For compound cytotoxicity assessment in MT-2 cells, the protocol was identical to that of the antiviral assay in MT-2 cells, except that uninfected cells and a 3-fold serial dilution of compounds were used. For cytotoxicity assessment in MT-4 cells, the protocol is identical to that of the antiviral assay in MT-2 cells, except that no virus was added.

The compounds of the present invention have shown antiviral EC50 values (nM) in the range of about 0.1 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

What is claimed:

1. A compound of Formula (I) or (II):

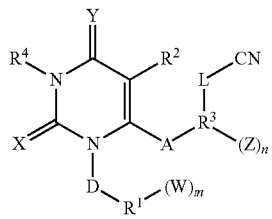

(I)

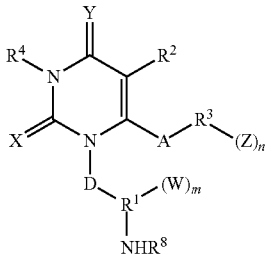

(II)

or a pharmaceutically acceptable salt thereof, wherein:
X and Y are independently O;
A is —O—, —S—, NR$^5$ or —C(R$^6$)$_2$—;
D is alkylene or substituted alkylene;
L is a covalent bond, alkylene, substituted alkylene, alkenylene, or substituted alkenylene;
R$^1$ is pyridyl or substituted pyridyl;
R$^2$ is H, halogen, nitro, alkyl, substituted alkyl, alkoxyalkyl, alkenyl, substituted alkenyl, alkynyl, substituted alkynyl, amino, alkylamino, dialkylamino, cycloalkyl, or substituted cycloalkyl;
R$^3$ is phenyl;
R$^4$ is H, alkyl, substituted alkyl, cycloalkyl, substituted cycloalkyl, arylalkyl, or substituted arylalkyl;
R$^8$ is H, —C(O)—O-alkyl, —C(O)—O-(substituted alkyl), —C(O)-alkyl-, or C(O)-(substituted alkyl);
R$^5$ is H, alkyl, substituted alkyl, arylalkyl, substituted arylalkyl, acyl, or substituted acyl;
each R$^6$ is independently H, alkyl, hydroxy, alkoxy, cyano, or halo; or each $R^6$, together with the carbon atom to which they are shown attached, form a —C(O)—, —C(S)—, —C(NR$^7$)—, or cycloalkyl;

$R^7$ is H, alkyl, substituted alkyl, hydroxy, or alkoxy;

each W and Z is independently selected from the group consisting of halo, nitro, hydroxy, amino, substituted amino, -amino-C(O)-alkylene-amino, sulfonamido, acetamido, trifluoroacetamido, azido, cyano, formyl, carbamoyl, alkyl, substituted alkyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, or oxide; and n and m are independently integers of from 0 to 4;

wherein a substituent of each substituted alkylene, substituted alkenylene, substituted alkyl, substituted alkenyl, substituted alkynyl, substituted cycloalkyl, substituted arylalkyl, substituted acyl, substituted heterocyclyl, substituted amino, substituted alkoxy, substituted cycloalkenyl, or substituted aryl is independently selected from the group consisting of —X, —R, —O—, =O, —OR, —SR, —S—, —NR$_2$, —N$^+$R$_3$, —CX$_3$, —CN, —OCN, —SCN, —NCS, —NO, —NO$_2$, =N$_2$, —N$_3$, —NHC(=O)R, —C(=O)R, —C(=O)NRR, —S(=O)$_2$O—, —S(=O)$_2$OH, —S(=O)$_2$R, —OS(=O)$_2$OR, —S(=O)$_2$NR, —S(=O)R, —OP(=O)(OR)$_2$, —N(=O)(OR)$_2$, —N(=O)(O—)$_2$, —N(=O)(OH)$_2$, —N(O)(OR)(O—), —C(=O)R, —C(=O)X, —C(S)R, —C(O)OR, —C(O)O—, —C(S)OR, —C(O)SR, —C(S)SR, —C(O)NRR, —C(S)NRR, and —C(=NR)NRR;

X is —F, —Cl, —Br, or —I; and each R is independently H, alkyl, aryl, arylalkyl, or heterocyclyl.

2. The compound of claim 1, wherein A is —C(R$^6$)$_2$—.

3. The compound of claim 2, wherein A is —C(O)—.

4. The compound of claim 3, wherein R$^3$ is phenyl and each Z is independently selected from the group consisting of —CN, alkyl, substituted alkyl, halo, and substituted alkenyl.

5. The compound of claim 4, wherein R$^3$—(Z)$_n$ or R$^3$-(L-CN)—(Z)$_n$ have the following structures:

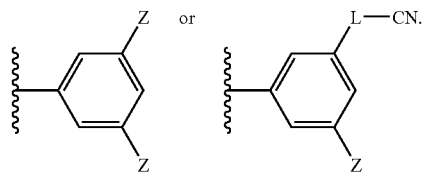

6. The compound of claim 5, wherein each Z is independently selected from the group consisting of —CN, —CH$_3$, —CH=CH—CN, —CH$_2$CH$_2$—CN, Cl, and Br.

7. The compound of claim 6, wherein R$^3$—(Z)$_n$ is selected from the group consisting of:

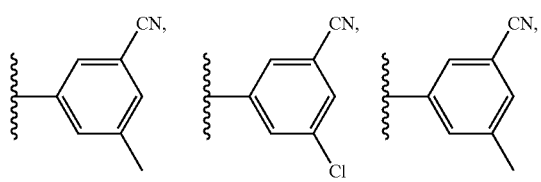

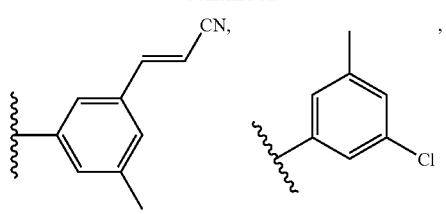

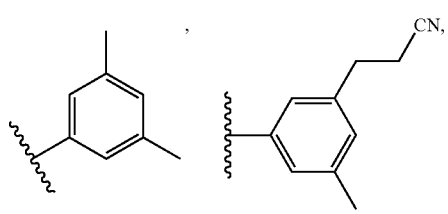

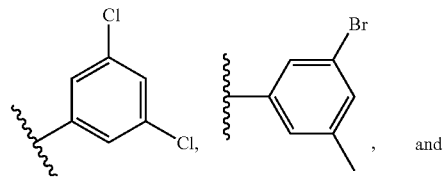

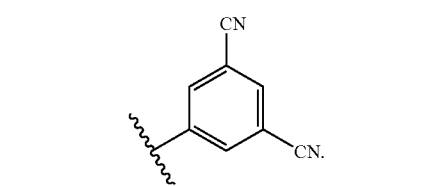

8. The compound of claim 1, wherein A is —O—.

9. The compound of claim 8, wherein R$^3$ is phenyl and each Z is independently selected from the group consisting of —CN, alkyl, substituted alkyl, halo, and substituted alkenyl.

10. The compound of claim 9, wherein R$^3$—(Z)$_n$ or R$^3$-(L-CN)—(Z)$_n$ have the following structures:

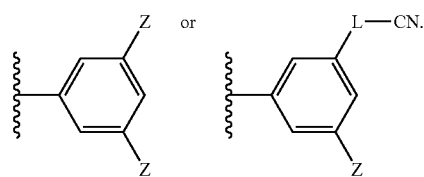

11. The compound of claim 10, wherein each Z is independently selected from the group consisting of —CN, —CH$_3$, —CH=CH—CN, —CH$_2$CH$_2$—CN, Cl, and Br.

12. The compound of claim 11, wherein R$^3$—(Z)$_n$ is selected from the group consisting of:

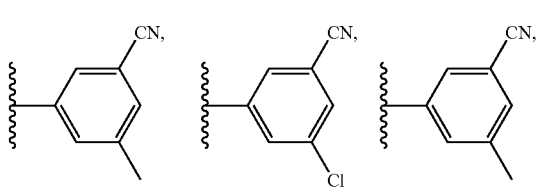

-continued

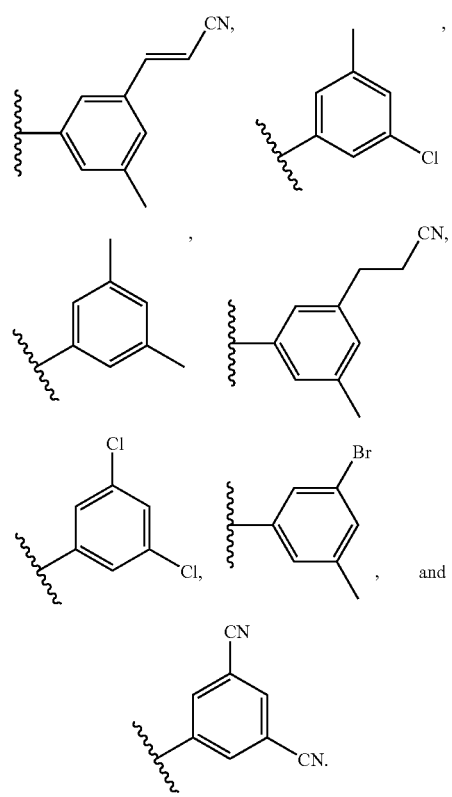

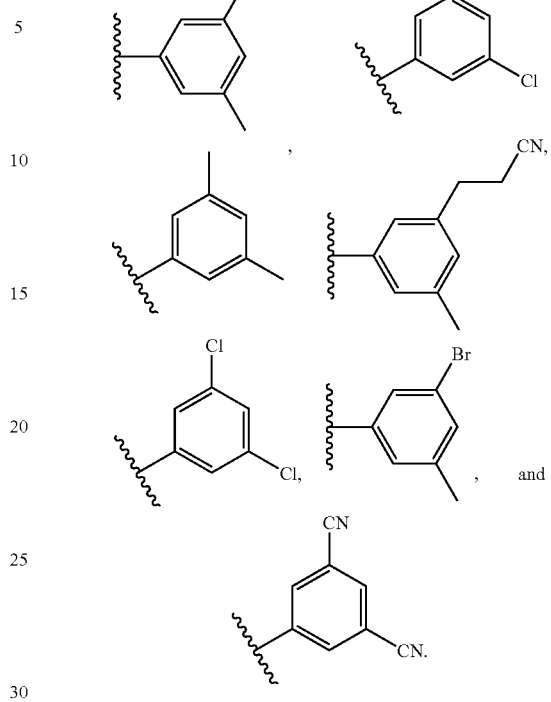

13. The compound of claim 1, wherein A is $NR^5$.

14. The compound of claim 13, wherein $R^3$ is phenyl, $R^5$ is H, and each Z is independently selected from the group consisting of —CN, alkyl, substituted alkyl, halo, and substituted alkenyl.

15. The compound of claim 14, wherein $R^3$—$(Z)_n$ or $R^3$-(L-CN)—$(Z)_n$ have the following structures:

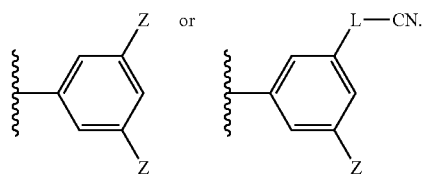

16. The compound of claim 15, wherein each Z is independently selected from the group consisting of —CN, —$CH_3$, —CH=CH—CN, —$CH_2CH_2$—CN, Cl, and Br.

17. The compound of claim 16, wherein $R^3$—$(Z)_n$ is selected from the group consisting of:

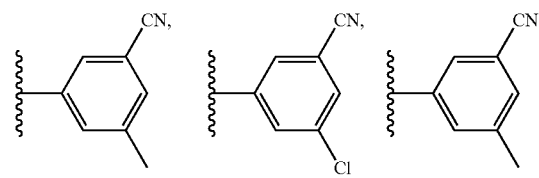

18. The compound of claim 1, wherein:
X and Y are both O;
A is —C(O)—; D is alkylene;
$R^1$ is pyridyl;
$R^2$ is alkyl; and
$R^3$ is phenyl.

19. The compound of claim 18, wherein:
D is —$CH_2$—;
$R^1$ is pyridyl;
$R^2$ is 2-propyl; and
$R^3$ is phenyl.

20. The compound of claim 19, wherein $R^1$ is 4-pyridyl.

21. The compound of claim 20, wherein each W is independently selected from the group consisting of halo, hydroxy, alkoxy, amino, substituted amino, -amino-C(O)-alkylene-amino, and sulfonamido.

22. The compound of claim 1, wherein $R^1$—$(W)_m$ is:

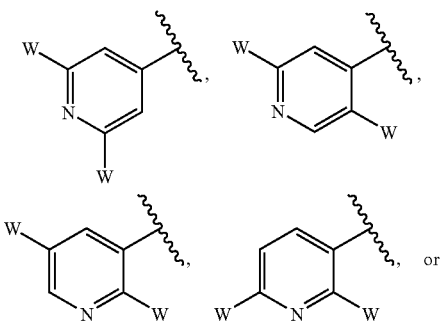

-continued

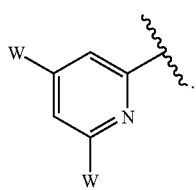

23. The compound of claim 22, wherein each W is independently selected from the group consisting of halo, hydroxy, alkoxy, amino, substituted amino, -amino-C(O)-alkylene-amino, and sulfonamido.

24. The compound of claim 23, wherein R¹—(W)$_m$ is selected from the group consisting of:

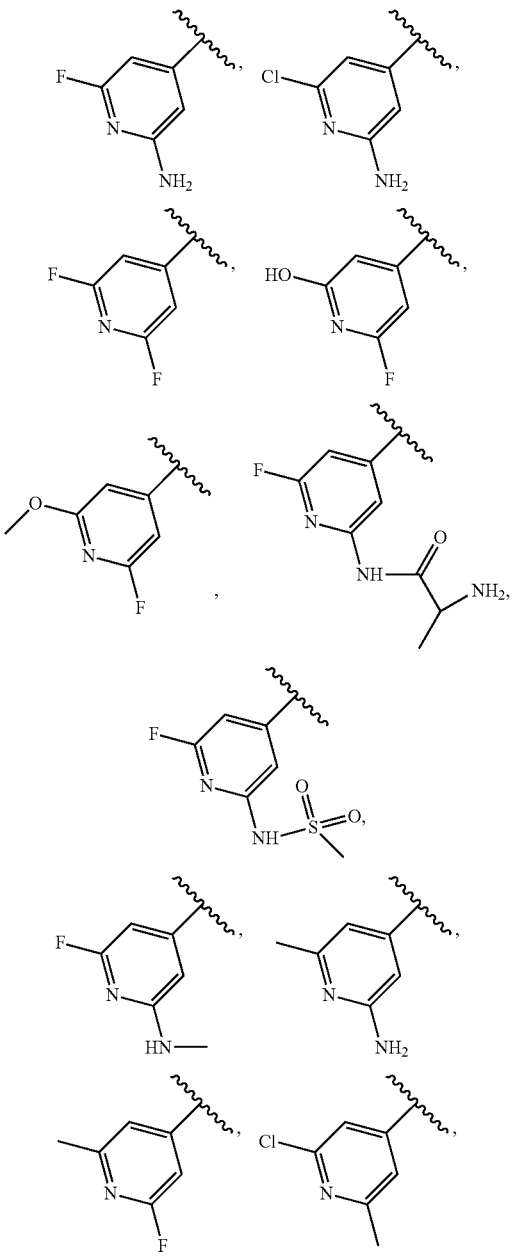

-continued

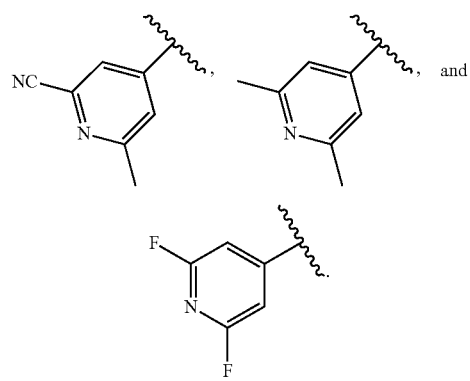

25. The compound of claim 1, wherein R¹—(W)$_m$ is:

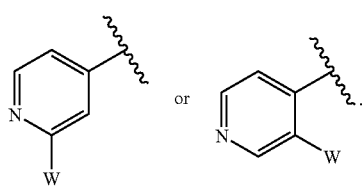

26. The compound of claim 25, wherein W is selected from the group consisting of halo, alkyl, cyano, —C(O)-amino, alkoxy, hydroxy, and amino.

27. The compound of claim 26, wherein R¹—(W)$_m$ is selected from the group consisting of:

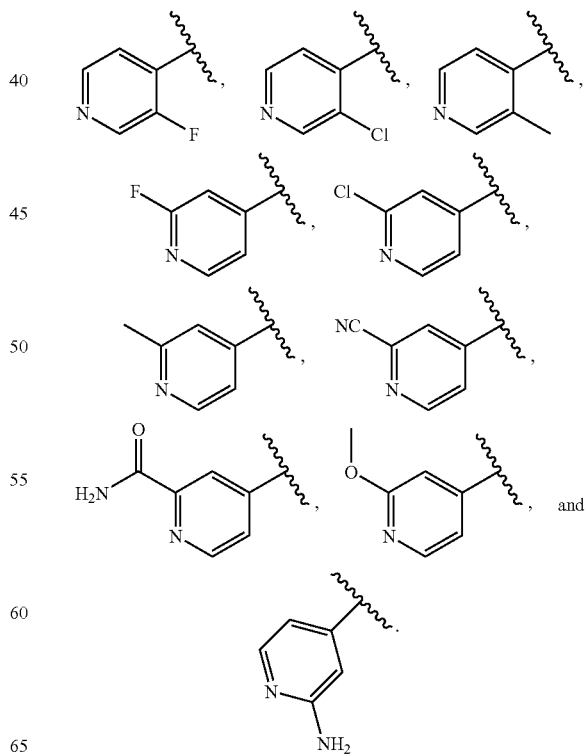

28. The compound of claim 1, wherein $R^1$—$(W)_m$ is:

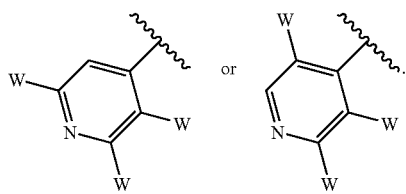

29. The compound of claim 28, wherein each W is independently selected from the group consisting of halo, hydroxy, alkoxy, amino, substituted amino, -amino-C(O)-alkylene-amino, and sulfonamido.

30. The compound of claim 1, wherein $R^2$ is alkyl, hydroxyalkyl, alkoxyalkyl, cycloalkyl, substituted cycloalkyl, halo, or amino.

31. The compound of claim 30, wherein $R^2$ is alkyl.

32. The compound of claim 1, wherein D is methylene.

33. The compound of claim 1, wherein $R^1$—$(W)_m$ is:

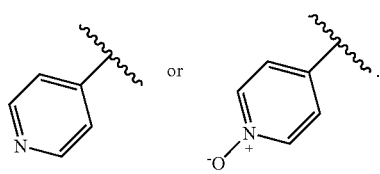

34. The compound of claim 1, selected from the group consisting of:

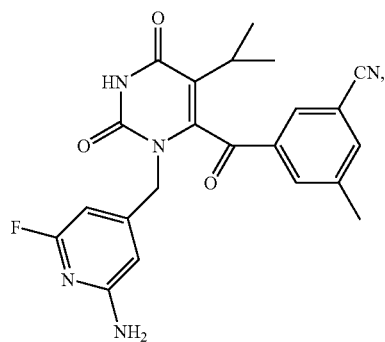

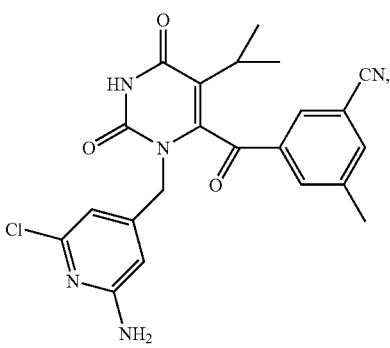

-continued

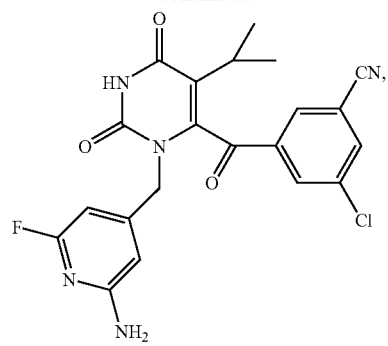

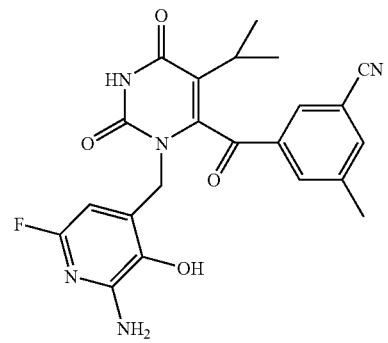

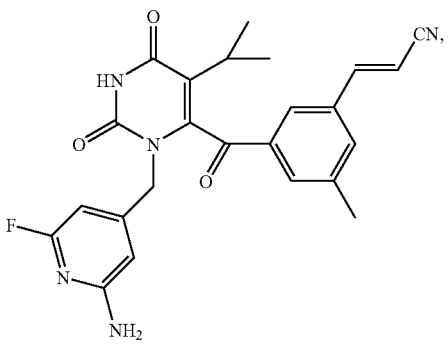

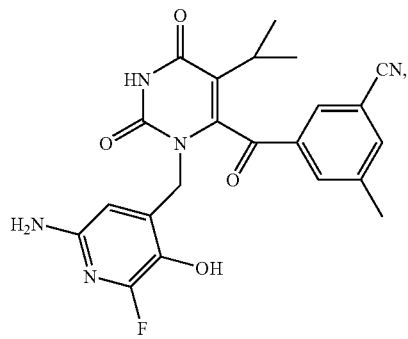

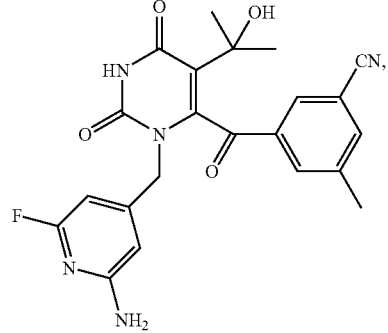

241
-continued
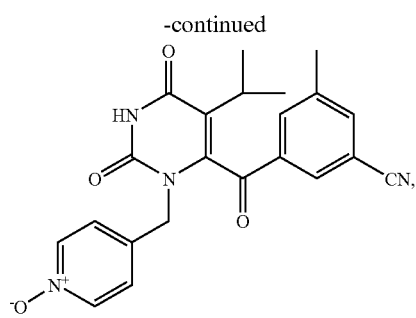
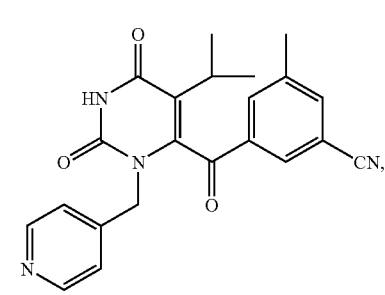
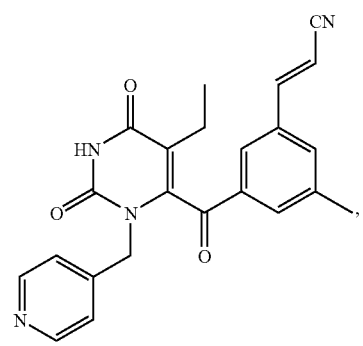
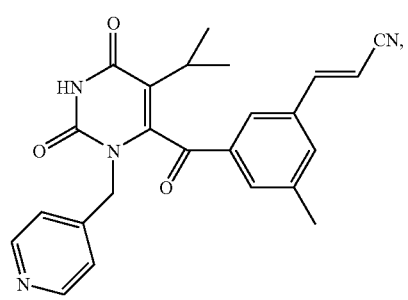
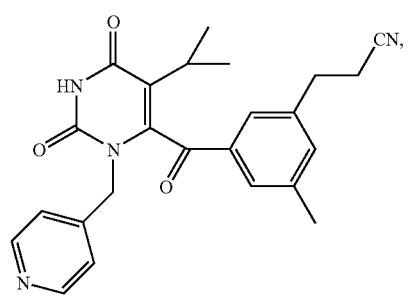
242
-continued
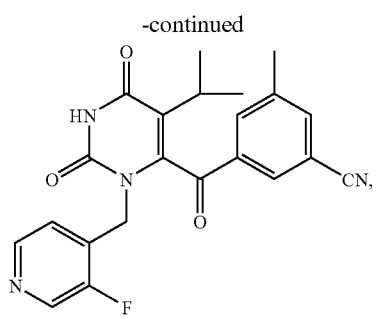
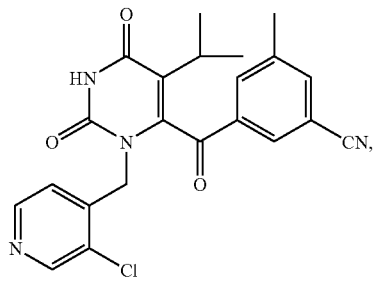
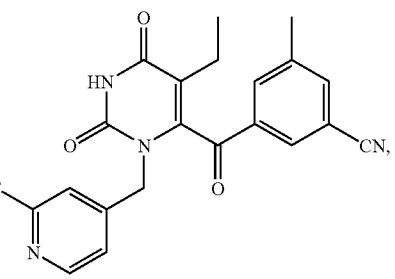
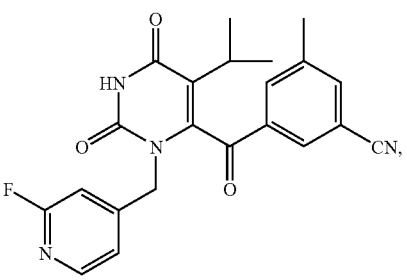
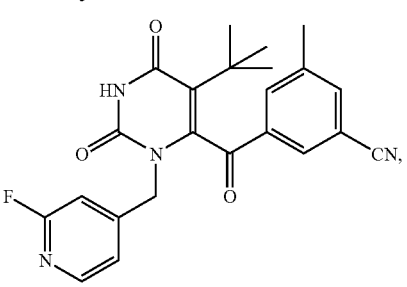

243
-continued
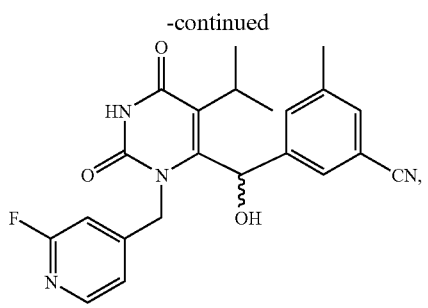
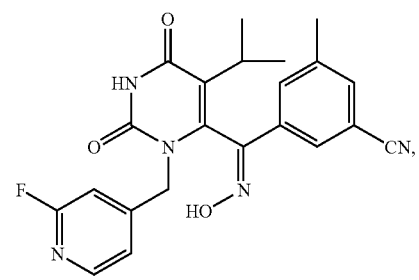
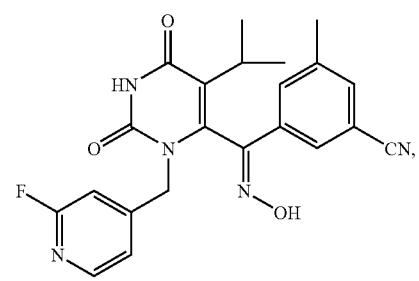
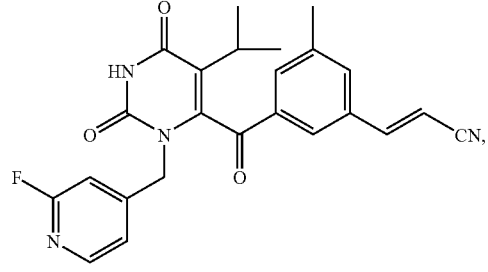
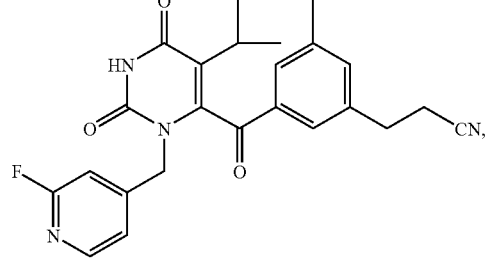
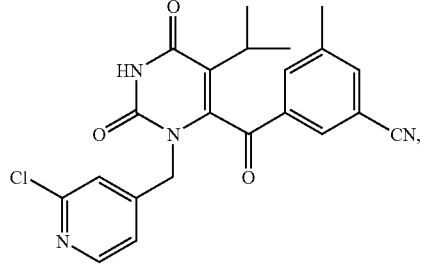
244
-continued
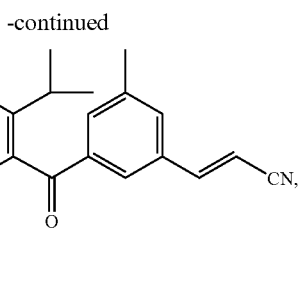
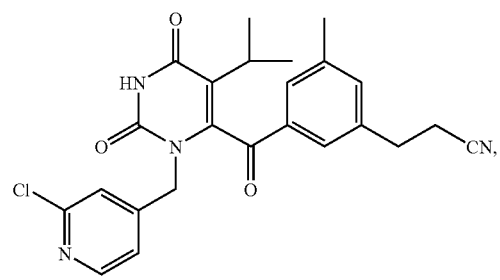
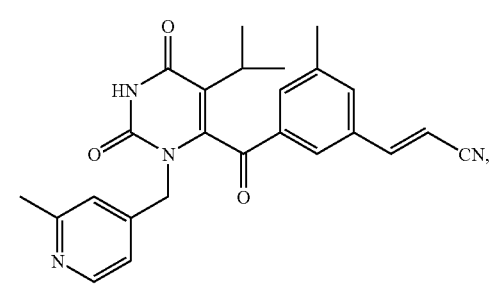
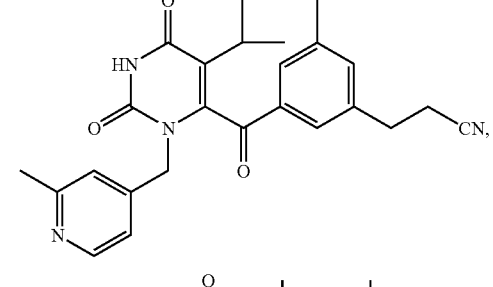
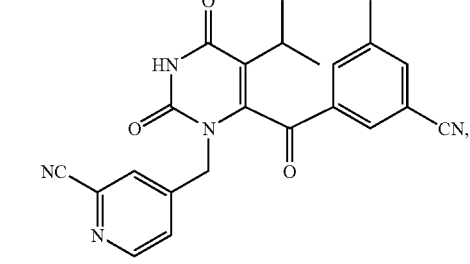
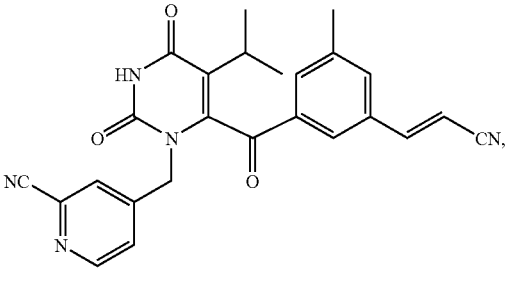

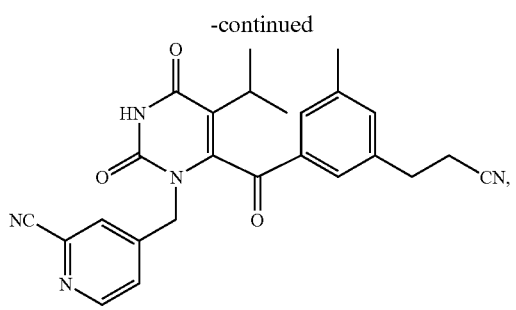
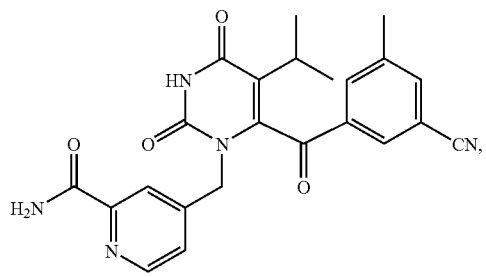
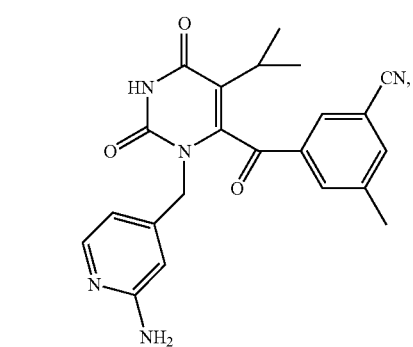
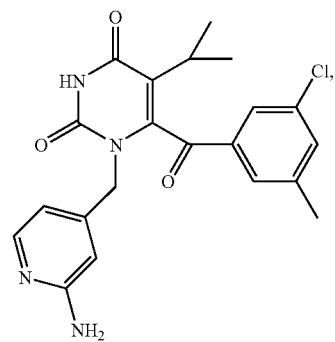
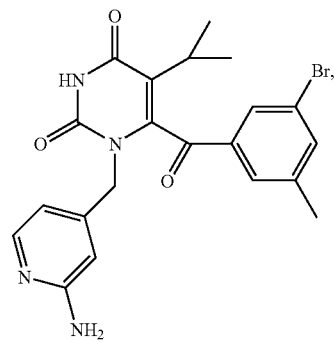
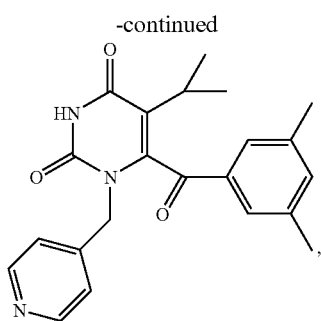
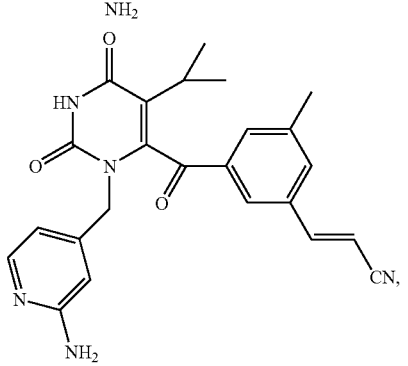
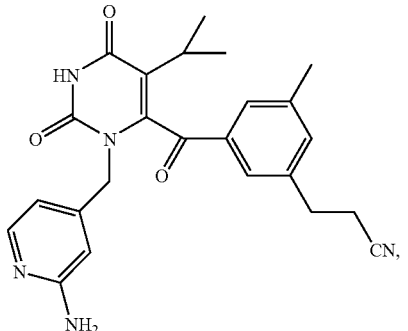
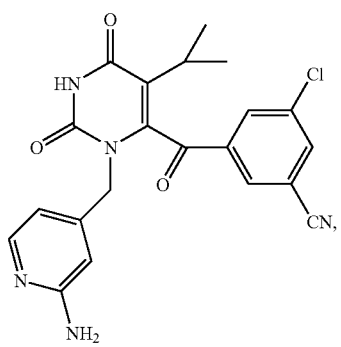
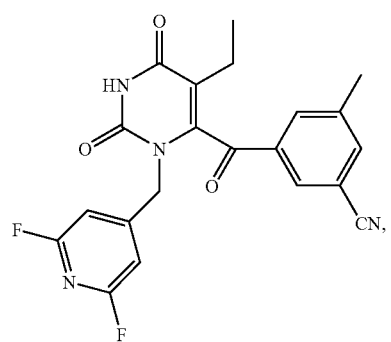

247
-continued
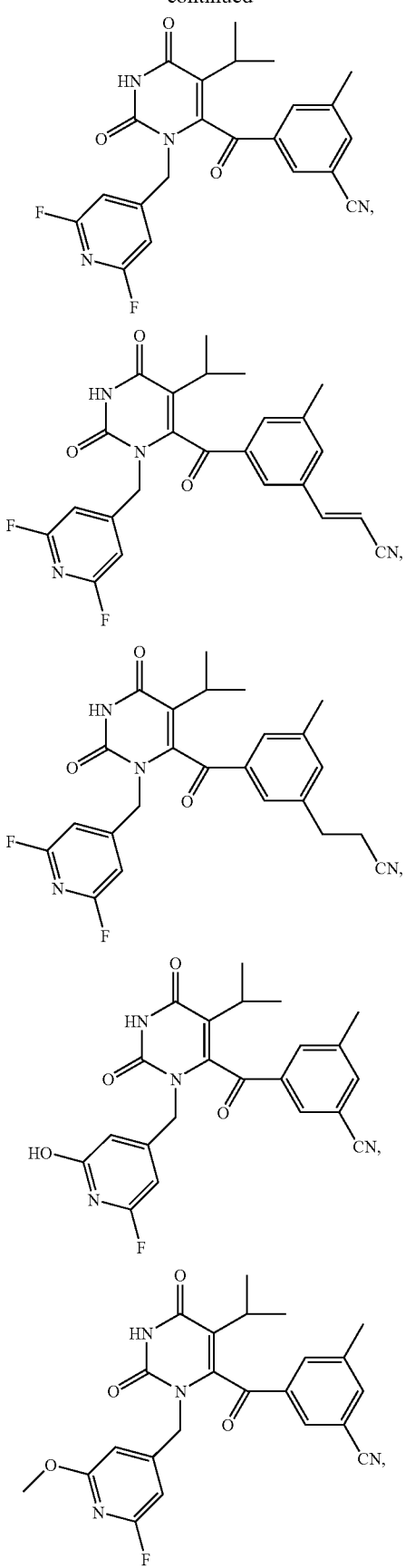
248
-continued
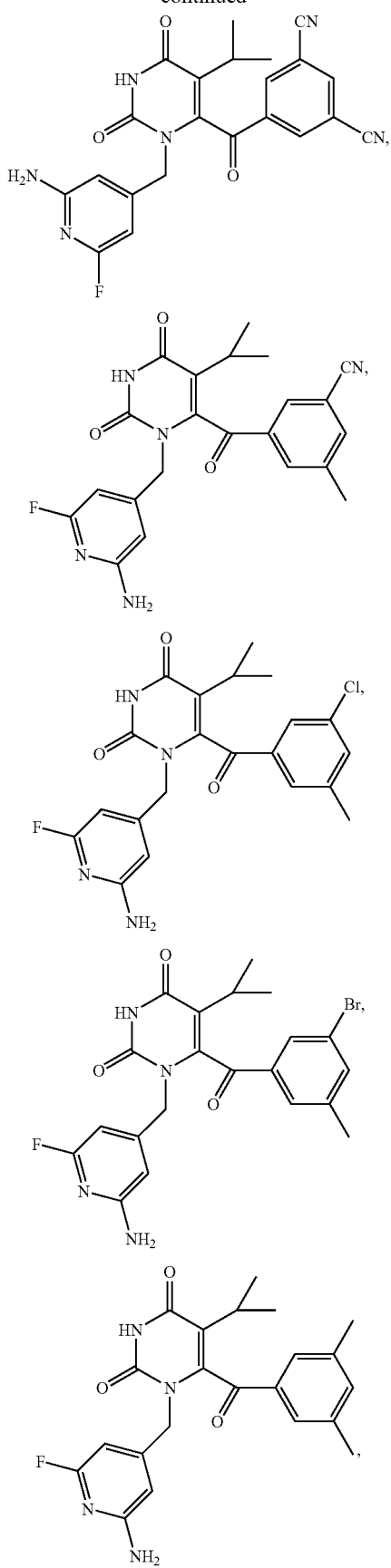

249
-continued
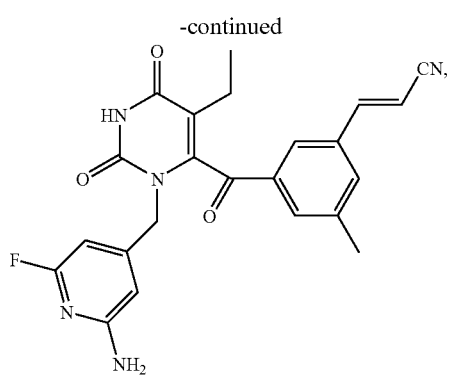
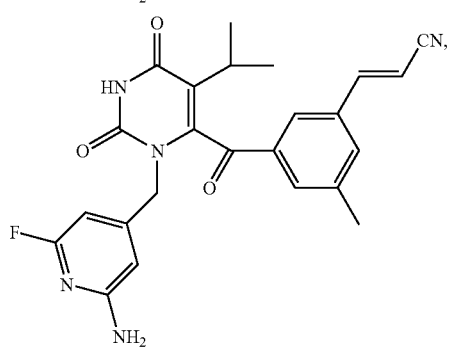
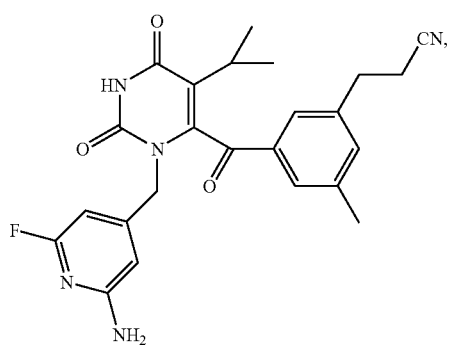
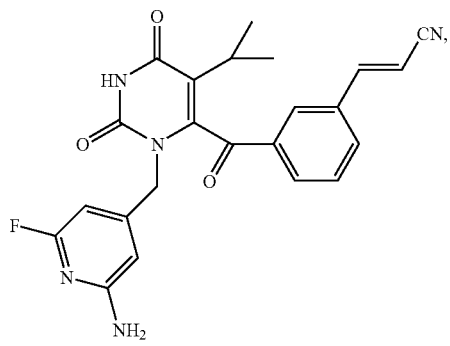
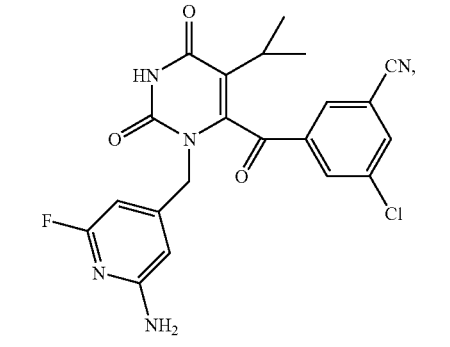
250
-continued
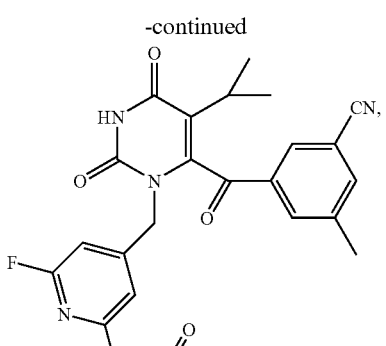
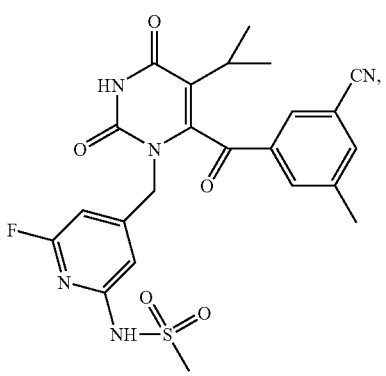
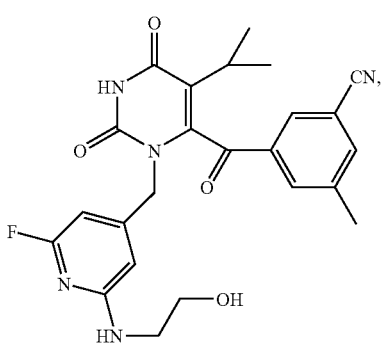
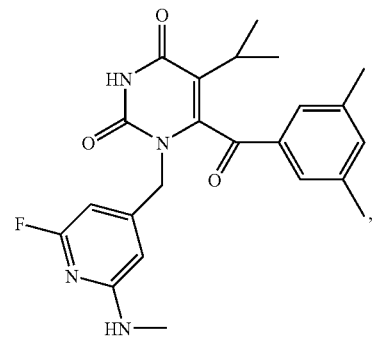

251
-continued
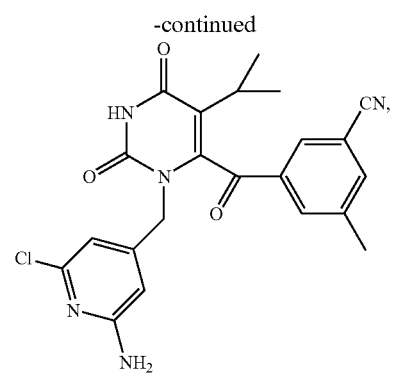
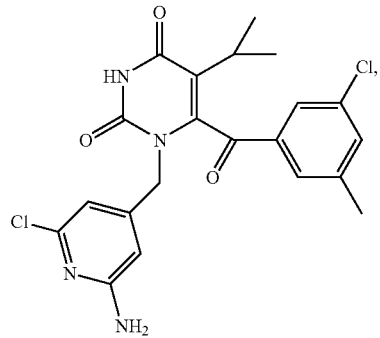
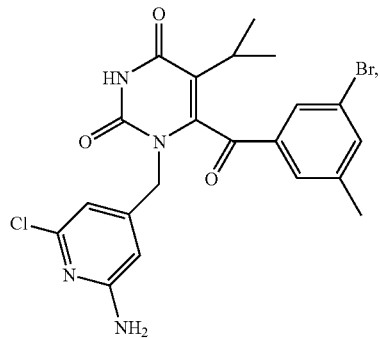
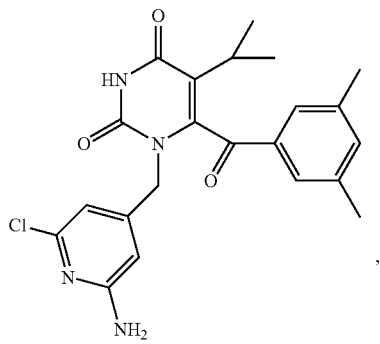
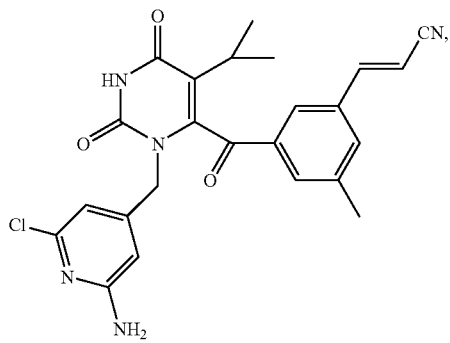
252
-continued
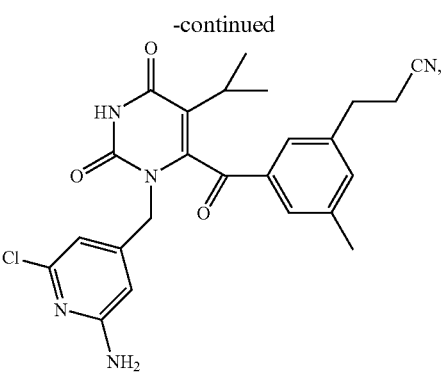
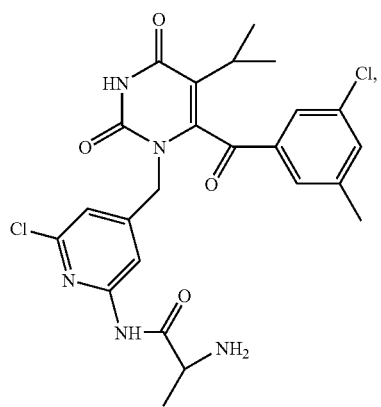
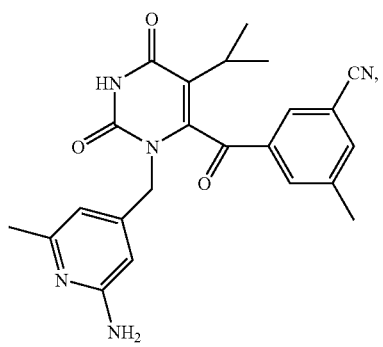
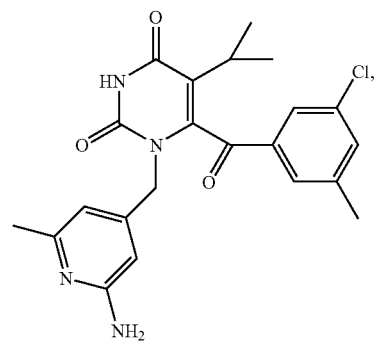

-continued
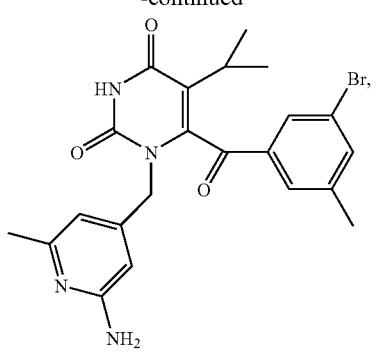
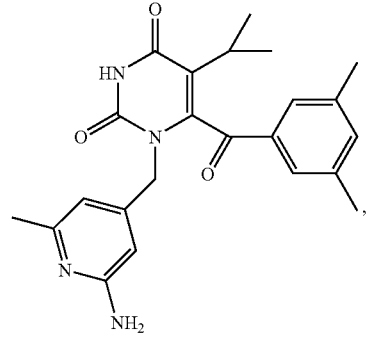
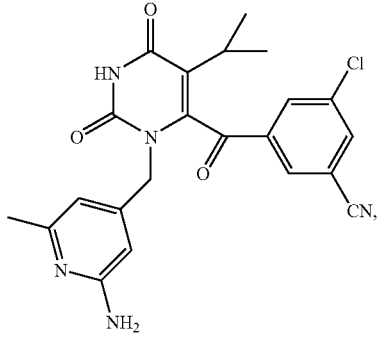
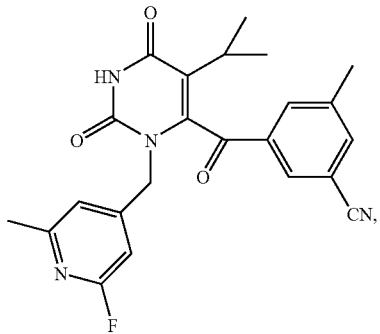
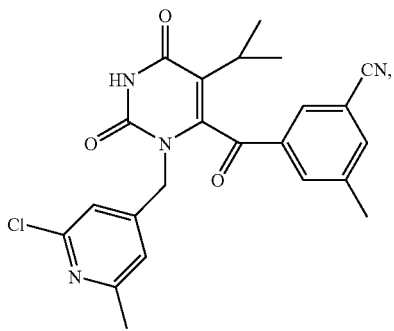
-continued
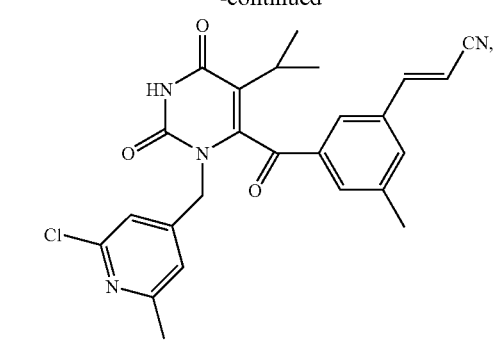
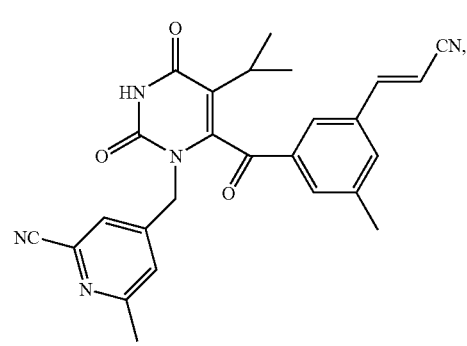
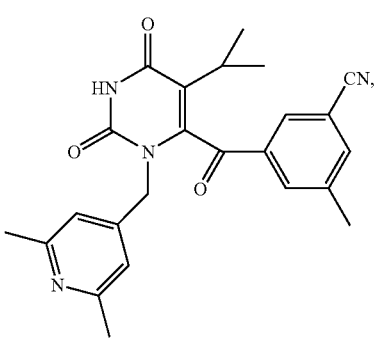
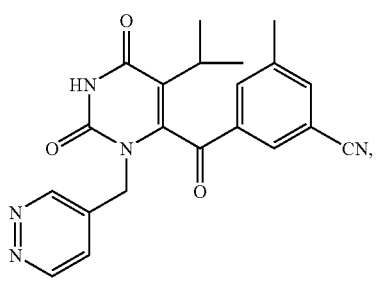
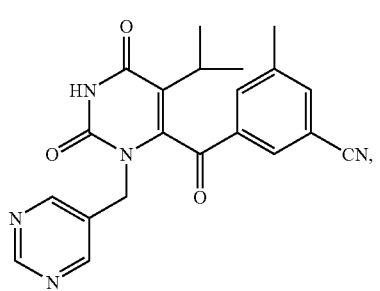

-continued
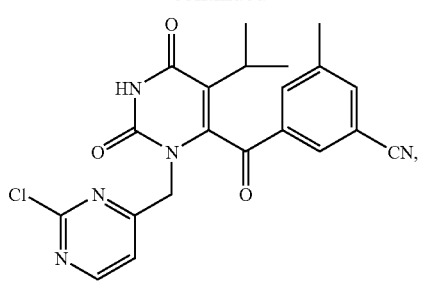
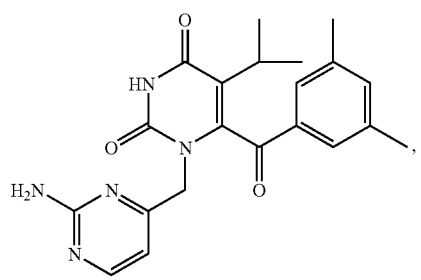
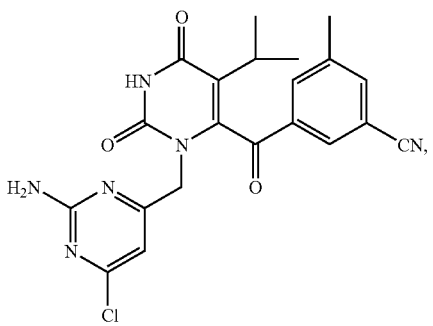
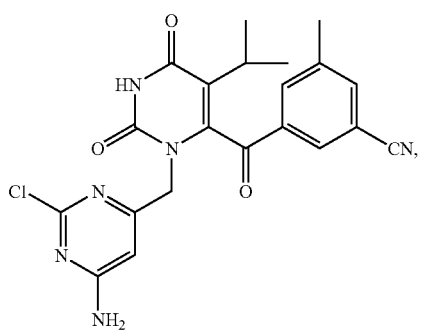
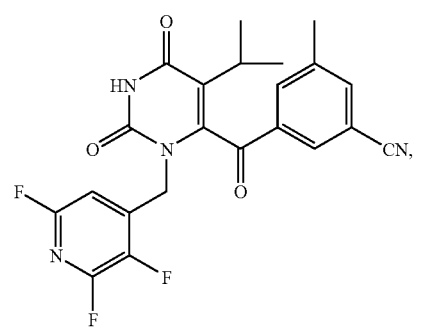
-continued
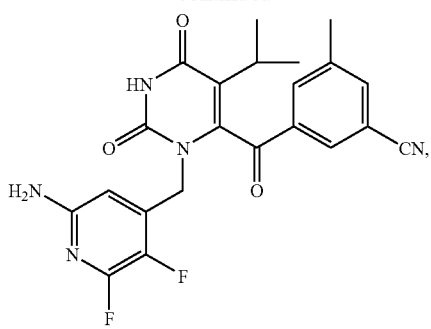
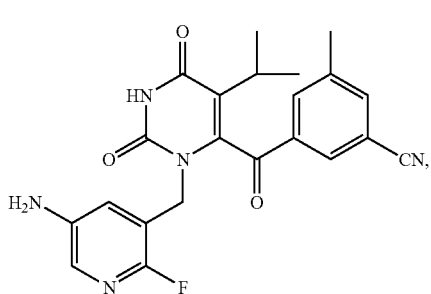
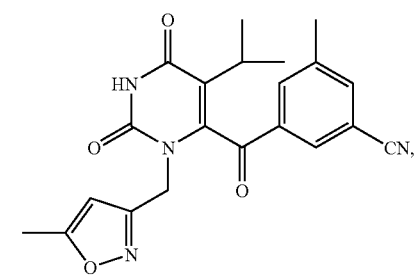
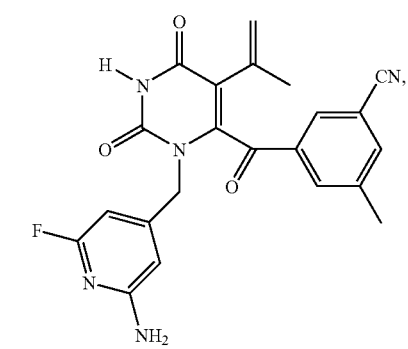
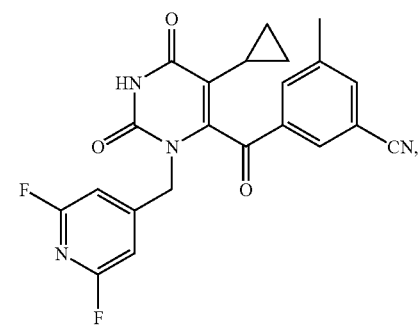

257
-continued
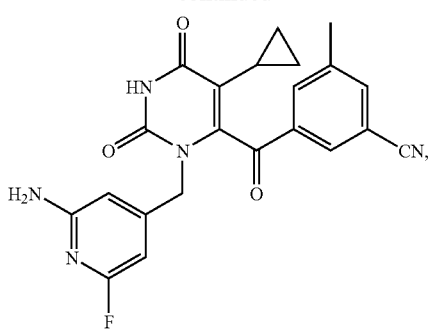
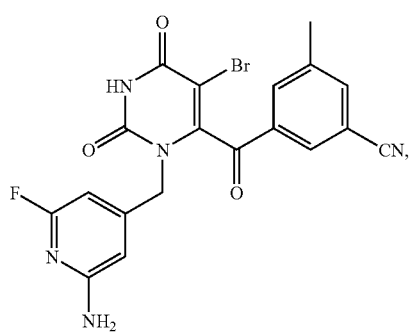
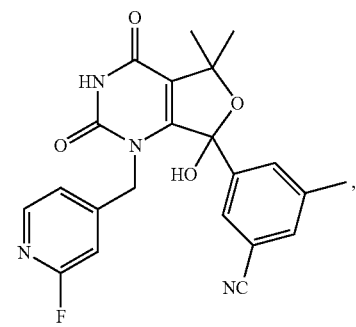
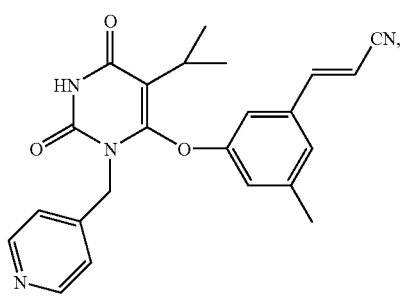
258
-continued
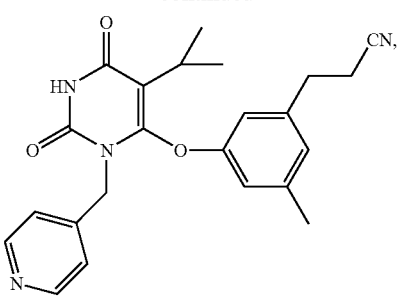
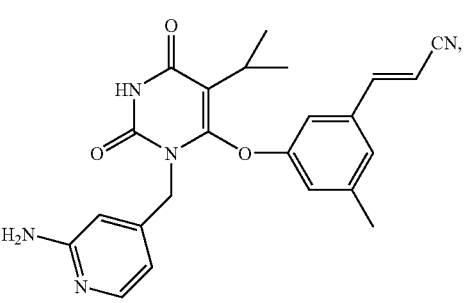
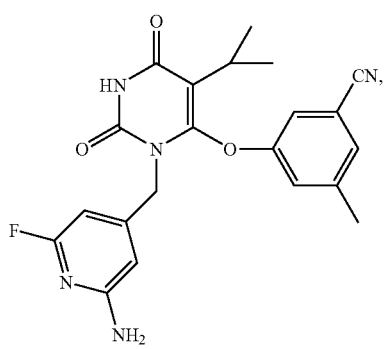
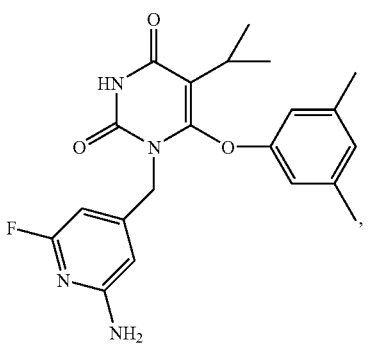

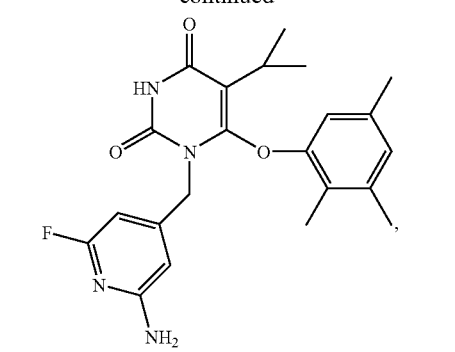
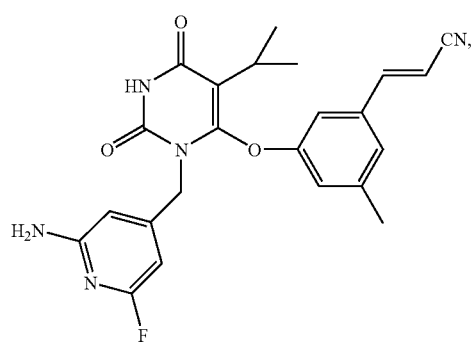
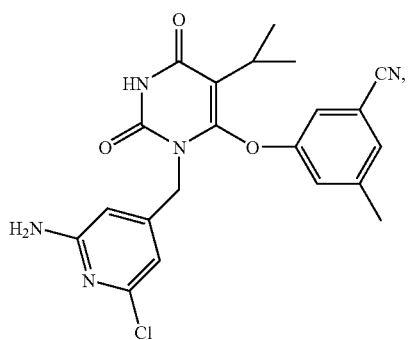
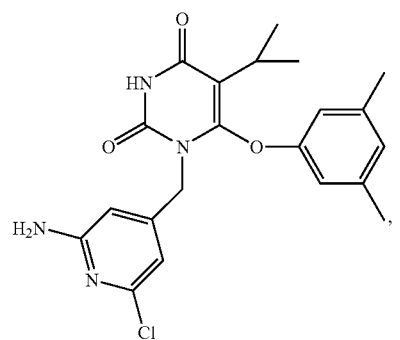
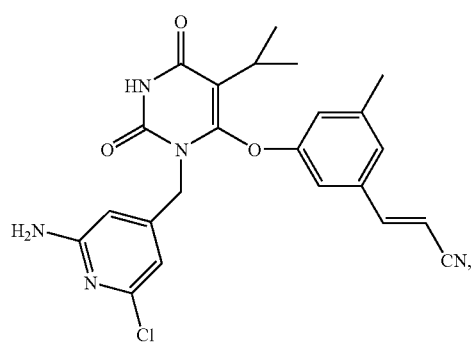
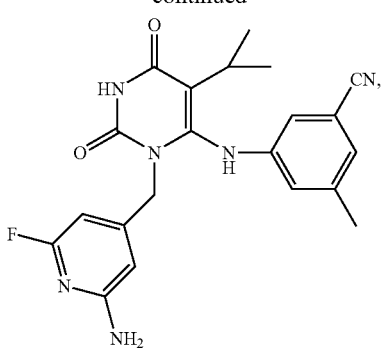
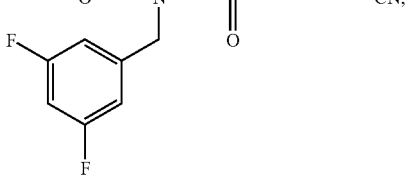
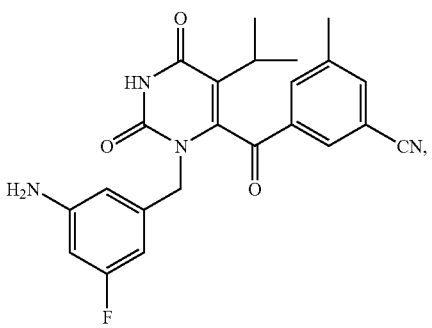
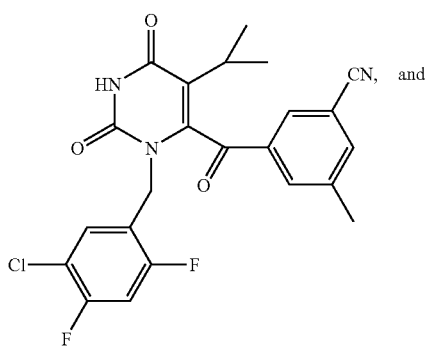
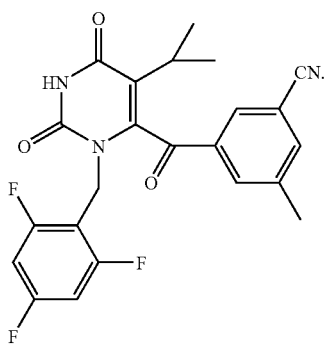

35. A pharmaceutical composition comprising a therapeutically effective amount of a compound of claim 1, and a pharmaceutically acceptable carrier.

36. A method for inhibiting HIV reverse transcriptase comprising: administering a therapeutically effective amount of a compound of claim 1, or a pharmaceutically acceptable salt thereof, to a patient in need of such treatment.

* * * * *